(12) United States Patent
Kennedy et al.

(10) Patent No.: US 11,976,329 B2
(45) Date of Patent: May 7, 2024

(54) METHODS AND SYSTEMS FOR DETECTING USUAL INTERSTITIAL PNEUMONIA

(71) Applicant: VERACYTE, INC., South San Francisco, CA (US)

(72) Inventors: Giulia C. Kennedy, South San Francisco, CA (US); Jing Huang, South San Francisco, CA (US); Yoonha Choi, South San Francisco, CA (US); Daniel Pankratz, South San Francisco, CA (US); Patric Sean Walsh, South San Francisco, CA (US)

(73) Assignee: Veracyte, Inc., South San Francisco, CA (US)

( * ) Notice: Subject to any disclaimer, the term of this patent is extended or adjusted under 35 U.S.C. 154(b) by 0 days.

(21) Appl. No.: 17/558,534

(22) Filed: Dec. 21, 2021

(65) Prior Publication Data
US 2022/0112561 A1    Apr. 14, 2022

Related U.S. Application Data

(63) Continuation of application No. 17/218,123, filed on Mar. 30, 2021, now abandoned, which is a continuation of application No. 16/292,573, filed on Mar. 5, 2019, now abandoned, which is a continuation of application No. PCT/US2017/050358, filed on Sep. 6, 2017.

(60) Provisional application No. 62/528,899, filed on Jul. 5, 2017, provisional application No. 62/384,609, filed on Sep. 7, 2016, provisional application No. 61/799,754, filed on Mar. 15, 2013.

(51) Int. Cl.
| | |
|---|---|
| *C12Q 1/68* | (2018.01) |
| *A61K 31/197* | (2006.01) |
| *A61K 31/4412* | (2006.01) |
| *A61K 31/52* | (2006.01) |
| *A61K 31/573* | (2006.01) |
| *C12Q 1/6806* | (2018.01) |
| *C12Q 1/686* | (2018.01) |
| *C12Q 1/6874* | (2018.01) |
| *C12Q 1/6883* | (2018.01) |
| *G01N 33/68* | (2006.01) |

(52) U.S. Cl.
CPC .......... *C12Q 1/6883* (2013.01); *A61K 31/197* (2013.01); *A61K 31/4412* (2013.01); *A61K 31/52* (2013.01); *A61K 31/573* (2013.01); *C12Q 1/6806* (2013.01); *C12Q 1/686* (2013.01); *C12Q 1/6874* (2013.01); *G01N 33/6893* (2013.01); *C12Q 2600/112* (2013.01); *C12Q 2600/158* (2013.01); *G01N 2800/12* (2013.01); *G01N 2800/60* (2013.01)

(58) Field of Classification Search
CPC ............. C12Q 1/6874; C12Q 2600/158
See application file for complete search history.

(56) References Cited

U.S. PATENT DOCUMENTS

| | | |
|---|---|---|
| 3,640,268 A | 2/1972 | Hugh |
| 3,645,691 A | 2/1972 | Guenter et al. |
| 3,687,808 A | 8/1972 | Merigan, Jr. et al. |
| 4,641,662 A | 2/1987 | Jaicks |
| 4,800,896 A | 1/1989 | Jalowayski |
| 5,130,238 A | 7/1992 | Malek et al. |
| 5,143,854 A | 9/1992 | Pirrung et al. |
| 5,288,514 A | 2/1994 | Ellman |
| 5,384,261 A | 1/1995 | Winkler et al. |
| 5,399,491 A | 3/1995 | Kacian et al. |
| 5,422,273 A | 6/1995 | Garrison et al. |
| 5,440,942 A | 8/1995 | Hubbard |
| 5,455,166 A | 10/1995 | Walker |
| 5,477,863 A | 12/1995 | Grant |
| 5,494,810 A | 2/1996 | Barany et al. |
| 5,538,848 A | 7/1996 | Livak et al. |
| 5,677,195 A | 10/1997 | Winkler et al. |
| 5,705,365 A | 1/1998 | Ryder et al. |
| 5,710,029 A | 1/1998 | Ryder et al. |
| 5,726,060 A | 3/1998 | Bridges |
| 5,795,782 A | 8/1998 | Church et al. |
| 5,830,711 A | 11/1998 | Barany et al. |
| 5,846,717 A | 12/1998 | Brow et al. |
| 5,854,033 A | 12/1998 | Lizardi |
| 5,876,978 A | 3/1999 | Willey et al. |
| 5,888,779 A | 3/1999 | Kacian et al. |
| 5,965,360 A | 10/1999 | Zain et al. |
| 5,985,557 A | 11/1999 | Prudent et al. |
| 5,989,815 A | 11/1999 | Skolnick et al. |

(Continued)

FOREIGN PATENT DOCUMENTS

| | | |
|---|---|---|
| CA | 2712773 A1 | 7/2009 |
| CN | 1620309 A | 5/2005 |

(Continued)

OTHER PUBLICATIONS

Cho et al. System biology of interstitial lung diseases: integration of mRNA and microRNA expression changes. 2011, BMC Medical Genomics, 4:8, p. 1-20.
Co-pending U.S. Appl. No. 16/551,645, inventors Kennedygiulia; C. et al., filed on Aug. 26, 2019.
Co-pending U.S. Appl. No. 16/557,278, inventors Wildejonathan; I. et al., filed on Aug. 30, 2019.
De Figueiredo-Pontes, Idenification and characterization of ALK kinase splicing isoforms on non-small-cell lung cancer, J Thorac Oncol, 9(2): 248-253, Feb. 2014. (Year: 2014).
EP14764225.0 European Search Report dated Jan. 19, 2017.
EP14764225.0 European Search Report dated Oct. 7, 2016.

(Continued)

*Primary Examiner* — Kenneth R Horlick
(74) *Attorney, Agent, or Firm* — Wilson Sonsini Goodrich & Rosati

(57) ABSTRACT

The present disclosure provides systems, methods, and classifiers for differentiating between samples as usual interstitial pneumonia (UIP) or non-UIP.

20 Claims, 34 Drawing Sheets

(56) References Cited

U.S. PATENT DOCUMENTS

| | | |
|---|---|---|
| 5,994,069 A | 11/1999 | Hall et al. |
| 6,001,567 A | 12/1999 | Brow et al. |
| 6,013,431 A | 1/2000 | Soederlund et al. |
| 6,015,714 A | 1/2000 | Baldarelli et al. |
| 6,022,692 A | 2/2000 | Coulie et al. |
| 6,027,887 A | 2/2000 | Zavada et al. |
| 6,085,907 A | 7/2000 | Hochmeister et al. |
| 6,090,543 A | 7/2000 | Prudent et al. |
| 6,136,182 A | 10/2000 | Dolan et al. |
| 6,225,051 B1 | 5/2001 | Sugiyama et al. |
| 6,251,639 B1 | 6/2001 | Kurn |
| 6,268,142 B1 | 7/2001 | Duff et al. |
| 6,410,278 B1 | 6/2002 | Notomi et al. |
| 6,436,642 B1 | 8/2002 | Gould-Rothberg et al. |
| 6,627,067 B1 | 9/2003 | Branton et al. |
| 6,667,154 B1 | 12/2003 | Wang et al. |
| 6,676,609 B1 | 1/2004 | Rutenberg et al. |
| 6,723,506 B2 | 4/2004 | Fletcher et al. |
| 6,746,846 B1 | 6/2004 | Wang et al. |
| 7,186,514 B2 | 3/2007 | Zavada et al. |
| 7,211,390 B2 | 5/2007 | Rothberg et al. |
| 7,238,485 B2 | 7/2007 | Akeson et al. |
| 7,244,559 B2 | 7/2007 | Rothberg et al. |
| 7,258,838 B2 | 8/2007 | Li et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordano et al. |
| 7,662,553 B2 | 2/2010 | Lenz |
| 7,767,391 B2 | 8/2010 | Scott et al. |
| 7,901,881 B2 | 3/2011 | Libutti et al. |
| 7,901,888 B2 | 3/2011 | Kebebew |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,293,880 B2 | 10/2012 | Cote et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,074,258 B2 | 7/2015 | Davicioni et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,482 B2 | 12/2015 | Davicioni et al. |
| 9,234,244 B2 | 1/2016 | Zeiger et al. |
| 9,495,515 B1 | 11/2016 | Kennedy et al. |
| 9,587,279 B2 | 3/2017 | Fahey, III et al. |
| 9,617,604 B2 | 4/2017 | Davicioni et al. |
| 9,708,667 B2 | 7/2017 | Barnett-Itzhaki et al. |
| 9,714,452 B2 | 7/2017 | Davicioni et al. |
| 9,856,537 B2 | 1/2018 | Kennedy et al. |
| 9,920,374 B2 | 3/2018 | Brody et al. |
| 9,994,907 B2 | 6/2018 | Davicioni et al. |
| 10,036,069 B2 | 7/2018 | Noth et al. |
| 10,114,924 B2 | 10/2018 | Kennedy et al. |
| 10,236,078 B2 | 3/2019 | Kennedy et al. |
| 10,422,009 B2 | 9/2019 | Davicioni et al. |
| 10,446,272 B2 | 10/2019 | Wilde et al. |
| 10,526,655 B2 | 1/2020 | Whitney et al. |
| 10,570,454 B2 | 2/2020 | Brody et al. |
| 10,672,504 B2 | 6/2020 | Kennedy et al. |
| 10,731,223 B2 | 8/2020 | Kennedy et al. |
| 10,808,285 B2 | 10/2020 | Brody et al. |
| 10,927,417 B2 | 2/2021 | Beane-Ebel et al. |
| 10,934,587 B2 | 3/2021 | Kennedy et al. |
| 10,961,582 B2 | 3/2021 | Noth et al. |
| 11,217,329 B1 | 1/2022 | Choi et al. |
| 2001/0051344 A1 | 12/2001 | Shalon et al. |
| 2002/0031496 A1 | 3/2002 | Firestein et al. |
| 2002/0076735 A1 | 6/2002 | Williams et al. |
| 2002/0081612 A1 | 6/2002 | Katz et al. |
| 2002/0094547 A1 | 7/2002 | Burstein |
| 2002/0160388 A1 | 10/2002 | Macina et al. |
| 2002/0169137 A1 | 11/2002 | Reiner et al. |
| 2003/0104499 A1 | 6/2003 | Pressman et al. |
| 2003/0116159 A1 | 6/2003 | Orr et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2004/0005294 A1 | 1/2004 | Lee |
| 2004/0009489 A1 | 1/2004 | Golub et al. |
| 2004/0019466 A1 | 1/2004 | Minor et al. |
| 2004/0058378 A1 | 3/2004 | Kong et al. |
| 2004/0063120 A1 | 4/2004 | Beer et al. |
| 2004/0197785 A1 | 10/2004 | Willey et al. |
| 2004/0241725 A1 | 12/2004 | Xiao et al. |
| 2004/0241728 A1 | 12/2004 | Liew |
| 2005/0042222 A1 | 2/2005 | Yamamoto et al. |
| 2005/0048533 A1 | 3/2005 | Sidransky et al. |
| 2005/0065447 A1 | 3/2005 | Lee et al. |
| 2005/0137805 A1 | 6/2005 | Lewin et al. |
| 2005/0240357 A1 | 10/2005 | Minor |
| 2005/0250125 A1 | 11/2005 | Novakoff |
| 2005/0260586 A1 | 11/2005 | Demuth et al. |
| 2005/0266409 A1 | 12/2005 | Brown et al. |
| 2005/0266443 A1 | 12/2005 | Croce et al. |
| 2006/0003171 A1 | 1/2006 | Igawa et al. |
| 2006/0019256 A1 | 1/2006 | Clarke et al. |
| 2006/0019272 A1 | 1/2006 | Geraci et al. |
| 2006/0019615 A1 | 1/2006 | Ditmer |
| 2006/0035244 A1 | 2/2006 | Riggins et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0127928 A1 | 6/2006 | Bacus et al. |
| 2006/0140960 A1 | 6/2006 | Wang et al. |
| 2006/0154278 A1 | 7/2006 | Brody et al. |
| 2006/0183144 A1 | 8/2006 | Willey et al. |
| 2006/0188909 A1 | 8/2006 | Willey et al. |
| 2006/0190192 A1 | 8/2006 | Willey et al. |
| 2006/0194216 A1 | 8/2006 | Willey et al. |
| 2006/0241869 A1 | 10/2006 | Schadt et al. |
| 2006/0252057 A1 | 11/2006 | Raponi et al. |
| 2006/0265138 A1 | 11/2006 | Bowtell et al. |
| 2007/0020657 A1 | 1/2007 | Grebe et al. |
| 2007/0031873 A1 | 2/2007 | Wang et al. |
| 2007/0037186 A1 | 2/2007 | Jiang et al. |
| 2007/0048738 A1 | 3/2007 | Donkena et al. |
| 2007/0065833 A1 | 3/2007 | Gupta |
| 2007/0092891 A1 | 4/2007 | Willey et al. |
| 2007/0092892 A1 | 4/2007 | Willey et al. |
| 2007/0092893 A1 | 4/2007 | Willey et al. |
| 2007/0099209 A1 | 5/2007 | Clarke et al. |
| 2007/0105133 A1 | 5/2007 | Clarke et al. |
| 2007/0148650 A1 | 6/2007 | Brody et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |
| 2007/0172844 A1 | 7/2007 | Lancaster et al. |
| 2007/0220621 A1 | 9/2007 | Clarke et al. |
| 2007/0238119 A1 | 10/2007 | Yu et al. |
| 2008/0028302 A1 | 1/2008 | Meschkat |
| 2008/0044824 A1 | 2/2008 | Giordano et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlin |

(56) References Cited

U.S. PATENT DOCUMENTS

| | | |
|---|---|---|
| 2008/0274457 A1 | 11/2008 | Eng et al. |
| 2008/0280302 A1 | 11/2008 | Kebebew |
| 2008/0281568 A1 | 11/2008 | Kao et al. |
| 2009/0020433 A1 | 1/2009 | Cohen et al. |
| 2009/0029477 A1 | 1/2009 | Meller et al. |
| 2009/0042184 A1* | 2/2009 | Mas .............. C12Q 1/6886 435/6.12 |
| 2009/0061454 A1 | 3/2009 | Brody et al. |
| 2009/0186951 A1 | 7/2009 | Brody et al. |
| 2009/0191535 A1 | 7/2009 | Connelly et al. |
| 2009/0204333 A1 | 8/2009 | Friend et al. |
| 2009/0246779 A1 | 10/2009 | Rabinovitch et al. |
| 2009/0280490 A1 | 11/2009 | Baker et al. |
| 2009/0291853 A1 | 11/2009 | Kim et al. |
| 2009/0311692 A1 | 12/2009 | Brody et al. |
| 2010/0035244 A1 | 2/2010 | Brody et al. |
| 2010/0055689 A1 | 3/2010 | Spira et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0119474 A1 | 5/2010 | Crystal et al. |
| 2010/0131286 A1 | 5/2010 | Houlgatte et al. |
| 2010/0131432 A1 | 5/2010 | Kennedy et al. |
| 2010/0143312 A1 | 6/2010 | Hariri et al. |
| 2010/0178653 A1 | 7/2010 | Aharonov et al. |
| 2010/0204058 A1 | 8/2010 | Chang et al. |
| 2010/0255486 A1 | 10/2010 | Showe et al. |
| 2010/0273674 A1 | 10/2010 | Kamalakaran et al. |
| 2010/0285979 A1 | 11/2010 | Zeiger et al. |
| 2010/0303813 A1 | 12/2010 | Carulli et al. |
| 2011/0053158 A1 | 3/2011 | Mambo et al. |
| 2011/0092375 A1 | 4/2011 | Zamore et al. |
| 2011/0152110 A1 | 6/2011 | Vierlinger et al. |
| 2011/0190150 A1 | 8/2011 | Brody et al. |
| 2011/0190156 A1 | 8/2011 | Whitfield et al. |
| 2011/0212855 A1 | 9/2011 | Rafnar et al. |
| 2011/0217315 A1* | 9/2011 | Schwartz .............. A61P 11/00 424/94.6 |
| 2011/0217717 A1 | 9/2011 | Brody et al. |
| 2011/0224313 A1 | 9/2011 | Tsao et al. |
| 2011/0229894 A1 | 9/2011 | Levy et al. |
| 2011/0230372 A1 | 9/2011 | Willman et al. |
| 2011/0269142 A1 | 11/2011 | Zavras |
| 2011/0287946 A1 | 11/2011 | Gudmundsson et al. |
| 2011/0294684 A1 | 12/2011 | Baty et al. |
| 2011/0312520 A1 | 12/2011 | Kennedy et al. |
| 2011/0312530 A1 | 12/2011 | Aharonov et al. |
| 2012/0015839 A1 | 1/2012 | Chinnaiyan |
| 2012/0015843 A1 | 1/2012 | Von et al. |
| 2012/0041686 A1 | 2/2012 | Brody et al. |
| 2012/0115735 A1 | 5/2012 | Vogelstein et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0190567 A1 | 7/2012 | Brody et al. |
| 2012/0208706 A1 | 8/2012 | Downing et al. |
| 2012/0214165 A1 | 8/2012 | Walfish et al. |
| 2012/0220474 A1 | 8/2012 | Kennedy et al. |
| 2012/0264626 A1 | 10/2012 | Nana-Sinkam et al. |
| 2012/0288860 A1* | 11/2012 | Van Hoek .............. C12Q 1/6883 435/6.12 |
| 2012/0322673 A1 | 12/2012 | Brody et al. |
| 2012/0329666 A1* | 12/2012 | Steele .............. G01N 33/6842 435/6.12 |
| 2013/0023434 A1 | 1/2013 | Van |
| 2013/0023437 A1 | 1/2013 | Brody et al. |
| 2013/0029873 A1 | 1/2013 | De et al. |
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0184999 A1 | 7/2013 | Ding |
| 2013/0196868 A1 | 8/2013 | Lebowitz et al. |
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2013/0302810 A1 | 11/2013 | Latham et al. |
| 2013/0303826 A1 | 11/2013 | Jurisica et al. |
| 2014/0030714 A1 | 1/2014 | Paschke et al. |
| 2014/0080731 A1 | 3/2014 | Davicioni et al. |
| 2014/0087961 A1 | 3/2014 | Sulem et al. |
| 2014/0099261 A1 | 4/2014 | Keutgen et al. |
| 2014/0121126 A1 | 5/2014 | Bivona et al. |
| 2014/0143188 A1 | 5/2014 | Mackey et al. |
| 2014/0179771 A1 | 6/2014 | Bancel et al. |
| 2014/0220006 A1 | 8/2014 | Aghvanyan et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0329251 A1 | 11/2014 | Moerman et al. |
| 2014/0349856 A1 | 11/2014 | Schnabel et al. |
| 2014/0349864 A1 | 11/2014 | Kennedy et al. |
| 2014/0371096 A1 | 12/2014 | Umbricht et al. |
| 2014/0378425 A1 | 12/2014 | Wilde et al. |
| 2015/0038376 A1 | 2/2015 | Tian et al. |
| 2015/0080243 A1 | 3/2015 | Whitney et al. |
| 2015/0088430 A1 | 3/2015 | Whitney et al. |
| 2015/0099665 A1 | 4/2015 | Rosenfeld et al. |
| 2015/0141470 A1 | 5/2015 | Garraway et al. |
| 2015/0152474 A1 | 6/2015 | Pawlowski et al. |
| 2015/0275306 A1 | 10/2015 | Bernards et al. |
| 2015/0299808 A1 | 10/2015 | Gonzalez et al. |
| 2015/0307947 A1 | 10/2015 | Basu et al. |
| 2015/0329915 A1 | 11/2015 | Davicioni et al. |
| 2015/0337385 A1 | 11/2015 | Harris et al. |
| 2015/0354008 A1 | 12/2015 | Brody et al. |
| 2015/0368724 A1 | 12/2015 | Aharonov et al. |
| 2016/0024583 A1 | 1/2016 | Whitney et al. |
| 2016/0024586 A1 | 1/2016 | Delfour et al. |
| 2016/0032400 A1 | 2/2016 | Gomis et al. |
| 2016/0068915 A1 | 3/2016 | Kennedy et al. |
| 2016/0115546 A1 | 4/2016 | Rosenfeld et al. |
| 2016/0120832 A1 | 5/2016 | Rabinowitz et al. |
| 2016/0130656 A1 | 5/2016 | Whitney et al. |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2017/0016076 A1 | 1/2017 | Barnett-Itzhaki et al. |
| 2017/0127976 A1 | 5/2017 | Phillips et al. |
| 2017/0145513 A1 | 5/2017 | Kennedy et al. |
| 2017/0166980 A1 | 6/2017 | Fahey, III et al. |
| 2017/0226591 A1 | 8/2017 | Brody et al. |
| 2017/0247759 A1 | 8/2017 | Wilde et al. |
| 2017/0328908 A1 | 11/2017 | Brody et al. |
| 2017/0329894 A1 | 11/2017 | Kennedy et al. |
| 2017/0335396 A1* | 11/2017 | Kennedy .............. C12Q 1/6876 |
| 2018/0016642 A1 | 1/2018 | Kennedy et al. |
| 2018/0030540 A1 | 2/2018 | Davicioni et al. |
| 2018/0068058 A1 | 3/2018 | Abdueva et al. |
| 2018/0112275 A1 | 4/2018 | Davicioni et al. |
| 2018/0122508 A1 | 5/2018 | Wilde et al. |
| 2018/0127832 A1 | 5/2018 | Kennedy et al. |
| 2018/0349548 A1 | 12/2018 | Walsh et al. |
| 2019/0080047 A1 | 3/2019 | Kennedy et al. |
| 2019/0100805 A1 | 4/2019 | Davicioni et al. |
| 2019/0100809 A1 | 4/2019 | Kennedy et al. |
| 2019/0172551 A1 | 6/2019 | Kennedy et al. |
| 2019/0292600 A1 | 9/2019 | Spira et al. |
| 2019/0330680 A1* | 10/2019 | Kennedy .............. C12Q 1/6837 |
| 2019/0376148 A1 | 12/2019 | Brody et al. |
| 2020/0096513 A1 | 3/2020 | Brody et al. |
| 2020/0115763 A1 | 4/2020 | Brody et al. |
| 2020/0143944 A1 | 5/2020 | Wilde et al. |
| 2020/0176078 A1 | 6/2020 | Kennedy et al. |
| 2020/0202974 A1 | 6/2020 | Kennedy et al. |
| 2020/0232045 A1 | 7/2020 | Brody et al. |
| 2020/0232046 A1 | 7/2020 | Kennedy |
| 2020/0248274 A1 | 8/2020 | Brody et al. |
| 2020/0405225 A1 | 12/2020 | Kennedy et al. |
| 2021/0040559 A1 | 2/2021 | Wilde et al. |
| 2021/0040562 A1 | 2/2021 | Whitney et al. |

(56) References Cited

U.S. PATENT DOCUMENTS

| | | | |
|---|---|---|---|
| 2021/0079471 | A1 | 3/2021 | Kennedy et al. |
| 2021/0238686 | A1 | 8/2021 | Kennedy et al. |
| 2021/0324464 | A1 | 10/2021 | Kennedy et al. |
| 2021/0332431 | A1 | 10/2021 | Wilde et al. |
| 2021/0355524 | A1 | 11/2021 | Kennedy et al. |
| 2021/0381062 | A1 | 12/2021 | Spira et al. |
| 2022/0235417 | A1 | 7/2022 | Noth et al. |

FOREIGN PATENT DOCUMENTS

| | | | |
|---|---|---|---|
| CN | 1688582 | A | 10/2005 |
| CN | 101014720 | A | 8/2007 |
| CN | 101501214 | A | 8/2009 |
| CN | 102640001 | A | 8/2012 |
| CN | 102858991 | A | 1/2013 |
| CN | 103038635 | A | 4/2013 |
| CN | 104334744 | A | 2/2015 |
| CN | 104853802 | A | 8/2015 |
| CN | 105247075 | A | 1/2016 |
| CN | 105378104 | A | 3/2016 |
| DE | 10219117 | C1 | 10/2003 |
| EP | 0684315 | A1 | 11/1995 |
| EP | 1403638 | A1 | 3/2004 |
| EP | 1975245 | A1 | 10/2008 |
| EP | 1975252 | A1 | 10/2008 |
| EP | 2231874 | A2 | 9/2010 |
| EP | 2295599 | A1 | 3/2011 |
| EP | 2366800 | A1 | 9/2011 |
| EP | 2971128 | A2 | 1/2016 |
| EP | 3215170 | A1 | 9/2017 |
| EP | 3360978 | A2 | 8/2018 |
| EP | 3510173 | A1 | 7/2019 |
| EP | 3770274 | A1 | 1/2021 |
| EP | 4219761 | A1 | 8/2023 |
| JP | 2004526154 | A | 8/2004 |
| JP | 2005168432 | A | 6/2005 |
| JP | 2005304497 | A | 11/2005 |
| JP | 2007513635 | A | 5/2007 |
| JP | 2008545400 | A | 12/2008 |
| JP | 2008545431 | A | 12/2008 |
| JP | 2013532295 | A | 8/2013 |
| JP | 2013212052 | A | 10/2013 |
| JP | 2015519966 | A | 7/2015 |
| JP | 2018504138 | A | 2/2018 |
| KR | 20080020083 | A | 3/2008 |
| KR | 20130017525 | | 2/2013 |
| WO | WO-9015070 | A1 | 12/1990 |
| WO | WO-9210092 | A1 | 6/1992 |
| WO | WO-9309668 | A1 | 5/1993 |
| WO | WO-9322684 | A1 | 11/1993 |
| WO | WO-9515331 | A1 | 6/1995 |
| WO | WO-9857145 | A1 | 12/1998 |
| WO | WO-9960160 | A1 | 11/1999 |
| WO | WO-0006780 | A1 | 2/2000 |
| WO | WO-0120035 | A2 | 3/2001 |
| WO | WO-0128428 | A1 | 4/2001 |
| WO | WO-0206791 | A2 | 1/2002 |
| WO | WO-0244331 | A2 | 6/2002 |
| WO | WO-02072866 | A2 | 9/2002 |
| WO | WO-02086443 | A2 | 10/2002 |
| WO | WO-03015613 | A2 | 2/2003 |
| WO | WO-03029273 | A2 | 4/2003 |
| WO | WO-03040325 | A2 | 5/2003 |
| WO | WO-03062389 | A2 | 7/2003 |
| WO | WO-03097666 | A2 | 11/2003 |
| WO | WO-2004005891 | A2 | 1/2004 |
| WO | WO-2004029055 | A1 | 4/2004 |
| WO | WO-2004091383 | A2 | 10/2004 |
| WO | WO-2004091511 | A2 | 10/2004 |
| WO | WO-2004111197 | A2 | 12/2004 |
| WO | WO-2005000098 | A2 | 1/2005 |
| WO | WO-2005005601 | A2 | 1/2005 |
| WO | WO-2005047451 | A2 | 5/2005 |
| WO | WO-2005085471 | A2 | 9/2005 |
| WO | WO-2005100608 | A2 | 10/2005 |
| WO | WO-2005005601 | A3 | 4/2006 |
| WO | WO-2006047484 | A2 | 5/2006 |
| WO | WO-2006062118 | A1 | 6/2006 |
| WO | WO-2006105252 | A2 | 10/2006 |
| WO | WO-2006110593 | A2 | 10/2006 |
| WO | WO-2006113467 | A2 | 10/2006 |
| WO | WO-2006127537 | A2 | 11/2006 |
| WO | WO-2006113467 | A3 | 4/2007 |
| WO | WO-2007038792 | A2 | 4/2007 |
| WO | WO-2007103541 | A2 | 9/2007 |
| WO | WO-2007038792 | A3 | 11/2007 |
| WO | WO-2007126882 | A2 | 11/2007 |
| WO | WO-2008104380 | A2 | 9/2008 |
| WO | WO-2008119776 | A1 | 10/2008 |
| WO | WO-2008130887 | A1 | 10/2008 |
| WO | WO-2008104380 | A3 | 11/2008 |
| WO | WO-2008140774 | A2 | 11/2008 |
| WO | WO-2009006323 | A2 | 1/2009 |
| WO | WO-2009020905 | A2 | 2/2009 |
| WO | WO-2009026605 | A2 | 3/2009 |
| WO | WO-2009029266 | A2 | 3/2009 |
| WO | WO-2009037337 | A1 | 3/2009 |
| WO | WO-2009039457 | A1 | 3/2009 |
| WO | WO-2006127537 | A3 | 4/2009 |
| WO | WO-2009042728 | A1 | 4/2009 |
| WO | WO-2009068591 | A2 | 6/2009 |
| WO | WO-2009079450 | A2 | 6/2009 |
| WO | WO-2009087139 | A1 | 7/2009 |
| WO | WO-2009096903 | A1 | 8/2009 |
| WO | WO-2009111881 | A1 | 9/2009 |
| WO | WO-2009121070 | A1 | 10/2009 |
| WO | WO-2009126271 | A1 | 10/2009 |
| WO | WO-2009143603 | A1 | 12/2009 |
| WO | WO-2010000907 | A1 | 1/2010 |
| WO | WO-2010018600 | A1 | 2/2010 |
| WO | WO-2010018601 | A2 | 2/2010 |
| WO | WO-2010028274 | A1 | 3/2010 |
| WO | WO-2010054233 | A1 | 5/2010 |
| WO | WO-2010056374 | A2 | 5/2010 |
| WO | WO-2010073248 | A2 | 7/2010 |
| WO | WO-2010056374 | A3 | 9/2010 |
| WO | WO-2010073248 | A3 | 9/2010 |
| WO | WO-2010099598 | A1 | 9/2010 |
| WO | WO-2010123626 | A1 | 10/2010 |
| WO | WO-2010124372 | A1 | 11/2010 |
| WO | WO-2010127322 | A1 | 11/2010 |
| WO | WO-2010129934 | A2 | 11/2010 |
| WO | WO-2011044142 | A1 | 4/2011 |
| WO | WO-2011079846 | A2 | 7/2011 |
| WO | WO-2011086174 | A2 | 7/2011 |
| WO | WO-2011094345 | A1 | 8/2011 |
| WO | WO-2011137060 | A1 | 11/2011 |
| WO | WO-2011143361 | A2 | 11/2011 |
| WO | WO-2012006632 | A2 | 1/2012 |
| WO | WO-2012055565 | A1 | 5/2012 |
| WO | WO-2012129237 | A2 | 9/2012 |
| WO | WO-2012149550 | A1 | 11/2012 |
| WO | WO-2013033640 | A1 | 3/2013 |
| WO | WO-2013049152 | A2 | 4/2013 |
| WO | WO-2013063544 | A1 | 5/2013 |
| WO | WO-2013074938 | A2 | 5/2013 |
| WO | WO-2013086429 | A2 | 6/2013 |
| WO | WO-2013086522 | A1 | 6/2013 |
| WO | WO-2013088457 | A1 | 6/2013 |
| WO | WO-2013148232 | A1 | 10/2013 |
| WO | WO-2013163568 | A2 | 10/2013 |
| WO | WO-2013177060 | A1 | 11/2013 |
| WO | WO-2013190092 | A1 | 12/2013 |
| WO | WO-2014043803 | A1 | 3/2014 |
| WO | WO-2014144564 | A2 | 9/2014 |
| WO | WO-2014144821 | A1 | 9/2014 |
| WO | WO-2014151764 | A2 | 9/2014 |
| WO | WO-2014186036 | A1 | 11/2014 |
| WO | WO-2015068157 | A1 | 5/2015 |
| WO | WO-2015071876 | A2 | 5/2015 |
| WO | WO-2016011068 | A1 | 1/2016 |
| WO | WO-2016073768 | A1 | 5/2016 |
| WO | WO-2016094330 | A2 | 6/2016 |
| WO | WO-2016141127 | A1 | 9/2016 |

(56) References Cited

FOREIGN PATENT DOCUMENTS

| WO | WO-2017065959 A2 | 4/2017 |
|---|---|---|
| WO | WO-2017197335 A1 | 11/2017 |
| WO | WO-2018009915 A1 | 1/2018 |
| WO | WO-2018048960 A1 | 3/2018 |
| WO | WO-2018223066 A1 | 12/2018 |
| WO | WO-2019023517 A2 | 1/2019 |

OTHER PUBLICATIONS

EP17849490.2 Extended Search Report dated Apr. 20, 2020.
European extended search report dated Mar. 28, 2018 for application No. 15857196.8.
Hummert et al. Creation and Comparison of Different Chip Definition Files for Affymetrix Microarrays. Proceedings of the International Conference on Bioinformatics and Computational Biology. BioComp'11, Jul. 18-21, 2011, Las Vegas, USA, 1(1): 16-22.
Key, Objective cough frequency in Idiopathic Pulomnary Fibrosis, Cough, 6:4, pp. 1-7, 2010. (Year: 2010).
Konishi, Gene Expression Profiles of Acute Exacerbations of Idiopathic Pulmonary Fibrosis, Am J Respir Crit Care Med, 180, 167-175, 2009. (Year: 2009).
Noble et al. Pirfenidone in patients with idiopathic pulmonary fibrosis (CAPACITY): two randomised trials. 2011, Lancet, 377, 1760-69.
Pankratz et al. Usual interstitial pneumonia can be detected in transbronchial biopsies using machine learning. Annals of the American Thoracic Society 14.11 (2017): 1646-1654.
PCT/US2014/029029 International Preliminary Report on Patentability dated Sep. 15, 2015.
PCT/US2014/029029 International Search Report dated Oct. 2, 2014.
PCT/US2014/029029 Written Opinion dated Oct. 2, 2014.
PCT/US2015/059309 International Search Report and Written Opinion dated Mar. 11, 2016.
PCT/US2017/050358 International Search Report dated Dec. 18, 2017.
"Quackenbush, et al. Microarray data normalization and transformation. Nature Genetics Supplement. Dec. 2002. vol. 32, p. 496-501".
Raghu et al. An official ATS/ERS/JRS/ALAT statement: idiopathic pulmonary fibrosis: evidence-based guidelines for diagnosis and management. American Journal of Respiratory and Critical Care Medicine (2011); 183.6: 788-824.
Selman et al. Gene expression profiles distinguish idiopathic pulmonary fibrosis from hypersensitivity pneumonitis. American Journal of Respiratory and Critical Care Medicine (2006); 173.2: 188-198.
U.S. Appl. No. 14/213,632 Office Action dated Jun. 10, 2015.
U.S. Appl. No. 14/213,632 Office Action dated Mar. 11, 2016.
U.S. Appl. No. 15/261,662 Office Action dated May 1, 2019.
U.S. Appl. No. 17/218,121 Office Action dated Jan. 24, 2022.
U.S. Appl. No. 17/218,121 Office Action dated Jun. 13, 2022.
U.S. Appl. No. 17/218,121 Office Action dated Oct. 17, 2022.
U.S. Appl. No. 17/218,125 Notice of Allowance dated Jan. 26, 2023.
U.S. Appl. No. 17/218,125 Office Action dated Feb. 17, 2022.
U.S. Appl. No. 17/218,125 Office Action dated Sep. 15, 2022.
U.S. Appl. No. 17/218,125 Office Action dated Sep. 28, 2021.
Yang et al. Expression of cilium-associated genes defines novel molecular subtypes of idiopathic pulmonary fibrosis. Thorax (2013): 68(12):1114-11121.
Yang et al. Gene expression profiling of familial and sporadic interstitial pneumonia. American Journal of Respiratory and Critical Care Medicine (2007); 175.1: 45-54.
Zhang, et al., Biomarkers in idiopathic pulmonary fibrosis, Current opinion in pulmonary medicine, vol. 18, No. 5, Sep. 1, 2012, 441-446.
PCT/US2012/065540 International Search Report and Written Opinion dated Mar. 27, 2013.
Abrahamson et al. Cystatins. Biochem. Soc. Symp. 70: 179-199 (2003).
Abratani, Hiroyuki. Characteristic Diagnosis of Cancer by Gene Expression Profiling. Personalized Diagnosis of Cancer by Gene Expression Profiling. English Translation. Journal of Clinical and Experimental Medicine (Igaku No Ayumi), Jun. 1, 2002, vol. 201, No. 9, p. 687-692.
Abrosimov et al. The cytoplasmic expression of MUC1 in papillary thyroid carcinoma of different histological variants and its correlation with cyclin D1 overexpression. Endocr Pathol. 2007;18(2):68-75.
Abubaker et al. Clinicopathological analysis of papillary thyroid cancer with PIK3CA alterations in a Middle Eastern population. J Clin Endocrinol Metab. 2008;93(2):611-8.
Accession N M_000441. 2008. *Homo sapiens* solute carrier family 26, member 4 (SLC26A4), mRNA (Year: 2008).
Adams, J.U., The Human Genome project set out to sequence all of the 3 billion nucleotides in the human genome. Exactly how was this daunting task done with such incredible speed and accuracy? DNA sequencing technologies. Nature Education, 2008; 1(1):193, pp. 1-6.
Adapt, The Peterson Institute for Cancer Research, probesets for ARSG, printed Jan. 10, 2013.
Adapt, The Peterson Institute for Cancer Research, probesets for FREM2, printed Jan. 10, 2013.
Adapt, The Peterson Institute for Cancer Research, probesets for GIMAP2, printed Jan. 10, 2013.
Adapt, The Peterson Institute for Cancer Research, probesets for HRASLS3, printed Jan. 10, 2013.
Adapt, The Peterson Institute for Cancer Research, probesets for PIGN, printed Jan. 10, 2013.
Adapt website. Paterson Institute for Cancer Research. Probesets for AUTS2. Printed Jul. 1, 2014. 2 pages.
Adapt website. Paterson Institute for Cancer Research. Probesets for FXYD6. Printed Jul. 1, 2014. 1 page.
Affymetrix CDKL2 ( https://www.affymetriix.com/analysis/netaffx/showresults.affx , Mar. 21, 2019).
Affymetrix: "Data Sheet Affymetrix(R) Genome-Wide Human SNP Array 6.0", 2007, pp. 1-4, XP002525407. Retrieved from the Internet: URL: http://www.affymetrix.com/support/technical/datasheets/genomewide_snp6_datasheet.pdf.
Affymetrix HG-U 133 Plus 2.0 Annotation File (filtered excerpt, obtained from http://www.affymetrix.com/Auth/analysis/downloads/na26/ivt/HG-U133_Pius_2.na26.annot.csv.zip on Mar. 18, 2013, 1 page) (Year: 2013).
Affymetrix HG-U 133A Annotation File (filtered excerpt, obtained from http://www.affymetrix.com/Auth/analysis/downloads/na35/ivt/HG-U133A.na35.annot.csv.zip on Apr. 29, 2016, 1 page) (Year: 2016).
Affymetrix HLA-F ( https://www.affymetrix.com/analysis/netaffx/showresults.affz , Mar. 21, 2019).
Affymetrix Technical Note: GeneChip® Gene 1.0 ST Array Design (created Sep. 5, 2007; downloaded from http://media.affymetrix.com/support/technical/technotes/gene_1_0_st_technote.pdf).
Affymetrix website for HG-U133A probe set list version 2004, Archived NetAffx Annotation Files (http://www.affymetrix.com/estore/catalog/131537/AFFY/Human+Genome+U133A+2.0+Array#1_3) printed Mar. 2015.
Afink, et al. Molecular characterization of iodotyrosine dehalogenase deficiency in patients with hypothyroidism. J Clin Endocrinol Metab. Dec. 2008;93(12):4894-901.
Aggarwal et al. Thyroid carcinoma-associated genetic mutations also occur in thyroid lymphomas. Mod Pathol. vol. 25 No. 9. May 11, 2012. pp. 1203-1211.
Agrawal, et al. Cancer Genome Atlas Research Network. Integrated genomic characterization of papillary thyroid carcinoma. Cell. Oct. 23, 2014;159(3):676-90. doi: 10.1016/j.cell.2014.09.050.
Akashi et al. Histopathologic analysis of sixteen autopsy cases of chronic hypersensitivity pneumonitis and comparison with idiopathic pulmonary fibrosis/usual interstitial pneumonia. American Journal of Clinical Pathology (2009); 131.3: 405-415.
Akester et al. Cancer in the thyroid is not always thyroid cancer. Hormones-Athens-2 (2003): 250-255.
Akita, et al. Molecular Biology of Lung Cancer. The Journal of the Japanese Respiratory Society, 42(5): (2004).

(56) References Cited

OTHER PUBLICATIONS

Aldred et al. Caveolin-1 and caveolin-2, together with three bone morphogenetic protein-related genes, may encode novel tumor suppressors down-regulated in sporadic follicular thyroid carcinogenesis. Cancer Res. 2003;63(11):2864-71.

Aldred et al. Papillary and follicular thyroid carcinomas show distinctly different microarray expression profiles and can be distinguished by a minimum of five genes. J Clin Oncol. 2004;22(17):3531-9.

Alexander et al. Preoperative diagnosis of benign thyroid nodules with indeterminate cytology. N Engl J Med. Aug. 23, 2012;367(8):705-15.

Ali et al. Use of the Afirma® Gene Expression Classifier for Preoperative Identification of Benign Thyroid Nodules with Indeterminate Fine Needle Aspiration Cytopathology. PLoS Currents 5:pp. 1-7 (2013).

Ambion, Inc. GeneAssist Pathway Atlas for PI3K Signaling. Accessed from <http://www5.appliedbiosystems.com/tools/pathway/pathwayproteins.php?pathway=PI3K> on May 3, 2011.

American Thoracic Society, American Thoracic Society/European Respiratory Society International Multidisciplinary Consensus Classification of the Idiopathic Interstitial Pneumonias. Am. J. Respir. Crit. Care Med. 165, 277-304, 2002.

American Thoracic Society. European Respiratory Society. Idiopathic pulmonary fibrosis: diagnosis and treatment. International consensus statement. Am J Respir Crit Care Med (2000); 161.2 pt 1: 646-664.

Anbazhagan et al. Classification of Small Cell Lung Cancer and Pulmonary Carcinoid by Gene Expression Profiles. Cancer Research, 59:5119-5122, (Oct. 15, 1999).

Anders et al. HTSeq-a Python framework to work with high-throughput sequencing data. Bioinformatics (2015); 31(2): 166-169.

Anderson et al. Deaths: Leading Causes for 2001. National Vital Statistics Report; 52(9): 1-88 (Nov. 7, 2003).

Anonymous: "Bronchogenic carcinoma / definition of bronchogenic carcinoma by Medicaldictionary," Feb. 13, 2019 (Feb. 13, 2019), retrieved from the internet: URL: https://medicaldictionary.thefreedictionary.com/bronchogenic+carcinoma [retrieved on Feb. 13, 2019].

Anonymous: "Bronchogenic carcinoma is a malignant neoplasm of the lung arising from theepithelium of the bronchus or bronchiole", Apr. 22, 2003 (Apr. 22, 2003), retrieved from theinternet:URL: http://www.meddean.luc.edu/lumen/meded/medicine/pulmonar/pathms/path19.htm [retrieved on Feb. 13, 2019].

Anthonisen et al. Effects of Smoking Intervention and the Use of an Inhaled Anticholinergic Bronchodilator on the Rate of Decline of FEV1. JAMA; 272(19):1497-1505 (Nov. 16, 1994).

Appleby et al. New technologies for ultra-high throughput genotyping in plants. Plant Genomics: Methods and Protocols (2009); 513: 19-39.

Arimura et al. Elevated Serum 6-Defensins Concentrations in Patients with Lung Cancer. Anticancer Res. Nov.-Dec. 2004;24(6):4051-7.

Arnesen et al. Expression of N-acetyl transferase human and human Arrest defective 1 proteins in thyroid neoplasms. Thyroid. 2005;15(10):1131-6.

Ashley. Towards precision medicine. Nature Reviews Genetics 17.9 (2016): 507.

Asseroshn et al. The feasibility of using fine needle aspiration from primary breast cancers for cDNA microarray analyses. Clinical Cancer Research 8.3 (2002): 794-801.

"Ausubel, et al. Current Protocols in Molecular Biology. Wiley & Sons, New York, 1995."

Auton et al. 1000 Genomes Project Consortium. A global reference for human genetic variation. Nature 526, 7571 (2015): 68.

"Bach, et al. Benefits and harms of CT screening for lung cancer: a systematic review. Jama 307.22 (2012): 2418-2429."

Bai et al. Mutational analysis of thyroid transcription factor-1 gene (TTF-1) in lung carcinomas. In Vitro Cell Dev Biol Anim. 2008;44(1-2):17-25.

Baker et al., Screening for bronchogenic carcinoma: The Surgical experience, J. Thorac Cardiovasc Surg, 1979; 78:876-882.

Baker, Stuart. The Central Role of Receiver Operating Characteristic (ROC) Curves in Evaluating Tests for the Early Detection of Cancer. Journal of the National Cancer Institute, 95(7): 511-515 (Apr. 2003).

Baldi; et al., "DNA microarrays and gene expression: from experiments to data analysis and modeling. Cambridge university press, 2002."

Baloch, et al. Our approach to follicular-patterned lesions of the thyroid. J Clin Pathol. Mar. 2007;60(3):244-50. Epub Jun. 23, 2006.

Banito et al. Aneuploidy and RAS mutations are mutually exclusive events in the development of well-differentiated thyroid follicular tumours. Clin Endocrinol (Oxf). 2007;67(5):706-11.

Barden et al. Classification of follicular thyroid tumors by molecular signature: results of gene profiling. Clin Cancer Res. 2003;9(5):1792-800.

Baris et al. Transcriptional profiling reveals coordinated upregulation of oxidative metabolism genes in thyroid oncocytic tumors. J Clin Endocrinol Metab. 2004;89(2):994-1005.

Bauer et al. A novel genomic signature with translational significance for human idiopathic pulmonary fibrosis. American Journal of Respiratory Cell and Molecular Biology (2015); 52.2: 217-231.

Beane et al. A Prediction Model for Lung Cancer Diagnosis that Integrates Genomic and Clinical Features. Cancer Prevention Research, 1:56-64 (2008).

Beane, et al., Characterizing the impact of smoking and lung cancer on the airway transcriptome using RNA-Seq. Cancer Prev Res 2011;4:803-817.

Beane et al. Reversible and permanent effects of tobacco smoke exposure on airway epithelial gene expression. Genome Biology 2007, 8:R201 (Sep. 25, 2007).

Beane-Ebel. Single-Cell RNA Sequencing of the Bronchial Epithelium in Smokers With Lung Cancer. U.S. Army Medical Research and Material Command. Jul. 2015 version. [retrieved on Sep. 19, 2017]. Retrieved from the Internet at http://www.dtic.mil/dtic/tr/fulltext/u2/a624219.pdf.

Beaudenon-Huibregtse, et al. Centralized molecular testing for oncogenic gene mutations complements the local cytopathologic diagnosis of thyroid nodules. Thyroid. Oct. 2014;24(10):1479-87. Epub Jun. 1, 20148.

Beer et al. Gene-expression profiles predict survival of patients with lung adenocarcinoma. Nature Medicine, 8: 816-824 (2002).

Belinksky et al. Aberrant promoter methylation in bronchial epithelium and sputum from current and former smokers. Cancer Res., 62(8): 2370-7 (2002).

Belperio, et al., Critical role for CXCR2 and CXCR2 ligands during the pathogenesis of ventilator-induced lung injury. J Clin Invest. 2002; 110(11): 1703-1716.

Belyavsky et al. PCR-based cDNA library construction: general cDNA libraries at the level of a few cells. Nucleic Acids Research (1989); 17.8: 2919-2932.

Benner, et al. Evolution, language and analogy in functional genomics. Trends in Genetics, 17:414-418 (2001).

Berbescu et al. Transbronchial biopsy in usual interstitial pneumonia. Chest Journal (May 2006); 129.5: 1126-1131.

Berman, Jeffrey S. Abstract Immunopathology of the nasal mucosa in sarcoidosis National Institutes of Health Grant No. 1 R21 HL077498-01 (Funding Start Date Sep. 15, 2004).

Bernard et al. Multiplex messenger assay: simultaneous, quantitative measurement of expression of many genes in the context of T cell activation. Nucleic Acids Research (1996); 24.8: 1435-1442.

Bessarabova, et al. Bimodal gene expression patterns in breast cancer. BMC Genomics. Feb. 10, 2010;11 Suppl 1:S8. doi: 10.1186/1471-2164-11-S1-S8.

Beum et al. Epidermal Growth Factor Downregulates Core 2 Enzymes in a Human Airway Adenocarcinoma Cell Line. Am. J. Respir. Cell Mol. Biol., 29:48-56 (Jan. 2003).

Bhattacharjee et al. Classification of human lung carcinoma by mRNA expression profiling reveals distinct adenocarcinoma subclasses. Proc Natl Acad Sci USA, 98(24): 13790-5 (Nov. 20, 2001).

Bild et al. Oncogenic Pathway Signatures in Human Cancers as a Guide to Targeted Therapies. Nature, 439: 353-357 (Jan. 2006).

(56) References Cited

OTHER PUBLICATIONS

Bjoraker et al. Prognostic significance of histopathologic subsets in idiopathic pulmonary fibrosis. American Journal of Respiratory and Critical Care Medicine (1998); 157.1: 199-203.
Blower et al. PLOS One. 2013. 8(10):e77700. (Year: 2013).
Bohula et al. The Efficacy of Small Interfering RNAs Targeted to the Type 1 Insulin-like Growth Factor Receptor (IGF1R) Is Influenced by Secondary Structure in the IGF1R Transcript. The Journal of Biological Chemistry 278(18): 15991-15997 (May 2003).
Bolstad, et al. A comparison of normalization methods for high density oligonucleotide array data based on variance and bias. Bioinformatics. Jan. 22, 2003;19(2):185-93.
Bonora et al. Novel germline variants identified in the inner mitochondrial membrane transporter TIMM44 and their role in predisposition to oncocytic thyroid carcinomas. Br J Cancer. 2006;95(11):1529-36.
Bosse et al. Molecular signature of smoking in human lung tissues. Cancer Research (2012); 72.15: 3753-3763.
Boulesteix, et al. Evaluating microarray-based classifiers: an overview. Cancer Inform. 2008;6:77-97. Epub Feb. 29, 2008.
Braakhuis et al. A Genetic Explanation of Slaughter's Concept of Field Cancerization Evidence and Clinical Implications. Cancer Research, 63: 1727-1730 (Apr. 2003).
Brambilla et al. p53 Mutant Immunophenotype and Deregulation of p53 Transcription Pathway (Bc12, Bax and Waf1) in Precursor Bronchial Lesions of Lunch Cancer. Clinical Cancer Research (4): 1609-1618 (1998).
Brasseur et al. Papillary thyroid carcinoma in a 9-year-old girl with ataxia-telangiectasia. Pediatr Blood Cancer. 2008;50(5):1058-60.
Brenner, et al., Gene Expression analysis by massively parallel signature sequencing (MPSS) on microbead arrays. Nature Biotechnology 18.6 (Jun. 2000): 630-634, doi:10.1038/76469.
British Thoracic society bronchoscopy committee, British Thoracic Society guidelines on diagnostic flexible bronchoscopy. Thorax, 2001, 56 (suppl I): i1-i21).
Brody, Jerome S. Abstract: Airway epithelial gene expression in COPD. National Institutes of Health. Grant No. 1RO1HL071771-01 (Funding Start Date Sep. 30, 2002).
Brozek et al. Thyroid cancer in two siblings with FAP syndrome and APC mutation. Int J Colorectal Dis. 2008;23(3):331-2.
Buckanovich et al. Nova, the paraneoplastic Ri antigen, is homologous to an RNA-binding protein and is specifically expressed in the developing motor system. Neuron (1993); 11.4: 657-672.
Bugalho et al. Mutation analysis of the RET proto-oncogene and early thyroidectomy: results of a Portuguese cancer centre. Surgery. 2007;141(1):90-5.
Byron et al. Translating RNA sequencing into clinical diagnostics: opportunities and challenges. Nature Reviews Genetics 17.5 (2016): 257.
Cameselle-Teijeiro et al. Follicular thyroid carcinoma with an unusual glomeruloid pattern of growth. Hum Pathol. 2008;39(10):1540-7.
Campbell, et al., Applying gene expression microarrays to pulmonary disease. Respirology, 16; 2011:407-418.
Camus et al. Interstitial lung disease induced by drugs and radiation. Respiration. Jul.-Aug. 2004;71(4):301-26.
Carda et al. Anaplastic carcinoma of the thyroid with rhabdomyosarcomatous differentiation: a report of two cases. Virchows Arch. 2005;446(1):46-51.
Carroll et al. Promising Molecular Techniques for Discriminating Among Follicular Thyroid Neoplasms. Surgical Oncology, Blackwell Scientific Publ., Oxford, GB, vol. 15, No. 2, Aug. 1, 2006, pp. 59-64.
Castro et al. Adenomas and follicular carcinomas of the thyroid display two major patterns of chromosomal changes. J Pathol. 2005;206(3):305-11.
Castro et al.PAX8-PPARgamma rearrangement is frequently detected in the follicular variant of papillary thyroid carcinoma. J Clin Endocrinol Metab. 2006;91(1):213-20.

Centeno et al. Classification of human tumors using gene expression profiles obtained after microarray analysis of fine-needle aspiration biopsy samples. Cancer Cytopathology: Interdisciplinary International Journal of the American Cancer Society 105.2 (2005): 101-109.
Cerutti et al. A preoperative diagnostic test that distinguishes benign from malignant thyroid carcinoma based on gene expression. J Clin Invest. 2004;113(8):1234-42.
Cerutti et al. Diagnosis of suspicious thyroid nodules using four protein biomarkers. Clin Cancer Res. 2006;12(11 Pt 1):3311-8.
Chan, et al. Integrating Transcriptomics and Proteomics. Drug Discovery and Development. Apr. 1, 2006. 4 pages. Published in G&P magazine 2006 vol. 6 No 3 pp. 20-26.
Chan et al. Integrating Transcriptomics and Proteomics. Genomics & Proteomics Magazine, 6(3), text of article reprinted and accessed from www.dddmag.com Published Oct. 4, 2007. http://www.dddmag.com/article/2007/10/integrating-transcriptomics-and-proteomics.
Chari et al. Effect of active smoking on the human bronchial epithelium transcriptome. BMC Genomics, 8:297 (Aug. 29, 2007).
Chaudhuri et al. Low sputum MMP-9/TIMP ratio is associated with airway narrowing in smokers with asthma. European Respiratory Journal (Jul. 3, 2014); 44(4): 895-904.
Chen et al. Discordant Protein and mRNA Expression in Lung Adenocarcinomas. Molecular and Cellular Proteomics, 1: 304-313 (2001).
Chen et al. Enrichr: interactive and collaborative HTML5 gene list enrichment analysis tool. BMC Bioinformatics (2013); 14: 128.
Chen et al: "Expression of dihydrodiol dehydrogenase in theresected stage I non-small cell lung cancer", Oncologyreports, vol. 9, No. 3 May 1, 2002, pp. 515-519.
Chen et al. Restricted kappa/lambda light chain ratio by flow cytometry in germinal center B cells in Hashimoto thyroiditis. Am J Clin Pathol. 2006;125(1):42-8.
Chen et al. Up-regulations of Tumor Interleukin-8 Expression by Infiltrating Macrophages: Its Correlation with Tumor Angiogenesis and Patient Survival in Non-Small Cell Lung Cancer. Clinical Cancer Research: p. 729, (Feb. 1, 2003).
Cheng et al. A Multi-Cancer Mesenchymal Transition Gene Expression Signature Is Associated with Prolonged Time to Recurrence in Glioblastoma. Plos One 7(4):e34705 (2012).
Cheng et al. Reduced expression levels of nucleotide excision repair genes in lung cancer: a case-control analysis. Carcinogenesis. 21(8):1527-1530 (2000).
Cheung, et al. Immunohistochemical diagnosis of papillary thyroid carcinoma. Mod Pathol. Apr. 2001;14(4):338-42.
Cheung, et al. Natural Variation in Human Gene Expression Assessed in Lymphoblastoid Cells. Nature Genetics. vol. 33 (2003): pp. 422-425.
Chevillard et al. Gene expression profiling of differentiated thyroid neoplasms: diagnostic and clinical implications. Clin Cancer Res. 2004;10(19):6586-97.
Chiappetta et al. The antiapoptotic protein BAG3 is expressed in thyroid carcinomas and modulates apoptosis mediated by tumor necrosis factor-related apoptosis-inducing ligand. J Clin Endocrinol Metab. 2007;92(3):1159-63.
Chinese Search Report for Application No. 2008801147951 dated Aug. 24, 2012.
Choi et al. Case-control association testing in the presence of unknown relationships. Genetic epidemiology 33.8 (2009): 668-678.
Choi etal. Model Assisted Statistics and Applications.2017. 12:265-273. (Year: 2017).
Chudova, et al. Molecular classification of thyroid nodules using high-dimensionality genomic data. J Clin Endocrinol Metab. Dec. 2010;95(12):5296-304. doi: 10.1210/jc.2010-1087. Epub Sep. 8, 2010.
Chung et al. Detection of BRAFV600E mutation on fine needle aspiration specimens of thyroid nodule refines cyto-pathology diagnosis, especially in BRAF600E mutation-prevalent area. Clin Endocrinol (Oxf). 2006;65(5):660-6.

(56) References Cited

OTHER PUBLICATIONS

Chung KW et al., Gene expression profiling of papillary thyroid carcinomasin Korean patients by oligonucleotide microarrays. Journal of the KoreanSurgical Society, Apr. 26, 2012, vol. 82, No. 5, pp. 271-280whole document.
Ciampi et al. BRAF copy number gains in thyroid tumors detected by fluorescence in situ hybridization. Endocr Pathol. 2005;16(2):99-105.
Cibas, et al. The Bethesda System for Reporting Thyroid Cytopathology. Am J Clin Pathol. Nov. 2009; 132(5):658-65. doi: 10.1309/AJCPPHLWMI3JV4LA.
Cirulli Uncovering the roles of rare variants in common disease through whole-genome sequencing. Nature Reviews Genetics 11.6 (2010): 415.
Clark et al. Altered Protein Kinase C (PKC) Isoforms in Non-Small Cell Lung Cancer Cells: PKCdelta Promotes Cellular Survival and Chemotherapeutic Resistance. Cancer Research, 63(4): 780-786 (2003).
Clark et al. Discovery of tissue-specific exons using comprehensive human exon microarrays. Genome Biol. 2007;8(4):R64.
Clinical cytopathology and aspiration biopsy: Fundamental principles and practice. McGraw Hill Professional, 2001.
Cogan, et al., Rare variants in RTEL1 Are associated with familial interstitial Pneumonia. American Journal of respiratory and critical care medicine, Mar. 15, 2015; 191(6):646-655.
Cohen et al. Mutational Analysis of BRAF in Fine Needle Aspiration Biopsies of the Thyroid: A Potential Application for the Preoperative Assessment of Thyroid Nodules. Clinical Cancer Research 10:2761-2765 (Apr. 2004).
Coleman et al. Of mouse and man—what is the value of the mouse in predicting gene expression in humans? Drug Discov Today 8(6) (Mar. 2003): 233-235.
Collard et al. Changes in clinical and physiologic variables predict survival in idiopathic pulmonary fibrosis. American Journal of Respiratory and Critical Care Medicine (May 2003); 168.5: 538-542.
Combined search report and examination report dated Oct. 1, 2013 for GB Application No. 1315760.7.
Cooper, et al. Management guidelines for patients with thyroid nodules and differentiated thyroid cancer. Thyroid. Feb. 2006; 16(2):109-42.
Cooper. Gene Expression Studies in Lung Cancer. The Molecular Genetics of Lung Cancer, pp. 167-186, (2005).
Co-pending U.S. Appl. No. 15/096,739, inventors Giulia; C. Kennedy et al., filed Apr. 12, 2016.
Co-pending U.S. Appl. No. 16/279,252, inventors Kennedygiulia; C et al., filed Feb. 19, 2019.
Co-pending U.S. Appl. No. 16/422,109, inventors Kennedygiulia; C. et al., filed May 24, 2019.
Co-pending U.S. Appl. No. 16/534,889, inventors Kennedygiulia; C. et al., filed Aug. 7, 2019.
Co-pending U.S. Appl. No. 16/541,041, inventors Kennedygiulia; C. et al., filed Sep. 5, 2019.
Co-pending U.S. Appl. No. 16/593,918, inventors Whitneyduncan; H. et al., filed Oct. 4, 2019.
Co-pending U.S. Appl. No. 16/594,586, inventors Kennedygiulia; C. et al., filed Oct. 7, 2019.
Co-pending U.S. Appl. No. 16/693,194, inventors Whitneyduncan; H. et al., filed Nov. 22, 2019.
Co-pending U.S. Appl. No. 16/721,783, inventors Kennedygiulia; C. et al., filed Dec. 19, 2019.
Co-pending U.S. Appl. No. 16/820,537, inventors Kennedygiulia; C. et al., filed Mar. 16, 2020.
Co-pending U.S. Appl. No. 16/820,599, inventors Kennedy; Giulia C. et al., filed Mar. 16, 2020.
Co-pending U.S. Appl. No. 16/886,477, inventors K; Giulia C. et al., filed May 28, 2020.
Co-pending U.S. Appl. No. 16/910,039, inventors Kennedy; Giulia C. et al., filed Jun. 23, 2020.
Co-pending U.S. Appl. No. 16/945,119, inventors Whitneyduncan; H. et al., filed Jul. 31, 2020.
Co-pending U.S. Appl. No. 17/003,228, inventors Kennedygiulia; C. et al., filed Aug. 26, 2020.
Co-pending U.S. Appl. No. 17/084,593, inventors Kennedygiulia; C. et al., filed Oct. 29, 2020.
Co-pending U.S. Appl. No. 17/084,622, inventors Kennedygiulia; C. et al., filed Oct. 29, 2020.
Co-pending U.S. Appl. No. 17/145,563, inventors Kennedygiulia; C. et al., filed Jan. 11, 2021.
Co-pending U.S. Appl. No. 17/169,082, inventors Kennedygiulia; C. et al., filed Feb. 5, 2021.
Co-pending U.S. Appl. No. 17/169,397, inventors Davicionielai et al., filed Feb. 5, 2021.
Co-pending U.S. Appl. No. 17/190,408, inventors Whitneyduncan; H. et al., filed Mar. 3, 2021.
Co-pending U.S. Appl. No. 17/322,681, inventors Kennedygiulia; C. et al., filed May 17, 2021.
Co-pending U.S. Appl. No. 17/338,585, inventors Kennedygiulia; C. et al., filed Jun. 3, 2021.
Co-pending U.S. Appl. No. 17/338,587, inventors Kennedygiulia; C. et al., filed Jun. 3, 2021.
Co-pending U.S. Appl. No. 17/409,670, inventors Kennedygiulia; C. et al., filed Aug. 23, 2021.
Co-pending U.S. Appl. No. 17/476,284, inventors Kennedygiulia; C. et al., filed Sep. 15, 2021.
Co-pending U.S. Appl. No. 17/501,856, inventors Whitneyduncan; H. et al., filed Oct. 14, 2021.
Co-pending U.S. Appl. No. 18/181,535, inventors Kennedy; Giulia C. et al., filed Mar. 9, 2023.
Cortes et al. Support-vector networks. Machine Learning. 1995; 20:273-297.
Costa et al. New somatic mutations and WNK1-B4GALNT3 gene fusion in papillary thyroid carcinoma. Oncotarget 6:11242-11251 (2015).
Cottin et al. Neglected evidence in idiopathic pulmonary fibrosis and the importance of early diagnosis and treatment. European Respiratory Review (Mar. 1, 2014); 23.131: 106-110.
Covey et al. Factors associated with pneumothorax and pneumothorax requiring treatment after percutaneous lung biopsy in 443 consecutive patients. Journal of Vascular and Interventional Radiology (2004); 15.5: 479-483.
Crawford et al. Normal Bronchial Epithelial Cell Expression of Glutathione Transferase P1, Glutathione Transferase M3, and Glutathione Peroxidase is Low in Subjects with Bronchogenic Carcinoma. Cancer Research, 60: 1609-1618 (Mar. 15, 2000).
Crescioli et al. Methimazole inhibits CXC chemokine ligand 10 secretion in human thyrocytes. J Endocrinol. 2007;195(1):145-55.
Cross et al. The promise of molecular profiling for cancer identification and treatment. Clinical medicine & research 2.3 (2004): 147-150.
Cummings, Sr. et al. Estimating the probability of malignancy in solitary pulmonary nodules. A Bayesian approach, Am Rev Respir Dis 1986;134:449-52 (1986).
Dai et al. Evolving gene/transcript definitions significantly alter the interpretation of GeneChip data. Nucleic Acids Research 33.20 (2005): e175-e175.
Danel et al. Quantitative Assessment of the Epithelial and Inflammatory Cell Populations in Large Airways of Normals and Individuals with Cystic Fibrosis. Am. Journal of Resp. and Critical Care Medicine 153:362-368 (1996).
Dauletbaev et al. Expression of Human Beta Defensin (HBD-1 and HBD-2) mRNA in Nasal Epithelia of Adult Cystic Fibrosis Patients, Healthy Individuals, and Individuals with Acute Cold. Respiration, 69:46-51 (2002).
De Lellis et al. The pathobiology of the human calcitonin (C)-cell: a review. Pathol Annu. 1981;16(Pt 2):25-52.
Del Senno et al. c-myc oncogene alterations in human thyroid carcinomas. Cancer Detect Prev. 1987;10(3-4):159-66.
Delehaye, et al., Elevated levels of calcitonin mRNA: A marker for the spontaneous development of medullary thyroid carcinoma in rats. Biochemical and biophysical research communications, Mar. 15, 1989; 159(2): 528-535.

(56) References Cited

OTHER PUBLICATIONS

Delellis et al. C-cell hyperplasia. An ultrastructural analysis. Lab Invest. 1977;36(3):237-48.
Delibasis, et al., "Computer-Aided Diagnosis of Thyroid Malignancy Using an Artificial Immune System Classification Algorithm," IEEE Transactions on Information Technology in Biomedicine, vol. 13, No. 5, pp. 680-686, Sep. 2009.
DeLong et al. Comparing the areas under two or more correlated receiver operating characteristic curves: a nonparametric approach. Biometrics (1988); 44(3): 837-845.
DeLuca et al. RNA-SeQC: RNA-seq metrics for quality control and process optimization. Bioinformatics (2012); 28.11: 1530-1532.
DeMeo et al. The SERPINE2 gene is associated with chronic obstructive pulmonary disease. Am J Hum Genet., 78(2): 253-264 (Feb. 2006).
Demoly et al. c-fos Proto-oncogene Expression in Bronchial Biopsies of Asthmatics. American Journal of Respiratory Cell and Molecular Biology 7:128-133 (1992).
Dempsey, et al. Lung disease and PKCs. Pharmacol Res., 55 6 : 545-59 2007.
DeMuth et al. The Gene Expression of Index c-myc X E2F-1/p21 Is Highly Predictive of Malignant Phenotype in Human Bronchial Epithelial Cells. Am. J. Cell Mol. Bio. (19): 18-24 (1998).
Deng et al. Ubiquitous Induction of Resistance to Platinum Drugs in Human Ovarian, Cervical, Germ-Cell and Lung Carcinoma Tumor Cells Overexpressing Isoforms 1 and 2 of Dihydrodiol Dehydrogenase. Cancer Chemother. PharmacoL, 54:301-307, (2004).
Denis et al. RING3 Kinase Transactivates Promoters of Cell Cycle Regulatory Genes through E2F1 Cell. Growth Differ; 11: 417-424 (Aug. 2000).
Depeursinge et al. Automated classification of usual interstitial pneumonia using regional volumetric texture analysis in high-resolution computed tomography. Invest Radiol. Apr. 2015;50(4):261-7.
DePianto et al. Heterogeneous gene expression signatures correspond to distinct lung pathologies and biomarkers of disease severity in idiopathic pulmonary fibrosis. Thorax (2015); 70.1: 48-56.
Derringer, et al. Malignant lymphoma of the thyroid gland: a clinicopathologic study of 108 cases. Am J Surg Pathol. May 2000;24(5):623-39.
Details for HG-U133A:217291_AT (Ceacams) (https://www.affymetrix.com/analysis/netaffx/fullrecord.affx?pk=HG-U133A:217291 _AT, downloaded Apr. 22, 2016).
DetailsforHG-U112A:823_AT (http://www.affymetrix.com/analysis/netaffx/fultrecord.affx?pk=HG-U133A:823 AT, downloaded Dec. 10, 2012).
DetailsforHG-U133A:202831_AT (https://www.affymetrix.com/analysis/netaffx/fullrecord.affx?pk=HG-U133A:202831AT, downloaded Dec. 10, 2012).
DetailsforHG-U133a-207469_S_AT (https://www.affymetrix.com/analysis/netaffx/fullrecod.affx?pk=HG-U133A:207469 S At, downloaded Dec. 10, 2012).
DetailsforHG-U133A:210519_S_AT (https://www.affvmetrix.com/analysis/netaffx/fullrecord.affx?pk=HG-U133A:210519 S AT downloaded Dec. 10, 2012).
Detterbeck et al. Screening for lung cancer: diagnosis and management of lung cancer: American College of Chest Physicians evidence-based clinical practice guidelines. Chest Journal (2013); 143.5_suppl: e78S-e92S.
Dettori et al. Aneuploidy in oncocytic lesions of the thyroid gland: diffuse accumulation of mitochondria within the cell is associated with trisomy 7 and progressive numerical chromosomal alterations. Genes Chromosomes Cancer. 2003;38(1):22-31.
Diaz-Uriarte et al. Gene selection and classification of microarray data using random forest. BMC Bioinformatics. 2006;7:3.
Ding et al. A high-throughput gene expression analysis technique using competitive PCR and matrix-assisted laser desorption ionization time-of-flight MS. Proceedings of the National Academy of Sciences USA (Mar. 2003); 100.6: 3059-3064.

Dobin et al.: Star: Ultrafast Universal RNA-Seq Aligner. Bioinformatics 29:15-21 (2012).
Doll et al. Mortality in relation to smoking: 40 years' observations on male British doctors. BMJ; 309:901-911 (Oct. 8, 1994).
Doris et al. Quantitative analysis of gene expression by ion-pair high-performance liquid chromatography. Journal of Chromatography A (1998); 806.1: 47-60.
Dou et al. PLOS Genetics. 2017. 13(9):e1007021. (Year:2017) .
Dougherty. The fundamental role of pattern recognition for gene-expression/microarray data in bioinformatics. Pattern recognition. 2005; 38:2226-2228.
Druckenthaner et al. Evidence for Somatostatin receptor 2 in thyroid tissue. Regul Pept. 2007;138(1):32-9.
Du Bois et al. Ascertainment of individual risk of mortality for patients with idiopathic pulmonary fibrosis. American Journal of Respiratory and Critical Care Medicine (2011); 184.4: 459-466.
Du Bois, R. M. Strategies for treating idiopathic pulmonary fibrosis. Nature reviews Drug Discovery (2010); 9.2: 129-140.
Durand et al. Evaluation of gene expression profiles in thyroid nodule biopsy material to diagnose thyroid cancer. J Clin Endocrinol Metab. 2008;93(4):1195-202.
Durante, et al. BRAF mutations in papillary thyroid carcinomas inhibit genes involved in iodine metabolism. J Clin Endocrinol Metab. Jul. 2007;92(7):2840-3. Epub May 8, 2007.
Durham et al. The Relationship Between COPD and Lung Cancer. Lung Cancer, 90:121-127, (2015).
Ebbert, et al. Lung Cancer Risk Reduction After Smoking Cessation: Observations From a Prospective Cohort of Women. J Clin Oncol; 21(5):921-926 (Mar. 1, 2003).
Elisabeth Brambilla, et al., "Advances in Brief p53 Mutant Immunophenotype and Deregulationof p53 Transcription Pathway (Bcl2, Bax, and Waft) in Precursor Bronchial Lesions of LungCancer", Clinical Cancer Research 4.7 (1998): 1609-1618.
Elisei et al. RET genetic screening in patients with medullary thyroid cancer and their relatives: experience with 807 individuals at one center. J Clin Endocrinol Metab. 2007;92(12):4725-9.
Elliot, et al., Transcriptome analysis of peripheral blood mononuclear cells in human subjects following a 36 h fast provides evidence of effects on genes regulating inflammation, apoptosis and energy metabolism. Genes & Nutrition; studying the relationship between genetics and nutrition in the improvement of human health, Berlin; Heidelberg: Springer, DE. Sep. 2014; 9(6): 1-11.
Ellis, et al., Rare variants in MYD88, IRAK4 and IKBKG and susceptibility to invasive Pneumococcal disease: A population-based case-control study. PLoS ONE, Apr. 2015; 10(4): 1-9.
EMBL database (Gene: CXCL2 ENSG00000081041. https://useast.ensembl.org/Homo_sapiens/Gene/Summary?g=ENSG00000081041;r=4:740 . . . , downloaded Jul. 20, 2020.
EMBL database (Gene: ZNF671 ENSG00000083814. https://useast.ensembl.org/Homo_sapiens/Gene/Summary?g=ENSG00000083814;r=19:57719 751-57727624, downloaded Jul. 20, 2020.
Enard, et al. Intra- and interspecific variation in primate gene expression patterns. Science. Apr. 12, 2002;296(5566):340-343. doi: 10.1126/science.1068996.
Endocrine website. http://www.endocrineweb.com/noduleus.html (Accessed Dec. 9, 2011) (last update Oct. 12, 2010).
Englisch, et al. Chemically Modified Oligonucleotides as Probes and Inhibitors. Angew. Chem. Int. Ed. Eng. 1991; 30:613-629.
Engstrom et al. Systematic evaluation of spliced alignment programs for RNA-seq data. Nature methods 10.12 (2013): 1185.
EP04776438.6 European Search Report dated Sep. 24, 2007.
EP12828537.6 European Search Report dated Apr. 16, 2015.
EP13782273.0 Extended Search Report dated Apr. 21, 2016.
EP14797859.7 Extended Search Report dated Oct. 19, 2016.
EP15822338.8 Extended Search Report dated Feb. 6, 2018.
EP16759458.9 European Search Report dated Sep. 6, 2018.
EP16759458.9 Extended European Search Report dated Sep. 6, 2018.
EP17185133.0 European Search Report dated Feb. 21, 2018.
EP18191806.1 European Search Report dated Jun. 28, 2019.
EP18810306.3 Extended European Search Report dated Mar. 3, 2021.

(56) References Cited

OTHER PUBLICATIONS

EP19190846.6 Extended European Search Report dated Feb. 3, 2020.
EP20178664.7 European Search Report dated May 3, 2021.
EP20182173.3 Extended European Search Report dated Dec. 10, 2020.
EP21185798.2 Extended European Search Report dated Oct. 29, 2021.
EP23158699 Extended European Search Report dated Jun. 30, 2023.
Erdogan et al. The prevalence of RET/PTC mutations in papillary thyroid cancers in Turkish population and its relation between tumor histopathology and prognostic factors. Exp Clin Endocrinol Diabetes. 2008;116(4):225-30.
Erkkila et al. Probabilistic analysis of gene expression measurements from heterogeneous tissues. Bioinformatics 26(20):2571-2577 (2010).
Ernst et al. Interventional pulmonary procedures: guidelines from the American College of Chest Physicians. CHEST Journal (May 2003); 123.5: 1693-1717.
Esperante, et al. Identification and characterization of four PAX8 rare sequence variants (p.T225M, p.L233L, p.G336S and p.A439A) in patients with congenital hypothyroidism and dysgenetic thyroid glands. Clin Endocrinol (Oxf). May 2008;68(5):828-35.
Eszlinger et al. Gene expression analysis reveals evidence for inactivation of the TGF-beta signaling cascade in autonomously functioning thyroid nodules. Oncogene. 2004;23(3):795-804.
Eszlinger et al. Meta- and reanalysis of gene expression profiles of hot and cold thyroid nodules and papillary thyroid carcinoma for gene groups. J Clin Endocrinol Metab. 2006;91(5):1934-42.
Eszlinger et al. Perspectives and limitations of microarray-based gene expression profiling of thyroid tumors. Endocr Rev. 2007;28(3):322-38.
Eszlinger et al., Perspectives and Limitations of Microarray-Based Gene Expression Profiling of Thyroid Tumors. Endocrine Reviews, 2007; 28:322-338.
Eszlinger, et al. Perspectives for Improved and More Accurate Classification of Thyroid Epithelial Tumors. J Clin Endocrinol Metab. Sep. 2008;93(9):3286-94. Epub Jul. 1, 2008.
European Search Report May 25, 2018 for EP172108505.
European search report and opinion dated Mar. 5, 2014 for EP Application No. 11781242.0.
European search report and opinion dated Apr. 28, 2016 for EP 16153243.7.
European search report and search opinion dated Jan. 28, 2013 for Application No. 10772919.6.
European search report and search opinion dated Nov. 27, 2012 for Application No. 09826462.5.
European Search Report for European Application No. EP 10195816, dated Oct. 13, 2011.
European Search Report in Application EP 04 81 0818, dated Oct. 28, 2010.
European Search Report in Application EP 08 83 2403, dated Oct. 22, 2010.
European Search Report in Application EP 09 72 4548, Jun. 16, 2011.
European Search Report in Application EP 10 18 4732, dated Mar. 21, 2011.
European Search Report in Application EP 10 18 4813, dated Mar. 21, 2011.
European Search Report in Application EP 10 18 4888, dated Mar. 21, 2011.
European Search Report in Application EP 10 19 5803, dated Jun. 20, 2011.
European Search Report in Application EP 10 19 5822, dated Jun. 20, 2011.
European Search Report in Application EP 12 17 0635, dated Apr. 22, 2013.
Extended European Search Report dated Apr. 22, 2016 for European Patent Application No. 13838743.6.
Extended European Search Report from EP 16186152.1, dated May 17, 2017.
Fahy, JV. Remodeling of the Airway Epithelium in Asthma. Am. J. Respir. Crit. Care Med. 164:S46-S51 (2001).
Ferrari, et al. An approach to estimate between- and within-group correlation coefficients in multicenter studies: plasma carotenoids as biomarkers of intake of fruits and vegetables. Am J Epidemiol. Sep. 15, 2005;162(6):591-8. Epub Aug. 10, 2005.
Fielding et al. Heterogeneous Nuclear Ribonucleoprotein A2B1 Up-Regulation in Bronchial Lavage Specimens: A Clinical Marker of Early Lung Cancer Detection. Clinical Cancer Research. 5:4048-4052 (1999).
Filicori, et al. Risk stratification of indeterminate thyroid fine-needle aspiration biopsy specimens based on mutation analysis. Surgery. Dec. 2011;150(6):1085-91.
Final Office action dated Aug. 28, 2018 for U.S. Appl. No. 13/105,756.
"Final Office action dated Sep. 7, 2018 for U.S. Appl. No. 14/775,379."
Final Office action dated Sep. 7, 2018 for U.S. Appl. No. 15/694,157.
Final Office Action for U.S. Appl. No. 11/294,834, filed Aug. 18, 2014.
Final Office Action for U.S. Appl. No. 12/234,588, filed Nov. 4, 2011.
Final Office Action for U.S. Appl. No. 12/414,555, filed Mar. 15, 2012.
Final Office Action for U.S. Appl. No. 13/323,655, filed Jul. 17, 2014.
Final Office Action for U.S. Appl. No. 13/346,444, filed Nov. 27, 2013.
Final Office Action for U.S. Appl. No. 13/524,749, filed Apr. 3, 2014.
Final Office Action for U.S. Appl. No. 14/500,475, filed Aug. 2, 2017.
Final Office Action for U.S. Appl. No. 14/500,475, filed Feb. 28, 2017.
Final Office Action for U.S. Appl. No. 14/613,210, filed Apr. 3, 2017.
Final Office Action for U.S. Appl. No. 15/644,721, filed Jun. 20, 2018.
Final Office Action for U.S. Serial No. U.S. Appl. No. 15/336,469, filed Jul. 10, 2020.
Final Office Action from U.S. Appl. No. 11/294,834, filed Aug. 22, 2016.
Final Office Action issued in Application No. U.S. Appl. No. 15/336,469, filed Jun. 25, 2021.
Finley et al. Advancing the molecular diagnosis of thyroid nodules: defining benign lesions by molecular profiling. Thyroid. 2005;15(6):562-8.
Finley et al. Discrimination of benign and malignant thyroid nodules by molecular profiling. Ann Surg. 2004;240(3):425-36; discussion 436-7.
Finley et al. Molecular analysis of Hurthle cell neoplasms by gene profiling. Surgery. 2004;136(6):1160-8.
Finley et al. Molecular profiling distinguishes papillary carcinoma from benign thyroid nodules. J Clin Endocrinol Metab. 2004;89(7):3214-23.
Finn, et al. Expression microarray analysis of papillary thyroid carcinoma and benign thyroid tissue: emphasis on the follicular variant and potential markers of malignancy. Virchows Arch. Mar. 2007;450(3):249-60.
Fishel, et al. Meta-analysis of gene expression data: a predictor-based approach. Bioinformatics. Jul. 1, 2007;23(13):1599-606. Epub Apr. 26, 2007.
Flaherty et al. Clinical significance of histological classification of idiopathic interstitial pneumonia. European Respiratory Journal (2002); 19.2: 275-283.
Flaherty et al. Histopathologic variability in usual and nonspecific interstitial pneumonias. American Journal of Respiratory and Critical Care Medicine (2001); 164.9: 1722-1727.
Flaherty et al. Idiopathic interstitial pneumonia: what is the effect of a multidisciplinary approach to diagnosis ?. American Journal of Respiratory and Critical Care Medicine (2004); 170.8: 904-910.
Flaherty et al. Radiological versus histological diagnosis in UIP and NSIP: survival implications. Thorax (Feb. 2003); 58.2: 143-148.

(56) References Cited

OTHER PUBLICATIONS

Fodor, et al. Light-directed, spatially addressable parallel chemical synthesis. Science. Feb. 15, 1991;251(4995):767-73.
Fontaine, et al. Increasing the number of thyroid lesions classes in microarray analysis improves the relevance of diagnostic markers. PLoS One. Oct. 29, 2009;4(10):e7632.
Fontaine et al. Microarray analysis refines classification of non-medullary thyroid tumours of uncertain malignancy. Oncogene. 2008;27(15):2228-36.
Fontaine-Delaruelle et al. Is transthoracic core needle biopsy under CT scan a good deal for benign diseases' diagnosis? European Respiratory Journal (2014); 44.Suppl 58: P679.
Foppiani et al. Uncommon association of germline mutations of RET proto-oncogene and CDKN2A gene. Eur J Endocrinol. 2008;158(3):417-22.
Fox et al. Applications of ultra-high-throughput sequencing. (ed. Belostotsky, D.A., Plant Systems Biology (2009); 5: 79-108.
Frampton, et al. Development and validation of a clinical cancer genomic profiling test based on massively parallel DNA sequencing. Nat Biotechnol. Nov. 2013;31(11):1023-31. Epub Oct. 20, 2013.
Franklin, et al. Widely Dispersed p53 Mutation in Respiratory Epithelium. The Journal of Clinical Investigation, 100(8): 2133-2137 (1997).
Frattini, et al. Alternative mutations of BRAF, RET and NTRK1 are associated with similar but distinct gene expression patterns in papillary thyroid cancer. Oncogene. Sep. 23, 2004;23(44):7436-40.
Freeman et al. DNA from Buccal Swabs Recruited by Mail: Evaluation of Storage Effects on Long-term Stability and Suitability for Multiplex Polymerase Chain Reaction Genotyping, Behavior Genetics, 33: 67 (2003).
Friedman et al. Regularization Paths for Generalized Linear Models via Coordinate Descent. J Stat Softw 33:1-22 (2010).
Fritz et al. Nasal mucosal gene expression in patients with allergic rhinitis with and without nasal polyps. Journal of Allergy Clin. Immunol, 112(6): 1057-1063 (Dec. 2003).
Frohman et al. Rapid production of full-length cDNAs from rare transcripts: amplification using a single gene-specific oligonucleotide primer. Proc Natl Acad Sci U S A. Dec. 1988;85(23):8998-9002.
Frohman On Beyond Classic RACE (Rapid Amplification of eDNA Ends) PCR Methods and Applications vol. 4, pp. S40-S58 (Year: 1994).
Fryknas et al. Molecular markers for discrimination of benign and malignant follicular thyroid tumors. Tumour Biol. 2006;27(4):211-20.
Fujarewicz, et al. A multi-gene approach to differentiate papillary thyroid carcinoma from benign lesions: gene selection using support vector machines with bootstrapping. Endocr Relat Cancer. Sep. 2007;14(3):809-26.
Fukumoto et al. Overexpression of the Aldo-Keto Reductase Family Protein AKR1B10 is Highly Correlated with Smokers' Non-Small Cell Lung Carcinomas. Clinical Cancer Research 11:1776-1785 (2005).
Furneaux et al. Selective expression of Purkinje-cell antigens in tumor tissue from patients with paraneoplastic cerebellar degeneration. New England Journal of Medicine (1990); 322.26: 1844-1851.
Gait. Chapter 16: Oligoribonucleotides. Antisense Research and Applications, Crookeand Lebleu Eds., CRC Press (pp. 289-302) (1993).
Garber et al. Diversity of gene expression in adenocarcinoma of the lung. PNAS, 98(24): 13784-13789 (Nov. 20, 2001).
Garcia-Alvarez et al. Tissue inhibitor of metalloproteinase-3 is up-regulated by transforming growth factor-131 in vitro and expressed in fibroblastic foci in vivo in idiopathic pulmonary fibrosis. Experimental Lung Research (Apr. 2006); 32(5): 201-214.
Garcia-Closas et al. Collection of Genomic DNA from Adults in Epidemiological Studies by Buccal Cytobrush and Mouthwash. Cancer Epidemiology, Biomarkers and Prevention, 10(6): 687-696 (2001).
Garcia-Lopez et al. Thyrocytes from autoimmune thyroid disorders produce the chemokines IP-10 and Mig and attract CXCR3+ lymphocytes. J Clin Endocrinol Metab. 2001;86(10):5008-16.
Gardina et al. Alternative splicing and differential gene expression in colon cancer detected by a whole genome exon array. BMC Genomics. 2006;7:325.
Gasparre et al. Disruptive mitochondrial DNA mutations in complex I subunits are markers of oncocytic phenotype in thyroid tumors. Proc Natl Acad Sci USA. 2007;104(21):9001-6.
Gebel, et al. Gene expression profiling in respiratory tissues from rats exposed to mainstream cigarette smoke. Carcinogenesis. Feb. 2004;25(2):169-78.
Gene Annot Website. Array Probesets for HOMER2, printed Jan. 2016.
Gene Annot website. Probesets for ALDH1B1. Printed Feb. 2018.
Gene Annot website. Probesets for AUTS2. Printed Feb. 2018.
Gene Annot website. Probesets for CFHR1. Printed Feb. 2018.
Gene Annot website. Probesets for CPE. Printed Feb. 2018.
Gene Annot website, Probesets for FN1. Printed Feb. 2018.
Gene Annot website. Probesets for GABRB2. Printed Feb. 2018.
Gene Annot website. Probesets for PLCB1. Printed Feb. 2018.
Gene Annot website. Probesets for PYGL. Printed Feb. 2018.
Gene Annot website. Probesets for ROS1. Printed Feb. 2018.
GeneAnnot Search for Affymetrix HG-U 133A microarray pro besets for TIMP1, printed Dec. 2018.
GeneAnnot Search for Affymetrix HG-U 133A microarray probesets for SLCA4, printed Dec. 2018.
GeneAnnot website. Probesets for AKT1. Printed Aug. 30, 2016. 1 page.
GeneAnnot website. Probesets for ALK. Printed Aug. 30, 2016. 1 page.
GeneAnnot website. Probesets for BRAF. Printed Aug. 30, 2016. 1 page.
GeneAnnot website. Probesets for CALCA. Printed Aug. 30, 2016. 1 page.
GeneAnnot website. Probesets for CTNNB1. Printed Aug. 30, 2016. 1 page.
GeneAnnot website. Probesets for EIF1AY. Printed Aug. 30, 2016. 1 page.
GeneAnnot website. Probesets for IGF2BP2. Printed Aug. 30, 2016. 1 page.
GeneAnnot website. Probesets for KRAS. Printed Feb. 7, 2017. 2 pages.
GeneAnnot website. Probesets for KRT7. Printed Aug. 30, 2016. 1 page.
GeneAnnot website. Probesets for MET. Printed Aug. 30, 2016. 1 page.
GeneAnnot website. Probesets for NTRK2. Printed Aug. 30, 2016. 1 page.
GeneAnnot website. Probesets for NTRK3. Printed Aug. 30, 2016. 2 pages.
GeneAnnot website. Probesets for PIK3CA. Printed Aug. 30, 2016. 1 page.
GeneAnnot website. Probesets for PPARGC1A. Printed Aug. 30, 2016. 1 page.
GeneAnnot website. Probesets for PROS1. Printed Nov. 8, 2016. 1 page.
GeneAnnot website. Probesets for PTEN. Printed Aug. 30, 2016. 2 pages.
GeneAnnot website. Probesets for PTH. Printed Aug. 30, 2016. 1 page.
GeneAnnot website. Probesets for RASA1. Printed Aug. 30, 2016. 1 page.
GeneAnnot website. Probesets for RET. Printed Aug. 30, 2016. 1 page.
GeneAnnot website. Probesets for RXRG. Printed Nov. 8, 2016. 1 page.
GeneAnnot website. Probesets for TP53. Printed Aug. 30, 2016. 1 page.
GeneAnnot website. Probesets for TSHR. Printed Aug. 30, 2016. 1 page.
GeneAnnot website. Probesets for TTF1. Printed Aug. 30, 2016. 1 page.

(56) References Cited

OTHER PUBLICATIONS

Geneloc CYP4F11. Geneloc Integrated Map for Chromosome 19: Exon structure for CYP4F11, https://genecards.weizmann.ac.il/ geneloc-bin/exon_struct.pl?disp_name=CYP4F11&chr_nr=19, accessed Dec. 13, 2019, pp. 1-2 (Year: 2019).

Geraghty et al. CT-guided transthoracic needle aspiration biopsy of pulmonary nodules: Needle size and pneumothorax rate 1. Radiology. Nov. 2003;229(2):475-81.

Gereben et al. Pretranslational regulation of type 2 deiodinase. Thyroid. 2005;15(8):855-64.

Gerstung, et al. Combining gene mutation with gene expression data improves outcome prediction in myelodysplastic syndromes. Nat Commun. Jan. 9, 2015;6:5901.

Gildea et al. Electromagnetic navigation diagnostic bronchoscopy: a prospective study. American Journal of Respiratory and Critical Care Medicine. Nov. 2006; 174(9):982-989.

Gill, et al. Nucleic acid isothermal amplification technologies: a review. Nucleosides Nucleotides Nucleic Acids. Mar. 2008;27(3):224-43.

Giordano et al. Delineation, functional validation, and bioinformatic evaluation of gene expression in thyroid follicular carcinomas with the PAX8-PPARG translocation. Clin Cancer Res. 2006;12(7 Pt 1):1983-93.

Giordano et al. Distinct transcriptional profiles of adrenocortical tumors uncovered by DNA microarray analysis. Am J Pathol. 2003;162(2):521-31.

Giordano et al. Molecular Classification of Papillary Thyroid Carcinoma; distinct BRAF, RAS and RET/PTC mutation-specific gene expression profiles discovered by DNA microarray Analysis Oncogene. Oncogene 24:6646-6656 (2005).

Giordano et al. Organ-specific molecular classification of primary lung, colon, and ovarian adenocarcinomas using gene expression profiles. Am J Pathol. 2001;159(4):1231-8.

Giordano. Genome-wide studies in thyroid neoplasia. Endocrinol Metab Clin North Am. 2008;37(2):311-31, vii-viii.

Golub, et al. Molecular classification of cancer: Discovery and class prediction by gene expression monitoring. Science, 286, 531-537, 1999.

Gombos, et al. Characterization of microarray gene expression profiles of early stage thyroid tumours. Cancer Genomics Proteomics. Nov.-Dec. 2007;4(6):403-9.

Gonzalez-Campora et al. Blood group antigens in differentiated thyroid neoplasms. Arch Pathol Lab Med. 1998;122(11):957-65.

Gorringe, et al., Loss of Heterozygosity. eLS, 2016; 1-8.

Gould et al. (1987). Synaptophysin expression in neuroendocrine neoplasms as determined by immunocytochemistry. Am J Pathol. 126(2):243-57.

Gould et al. A clinical model to estimate the pretest probability of lung cancer in patients with solitary pulmonary nodules. Chest Journal (2007); 131.2: 383-388.

Gould et al. Evaluation of individuals with pulmonary nodules: When is it lung cancer ?: Diagnosis and management of lung cancer: American College of Chest Physicians evidence-based clinical practice guidelines. CHEST Journal (2013); 143.5_suppl: e93S-e120S.

Gould et al. Recent trends in the identification of incidental pulmonary nodules. Am J Respir Crit Care Med. Nov. 15, 2015;192(10):1208-14.

Gower A C et al.: "Transcriptomic studies of the airway field of injury associated with smoking-related lung disease", Proceedings of the American Thoracic Society May 1, 2011 American Thoracic Society USA, val. 8, No. 2, May 1, 2011 (May 1, 2011 ), pp. 173-179.

Goy, A et al., 'The feasibility of gene expression profiling generated in fine-needle aspiration specimensfrom patients with follicular lymphoma and diffuse large B-cell lymphoma', Cancer. 2006 vol. 108 pp. 10-20.

Greenbaum, et al. Comparing protein abundance and mRNA expression levels on a genomic scale. Genome Biol. 2003;4(9):117. Epub Aug. 29, 2003.

Greenbaum, et al. Interrelating different types of genomic data, from proteome to secretome: 'oming in on function. Genome Res. Sep. 2001; 11(9):1463-8.

Greenlee et al. Cancer Statistics, 2001. CA Cancer J Clin; 51(1):15-36 (2001).

Grepmeier et al. Deletions at chromosome 2q and 12p are early frequent molecular alterations in bronchial epithelium and NSCLC of long-term smokers. Int J Oncol., 27(2):481-8(2005).

Griffith, et al. Biomarker panel diagnosis of thyroid cancer: a critical review. Expert Rev Anticancer Ther. Sep. 2008;8(9):1399-413.

Griffith et al. Meta-analysis and meta-review of thyroid cancer gene expression profiling studies identifies important diagnostic biomarkers. J Clin Oncol. 2006;24(31):5043-51.

Grogan et al. Thoracic operations for pulmonary nodules are frequently not futile in patients with benign disease. Journal of Thoracic Oncology (2011); 6.10: 1720-1725.

Guajardo et al. Altered gene expression profiles in nasal respiratory epithelium reflect stable versus actue childhood asthma. J. Allergy Clin Immunol; 115(2): 243-251 (2005).

Guatelli et al. Isothermal, in vitro amplification of nucleic acids by a multienzyme reaction modeled after retroviral replication. pnas usa 87(5):1874-1878 (1990).

Gulati, Mridu. Diagnostic assessment of patients with interstitial lung disease. Prim Care Respir J. Jun. 2011;20(2):120-7.

Gurney, JW. Determining the likelihood of malignancy in solitary pulmonary nodules with Bayesian analysis Part 1 Theory. Radiology 1993;186:405-13 (2005).

Gustafson et al. Airway P13K Pathway Activation is an Early and Reversible Even in Lung Cancer Development. <www.sciencetransmlationmedicine.org>. 2(26) (2010) .</www.sciencetransmlationmedicine.org>.

Ha et al. Localized non-Hodgkin lymphoma involving the thyroid gland. Cancer91.4 (2001): 629-635.

Hackett, et al., The Human Airway epithelial basal cell transcriptome, PLOS ONE, 2011; 6(5): e18378 pp. 1-22.

Hackett et al. Variability of antioxidant-related gene expression in the airway epithelium of cigarette smokers. Am J Respir Cell Mol Biol., 29: 331-43 (Apr. 2003).

Hadd, et al. Targeted, high-depth, next-generation sequencing of cancer genes in formalin-fixed, paraffin-embedded and fine-needle aspiration tumor specimens. J Mol Diagn. Mar. 2013;15(2):234-47. doi: 10.1016/j.jmoldx.2012.11.006. Epub Jan. 13, 2013.

Hamada, et al. Diagnostic usefulness of PCR profiling of the differentially expressed marker genes in thyroid papillary carcinomas. Cancer Lett. Jun. 28, 2005;224(2):289-301. Epub Nov. 18, 2004.

Hamilton et al. Diagnosis of lung cancer in primary care: a structured review. Fam Pract. Dec. 2004;21(6):605-11.

Hanley et al. The meaning and use of the area under a receiver operating characteristic (ROC) curve. Radiology. Apr. 1982;143(1):29-36.

Harach et al. Histology of familial thyroid tumours linked to a gene mapping to chromosome 19p13.2. J Pathol. 1999;189(3):387-93.

Hartigan, et al. The dip test of unimodality. Annals of Statistics. 1985; 13(1):70-84.

Haugen, et al. Development of a novel molecular classifier to accurately identify benign thyroid nodules in patients with indeterminate FNA cytology. Abstract presented at 14th International Thyroid Congress. Sep. 15, 2010.

Haugen et al. Increased expression of genes encoding mitochondrial proteins in papillary thyroid carcinomas. Thyroid. 2003;13(7):613-20.

Hawthorn, et al. TIMP1 and SERPIN-A overexpression and TFF3 and CRABP1 underexpression as biomarkers for papillary thyroid carcinoma. Head Neck. Dec. 2004;26(12):1069-83.

He, et al. A susceptibility locus for papillary thyroid carcinoma on chromosome 8q24. Cancer Res. Jan. 15, 2009;69(2):625-31.

He et al. The role of microRNA genes in papillary thyroid carcinoma. Proc Natl Acad Sci USA. 2005;102(52):19075-80.

Hecht, SS. Tobacco carcinogens, their biomarkers and tobacco-induced cancer. Nature Review Cancer; 3:733-744 (Oct. 2003).

(56) References Cited

OTHER PUBLICATIONS

Hellmann et al. Gene Expression Profiling of Cultured Human Bronchia Epithelial and Lung Cacinoma Cells. Toxicological Sciences, 61: 154-163 (2001).
Hellwig, et al. Comparison of scores for bimodality of gene expression distributions and genome-wide evaluation of the prognostic relevance of high-scoring genes. BMC Bioinformatics. May 25, 2010;11:276. doi: 10.1186/1471-2105-11-276.
Hemmer et al. Comparison of benign and malignant follicular thyroid tumours by comparative genomic hybridization. Br J Cancer. 1998;78(8):1012-7.
Hemmer, et al. DNA copy number changes in thyroid carcinoma. Am J Pathol. May 1999;154(5):1539-47.
Hennessy et al. Exploiting the PI3KAKT Pathway for Cancer Drug Discovery Nature vol. 4:988-1004 (2005).
Heuer et al. Different cytokine mRNA profiles in Graves' disease, Hashimoto's thyroiditis, and nonautoimmune thyroid disorders determined by quantitative reverse transcriptase polymerase chain reaction (RT-PCR). Thyroid. 1996;6(2):97-106.
Hindiyeh et al. Evaluation of a Multiplex Real-Time Reverse Transcriptase PCR Assay for Detection and Differentiation of Influenza Viruses A and B during the 2001-2002 Influenza Season in Israel. Journal of Clinical Microbiology, 2005, 43(2):589-595. doi: 10.1128/JCM.43.2.589-595.2005.
Hirsch et al. Early Detection of Lung Cancer: Clinical Perspectives of Recent Advances in Biology and Radiology. Clinical Cancer Research (7): 5-22 (2001).
Hodnett et al. Fibrosing interstitial lung disease: a practical HRCT based approach to diagnosis and management and review of the literature. Am J Respir Crit Care Med (2013); 188.2: 141-149.
Holden et al. Tyrosine kinase activating mutations in human malignancies: implications for diagnostic pathology. Exp Mol Pathol. 2008; 85(1):68-75.
Holland, et al., Detection of specific polymerase chain reaction product by utilizing the 5' to 3' exonuclease activity of Thermus aquaticus DNA polymerase. PNAS (USA) 88:7276-7280, 1991.
Hoshikawa, et al. Hypoxia Induces Different Genes in the Lungs of Rats Compared With Mice. Physiological Genomics. vol. 12, Issue. 3 (2003): pp. 209-219.
Hou et al. Genetic alterations and their relationship in the phosphatidylinositol 3-kinase/Akt pathway in thyroid cancer. Clin Cancer Res. 2007;13(4):1161-70.
Howlader et al. SEER stat fact sheets: lung and bronchus cancer. Bethesda: National Cancer Institute (2011). http://seer.cancer.gov/statfacts/html/lungb.html [Downloaded Oct. 18, 2016], 9 pages.
Hsu et al. Characterization of a novel tripartite nuclear localization sequence in the EGFR family. J Biol Chem. 2007;282(14):10432-40.
Hsu et al. Overexpression of dihydrodiol dehydrogenase as a prognostic marker of non-small cell lung cancer. Cancer research, Mar. 2001; 61(6): 2727-2731.
Hu et al. Nature Protocols. 2006. 1 (4): 17 43. (Year: 2006).
Huang et al. A genome-wide approach to identify genetic variants that contribute to etoposide-induced cytotoxicity. Proc Natl Acad Sci USA. 2007;104(23):9758-63.
Huang et al. A tool for RNA sequencing sample identity check. Bioinformatics 29.11 (2013): 1463-1464.
Huang et al. Gene expression in papillary thyroid carcinoma reveals highly consistent profiles. Proc Natl Acad Sci USA. 2001;98(26):15044-9.
Huang et al. Systematic and integrative analysis of large gene lists using DAVID bioinformatics resources. Nature protocols 4:44-57 (2009).
Human hg 19 chr5 (Human hg 19 chr5: 136368834-136368864 UCSC Genome Browser v410, 2009) (Year: 2009).
Human hg19 chr11 (Human hg19 chr11 :30509671-30509898 UCSC Genome Browser v410, 2009) (Year: 2009).
Hunt, et al. A microdissection and molecular genotyping assay to confirm the identity of tissue floaters in paraffin-embedded tissue blocks Arch Pathol Lab Med. 2003; 127(2):213-217.
Hviid et al. HLA-G polymorphisms and HLA-G expression in sarcoidosis. Sarcoidosis, vasculitis, and diffuse lung diseases: official journal of WASOG/World Association of Sarcoidosis and Other Granulomatous Disorders (Mar. 23, 2006); 23.1: 30-37.
Ikeda et al. Malignancy associated changes in bronchial epithelial cells and clinical application as a biomarker. Lung Cancer, 19(3): 161-166 (1998).
Imelfort et al. De novo sequencing of plant genomes using second-generation technologies. Briefings in Bioinformatics (2009); 10.6: 609-618.
Inaji et al. Demonstration and diagnostic significance of pro-gastrin-releasing peptide in medullary thyroid carcinoma. Oncology. 2000;59(2):122-5.
International search report and written opinion dated Jan. 19, 2012 for PCT Application No. US2011/36143.
International search report and written opinion dated Feb. 25, 2011 for PCT Application No. US2010/034140.
International search report and written opinion dated Feb. 25, 2013 for PCT Application No. US2012/068804.
International search report and written opinion dated Apr. 17, 2015 for PCT/US2014/026411.
International search report and written opinion dated May 8, 2013 for PCT Application No. US2012/068587.
International Search Report and Written Opinion dated Nov. 18, 2013 for International PCT Patent Application No. PCT/CA2013/050686.
International Search Report dated Aug. 28, 2014 for International PCT Patent Application No. PCT/US2014/025715.
International search report dated Jul. 29, 2010 for PCT Application No. US2009/06162.
International Search Report for PCT/CA2010/000266, dated Jul. 12, 2010.
International Search Report for PCT/CA2010/000621, completed Jul. 14, 2010.
International search report with written opinion dated Apr. 4, 2017 for PCT/US2016/053578.
International search report with written opinion dated Jun. 2, 2016 for PCT/US2016/020583.
Irizarry, et al. Exploration, normalization, and summaries of high density oligonucleotide array probe level data. Biostatistics. Apr. 2003;4(2):249-64.
Irizarry et al. Summaries of Affymetrix GeneChip probe level data. Nucleic Acids Res 31(4):e15 (Feb. 2003).
Ito, et al. Distant and lymph node metastases of thyroid nodules with No. pathological evidence of malignancy: a limitation of pathological examination. Endocr J. Oct. 2008;55(5):889-94. Epub Jun. 1, 20084.
Ito et al. Simultaneous expression of keratan sulphate epitope (a sulphated poly-N-acetyllactosamine) and blood group ABH antigens in papillary carcinomas of the human thyroid gland. Histochem J. 1996;28(9):613-23.
Ivana et al. Expression of cilium-associated genes defines novel molecular subtypes of idiopathic pulmonary fibrosis. Thorax(2013): thoraxjnl-2012.
Ivana et al. Gene expression profiling of familial and sporadic interstitial pneumonia. American journal of respiratory and critical care medicine 175.1 (2007): 45-54.
Jacques et al. Two-step differential expression analysis reveals a new set of genes involved in thyroid oncocytic tumors. J Clin Endocrinol Metab. 2005;90(4):2314-20.
Jang et al. Activation of melanoma antigen tumor antigens occurs early in lung carcinogenesis. Cancer Research 61: 7959-7963 (2001).
Jarzab et al. Gene Expression Profile of Papillary Thyroid Cancer: Sources of Variability and Diagnostic Implications. Cancer Res. 2005;65(4):1587-1597.
Jazdzewski et al. Common SNP in pre-miR-146a decreases mature miR expression and predisposes to papillary thyroid carcinoma. Proc Natl Acad Sci USA. 2008;105(20):7269-74.
Ji et al., Long-term impact of initial surgical and medical therapy on young patients with papillary thyroid cancer and bilateral cervical metastases. Chinese Medical Journal, 2008; 121 (1) :63-66.

(56) References Cited

OTHER PUBLICATIONS

Jin et al. The Cystic fibrosis transmembrane conductance regulator as a biomarker in non-small cell lung cancer. International Journal of Oncology, 2015; 46: 2107-2115.
Jo, et al. Influence of the Braf V600E mutation on expression of vascular endothelial growth factor in papillary thyroid cancer. J Clin Endocrinol Metab. Sep. 2006;91(9):3667-70. Epub Jun. 13, 2006.
Johansson, et al. Confirmation of a BRAF mutation-associated gene expression signature in melanoma. Pigment Cell Res. Jun. 2007;20(3):216-21.
Johnson et al. Adjusting batch effects in microarray expression data using empirical Bayes methods. Biostatistics (2007); 8.1: 118-127.
Jones et al., Value and accuracy of cytology in addition to histology in the diagnosis of lung cancer at flexible bronchoscopy. Respiratory Medicine, 2001; 95: 374-378.
Jonigk et al. Molecular profiling in lung biopsies of human pulmonary allografts to predict chronic lung allograft dysfunction. The American Journal of Pathology (2015); 185.12: 3178-3188.
Joseph et al. Lack of mutations in the thyroid hormone receptor (TR) alpha and beta genes but frequent hypermethylation of the TRbeta gene in differentiated thyroid tumors. J Clin Endocrinol Metab. 2007;92(12):4766-70.
Joshua D Campbell et al: "A gene expression signature of emphysema-related lung destruction and its reversal by the tripeptide GHK", Genome Med, Biomed Central L To, London, UK, vol. 4, No. 8, Aug. 31, 2012 (Aug. 31, 2012 ), p. 67.
Jovanovic et al. Most multifocal papillary thyroid carcinomas acquire genetic and morphotype diversity through subclonal evolution following the intra-glandular spread of the initial neoplastic clone. J Pathol. 2008;215(2):145-54.
Jun et al. Detecting and estimating contamination of human DNA samples in sequencing and array-based genotype data. The American Journal of Human Genetics 91.5 (2012): 839-848.
Jung et al., Expression of MAGE and GAGE genes in the bronchogenic cancer tissues obtained by bronchoscopy. Korean journal of medicine, 2002, 62(1): 58-68.
Kadara et al. Transcriptomic architecture of the adjacent airway field cancerization in non-small cell lung cancer. Journal of the National Cancer Institute (2014); 106.3: dju004.
Kakudo et al. Immunohistochemical study of substance P-like immunoreactivity in human thyroid and medullary carcinoma of the thyroid. J Submicrosc Cytol. 1983;15(2):563-8.
Kanehisa. Use of statistical criteria for screening potential homologies in nucleic acid sequences. Nucleic Acids Res. Jan. 11, 1984;12(1 Pt 1):203-13.
Kang et al. High prevalence of RET, RAS, and ERK expression in Hashimoto's thyroiditis and in papillary thyroid carcinoma in the Korean population. Thyroid. 2007;17(11):1031-8.
Kannengiesser, et al. Gene expression signature associated with BRAF mutations in human primary cutaneous melanomas. Mol Oncol. Apr. 2008; 1(4):425-30. doi: 10.1016/j.molonc.2008.01.002. Epub Jan. 12, 2008.
Kanner et al. Effects of randomized assignment to a smoking cessation intervention and changes in smoking habits on respiratory symptoms in smokers with early chronic obstructive pulmonary disease: the lung health study. American Journal of Medicine; 106:410-416 (1999).
Kao, et al. Tumor-associated Antigen L6 and the Invasion of Human Lung Cancer Cells. Clin Cancer Res. 9:2807-2816 (Jul. 2003).
Kapadia, et al. Malignant lymphoma of the thyroid gland: a clinicopathologic study. Head Neck Surg. Mar.-Apr. 1982;4(4):270-80.
Kasraeian, et al. A comparison of fine-needle aspiration, core biopsy, and surgical biopsy in the diagnosis of extremity soft tissue masses. Clin Orthop Relat Res. Nov. 2010;468(11):2992-3002. doi: 10.1007/s11999-010-1401-x.
Katoh et al. Thyroid transcription factor-1 in normal, hyperplastic, and neoplastic follicular thyroid cells examined by immunohistochemistry and nonradioactive in situ hybridization. Mod Pathol. 2000;13(5):570-6.
Katz et al. Automated detection of genetic abnormalities combined with cytology in sputum is a sensitive predictor of lung cancer. Modern Pathology;21:950-960 (2008).
Katzenstein, Anna-Luise A. Smoking-related interstitial fibrosis (SRIF), pathogenesis and treatment of usual interstitial pneumonia (UIP), and transbronchial biopsy in UIP. Modern Pathology (2012); 25: S68-S78.
Katzenstein et al. Diagnosis of usual interstitial pneumonia and distinction from other fibrosing interstitial lung diseases. Erratum to Diagnosis of usual interstitial pneumonia and distinction from other fibrosing interstitial lung diseases. [Hum Pathol (2008); 39: 1275-1294]. Human Pathology (2008); 39.11: 1562-1581.
Katzenstein et al. Idiopathic Pulmonary Fibrosis. Am J Respir Crit Care Med (1998); 157: 1301-1315.
Katzenstein et al. Usual interstitial pneumonia: histologic study of biopsy and explant specimens. The American Journal of Surgical Pathology (2002); 26.12: 1567-1577.
Kauffmann et al. arrayQualityMetrics—a bioconductor package for quality assessment of microarray data. Bioinformatics (2009); 25.3: 415-416.
Kawai, et al. Recent Advances of DNA chip application. Latest Situation in DNA Chip Applications. English Translation. Protein Nucleic Acid and Enzyme, Aug. 1, 2000, vol. 45, No. 11, p. 47-53.
Kazemi-Noureini et al. Differential gene expression between squamous cell carcinoma of esophageus and its normal epithelium; altered pattern of mal, akric2, and rab11a expression. World J Gastroenterol. Jun. 15, 2004; 10(12): 1716-1721.
Kebebew et al. Diagnostic and extent of disease multigene assay for malignant thyroid neoplasms. Cancer. 2006;106(12):2592-7.
Kebebew et al. Diagnostic and prognostic value of angiogenesis-modulating genes in malignant thyroid neoplasms. Surgery. Dec. 2005;138(6):1102-9; discussion 1109-10.
Kebebew, et al. The prevalence and prognostic value of BRAF mutation in thyroid cancer. Ann Surg. Sep. 2007;246(3):466-70; discussion 470-1.
Kelmemi et al. BMC Medical Genetics. 2015. 16:50.(Year: 2015).
Khan et al. Classification and Diagnostic Prediction of Cancers Using Gene Expression Profiling and Artificial Neural Networks. Nature Medicine, 7(6):673-679, (Jun. 2001).
Kim, et al., Classification of usual interstitial pneumonia in patients with interstitial lung disease: Assessment of a machine learning approach using high-dimensional transcriptional data. The Lancet respiratory medicine, elsevier oxford, Jun. 2015; 3(6): 473-482.
Kim et al. Diagnostic use of molecular markers in the evaluation of thyroid nodules. Endocrine Practice Sep./Oct. 2012, vol. 18, No. 5, pp. 796-802 (Year: 2012).
Kim et al. Identification of bronchioalveolar stem cells in normal lung and lung cancer. Cell (2005); 121.6: 823-835.
King et al. Idiopathic pulmonary fibrosis. The Lancet (2011); 378.9807: 1949-1961.
King Jr. et al. A phase 3 trial of pirfenidone in patients with idiopathic pulmonary fibrosis. N Engl J Med. May 29, 2014;370(22):2083-92.
King, T.E., Clinical advances in the diagnosis and therapy of the interstitial lung diseases. Am J Resp. Crit care med. vol. 172; 2005: 268-279.
Kiss, et al. Anatomisk Atlas over Manniskokroppen, band II. Natur och Kultur Stockholm, Stockholm, Sweden ISBN: 91-27-67278-6; 1973.
Kitahara et al. Alternations of Gene Expression during Colorectal Carcinogenesis Revealed by cDNA Microarrays after Laser-Capture Microdissection of Tumor Tissues and Normal Epithelia. Cancer Research, 61: 3544-3549 (May 1, 2001).
Knudsen et al. Ri antibodies in patients with breast, ovarian or small cell lung cancer determined by a sensitive immunoprecipitation technique. Cancer Immunology Immunotherapy 55.10 (Jan. 2006): 1280-1284.
Kocarnik et al. Replication of Associations Between GWAS SNPs and Melanoma Risk in the Population Architecture Using Genomics and Epidemiology (PAGE) Study. Journal of Investigative Dermatology, 134:2049-2052, (Feb. 27, 2014).

(56) References Cited

OTHER PUBLICATIONS

Korn et al., Glucocorticoid receptor mRNA levels in bronchial epithelial cells of patients with COPD: influence of glucocorticoids. Respiratory Medicine, 1998; 92: 1102-1109.

Koshkin et al. LNA (locked nucleic acids): An RNA mimic forming exceedingly stable LNA: LNA duplexes. J Am Chem Soc 120:13252-13253 (1998).

Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).

Kraft et al. Expression of epithelial markers in nocturnal asthma. Journal of Allergy and Clinical Immunology, 102(3): 376-381 (1998).

Krause, et al. Characterisation of DEHAL1 expression in thyroid pathologies. Eur J Endocrinol. Mar. 2007;156(3):295-301.

Krawczak, et al. The mutational spectrum of single base-pair substitutions in mRNA splice junctions of human genes: causes and consequences. Hum Genet. Sep.-Oct. 1992;90(1-2):41-54.

Kreula, et al. Sample size in fine needle aspiration biopsy. Br J Surg. Dec. 1989;76(12):1270-2.

Kristensen, et al. Genetic variation in putative regulatory loci controlling gene expression in breast cancer. Proc Natl Acad Sci U S A. May 16, 2006;103(20):7735-40. Epub May 9, 2006.

Kroese et al. Genetic tests and their evaluation: Can we answer the key questions? Genetics in Medicine 6:475-480 (2004).

Kroschwitz. The Concise Encyclopedia of Polymer Science and Engineering. (pp. 858-859) (1990).

Kumar, et al. The first analogues of LNA (locked nucleic acids): phosphorothioate-LNA and 2'- thio-LNA. Bioorg Med Chem Lett. Aug. 18, 1998;8(16):2219-22.

Kuriakose et al. Selection and validation of differentially expressed genes in head and neck cancer. Cellular and Molecular Life Sciences CMLS 61. (11):1372-83, Jul. 2004.

Kwan, et al. Heritability of alternative splicing in the human genome. Genome Res. Aug. 2007;17(8):1210-8.

Kwoh et al. Transcription-based amplification system and detection of amplified human immunodeficiency virus type 1 with a bead-based sandwich hybridization format. PNAS USA 86(4):1173-1177 (1989).

Lacobuzio-Donahue et al., Highly Expressed Genes in Pancreatic Ductal Adenocarcinomas: A Comprehensive Characterization and Comparison of the Transcription Profiles Obtained from Three Major Technologies. Cancer Research, Dec. 2003; 63: 8614-8622.

Lacroix, et al. PAX8 and peroxisome proliferator-activated receptor gamma 1 gene expression status in benign and malignant thyroid tissues. Eur J Endocrinol. Sep. 2004;151(3):367-74.

Lacroix et al. Sensitive Detection of Rare Cancer Cell in Sputum and Peripheral Blood Samples of Patients with Lunch Cancer by Preprogrp-Specific TR-PCR. Int. J. Cancer, vol. 92: 1-8 (2001).

Lam et al. A Phase I Study of myo-Inositol for Lung Cancer Chemoprevention. Cancer Epidemiology, Biomarkers & Prevention 15(8): 1526-1531 (Aug. 2006).

Lampe et al. Signatures of environmental exposures using peripheral leukocyte gene expression: tobacco smoke. Cancer Epidemiology Biomarkers & Prevention (2004); 13.3: 445- 453.

Landegren, et al., A ligase-mediated gene detection technique. Science. Aug. 26, 1988;241(4869):1077-80.

Lander, et al. Initial sequencing and analysis of the human genome. Nature 409:860-921 (Feb. 15, 2001).

Langford et al. Is the Property of Being Positively Correlated Transitive. The American Statistician. 55(4):322-325 (2001).

Lau et al. Thyroid transcription factor-1: a review. Appl Immunohistochem Mol Morphol. 2002;10(2):97-102.

Lauter et al. Mutational analysis of CDKN1B, a candidate tumor-suppressor gene, in refractory secondary/tertiary hyperparathyroidism. Kidney Int. 2008;73(10):1137-40.

Lee, et al., Expression of mRNA of Trefoil Factor Peptides in Human Nasal Mucosa. Acta Oto-Laryngologica. 2001;121(7):849-853.

Lee et al. NGSCheckMate: software for validating sample identity in next-generation sequencing studies within and across data types. Nucleic acids research 45.11 (2017).

Lewis et al. Cotinine levels and self-reported smoking status in patients attending a bronchoscopy clinic. Biomarkers (2003); 8.3-4: 218-228.

Li et al. Gene expression profiling in human lung fibroblast following cadmium exposure. Food and Chemical Toxicology (2008); 46.3: 1131-1137.

Li, Lexin. Survival prediction of diffuse large-B-cell lymphoma based on both clinical and gene expression information. Bioinformatics 2006; 22:466-71, (Feb. 2006).

Li, X et al. American Journal of Respiratory and Critical Care Medicine 183(1 Supp.): abstract A6176 (May 1, 2011) (3 pages).

Liao et al. Expression and significance of PTEN/PI3K signal transduction-related proteins in nonsmall cell lung cancer. Ai Zheng 25: 10, p. 1238-42. Abstract (Oct. 2006).

Lima et al. Thyroid Peroxidase and Thyroglobulin Expression in Normal Human Thyroid Glands. Endocr Pathol. 1998;9(1):333-338.

Lin et al. Effects of Dexamethasone on Acute Lung Injury Rat Cells Signal Transduction Systems ERK and P13-K. Medical Journal of Chinese People's Liberation Army 6(31): 592-594 (Sep. 2006).

Lin et al. Expression of sodium iodide symporter in benign and malignant human thyroid tissues. Endocr Pathol. 2001;12(1):15-21.

Lin, et al. Thyroid ultrasonography with fine-needle aspiration cytology for the diagnosis of thyroid cancer. J Clin Ultrasound. Mar.-Apr. 1997;25(3):111-8.

Liu et al. An oligonucleotide microchip for genome-wide microRNA profiling in human and mouse tissues. Proc Natl Acad Sci USA, 2004, 101(26):9740-9744.

Liu et al. Effects of physiological versus pharmacological g-carotene supplementation on cell proliferation and histopathological changes in the lungs of cigarette smoke-exposed ferrets. Carcinogenesis, 21: 2245-2253 (2000).

Liu et al. Highly prevalent genetic alterations in receptor tyrosine kinases and phosphatidylinositol 3-kinase/akt and mitogen-activated protein kinase pathways in anaplastic and follicular thyroid cancers. J Clin Endocrinol Metab. 2008;93(8):3106-16.

Liu, et al. Quantitative Proteome Analysis Reveals Annexin A3 as a Novel Biomarker in Lung Adenocarcinoma. Journal of Pathology, 217: 54-64 (2009).

Liu, Y. 'Active learning with support vector machine applied to gene expression data for cancer classification', J Chem Inf Comput Sci. 2004, vol. 44, pp. 1936-1941.

Lockstone et al. Gene set analysis of lung samples provides insight into pathogenesis of progressive, fibrotic pulmonary sarcoidosis. American Journal of Respiratory and Critical Care Medicine (2010); 181.12: 1367-1375.

Love, et al. Moderated estimation of fold change and dispersion for RNA-seq data with DESeq2. Genome Biol. Dec. 5, 2014;15(12):550.

Lubitz et al. 2006;Microarray analysis of thyroid nodule fine-needle aspirates accurately classifies benign and malignant lesions. J Mol Diagn. 8(4):490-8; quiz 528.

Lubitz et al. Molecular analysis of minimally invasive follicular carcinomas by gene profiling. Surgery. 2005;138(6):1042-8; discussion 1048-9.

Lubitz, et al., The differentiation of Benign and malignant thyroid nodules. Advances in sur. Jan. 1, 2005; 39(1): 355-377.

Lucentini, J. Gene Association Studies Typically Wrong. The Scientist, 18(24):20 (2004).

Lui et al. 2008;CREB3L2-PPARgamma fusion mutation identifies a thyroid signaling pathway regulated by intramembrane proteolysis. Cancer Res. 68(17):7156-64.

Machens et al. Genotype-phenotype based surgical concept of hereditary medullary thyroid carcinoma. World J Surg. 2007;31(5):957-68.

Mackay, et al. Targeting the protein kinase C family: are we there yet? Nature Reviews Cancer. 7(7):554-62 (Jul. 1, 2007).

MacMahon et al. Guidelines for management of small pulmonary nodules detected on CT scans: a statement from the Fleischner Society 1. Radiology (2005); 237.2: 395-400.

(56) References Cited

OTHER PUBLICATIONS

Majewski, K et al., Serum concentrations of antimicrobial peptide cathelicidin LL-37 in patients with bacterial lung infections. Cent Eur J Immunol. 2018; 43(4): 453-457.
Mak (Thesis: "Expression of CFTR mRNA Epithelium and Vas Deferens", 1997, Univ of Toronto).
Manichaikul, et al. Robust relationship inference in genome-wide association studies. Bioinformatics. Nov. 15, 2010;26(22):2867-73. Epub Oct. 5, 2010.
Mannino et al. Low lung function and incident lung cancer in the United States: data From the First National Health and Nutrition Examination Survey follow-up. Arch Intern Med. 163(12):1475-80 (Jun. 23, 2003).
Margulies, et al. Genome sequencing in microfabricated high-density picolitre reactors. Nature. Sep. 15, 2005;437(7057):376-80. Epub Jul. 3, 20051.
Mariani Thomas J et al: "Molecular markers for quantitative and discrete COPD phenotypes", The FASEB Journal, Federation of American Societies for Experimental Biology, US, vol. 21, No. 5, Apr. 1, 2007 (Apr. 1, 2007 ), p. A8.
Marinov et al. Targeting mTOR signaling in lung cancer. Critical Reviews in Oncology/Hematology 63: 172-182 (Aug. 2007).
Marsh, et al. Genome-wide copy number imbalances identified in familial and sporadic medullary thyroid carcinoma. J Clin Endocrinol Metab. Apr. 2003;88(4):1866-72.
Martin. A New Access to 2'-O-Alkylated Ribonucleosides and Properties of 2'-O-Alkylated Oligoribonucleotides. Helv. Chim. Acta. 1995; 78:486-504. (in German with English abstract).
Masini-Repiso et al. Ultrastructural localization of thyroid peroxidase, hydrogen peroxide-generating sites, and monoamine oxidase in benign and malignant thyroid diseases. Hum Pathol. 2004; 35(4):436-46.
Mason, et al. Bimodal distribution of RNA expression levels in human skeletal muscle tissue. BMC Genomics. Feb. 7, 2011;12:98. doi: 10.1186/1471-2164-12-98.
Matsubayashi et al. Gastrin-releasing peptide immunoreactivity in medullary thyroid carcinoma. Cancer. 1984;53(11):2472-7.
Maximo et al. Somatic and germline mutation in GRIM-19, a dual function gene involved in mitochondrial metabolism and cell death, is linked to mitochondrion-rich (Hurthle cell) tumours of the thyroid. Br J Cancer. 2005;92(10):1892-8.
May et al., How Many Species Are There on Earth? Science, 1988; vol. 241: p. 1441.
May, Robert M. How Many Species Are There on Earth? Science, 241: 1141-1449 (1988).
Mazzanti, et al. Using gene expression profiling to differentiate benign versus malignant thyroid tumors. Cancer Res. Apr. 15, 2004;64(8):2898-903.
McCarroll, et al. Integrated detection and population-genetic analysis of SNPs and copy number variation. Nature Genetics 40, 1166-1174 (2008).
McWilliams et al. Probability of cancer in pulmonary nodules detected on first screening CT. New England Journal of Medicine (2013); 369.10: 910-919.
Medical News: Targeted, Oral Agent Enzastaurin Shows Favorable Results in Late-Stage Lung Cancer. (Jun. 11, 2007), Retrieved from the Internet URL: https://www.medicalnewstoday.com/releases/73761.php.
Memoli et al. Meta-analysis of guided bronchoscopy for the evaluation of the pulmonary nodule. CHEST Journal (2012); 142.2: 385-393.
Merrium-Webster.com ( http://www.merriam-webstercom/dictionary/questionnaire), downloaded Oct. 26, 2013.
Meyer et al. Support vector machines. The Interface to libsvm in package e1071. FH Technikum Wien, Austria (2015); pp. 1-8.
Mi, et al., The PANTHER database of protein families, subfamilies, functions and pathways, Neucleic acids research, 2005, 3: D284-88.
Michalczyk et al. Fresh and cultured buccal cells as a source of mRNA and protein for molecular analysis. Biotechniques. Aug. 2004;37(2):262-4, 266-9.

Miklos, et al. Microarray reality checks in the context of a complex disease. Nature Biotechnology, 22:5 (May 2005).
Mineva, et al. Differential expression of alphaB-crystallin and Hsp27-1 in anaplastic thyroid carcinomas because of tumor-specific alphaB-crystallin gene (CRYAB) silencing. Cell Stress Chaperones. 2005 Autumn;10(3):171-84.
Minhyeok; Lee et al., "Copy number Variations of Chromosome 17p13.1 Might be Linked to High Risk of Lung Cancer in Heavy Smokers", Mol Biol Rep, 2011, 38, 5211-5217.
Mitomo et al. Downregulation of miR-138 is associated with overexpression of human telomerase reverse transcriptase protein in human anaplastic thyroid carcinoma cell lines. Cancer Sci. 2008;99(2):280-6.
Miura et al. Laser capture microdissection and microarray expression analysis of lung adenocarcinoma reveals tobacco smoking- and prognosis-related molecular profiles. Cancer Res., 62(11): 3244-50 (Jun. 1, 2002).
Miyamoto et al. Potential Marker of Oral Squamous Cell Carcinoma Aggressiveness Detected by Fluorescence in Situ Hybridization in Fine-Needle Aspiration Biopsies. Cancer American Cancer Society 95(10):2152-2159 (Jun. 6, 2002).
Mizukami, et al. Late bone metastasis from an encapsulated follicular carcinoma of the thyroid without capsular and vascular invasion. Pathol Int. Jun. 1996; 46(6):457-61.
Modrek et al. Genome-wide detection of alternative splicing in expressed sequences of human genes. Nucleic Acids Research, 29(13): 2850-2859 (2001).
Moller et al. Altered Ratio of Endothelin ETA- and ETB Receptor mRNA in Bronchial Biopsies from Patients with Asthma and Chronic Airway Obstruction. (European Journal of Pharmacology, 1999, 365: R1-R3).
Mollerup et al. Sex Differences in Lung CYP1A1 Expression and DNA Adduct Levels among Lung Cancer Patients. Cancer Research, 1999, 59: 3317-3320 (1999).
Mongiat et al. Fibroblast Growth Factor-binding Protein Is a Novel Partner for Perlecan Protein Core. The Journal of Biological Chemistry; 276(13):10263-10271 (Mar. 30, 2001).
Montero-Conde et al. Molecular profiling related to poor prognosis in thyroid carcinoma. Combining gene expression data and biological information. Oncogene. 2008;27(11):1554-61.
Monti et al. Consensus Clustering: A Resampling-Based Method for Class Discovery and Visualization of Gene Expression Microarray Data. Machine Learning (Jul. 2003); 52(1): 91-118.
Morales et al. Accuracy of self-reported tobacco use in newly diagnosed cancer patients. Cancer Causes & Control (2013); 24.6: 1223-1230.
Moreno, et al. Mutations in the iodotyrosine deiodinase gene and hypothyroidism. N Engl J Med. Apr. 24, 2008;358(17):1811-8. doi: 10.1056/NEJMoa0706819.
Morin et al.: Profiling the HeLa S3 transcriptome using randomly primed cDNA and massively parallel short-read sequencing. Biotechniques. 45:81-94 (2008).
Morozova et al. Applications of next-generation sequencing technologies in functional genomics. Genomics (2008); 92.5: 255-264.
Murphy et al. Identification of immunohistochemical biomarkers for papillary thyroid carcinoma using gene expression profiling. Hum Pathol. 2008;39(3):420-6.
Nakano et al. Apoptosis-induced decrease of intrathyroidal CD4(+)CD25(+) regulatory T cells in autoimmune thyroid diseases. Thyroid. 2007;17(1):25-31.
Nakashima et al. Foci formation of P53-binding protein 1 in thyroid tumors: activation of genomic instability during thyroid carcinogenesis. Int J Cancer. 2008;122(5):1082-8.
Nakashima et al. RET oncogene amplification in thyroid cancer: correlations with radiation-associated and high-grade malignancy. Hum Pathol. 2007;38(4):621-8.
Nakayama et al. High molecular weight caldesmon positive stromal cells in the capsule of thyroid follicular tumours and tumour-like lesions. J Clin Pathol. 2002;55(12):917-20.
Nam, et al. Braf V600E mutation analysis of thyroid nodules needle aspirates in relation to their ultrasongraphic classification: a potential guide for selection of samples for molecular analysis. Thyroid. Mar. 2010;20(3):273-9. doi: 10.1089/thy.2009.0226.

(56) References Cited

OTHER PUBLICATIONS

National Cancer Institute web page: "Common Cancer Types", captured by WayBack machine on Dec. 4, 2011, http://www.cancer.gov/cancertopics/types/commoncancers.
National Lung Screening Trial Research Team et al. Reduced lung-cancer mortality with low-dose computed tomographic screening. N Engl J Med 365:395-409 (2011).
NCBI gene report for LOC100131599. Printed Feb. 2018.
Neonakis et al. Expression of calcitonin and somatostatin peptide and mRNA in medullary thyroid carcinoma. World J Surg. 1994;18(4):588-93.
Neubauer et al. Cure of Helicobacter pylori Infection and Duration of Remission of Low-Grade Gastric Mucosa-Associated Lymphoid Tissue Lymphoma. J. Natl. Cancer Inst., 89(18): 1350-1355 (Sep. 17, 1997).
Newton et al. On Differential Variability of Expression Ratios: Improving Statistical Inference about Gene Expression Changes from Microarray Data. Journal of Computational Biology, 8: 37-52 (2001).
Nicholson et al. Inter-observer variation between pathologists in diffuse parenchymal lung disease. Thorax (2004); 59.6: 500-505.
Nicholson et al. The relationship between individual histologic features and disease progression in idiopathic pulmonary fibrosis. American Journal of Respiratory and Critical Care Medicine (2002); 166.2: 173-177.
Nielsen et al. Aquaporins in complex tissues. II. Subcellular distribution in respiratory and glandular tissues of rat. American Journal of Physiology-Cell Physiology (1997); 273.5: C1549-C1561.
Nielsen et al. Sequence-selective recognition of DNA by strand displacement with a thymine-substituted polyamide. Science 254:1497-1500 (1991).
Nikiforov et al. Impact of Mutational Testing on the Diagnosis and Management of Patients with Cytologically Indeterminate Thyroid Nodules: A Prospective Analysis of 1056 FNA Samples Journal of Clinical Endocrinology and Metabolism vol. 96, pp. 3390-3397 (Year: 2011).
Nikiforova, et al. Highly accurate diagnosis of cancer in thyroid nodules with follicular neoplasm/suspicious for a follicular neoplasm cytology by ThyroSeq v2 next-generation sequencing assay. Cancer. Dec. 1, 2014;120(23):3627-34. Epub Sep. 10, 2014.
Nikiforova et al. MicroRNA expression profiling of thyroid tumors: biological significance and diagnostic utility. J Clin Endocrinol Metab. 2008;93(5):1600-8.
Nikiforova, et al. Molecular diagnostics and predictors in thyroid cancer. Thyroid. Dec. 2009;19(12):1351-61.
Nikiforova, et al. Targeted Next-Generation Sequencing Panel (ThyroSeq) for Detection of Mutations in Thyroid Cancer. J Clin Endocrinol Metab. Nov. 2013; 98(11): E1852-E1860.
Nikolova et al. Genome-wide gene expression profiles of thyroid carcinoma: Identification of molecular targets for treatment of thyroid carcinoma. 2008;Oncol Rep. 20(1):105-21.
Non-Final Office Action for U.S. Appl. No. 15/644,721, filed Mar. 7, 2019.
Non-Final Office Action for U.S. Appl. No. 10/579,376, filed Jul. 9, 2008.
Non-Final Office Action for U.S. Appl. No. 11/294,834, filed Dec. 15, 2015.
Non-Final Office Action for U.S. Appl. No. 11/294,834, filed Jan. 29, 2014.
Non-Final Office Action for U.S. Appl. No. 11/294,834, filed Jun. 24, 2008.
Non-Final Office Action for U.S. Appl. No. 12/234,588, filed Jun. 27, 2011.
Non-Final Office Action for U.S. Appl. No. 12/414,555, filed Nov. 30, 2011.
Non-Final Office Action for U.S. Appl. No. 12/884,714, filed Sep. 23, 2011.
Non-Final Office Action for U.S. Appl. No. 13/323,655, filed Apr. 9, 2013.
Non-Final Office Action for U.S. Appl. No. 13/323,655, filed Nov. 7, 2013.
Non-Final Office Action for U.S. Appl. No. 13/346,444, filed Dec. 12, 2012.
Non-Final Office Action for U.S. Appl. No. 13/524,749, filed Sep. 9, 2013.
Non-Final Office Action for U.S. Appl. No. 14/584,960, filed Apr. 27, 2016.
Non-Final Office Action for U.S. Appl. No. 14/613,210, filed Dec. 6, 2016.
Non-Final Office Action for U.S. Appl. No. 15/439,891, filed Jun. 14, 2017.
Non-Final Office Action for U.S. Appl. No. 12/234,588, filed Mar. 28, 2014.
Notice of allowance dated Mar. 27, 2015 for U.S. Appl. No. 13/254,571.
Notice of Allowance dated Mar. 30, 2017 for U.S. Appl. No. 14/727,801.
Notice of Allowance dated Apr. 3, 2018 for U.S. Appl. No. 14/020,183
Notice of allowance dated Jun. 13, 2013 for U.S. Appl. No. 12/592,065.
Notice of allowance dated Jul. 30, 2015 for U.S. Appl. No. 13/258,429.
Notice of Allowance dated Aug. 21, 2017 for U.S. Appl. No. 15/274,492.
Notice of allowance dated Sep. 13, 2016 for U.S. Appl. No. 12/964,666.
Notice of allowance dated Oct. 18, 2013 for U.S. Appl. No. 13/318,751.
Notice of allowance dated Oct. 24, 2018 for U.S. Appl. No. 15/661,496.
Notice of allowance dated Nov. 28, 2016 for USA U.S. Appl. No. 14/926,349.
Notice of allowance dated Sep. 13, 2018 for U.S. Appl. No. 15/851,377.
Notice of Allowance issued in U.S. Appl. No. 15/644,721, filed Sep. 30, 2020.
Notterman et al. Tumor Biology and Microarray Analysis of Solid Tumors: Colorectal Cancer as a Model System. Microarrays and Cancer Research, Warrington et al.(eds.), Eaton Publishing, Westborough, MA, pp. xi-xvi, (2002).
Nucera, et al. BRAF(V600E) mutation and the biology of papillary thyroid cancer. Endocr Relat Cancer. Mar. 2008; 15(1):191-205. doi: 10.1677/ERC-07-0212.
Oerntoft, et al. Genome-wide study of gene copy Number transcripts, and protein levels in pairs of non-invasive and invasive human transitional cell carcinomas. Mol Cell Proteomics. Jan. 2002;1(1):37-45.
Office action dated Jan. 5, 2015 for U.S. Appl. No. 14/086,716.
Office Action dated Jan. 12, 2018 for U.S. Appl. No. 13/589,022.
Office action dated Jan. 16, 2013 for U.S. Appl. No. 12/592,065.
Office action dated Jan. 16, 2015 for U.S. Appl. No. 13/258,429.
Office action dated Jan. 16, 2018 for U.S. Appl. No. 13/105,756.
Office action dated Jan. 22, 2016 for U.S. Appl. No. 13/708,439.
Office Action dated Jan. 25, 2018 for U.S. Appl. No. 15/626,401.
Office action dated Feb. 4, 2014 for U.S. Appl. No. 13/708,439.
Office Action dated Feb. 13, 2017 for U.S. Appl. No. 15/164,241.
Office action dated Feb. 26, 2016 for U.S. Appl. No. 14/926,349.
Office action dated Feb. 27, 2015 for U.S. Appl. No. 13/710,134.
Office Action dated Mar. 2, 2018 for U.S. Appl. No. 13/589,022.
Office action dated Mar. 9, 2016 for U.S. Appl. No. 13/589,022.
Office Action dated Mar. 9, 2017 for U.S. Appl. No. 13/710,134.
Office action dated Mar. 11, 2014 for U.S. Appl. No. 13/254,571.
Office Action dated Mar. 21, 2017 for U.S. Appl. No. 15/164,217.
Office Action dated Mar. 21, 2017 for U.S. Appl. No. 15/164,230.
Office Action dated Mar. 23, 2015 for U.S. Appl. No. 13/589,022.
Office Action dated Mar. 23, 2017 for U.S. Appl. No. 15/164,220.
Office Action dated Mar. 23, 2017 for U.S. Appl. No. 15/274,492.
Office action dated Mar. 27, 18 for U.S. Appl. No. 114/153,219.
Office action dated Mar. 29, 18 for U.S. Appl. No. 14/086,716.
Office action dated Apr. 6, 2012 for U.S. Appl. No. 12/964,666.
Office action dated Apr. 8, 2014 for U.S. Appl. No. 13/258,429.
Office action dated Apr. 18, 2013 for U.S. Appl. No. 13/318,751.

(56) References Cited

OTHER PUBLICATIONS

Office action dated Apr. 27, 2015 for U.S. Appl. No. 12/964,666.
Office Action dated May 5, 2017 for U.S. Appl. No. 14/020,183.
Office action dated May 8, 2014 for U.S. Appl. No. 13/105,756.
Office action dated May 9, 2016 for U.S. Appl. No. 12/964,666.
Office action dated May 16, 2016 for U.S. Appl. No. 14/153,219.
Office action dated May 27, 2015 for U.S. Appl. No. 13/105,756.
Office action dated Jun. 6, 2012 for U.S. Appl. No. 12/592,065.
Office action dated Jun. 10, 2014 for U.S. Appl. No. 13/708,439.
Office Action dated Jun. 12, 2017 for U.S. Appl. No. 13/105,756.
Office action dated Jun. 15, 2018 for U.S. Appl. No. 15/661,496.
Office action dated Jun. 15, 2018 for U.S. Appl. No. 15/851,377.
Office action dated Jun. 20, 2014 for U.S. Appl. No. 12/964,666.
Office Action dated Jun. 23, 2017 for U.S. Appl. No. 14/153,219.
Office action dated Jun. 29, 2018 for U.S. Appl. No. 15/702,126.
Office Action dated Jul. 5, 2017 for U.S. Appl. No. 14/086,716.
Office action dated Jul. 6, 2011 for U.S. Appl. No. 12/964,666.
Office action dated Jul. 10, 2014 for U.S. Appl. No. 13/589,022.
Office action dated Jul. 26, 2016 for U.S. Appl. No. 13/710,134.
Office action dated Jul. 30, 2014 for U.S. Appl. No. 13/710,134.
Office action dated Aug. 10, 2016 for U.S. Appl. No. 14/086,716.
Office Action dated Aug. 29, 2017 for U.S. Appl. No. 15/185,960.
Office action dated Sep. 2, 2015 for U.S. Appl. No. 14/086,716.
Office action dated Sep. 7, 2016 for U.S. Appl. No. 14/727,801.
Office action dated Sep. 8, 2016 for U.S. Appl. No. 15/164,241.
Office action dated Sep. 10, 2018 for U.S. Appl. No. 15/702,217.
Office action dated Sep. 11, 2012 for U.S. Appl. No. 13/318,751.
Office action dated Sep. 11, 2013 for U.S. Appl. No. 13/258,429.
Office action dated Sep. 19, 2016 for U.S. Appl. No. 15/164,217.
Office action dated Sep. 19, 2016 for U.S. Appl. No. 15/164,220.
Office action dated Sep. 19, 2016 for U.S. Appl. No. 15/164,230.
Office action dated Sep. 19, 2018 for U.S. Appl. No. 15/096,739.
"Office action dated Oct. 9, 2018 for U.S. Appl. No. 14/690,182."
Office Action dated Oct. 12, 2017 for U.S. Appl. No. 13/589,022.
Office action dated Oct. 17, 2013 for U.S. Appl. No. 13/105,756.
Office action dated Nov. 7, 2016 for U.S. Appl. No. 13/105,756.
Office Action dated Nov. 9, 2018 for U.S. Appl. No. 14/851,864.
Office action dated Nov. 17, 2016 for U.S. Appl. No. 13/589,022.
Office action dated Nov. 18, 2016 for U.S. Appl. No. 14/153,219.
Office action dated Nov. 19, 2015 for U.S. Appl. No. 13/710,134.
Office Action dated Nov. 20, 2018 for U.S. Appl. No. 13/589,022.
Office action dated Nov. 29, 2013 for U.S. Appl. No. 13/710,134.
Office Action dated Nov. 29, 2018 for U.S. Appl. No. 15/626,401.
Office action dated Nov. 30, 2016 for U.S. Appl. No. 13/708,439.
Office action dated Dec. 4, 2014 for U.S. Appl. No. 13/254,571.
Office Action dated Dec. 12, 2018 for U.S. Appl. No. 14/086,716.
Office action dated Dec. 13, 18 for U.S. Appl. No. 14/153,219.
Office action dated Dec. 17, 2015 for U.S. Appl. No. 13/105,756.
Office Action dated Dec. 26, 2017 for U.S. Appl. No. 15/185,960.
Ohtsuka et al. ADAM28 is overexpressed in human non-small cell lung carcinomas and correlates with cell proliferation and lymph node metastasis. International Journal of Cancer, 118 2 : 263-273, Jan. 2006.
Okudela et al. K-ras Gene Mutation Enhances Motility of Immortalized Airway Cells and Lung Adenocarcinoma Cells Via Akt Activation: Possible Contribution to Non-Invasive Expansion of Lung Adenocarcinoma. Am J Pathol. Jan. 2004; 164(1): 91-100.
Oler, et al. Gene expression profiling of papillary thyroid carcinoma identifies transcripts correlated with BRAF mutational status and lymph node metastasis. Clin Cancer Res. Aug. 1, 2008;14(15):4735-42. doi: 10.1158/1078-0432.CCR-07-4372.
Ooi et al. Molecular Profiling of Premalignant Lesions in Lung Squamous Cell Carcinomas Identifies Mechanisms Involved in Stepwise Carcinogenesis. Cancer Prevention Research, 7(5):487-495, (Mar. 11, 2014).
Oshlack et al. FRom RNA-seq reads to differential expression results Genome Biology vol. 11, article 220 (Year: 201 0).
Ost et al. The solitary pulmonary nodule. New England Journal of Medicine (Jun. 19, 2003); 348.25: 2535-2542.
Oster et al. Identification and validation of highly frequent CpG island hypermethylation in colorectal adenomas and carcinomas. International Journal of Cancer (2011); 129.12: 2855-2866.
Otsubo et al. TSPAN2 is involved in cell invasion and motility during lung cancer progression. Cell Reports (2014); 7.2: 527-538.
Owens, et al. Metastatic breast carcinoma involving the thyroid gland diagnosed by fine-needle aspiration: a case report. Diagn Cytopathol. Aug. 2005;33(2):110-5.
Pallante et al. MicroRNA deregulation in human thyroid papillary carcinomas. Endocr Relat Cancer. 2006;13(2):497-508.
Panicker et al. A common variation in deiodinase 1 gene DIO1 is associated with the relative levels of free thyroxine and triiodothyronine. J Clin Endocrinol Metab. 2008;93(8):3075-81.
Pardo et al. Up-regulation and profibrotic role of osteopontin in human idiopathic pulmonary fibrosis. PLoS Med (2005); 2.9: e251.
Paull, D.E et al., 'Gene expression profiles from needle biopsies provide useful signatures of non-smallcell lung carcinomas', Biomark Insights. 2007, vol. 2, pp. 253-259.
Pavelic, et al. Molecular genetic alterations of FHIT and p53 genes in benign and malignant thyroid gland lesions. Mutat Res. Jul. 25, 2006;599(1-2):45-57. Epub May 15, 2006.
Pavey, et al. Microarray expression profiling in melanoma reveals a BRAF mutation signature. Oncogene. May 20, 2004;23(23):4060-7.
PCT/US2004/018460 International Preliminary Report on Patentability dated Dec. 13, 2005.
PCT/US2004/018460 International Search Report dated Nov. 2, 2005.
PCT/US2004/018460 Written Opinion dated Nov. 2, 2005.
PCT/US2004/018492 International Search Report dated May 30, 2006.
PCT/US2004/018492 Written Opinion dated May 30, 2006.
PCT/US2006/014132 International Search Report dated Feb. 5, 2007.
PCT/US2007/006006 International Search Report dated Nov. 15, 2007.
PCT/US2008/077136 International Search Report dated Dec. 12, 2008.
PCT/US2012/053531 International Preliminary Report on Patentability dated Mar. 4, 2014.
PCT/US2012/053531 International Search Report dated Jan. 17, 2013.
PCT/US2012/053531 Written Opinion dated Jan. 17, 2013.
PCT/US2012/057263 International Search Report dated Apr. 5, 2013.
PCT/US2013/038449 International Search Report dated Dec. 16, 2013.
PCT/US2015/040437 International Search Report dated Dec. 21, 2015.
PCT/US2017/032517 International Search Report dated Oct. 2, 2017.
PCT/US2017/041267 International Search Report dated Dec. 15, 2017.
PCT/US2018/035702 International Search Report and Written Opinion dated Sep. 12, 2018.
PCT/US2018/043984 International Search Report and Written Opinion dated Jan. 21, 2019.
Peluso et al. Comparison of DNA adduct levels in nasal mucosa, lymphocytes and bronchial mucosa of cigarette smokers and interaction with metabolic gene polymorphisms. Carcinogenesis 25(12): 2459-2465 (2004).
Penland, et al. RNA expression analysis of formalin-fixed paraffin-embedded tumors. Lab Invest. Apr. 2007;87(4):383-91.
Penning et al. Genomics of smoking exposure and cessation: lessons for cancer prevention and treatment. Cancer Prevention Research (2008); 1.2: 80-83.
Perez et al. Incidence, prevalence, and clinical course of idiopathic pulmonary fibrosis: a population-based study. CHEST Journal (2010); 137.1: 129-137.
Phenekos et al. Th1 and Th2 serum cytokine profiles characterize patients with Hashimoto's thyroiditis (Th1) and Graves' disease (Th2). Neuroimmunomodulation. 2004;11(4):209-13.

(56) References Cited

OTHER PUBLICATIONS

Pinto et al. mRNA expression of tachykinins and tachykinin receptors in different human tissues. Eur J Pharmacol. 2004;494(2-3):233-9.
Piotrowski et al. The selected genetic polymorphisms of metalloproteinases MMP2, 7, 9 and MMP inhibitor TIMP2 in sarcoidosis. Medical Science Monitor (2011); 17.10: CR598-CR607.
Pita et al. Gene expression profiling associated with the progression to poorly differentiated thyroid carcinomas. Br J Cancer. 2009;101(10):1782-1791.
Pittman et al. Integrated modeling of clinical and gene expression information for personalized prediction of disease outcomes. Proc Natl Acad Sci U S A. Jun. 1, 2004;101(22):8431-6.
Platform GPL6244 https://www.ncbi.nlm.nih.gov/geo/query/acc.cgi?acc=gpl6244, Submission Date Dec. 5, 2007 [Downloaded Oct. 18, 2016], 3 pages.
Poletti et al. Invasive diagnostic techniques in idiopathic interstitial pneumonias. Respirology (2016); 21.1: 44-50.
Potti et al. A Genomic Strategy to Refine Prognosis in Early-Stage Non Small-Cell Lung Cancer. The New England Journal of Medicine 2006; 335(6):570-580 (Aug. 2006).
Potti et al. Genomic Signatures to Guide the Use of Chemotherapeutics. Nature Medicine, 12(11): 1294-1300 (Oct. 2006).
Powell et al. Gene expression in lung adenocarcinomas of smokers and nonsmokers. American Journal of Respiratory Cell and Molecular Biology, 29: 157-162 (Aug. 2003).
Powell et al. Patterns of allelic loss differ in lung adenocarcinomas of smokers and nonsmokers. Lung Cancer, 39 1 : 23-29 (2003).
Powell, et al., Loss of Heterozygosity in epithelial cells obtained by bronchial brushing: clinical utility in lung cancer. Clinical cancer research, Aug. 1999, 5: 2025-2034.
Prasad et al. Identification of genes differentially expressed in benign versus malignant thyroid tumors. Clin Cancer Res. 2008;14(11):3327-37.
Printout from database NCBIGEO accession No. GSE4115 [Online] NCB dated Feb. 27, 2006.
Proctor, RN. Tobacco and the global lung cancer epidemic. Nature Reviews Cancer, 1: 82-86 (Oct. 2001).
Puissegur et al. miR-210 is overexpressed in late stages of lung cancer and mediates mitochondrial alterations associated with modulation of HIF-1 activity. Cell Death Differ. 18(3):465-478 (2011).
Puskas, et al. Gene profiling identifies genes specific for well-differentiated epithelial thyroid tumors. Cell Mol Biol (Noisy-le-grand). Sep. 5, 2005;51(2):177-86.
Pusztai, L. et al., 'Gene expression profiles obtained from fine-needle aspirations of breast cancer reliablyidentify routine prognostic markers and reveal large-scale molecular differences between estrogen-negative andestrogen-positive tumors', Clin Cancer Res. 2003, vol. 9, pp. 2406-2415.
Qian, et al. Renal cell carcinoma metastatic to Hurthle cell adenoma of thyroid. Ann Diagn Pathol. Oct. 2004;8(5):305-8.
R Core Team (2021). R: A language and environment for statistical computing. R Foundation for Statistical Computing, Vienna, Austria. URL: https://www.R-project.org/. Copy of homepage provided (3 pages); obtained online on Sep. 11, 2023.
Ramaswamy, et al. "Multiclass cancer diagnosisusing tumor gene expression signatures" Proceedings of the National Academyof Sciences Dec. 2001, 98 (26) 15149-15154.
Rekha Vij et al: "Peripheral blood biomarkers in IDP", Translational Research, vol. 159, No. 4, (Apr. 1, 2012), pp. 218-227, XP055240430,ISSN: 1931-5244, DOI: 10.1016/j.trsl.2012.01.012.
Reyes, et al. Identification of kallikrein 7, kallikrein 10 and secreted frizzled-related protein 2 as candidate molecular markers for papillary thyroid carcinoma using microarray analysis. Proc Amer Assoc Cancer Res. 2005, vol. 46, Abstract #38.
Reynolds et al. Pre-protachykinin-A mRNA is increased in the airway epithelium of smokers with chronic bronchitis. Respiratory, 6:187-197 (2001).
Richeldi et al. Efficacy and safety of nintedanib in idiopathic pulmonary fibrosis. N Engl J Med. May 29, 2014;370(22):2071-82.

Riise et al. Bronchial Brush Biopsies for Studies of Epithelial Inflammation in Stable Asthma and Nonobstructive Chronic Bronchitis. European Respiratory Journal, 9: 1665-1671 (1996).
Riley, et al., Ectopic synthesis of high-Mr calcitonin by the BEN lung carcinoma cell line reflects aberrant proteolytic processing. FEBS lettes, Mar. 17, 1986; 198(1): 71-79.
Ringel et al. Expression of the sodium iodide symporter and thyroglobulin genes are reduced in papillary thyroid cancer. Mod Pathol. 2001;14(4):289-96.
Rivera et al. Establishing the diagnosis of lung cancer: Diagnosis and management of lung cancer: American College of Chest Physicians evidence-based clinical practice guidelines. CHEST Journal 143.5_suppl (2013): e142S-e165S.
Robin et al. pROC: an open-source package for R and S+ to analyze and compare ROC curves. BMC Bioinformatics 12:77 (2011).
Robinson; et al., "A comparison of Affymetrix gene expression arrays. BMC bioinformatics 8.1 (2007): 449."
Robinson, et al. A comparison of Affymetrix gene expression arrays. BMC Bioinformatics. Nov. 15, 2007;8:449.
Robinson et al. A dynamic programming approach for the alignment of signal peaks in multiple gas chromatography-mass spectrometry experiments. BMC bioinformatics 8.1 (2007): 419.
Rodrigues-Serpa, et al. Loss of heterozygosity in follicular and papillary thyroid carcinomas. Cancer Genet Cytogenet. Feb. 2003;141(1):26-31.
Ronaghi et al. Real-time DNA sequencing using detection of pyrophosphate release. Anal Biochem. 1996; 242(1):84-89.
Roque, et al. Chromosome imbalances in thyroid follicular neoplasms: a comparison between follicular adenomas and carcinomas. Genes Chromosomes Cancer. Mar. 2003;36(3):292-302.
Ros et al. Thyroid-specific Gene Expression in the Multi-Step Process of Thyroid Carcinogenesis, Biochimie, Masson, Paris, FR, vol. 81, No. 4, Apr. 1, 1999, pp. 389-396.
Rosai et al. Pitfalls in the diagnosis of thyroid neoplasms. Pathol Res Pract. 1987;182(2):169-79.
Rosen et al. A six-gene model for differentiating benign from malignant thyroid tumors on the basis of gene expression. Surgery. 2005;138(6):1050-6; discussion 1056-7.
Roura-Mir et al. Single-cell analysis of intrathyroidal lymphocytes shows differential cytokine expression in Hashimoto's and Graves' disease. Eur J Immunol. 1997;27(12):3290-302.
Rouskin et al. Genome-wide probing of RNA structure reveals active unfolding of mRNA structures in vivo. Nature. Jan. 30, 2014;505(7485):701-5.
Rowe et al. Utility of Braf V600E Mutation Detection in Cytologically Indeterminate Thyroid Nodules. CytoJoural 3(10):1-10 (Apr. 2006).
Rusznak et al. Effect of Cigarette Smoke on the Permeability and IL-1B and sICAM-1 Release from Cultured Human Bronchial Epithelial Cells of Never-Smokers, Smokers, and Patients with Chronic Obstructive Pulmonary Disease. Am. J. Respir. Cell Mol. Biol., 23:530-536 (2000).
Saal et al. Poor Prognosis in Carcinoma is Associated with A Gene Expression Signature of Aberrant PTEN Tumor Suppressor Pathway Activitiy. PNAS 104(18):7564-7569 (2007).
Sabo-Attwood, et al. Gene Expression Profiles Reveal Increased mClca3 (Gob5) Expression and Mucin Production in a Murine Model of Asbestos-Induced Fibrogenesis. American Journal of Pathology. vol. 167 No. 5; Nov. 2005: pp. 1243-1256.
Saeys, et al. A review of feature selection techniques in bioinformatics. Bioinformatics. Oct. 1, 2007;23(19):2507-17. Epub Aug. 24, 2007.
Saheki et al. Pathogenesis and pathophysiology of citrin (a mitochondrial aspartate glutamate carrier) deficiency. Metabolic Brain Disease; 17(4):335-346 (Dec. 2002).
Saito-Hisaminato et al. Genome-Wide Profiling of Gene Expression in 29 Normal Human Tissues with a cNDA Microarray. DNA Research, 2002, 9:35-45.
Saiz et al. Immunohistochemical expression of cyclin D1, E2F-1, and Ki-67 in benign and malignant thyroid lesions. J Pathol. 2002; 198(2):157-62.

(56) References Cited

OTHER PUBLICATIONS

Salemi et al. Cerebellar degeneration-related autoantigen 1 (CDR1) gene expression in prostate cancer cell lines. Int J Biol Markers (2014); 29.3: e288-290.
Salvatore et al. A cell proliferation and chromosomal instability signature in anaplastic thyroid carcinoma. Cancer Res. 2007;67(21):10148-58.
Sambrook; et al., "Molecular Cloning: A Laboratory Manual. Second edition, Cold Spring Harbor Laboratory Press, 1989."
Sanghvi. Heterocyclic base modifications in nucleic acids and their applications in antisense oligonucleotides. in Antisense Research and Applications. Crooke, S. T. and Lebleu, B., ed., CRC Press. 1993; Ch 15 274-285.
Santarpia et al. Phosphatidylinositol 3-kinase/akt and ras/raf-mitogen-activated protein kinase pathway mutations in anaplastic thyroid cancer. J Clin Endocrinol Metab. 2008;93(1):278-84.
Santiyagu M. Savarimuthu Francis et al: "Genes and Gene Ontologies Common to Airflow Obstruction and Emphysema in the Lungs of Patients with COPD", PLOS ONE, vol. 6, No. 3, 2011, p. e17442.
Sapio, et al., Detection of RETIPTC, TRK and BRAF mutations in preoperative diagnosis of thyroid nodules with indeterminate cytological findings, C]Jnica1 Endocrinology, 2007, 66: 678-683.
Satake et al. Overview of the primary structure, tissue-distribution, and functions of tachykinins and their receptors. Curr Drug Targets. 2006;7(8):963-74.
Savagner et al. Defective mitochondrial ATP synthesis in oxyphilic thyroid tumors. J Clin Endocrinol Metab. 2001;86(10):4920-5.
Savagner et al. PGC-1-related coactivator and targets are upregulated in thyroid oncocytoma. Biochem Biophys Res Commun. 2003;310(3):779-84.
Schembri et al. MicroRNAs as modulators of smoking-induced gene expression changes in human airway epithelium. Proc Natl Acad Sci U S A, 106(7),2319-24 (Feb. 2009).
Schiff, et al. Epidermal growth factor receptor (EGFR) is overexpressed in anaplastic thyroid cancer, and the EGFR inhibitor gefitinib inhibits the growth of anaplastic thyroid cancer. Clin Cancer Res. Dec. 15, 2004;10(24):8594-602.
Schraufangel. "Interstitial Lung Disease," Chapter 10, pp. 99-107, in Breathing in America: Diseases, Progress and Hope, American Thoracic Society (2010).
Schraufnagel, Dean. Breathing in America: Diseases, Progress, and Hope. The American Thoracic Society. Published 2010. 282 pages.
Schroeder, et al. The RIN: an RNA integrity number for assigning integrity values to RNA measurements. BMC Mol Biol. Jan. 31, 2006;7:3.
Schulz et al. Activation of bronchial epithelial cells in smokers without airway obstruction and patients with COPD. Chest. May 2004;125(5):1706-13.
Schulz et al. Upregulation of MCAM in primary bronchial epithelial cells from patients with COPD. European Respiratory Journal (Sep. 2003); 22.3: 450-456.
Selman et al. Idiopathic pulmonary fibrosis: aberrant recapitulation of developmental programs ?. PLoS medicine 5.3 (2008): e62.
Selman et al. Revealing the pathogenic and aging-related mechanisms of the enigmatic idiopathic pulmonary fibrosis. An integral model. Am J Respir Crit Care Med. May 15, 2014;189(10):1161-72.
Selman, M. et al., Accelerated variant of idiopathic pulmonary fibrosis: Clinical behavior and gene expression pattern. Plos One, May 2007, Issue 5, e482, 11 Pages.
Shah et al. SIEGE: Smoking Induced Pithelial Gene Expression Database. Nucleic Acids Research, 33: D573-D579 (2005).
Shalon, D. et al. A DNA microarray system for analyzing complex DNA samples using two-color fluorescent probe hybridization. Genome research, 6(7): 639-645 (Jul. 1996).
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE. 1117839.

Sheu et al. The C allele of the GNB3 C825T polymorphism of the G protein beta3-subunit is associated with an increased risk for the development of oncocytic thyroid tumours. J Pathol. 2007;211(1):60-6.
Shi, et al. Combined analysis of gene expression, DNA copy number and mutation profiling data to display biological process anomalies in individual breast cancers. Breast Cancer Res Treat. Apr. 2014;144(3):561-8. Epub Mar. 12, 2014.
Shibru, et al. Does the 3-gene diagnostic assay accurately distinguish benign from malignant thyroid neoplasms? Cancer. Sep. 1, 2008;113(5):930-5.
Shibuya et al., Increased telomerase activity and elevated hTERT mRNA expression during multistage carcinogenesis of squamous cell carcinoma of the lung. Cancer, Aug. 2001; 92(4): 849-855.
Shields, PG. Molecular epidemiology of lung cancer. Annals of Oncology, 10(5):S7-S11 (1999).
Shih et al. A new Mel-CAM (CD146)-specific monoclonal antibody, MN-4, on paraffin-embedded tissue. Modern Pathology: an Official Journal of the United States and Canadian Academy of Pathology, Inc (1998); 11.11: 1098-1106.
Shim et al. Histopathologic findings of transbronchial biopsy in usual interstitial pneumonia. Pathology International (2010); 60.5: 373-377.
Shipp, et al. Diffuse large B-cell lymphoma outcome prediction by gene-expression profiling and supervised machine learning. Nat Med. Jan. 2002;8(1):68-74.
Shirasawa, S. Susceptibility genes for the development of autoimmune thyroid disease. Nippon Rinsho. Dec. 2006;64(12):2208-14. (Abstract only).
Shriver et al. Sex-Specific Expression of Gastrin-Releasing Peptide Receptor: Relationship to Smoking History and Risk of Lung Cancer. J. Natl. Cancer Inst., 92: 24-33 (2000).
Shvero et al. Immunohistochemical profile and treatment of uncommon types of thyroid carcinomas. Oncol Rep. 2003;10(6):2075-8.
Silvestri et al. A bronchial genomic classifier for the diagnostic evaluation of lung cancer. N Engl J Med. Jul. 16, 2015;373(3):243-51.
Silvestri et al. Latest advances in advanced diagnostic and therapeutic pulmonary procedures. CHEST Journal (2012); 142.6: 1636-1644.
Simon et al. Up-regulation of MUC18 in airway epithelial cells by IL-13: implications in bacterial adherence. American Journal of Respiratory Cell and Molecular Biology (2011); 44.5: 606-613.
Singh et al. LNA (locked nucleic acids): synthesis and high-affinity nucleic acid recognition. Chem Commun 4:455-456 (1998).
Singh et al. Screening for genetic aberrations in papillary thyroid cancer by using comparative genomic hybridization. Surgery. 2000;128(6):888-93;discussion 893-4.
Singh et al. Synthesis of 2'-amino-LNA: A novel conformationally restricted high-affinity oligonucleotide analogues with a handle. J Bio Chem 63:10035-10039 (1998).
Singhal et al. Alterations in cell cycle genes in early stage lung adenocarcinoma identified by expression profiling. Cancer Biol Ther. May-Jun. 2003;2(3):291-8.
Singhal S et al.: "Gene expression profiling of Non-small cell lung cancer", Lung Cancer, val. 60, No. 3, Jun. 1, 2008 (Jun. 1, 2008 ), pp. 313-324, XP022690999.
Siragusa et al. MUC1 oncoprotein promotes refractoriness to chemotherapy in thyroid cancer cells. Cancer Res. 2007;67(11):5522-30.
Siraj, et al., Genome-wide expression analysis of middle eastern papillary thyroid cancer reveals c-MET as a novel target for cancer therapy. The journal of pathology. Oct. 1, 2007; 213(2): 190-199.
Slonim, Donna. From Patterns to Pathways: Gene Expression Data Analysis Comes of Age. Nature Genetics Supplement, 32: 502-508, 2002.
Smirnov et al. Global gene expression profiling of circulating endothelial cells in patients with metastatic carcinomas. Cancer Res. Mar. 15, 2006;66(6):2918-22.
Smith et al. Methylation status of genes in papillary thyroid carcinoma. Arch Otolaryngol Head Neck Surg. 2007;133(10):1006-11.

(56) References Cited

OTHER PUBLICATIONS

Smith et al. Prevalence of benign disease in patients undergoing resection for suspected lung cancer. The Annals of Thoracic Surgery (May 2006); 81.5: 1824-1829.
Smyth. Limma: Linear Models for Microarray Data. In: Bioinformatics and Computational Biology Solutions using R and Bioconductor, R. Gentleman, V. Carey, S. Dudoit, R. Irizarry, W. Huber (eds.), Springer, New York. 2005; pp. 397-420.
Smyth. Linear models and empirical bayes methods for assessing differential expression in microarray experiments. Stat Appl Genet Mol Biol. 2004;3:Article3. Epub Feb. 12, 2004.
Song Kim, et al., Phase II clinical and exploratory biomarker study of dacomitinib in recurrent and/or metastatic esophageal squamous cell carcinoma. Oncotarget, Oct. 9, 2015, vol. 6, No. 42, p. 44971-44984.
Soni et al., Progress toward ultrafast DNA sequencing using solid-state nanopores. Clin Chem. 53(11):1996-2001 (2007).
Sotos, et al. The Transitivity Misconception of Pearson's Correlation Coefficient. Statistics Education Research Journal. 8(2):33-55 (2009).
Soumyaroop Bhattacharya1 et al.: "Molecular biomarkers for quantitative and discrete COPD phenotypes", American Journal of Respiratory Cell and Molecular Biology, American Lung Association, val. 40, No. 3, (Oct. 10, 2008), pp. 359-367.
Spargo, et al. Detection of M. tuberculosis DNA using thermophilic strand displacement amplification. Mol Cell Probes. Aug. 1996;10(4):247-56.
Speed et al. Nature Reviews. 2015. 16:33. (Year: 2015).
Spira, Avrum E. Abstract: Airway gene expression in smokers: an early diagnostic biomarker for lung cancer. National Institutes of Health Grant No. 1 RO1 CA124640-01 (Funding Start Date May 1, 2007).
Spira, Avrum E. Abstract: The airway transcriptome as a biomarker for lung cancer. National Institutes of Health Grant No. 1 R21 CA106506-01A2 (Funding Start Date Aug. 9, 2005).
Spira, et al. Airway epithelial gene expression in the diagnostic evaluation of smokers with suspect lung cancer. Nature Medicine 13: 361-366 (2007).
Spira, et al. Effects of cigarette smoke on the human airway epithelial cell transcriptome. PNAS, 101: 27, p. 10143-10148 (Jul. 6, 2004).
Spira et al. Gene Expression Profiling of Human Lung Tissue from Smokers with Severe Emphysema. Am J Respir Cell Mol Biol. Dec. 2004;31(6):601-10.
Spira, et al. Impact of cigarette smoke on the normal airway transcriptome. Chest. 125 (5 Suppl):115S (May 2004).
Spira et al. Noninvasive method for obtaining RNA from buccal mucosa epithelial cells for gene expression profiling. Biotechniques, 36(3): 484-7 (Apr. 2004).
Spivack, et al. Gene-environment interaction signatures by quantitative mRNA profiling in exfoliated buccal mucosal cells. Cancer Res. Sep. 15, 2004;64(18):6805-13.
Sridhar et al. Smoking-induced gene expression changes in the bronchial airway are reflected in nasal and buccal epithelium. BMC Genomics, 9: 259 (May 2008).
St. Croix et al. Genes Expressed in Human Tumor Endothelium. Science, 289:1197-1202, (Aug. 18, 2000).
Stanta et al. The biochemical and immunohistochemical profile of thyroid neoplasia. Pathol Annu. 1988;23 Pt 1: 129-57.
Steiling et al.: "A Dynamic Bronchial AirwayGene Expression Signature of Chronic Obstructive Pulmonary Disease and LungFunction impairment", American Journal of Respiratory and Critical Caremedicine, vol. 187, No. 9, (Mar. 7, 2013), pp. 933-942.
Steiling et al. The field of tissue injury in the lung and airway. Cancer Prevention Research (2008); 1.6: 396-403.
Steiling K et al.: "Airway gene expression in chronic obstructive pulmonary disease", Proceedings of the American Thoracic Society 20091215 American Thoracic Society USA, val. 6, No. 8, Dec. 15, 2009 (Dec. 15, 2009), pp. 697-700,1SSN: 1546-3222.
Stephenson et al. Integration of gene expression profiling and clinical variables to predict prostate carcinoma recurrence after radical prostatectomy, Cancer 2005; 104:290-8, 2005.
Stewart, JH. Lung Carcinoma in African Americans, A Review of the Current Literature. Cancer; 91(12): 2476-2482 (Jun. 15, 2001).
Strausberg et al. Reading the Molecular Signatures of Cancer. Microarrays and Cancer Research, Warrington et al. (eds.), Eaton Publishing, Westborough, MA, pp. 81-111, (2002).
Su et al. Molecular Classification of Human Carcinomas by Use of Gene Expression Signatures. Cancer Research, 61:7388-7393, (Oct. 15, 2001).
Subramaniam et al. Clonal characterization of sporadic cribriform-morular variant of papillary thyroid carcinoma by laser microdissection-based APC mutation analysis. Am J Clin Pathol. 2007;128(6):994-1001.
Subramanian et al. Gene set enrichment analysis: a knowledge-based approach for interpreting genome-wide expression profiles. PNAS USA 102:15545-15550 (2005).
Sugita et al. Combined Use of Oligonucleotide and Tissue Microarrays Identifies Cancer/Testis Antigens as Biomarkers in Lung Carcinoma. Cancer Research. Jul. 2002. vol. 62, Issue 14, pp. 3971-3979.
Sumikawa et al. Computed tomography findings in pathological usual interstitial pneumonia: relationship to survival. American Journal of Respiratory and Critical Care Medicine (2008); 177.4: 433-439.
Suomalainen et al. Quantitative analysis of human DNA sequences by PCR and solid-phase minisequencing. Molecular Biotechnology (2000); 15.2: 123-131.
Supplementary European search report and opinion dated Oct. 12, 2016 for EP Application No. 14770813.
Supplementary European Search Report for European Application No. EP 17 79 6983, Issued Feb. 3, 2020.
Suykens et al. Least squares support vector machine classifiers. Neural Processing Letters (1999); 9.3: 293-300.
Suzanne A Eccles et al: "Metastasis: recent discoveries and novel treatment strategies", The Lancet, val. 369, No. 9574, May 1, 2007 (May 1, 2007 ), pp. 1742-1757, XP055231616.
Swensen et al. Solitary pulmonary nodules: clinical prediction model versus physicians. Mayo Clinic Proc 1999; 74:319-29 (1999).
Swensen et al. The probability of malignancy in solitary pulmonary nodules. Application to small radiologically indeterminate nodules. Arch Intern Med 1997; 157:849-55, 1997.
Symmans, et al. Total RNA Yield and Microarray Gene Expression Profiles from Fine-Needle Aspiration Biopsy and Core-Needle Biopsy Samples of Breast Carcinoma. 2003; Cancer 97(12): 2960-2971.
Takakura et al. Oncogenic role of miR-17-92 cluster in anaplastic thyroid cancer cells. Cancer Sci. 2008;99(6):1147-54.
Takano et al. Expression of oncofetal fibronectin messenger ribonucleic acid in fibroblasts in the thyroid: a possible cause of false positive results in molecular-based diagnosis of thyroid carcinomas. J Clin Endocrinol Metab. 2000;85(2):765-8.
Takano et al. Preoperative diagnosis of thyroid papillary and anaplastic carcinomas by real-time quantitative reverse transcription-polymerase chain reaction of oncofetal fibronectin messenger RNA. Cancer Res. 1999;59(18):4542-5.
Takizawa et al. Increased expression of transforming growth factor-beta1 in small airway epithelium from tobacco smokers and patients with chronic obstructive pulmonary disease (COPD). American Journal of Respiratory and Critical Care Medicine, 163:1476-1483 (2001).
Tamir et al. Expression and development of a functional plasmalemmal 5-hydroxytryptamine transporter by thyroid follicular cells. Endocrinology. 1996;137(10):4475-86.
Tanaka et al. Trial to establish an animal model of paraneoplastic cerebellar degeneration with anti-Yo antibody: 1. Mouse strains bearing different MHC molecules produce antibodies on immunization with recombinant Yo protein, but do not cause Purkinje cell loss. Clinical Neurology and Neurosurgery (1995); 97.1: 95-100.

(56) References Cited

OTHER PUBLICATIONS

Taniguchi et al. Differentiation of follicular thyroid adenoma from carcinoma by means of gene expression profiling with adapter-tagged competitive polymerase chain reaction. Oncology. 2005;69(5):428-35.
Tanoue et al. Lung cancer screening. American Journal of Respiratory and Critical Care Medicine (2015); 191.1: 19-33.
Tarca et al. Analysis of microarray experiments of gene expression profiling. Am J Obstet Gynecol 195(2): 373-388 (Aug. 2006).
Terada. Brain metastasis from thyroid adenomatous nodules or an encapsulated thyroid follicular tumor without capsular and vascular invasion: a case report. Cases J. Jul. 17, 2009;2:7180. doi: 10.4076/1757-1626-2-7180.
Tetzlaff et al. Differential expression of miRNAs in papillary thyroid carcinoma compared to multinodular goiter using formalin fixed paraffin embedded tissues. Endocr Pathol. 2007;18(3):163-73.
Theocharis et al. Metallothionein: a multifunctional protein from toxicity to cancer. Int Biol Markers, 18(3):162-169 (2003).
Thisteda. What is a P-value. Departments of Statistics and Health Studies. The University of Chicago. (May 25, 1988).
Thompson et al. Primary smooth muscle tumors of the thyroid gland. Cancer. 1997;79(3):579-87.
Thornton et al. Estimating kinship in admixed populations. The American Journal of Human Genetics 91.1 (2012): 122-138.
Thurston et al. Modeling lung cancer risk in case-control studies using a new dose metric of smoking. Cancer Epidemiol Biomarkers Prev 2005; 14(10): 2296-302 (2005).
Tian, et al. A combined oncogenic pathway signature of BRAF, KRAS and PI3KCA mutation improves colorectal cancer classification and cetuximab treatment prediction. Gut. Apr. 2013;62(4):540-9. doi: 10.1136/gutjnl-2012-302423. Epub Jul. 14, 2012.
Tian, et al. Effects of Gender on Gene Expression in the Blood of Ischemic Stroke Patients. Journal of Cerebral Blood Flow & Metabolism. J Cereb Blood Flow Metab. May 2012;32(5):780-91. doi: 10.1038/jcbfm.2011.179. Epub Dec. 14, 2011.
Tibshirani. Regression shrinkage and selection via the lasso. Journal of the Royal Statistical Society Series B (Methodological) 58:267-288 (1996).
Tichelaar et al. Increased staining for phospho-Akt, p65/RELA and cIAP-2 in pre-neoplastic human bronchial biopsies. BMC Cancer 5(155):1-13 (2005).
Tjarda Van Heek et al., Gene expression profiling identifies markers of ampullary adenocarcinoma. (Cancer biology & Therapy, 2004, 3(7):651-656.).
Tockman, et al., Considerations in Bringing a Cancer Biomarker to Clinical Application. Cancer Res May 1, 1992; (52): 2711s-2718s.
Todaro et al. Autocrine production of interleukin-4 and interleukin-10 is required for survival and growth of thyroid cancer cells. Cancer Res. 2006;66(3):1491-9.
Tokunaga et al., Enhanced expression of a Glyceraldehyde-3-phosphate Dehydrogenase Gene in human lung cancers. (Cancer Research, 1987, 47: 5616-5619).
Tomassetti et al. Bronchoscopic lung cryobiopsy increases diagnostic confidence in the multidisciplinary diagnosis of idiopathic pulmonary fibrosis. American Journal of Respiratory and Critical Care Medicine (2016); 193.7: 745-752.
Tomassetti et al. Transbronchial biopsy is useful in predicting UIP pattern. Respiratory Research (2012); 13.1: 96.
Trahan et al. Role of surgical lung biopsy in separating chronic hypersensitivity pneumonia from usual interstitial pneumonia/idiopathic pulmonary fibrosis: analysis of 31 biopsies from 15 patients. CHEST Journal (2008); 134.1: 126-132.
Trapnell, et al. TopHat: discovering splice junctions with RNA-Seq. Bioinformatics. May 1, 2009;25(9):1105-11. doi: 10.1093/bioinformatics/btp120. Epub Mar. 16, 2009.
Travis et al. An official American Thoracic Society/European Respiratory Society statement: Update of the international multidisciplinary classification of the idiopathic interstitial pneumonias. Am J Respir Crit Care Med (2013); 188.6: 733-748.
Treutlein et al. Reconstructing lineage hierarchies of the distal lung epithelium using single-cell RNA-seq. Nature. May 15, 2014;509(7500):371-5. doi: 10.1038/nature13173. Epub Apr. 13, 2014.
Trovato, et al., Expression of the hepatocyte growth factor and c-met in normal thyroid, non-neoplastic, and neoplastic nodules. Thyroid, Jan. 1, 1998; 8(2): 125-131.
Trovisco et al. Molecular Genetics of Papillary Thyroid Carcinoma—Great Expectations . . . Arq Bras Endocrinol Metab, Jul. 1, 2007, pp. 643-653.
Trunk et al. The management and evaluation of the solitary pulmonary nodule. Chest 1974; 66:236-9 (1974).
Tsao et al. Increased Phospho-AKT (Ser4(3) Expression in Bronchial Dysplasia: Implications for Lunch Cancer Prevention Studies. Cancer Epidemiology Biomarkers & Prevention. 12:660-664 (2003).
Tsukamoto et al. Involvement of gicerin, a cell adhesion molecule, in tracheal development and regeneration. Cell Growth and Differentiation-Publication Cell Growth & Differentiation (1996); 7.12: 1761-1768.
Tsukamoto et al. The role of gicerin, a novel cell adhesion molecule, in development, regeneration and neoplasia. Histology and Histopathology (2001); 16.2: 563-571.
Tukey et al. Population-based estimates of transbronchial lung biopsy utilization and complications. Respiratory Medicine (2012); 106.11: 1559-1565.
Tukey. Exploratory Data Analysis: Past, Present, and Future. Technical Report No. 302. Department of Statistics, Princeton University. 1971-1977. 1993.
Tzen, et al. Is atypical follicular adenoma of the thyroid a preinvasive malignancy? Hum Pathol. Jul. 2003;34(7):666-9.
Ueda, et al. Analysis of PAX8 Gene in Congenital Hypothyroidism Mass Screening Positive Subjects. Folia Endocrinologica Japonica. Mar. 30, 2007, vol. 82, No. 4, p. 859. (in Japanese with English translation).
Ullmannová, et al. The use of housekeeping genes (HKG) as an internal control for the detection of gene expression by quantitative real-time RT-PCR. Folia Biol (Praha). 2003;49(6):211-6.
Ung et al. 18Fluorodeoxyglucose positron emission tomography in the diagnosis and staging of lung cancer: a systematic review. J Nat'l Cancer Institute, 99(23): 1753-67 (2007).
Unger et al. Array CGH demonstrates characteristic aberration signatures in human papillary thyroid carcinomas governed by RET/PTC. Oncogene. 2008;27(33):4592-602.
U.S. Appl. No. 14/153,219 Notice of Allowance dated Oct. 27, 2020.
U.S. Appl. No. 14/153,219 Office Action dated Apr. 17, 2020.
U.S. Appl. No. 14/153,219 Office Action dated Sep. 26, 2019.
U.S. Appl. No. 14/358,945 Notice of Allowance dated Mar. 29, 2018.
U.S. Appl. No. 14/358,945 Office Action dated Apr. 11, 2017.
U.S. Appl. No. 14/358,945 Office Action dated Oct. 19, 2017.
U.S. Appl. No. 14/500,475 Notice of Allowance dated Oct. 15, 2019.
U.S. Appl. No. 14/500,475 Office Action dated Mar. 26, 2018.
U.S. Appl. No. 14/500,475 Office Action dated May 14, 2019.
U.S. Appl. No. 14/613,210 Notice of Allowance dated Oct. 31, 2017.
U.S. Appl. No. 14/690,182 Office Action dated Apr. 20, 2018.
U.S. Appl. No. 14/690,182 Office Action dated Mar. 22, 2019.
U.S. Appl. No. 14/775,379 Notice of Allowance dated Oct. 11, 2019.
U.S. Appl. No. 14/775,379 Office Action dated Apr. 4, 2019.
U.S. Appl. No. 14/775,379 Office Action dated Nov. 16, 2017.
U.S. Appl. No. 14/799,472 Office Action dated Jan. 18, 2018.
U.S. Appl. No. 14/799,472 Office Action dated Jul. 5, 2019.
U.S. Appl. No. 14/799,472 Office Action dated Nov. 6, 2018.
U.S. Appl. No. 14/799,472 Office Action dated Oct. 13, 2016.
U.S. Appl. No. 14/851,864 Office Action dated May 14, 2019.
U.S. Appl. No. 15/096,739 Office Action dated Jun. 6, 2019.
U.S. Appl. No. 15/096,739 Office Action dated Mar. 13, 2020.
U.S. Appl. No. 15/096,739 Office Action dated Sep. 24, 2020.
U.S. Appl. No. 15/185,960 Office Action dated Dec. 21, 2018.
U.S. Appl. No. 15/336,469 Office Action dated Apr. 10, 2018.

(56) References Cited

OTHER PUBLICATIONS

U.S. Appl. No. 15/439,891 Office Action dated Dec. 28, 2018.
U.S. Appl. No. 15/439,891 Office Action dated Feb. 14, 2018.
U.S. Appl. No. 15/439,891 Office Action dated Jun. 18, 2019.
U.S. Appl. No. 15/440,575 Office Action dated Apr. 9, 2019.
U.S. Appl. No. 15/440,575 Office Action dated Aug. 13, 2020.
U.S. Appl. No. 15/440,575 Office Action dated Dec. 23, 2019.
U.S. Appl. No. 15/440,575 Office Action dated Mar. 22, 2021.
U.S. Appl. No. 15/523,654 Office Action dated Mar. 27, 2019.
U.S. Appl. No. 15/618,656 Office Action dated Aug. 18, 2020.
U.S. Appl. No. 15/618,656 Office Action dated Aug. 18, 2021.
U.S. Appl. No. 15/618,656 Office Action dated Dec. 18, 2019.
U.S. Appl. No. 15/626,401 Notice of Allowance dated Jul. 15, 2019.
U.S. Appl. No. 15/626,401 Notice of Allowance dated May 10, 2019.
U.S. Appl. No. 15/644,721 Office Action dated Dec. 27, 2017.
U.S. Appl. No. 15/661,496 Notice of Allowance dated Feb. 11, 2019.
U.S. Appl. No. 15/694,157 Office Action dated Mar. 7, 2019.
U.S. Appl. No. 15/702,126 Notice of Allowance dated Jun. 8, 2020.
U.S. Appl. No. 15/702,126 Office Action dated Apr. 19, 2019.
U.S. Appl. No. 15/702,217 Notice of Allowance dated Jun. 18, 2019.
U.S. Appl. No. 15/888,831 Office Action dated Jul. 24, 2018.
U.S. Appl. No. 15/888,831 Office Action dated Mar. 27, 2018.
U.S. Appl. No. 15/888,831 Office Action dated Mar. 27, 2019.
U.S. Appl. No. 15/888,831 Office Action dated Oct. 10, 2019.
U.S. Appl. No. 16/017,899 Notice of Allowance dated Sep. 16, 2021.
U.S. Appl. No. 16/017,899 Office Action dated Feb. 11, 2021.
U.S. Appl. No. 16/031,384 Notice of Allowance dated Nov. 18, 2020.
U.S. Appl. No. 16/031,384 Office Action dated Jan. 10, 2020.
U.S. Appl. No. 16/031,384 Office Action dated Jul. 24, 2020.
U.S. Appl. No. 16/292,573 Office Action dated Jul. 30, 2020.
U.S. Appl. No. 16/292,573 Office Action dated Mar. 19, 2021.
U.S. Appl. No. 16/300,947 Office Action dated Oct. 22, 2020.
U.S. Appl. No. 16/353,248 Notice of Allowance dated Apr. 20, 2020.
U.S. Appl. No. 16/353,248 Notice of Allowance dated Feb. 28, 2020.
U.S. Appl. No. 16/353,248 Office Action dated Oct. 28, 2019.
U.S. Appl. No. 16/510,584 Office Action dated Apr. 23, 2020.
U.S. Appl. No. 16/510,584 Office Action dated Aug. 25, 2021.
U.S. Appl. No. 16/510,584 Office Action dated Feb. 11, 2021.
U.S. Appl. No. 16/510,584 Office Action dated Jan. 16, 2020.
U.S. Appl. No. 16/510,584 Office Action dated Sep. 30, 2020.
U.S. Appl. No. 16/579,798 Office Action dated Jul. 20, 2021.
U.S. Appl. No. 16/696,888 Office Action dated Dec. 21, 2021.
U.S. Appl. No. 16/751,145 Office Action dated Aug. 18, 2021.
U.S. Appl. No. 16/810,827 Office Action dated Apr. 22, 2021.
U.S. Appl. No. 16/810,827 Office Action dated Aug. 10, 2020.
U.S. Appl. No. 16/810,827 Office Action dated Aug. 23, 2021.
U.S. Appl. No. 16/810,827 Office Action dated Nov. 23, 2020.
U.S. Appl. No. 17/218,121 Office Action dated Apr. 3, 2023.
U.S. Appl. No. 17/218,121 Office Action dated Sep. 28, 2021.
U.S. Appl. No. 17/218,127 Office Action dated Aug. 13, 2021.
Van Allen et al. Whole-exome sequencing and clinical interpretation of formalin-fixed, paraffin-embedded tumor samples to guide precision cancer medicine. Nature medicine 20.6 (2014): 682.
Van Der Laan, et al. A new algorithm for hybrid hierarchical clustering with visualization and the bootstrap. Journal of Statistical Planning and Inference. Dec. 2003. 117(2):275-303.
Van Dyck, E. et al., Bronchial airway gene expression in smokers with lung or head and neck cancer. Cancer Medicine, Apr. 2014; 3(2): 322-336.
Vasko, et al. Gene expression and functional evidence of epithelial-to-mesenchymal transition in papillary thyroid carcinoma invasion. Proc Natl Acad Sci U S A. Feb. 20, 2007;104(8):2803-8. Epub Feb. 12, 2007.
Viale et al. Coexpression of cytokeratins and vimentin in normal and diseased thyroid glands. Lack of diagnostic utility of vimentin immunostaining. Am J Surg Pathol. 1989;13(12):1034-40.
Viney et al. Regulation of the cell-specific calcitonin/calcitonin gene-related peptide enhancer by USF and the Foxa2 forkhead protein. J Biol Chem. 2004;279(48):49948-55.
Visone et al. MicroRNAs (miR)-221 and miR-222, both overexpressed in human thyroid papillary carcinomas, regulate p27Kip1 protein levels and cell cycle. Endocr Relat Cancer. 2007;14(3):791-8.
Visone et al. Specific microRNAs are downregulated in human thyroid anaplastic carcinomas. Oncogene. 2007;26(54):7590-5.
Volm et al. Prognostic significance of the expression of c-fos, c-jun and c-erbB-1 oncogene products in human squamous cell lung carcinomas. J Cancer Res Clin Oncol, 119: 507-510 (1993).
Voynow et al. UC2, and MUC5/5AC in Nasal Epithelial Cells of Cystic Fibrosis, Allergic Rhinitis, and Normal Individuals. Lung 176: 345-354 (1998).
Wahidi, et al. Evidence for the treatment of patients with pulmonary nodules: when is it lung cancer? ACCP evidence-based clinical practice guidelines 2nd Edition. Chest 2007; 132:94-1075 (2007).
Wang et al. Association of the T1799A BRAF mutation with tumor extrathyroidal invasion, higher peripheral platelet counts, and over-expression of platelet-derived growth factor-B in papillary thyroid cancer. Endocr Relat Cancer. 2008;15(1):183-90.
Wang et al. RNA-seq: a revolutionary tool for transcriptomics. Nature Reviews Genetics 10:57-63 (2009).
Wang et al. The expression analysis of ICOS-L on activated T cells and immature dendritic cells as well as malignant B cells and Grave's-disease-derived thyroid tissues by two novel mAbs against human ICOS-L. Tissue Antigens. 2007;69(1):62-72.
Wardlaw et al. Effect of cigarette smoke on CYP1A1, CYP1A2 and CYP2B1/2 of nasal mucosae in F344 rats. Carcinogenesis 19(4): 655-662 (1998).
Watanabe et al. Decrease of intrathyroidal CD161+Valpha24+Vbeta11+ NKT cells in Graves' disease. Endocr J. 2008; 55(1):199-203.
Wattel, et al. Gene expression in thyroid autonomous adenomas provides insight into their physiopathology. Oncogene. Oct. 20, 2005;24(46):6902-16.
Watters et al. Developing Gene Expression Signatures of Pathway Deregulation in Tumors. Molecular Cancer Therapeutics, 5: 2444-2449, Oct. 2006.
Weber et al. A limited set of human MicroRNA is deregulated in follicular thyroid carcinoma. J Clin Endocrinol Metab. 2006;91(9):3584-91. Epub Jul. 5, 2006.
Weber et al. Genetic classification of benign and malignant thyroid follicular neoplasia based on a three-gene combination. J Clin Endocrinol Metab. 2005;90(5):2512-21.
Weber et al. Silencing of the maternally imprinted tumor suppressor ARHI contributes to follicular thyroid carcinogenesis. J Clin Endocrinol Metab. 2005;90(2):1149-55.
Wells, Athol U. Managing diagnostic procedures in idiopathic pulmonary fibrosis. European Respiratory Review (2013); 22.128: 158-162.
Wells, Athol U. The revised ATS/ERS/JRS/ALAT diagnostic criteria for idiopathic pulmonary fibrosis (IPF)-practical implications. Respiratory Research (2013); 14(Suppl 1):S2.
Weng et al., Association between the risk of lung cancer and influenza: a population-based nested case-control study. International Journal of infectious diseases, 2019, 88: 8-13.
Wessagowit, et al. Normal and abnormal mechanisms of gene splicing and relevance to inherited skin diseases. J Dermatol Sci. Nov. 2005;40(2):73-84. Epub Jul. 27, 2005.
Wessels, et al., A protocol for building and evaluating predictors of disease state based on microarray data, Bioinformatics, 2005, 21:3755-3762).
West et al. Embracing the complexity of genomic data for personalized medicine. Genome Res 2006; 16:559-66, May 2006.
West et al. Rapid Akt Activation by Nicotine and Tobacco Carcinogen Modulates the Phenotype of Normal Human Airway Epithelial Cells. The Journal of Clinical Investigation. 111(1):81-90 (Jan. 2003).

(56) References Cited

OTHER PUBLICATIONS

Wharam, et al. Specific detection of DNA and RNA targets using a novel isothermal nucleic acid amplification assay based on the formation of a three-way junction structure. Nucleic Acids Res. Jun. 1, 2001;29(11):E54-4.

Whitehead, et al. Variation in Tissue-specific Gene Expression Among Natural Populations. Genome Biology. vol. 6, Issue. 2 (2005): pp. R13-R13.14.

Whitney et al. Derivation of a bronchial genomic classifier for lung cancer in a prospective study of patients undergoing diagnostic bronchoscopy. BMC Med Genomics. May 6, 2015;8:18.

Wiener et al. An official American Thoracic Society/American College of Chest Physicians policy statement: implementation of low-dose computed tomography lung cancer screening programs in clinical practice. Am J Respir Crit Care Med. Oct. 1, 2015;192(7):881-91.

Wiener et al. Population-based risk for complications after transthoracic needle lung biopsy of a pulmonary nodule: an analysis of discharge records. Annals of Internal Medicine (2011); 155.3: 137-144.

Wiener et al. Risks of transthoracic needle biopsy: how high? Clinical Pulmonary Medicine (2013); 20.1: 29-35.

Wilkerson et al. ConsensusClusterPlus: a class discovery tool with confidence assessments and item tracking. Bioinformatics (2010); 26.12: 1572-1573.

Willey et al. Quantitative RT-PCR Measurement of Cytochromes p450 1A1, 161, and 2B7, Microsomal Epoxide Hydrolase, and NADPH Oxidoreductase Expression in Lung Cells of Smokers and Nonsmokers. Am. J. Respir. Cell Mol. Biol., 1997, 17:114-124.

Wiseman et al. Molecular phenotyping of thyroid tumors identifies a Marker panel for differentiated thyroid cancer diagnosis. Ann Surg Oncol. 2008;15(10):2811-26.

Wistuba et al. High resolution chromosome 3p allelotyping of human lung cancer and preneoplastic/preinvasive bronchial epithelium reveals multiple, discontinuous sites of 3p allele loss and three regions of frequent breakpoints. Cancer Res., 60(7): 1949-60 (Apr. 1, 2000).

Wistuba et al. Molecular damage in the bronchial epithelium of current and former smokers. J Natl Cancer Inst., 89(18): 1366-73 (Sep. 17, 1997).

Woenckhaus et al. Expression Profiling of Non-Small Cell Lung Cancers and Bronchi of Smokers and Non Smokers. Study Group: Molecular Pathology/Pathology—Research and Practice, 200:p. 255, (2004).

Woenckhaus et al. Smoking and cancer-related gene expression in bronchial epithelium and non-small-cell lung cancers. Journal of Pathology, 210: 192-204 (Oct. 2006).

Wojnarowski et al. Cytokine Expression in Bronchial Biopsies of Cystic Fibrosis Patients With and Without Acute Exacerbation. (Eur Respir, 1999, 14: 1136-114).

Wong et al. Development of a quantitative assay for SARS coronavirus and correlation of GAPDH mRNA with SARS coronavirus in clinical specimens. J Clin Pathol, 2005, 58: 276-280, doi: 10.1136/jcp.2004016592.

Woodcock et al. The treatment of idiopathic pulmonary fibrosis. F1000Prime Rep. Mar. 3, 2014;6:16.

Wreesmann et al. Genome-wide profiling of papillary thyroid cancer identifies MUC1 as an independent prognostic marker. Cancer Res. 2004;64(11):3780-9.

Written Opinion of the International Searching Authority for PCT/CA2010/000621, dated Aug. 11, 2010.

Wu, et al. A comparative study of 200 fine needle aspiration biopsies performed by clinicians and cytopathologists. Laryngoscope. Jul. 2006; 116(7):1212-5.

Wu et al. Uncommon mutation, but common amplifications, of the PIK3CA gene in thyroid tumors. J Clin Endocrinol Metab. 2005;90(8):4688-93.

Wu, Thomas D. Analysing gene expression data from DNA microarrays to identify candidate genes. Journal of Pathology, 195:53-65 (2001).

Wuenschell et al. Embryonic mouse lung epithelial progenitor cells co-express immunohistochemical markers of diverse mature cell lineages. Journal of Histochemistry and Cytochemistry (1996); 44.2: 113-123.

Xing et al. BRAF V600E and TERT Promoter Mutations Cooperatively Identify the Most Aggressive Papillary Thyroid Cancer With Highest Recurrence Journal of Clinical Oncology vol. 32, pp. 2718-2726 (Year: 2014).

Xu et al. Differential expression of galectin-1 and galectin-3 in thyroid tumors. Potential diagnostic implications. Am J Pathol. 1995;147(3):815-22.

Yan, et al. Isothermal amplified detection of DNA and RNA. Mol Biosyst. May 2014; 10(5):970-1003.

Yang et al. C-myc, N-myc, N-ras, and c-erb-B: lack of amplification or rearrangement in human medullary thyroid carcinoma and a derivative cell line. Anticancer Res. 1990;10(1):189-92.

Yang et al. Reduction of Dihydrodiol Dehydrogenase Expression in Resected Hepatocellular Carcinoma. Oncol Rep., 10(2):271-276, (2003).

Yang, I.V., et al., Epigenetics of Idiopathic Pulmonary Fibrosis. Transl Res. Jan. 2015; 165(1): 48-60.

Yang Ivana V. et al: "The Peripheral Blood Transcriptome Identifies the Presence and Extent of Disease in Idiopathic Pulmonary Fibrosis", PLOS ONE, vol. 7, No. 6, Sep. 30, 2011 (Sep. 30, 2011), p. e37708, XP055819869,DOI: 10.1371 /journal.pone.0037708.

Yano et al. Gene expression profiling identifies platelet-derived growth factor as a diagnostic molecular marker for papillary thyroid carcinoma. Clin Cancer Res. 2004;10(6):2035-43.

Yatabe et al. Epidermal growth factor receptor gene amplification is acquired in association with tumor progression of EGFR-mutated lung cancer. Cancer Res. 2008;68(7):2106-11.

Yeh et al. Differentiated thyroid cancer cell invasion is regulated through epidermal growth factor receptor-dependent activation of matrix metalloproteinase (MMP)-2/gelatinase A. Endocr Relat Cancer. 2006;13(4):1173-83.

Yeh et al. Somatic mitochondrial DNA (mtDNA) mutations in papillary thyroid carcinomas and differential mtDNA sequence variants in cases with thyroid tumours. Oncogene. 2000;19(16):2060-6.

Yen-Tsung; Huang et al., "Genome-Wide Analysis of Survival in Early-Stage Non-Small-Cell Lung Cancer", Journal of Clinical Oncology, Jun. 1, 2009, 27 (16), 2660-2667.

Yoneda et al. Development of High-Density DNA Microarray Membrane for Profiling Smoke- and Hydrogen Peroxide-Induced Genes in a Human Bronchial Epithelial Cell Line. American Journal of Respiratory and Critical Care Medicine, 164:S86-S89, (2001).

Yoon et al. Identification of a novel noncoding RNA gene, NAMA, that is downregulated in papillary thyroid carcinoma with BRAF mutation and associated with growth arrest. Int J Cancer. 2007;121(4):767-75.

Yousefi et al. A SNP panel for identification of DNA and RNA specimens. BMC genomics 19.1 (2018): 90.

Yukinawa, et al. A multi-class predictor based on a probabilistic model: application to gene expression profiling-based diagnosis of thyroid tumors. BMC Genomics. Jul. 27, 2006;7:190.

Yu-Rong, et al. Tumor-associated antisen L6 and the invasion of human lung cancer cells. Clinical Cancer Research, Jul. 2003; vol. 9: 2807-2816.

Zabel et al. S-100 protein and neuron-specific enolase in parathyroid glands and C-cells of the thyroid. Histochemistry. 1987;86(4):389-92.

Zabner et al. Comparison of DNA-Lipid Complexes and DNA Alone for Gene Transfer to Cystic Fibrosis Airway Epithelia in vivo. (J Clin Invest, 1997, 100(6): 1529-1537.).

Zanna et al. Trop-1 are conserved growth stimulatory molecules that mark early stages of tumor progression. Cancer. 2007;110(2):452-64.

Zeeberg et al. GoMiner: a resource for biological interpretation of genomic and proteomic data. Genome Biology, 4(4):R28.1-R28.8 (Mar. 2003).

Zemke et al. Molecular staging of epithelial maturation using secretory cell-specific genes as markers. American Journal of Respiratory Cell and Molecular Biology (2009); 40.3: 340-348.

(56) References Cited

OTHER PUBLICATIONS

Zeng et al. The contributions of oestrogen receptor isoforms to the development of papillary and anaplastic thyroid carcinomas. J Pathol. 2008;214(4):425-33.
Zeskind Julie E et al.: "Translating the COPD transcriptome: insights into pathogenesis and tools for clinical anagement.", Proceedings of the American Thoracic Society Dec. 1, 2008, vol. 5, No. 8, Dec. 1, 2008 (Dec. 1, 2008), pp. 834-841.
Zhang, et al. Association between single-nucleotide polymorphisms of BRAF and papillary thyroid carcinoma in a Chinese population. Thyroid. Jan. 2013;23(1):38-44. doi: 10.1089/thy.2012.0228.
Zhang, et al. CDC23 Regulates Cancer Cell Phenotype and is Overexpressed in Papillary Thyroid Cancer. Endocr Relat Cancer. Endocr Relat Cancer. Nov. 28, 2011;18(6):731-42. doi: 10.1530/ERC-11-0181. Print 2011.
Zhang et al. Comparison of smoking-induced gene expression on Affymetrix Exon and 3'-based expression arrays. Genome Inform. 18: 247-57 (2007).
Zhang, et al., Identifying driver mutations from sequencing data of heterogeneous tumors in the era of personalized genome sequencing. Briefings in bioinformatics 15.2 (2014): 244-255.
Zhang et al. Regulation of tumor necrosis factor-related apoptosis-inducing ligand-induced apoptosis by DJ-1 in thyroid cancer cells. Endocr Relat Cancer. 2008;15(2):535-44.
Zhang et al. Similarities and differences between smoking-related gene expression in nasal and bronchial epithelium. Physiological Genomics (2010); 41(1), 1-8.
Zhou et al. RET proto-oncogene mutations are restricted to codons 634 and 918 in mainland Chinese families with MEN2A and MEN2B. Clin Endocrinol (Oxf). 2007;67(4):570-6.
Zhu et al. U1 snRNP-dependent function of TIAR in the regulation of alternative RNA processing of the human calcitonin/CGRP pre-mRNA. Mol Cell Biol. 2003;23(17):5959-71.
Zochbauer-Muller et al. 5' CpG Island Methylation of the FHIT Gene is Correlated with Loss of Gene Expression in Lung and Breast. Cancer Research, 61:3581-3585, (May 2, 2001).

\* cited by examiner

|  | Classification result | |
|---|---|---|
| Pathology Label | Non-UIP | UIP |
| Non-UIP | 54 | 5 |
| UIP | 39 | 72 |

| | |
|---|---|
| AUC | 0.85 [0.78-0.91] |
| Sensitivity | 0.65 [0.25, 0.82] |
| Specificity | 0.92 [0.81, 0.97] |

FIG. 3B

| Pathology Label | | Classification result | |
| --- | --- | --- | --- |
| | | Non-UIP | UIP |
| | Non-UIP | 32 | 5 |
| | UIP | 28 | 48 |

| | |
| --- | --- |
| AUC | 0.86 [0.79-0.93] |
| Sensitivity | 0.63 [0.43, 0.87] |
| Specificity | 0.86 [0.73, 0.97] |

FIG. 3D

All subjects in the primary analysis (N=49)

| Envisia Result | UIP reference standard (N=24) | Non-UIP reference standard (N=25) |
|---|---|---|
| UIP | 16 | 3 |
| Non-UIP | 8 | 22 |
| Sensitivity | 67% [CI:45%-84%] | |
| Specificity | 88% [CI:68%-97%] | |
| NPV | 73% | |
| PPV | 84% | |

FIG. 10B

| Central Radiology Result | UIP reference standard (N=23) | Non-UIP reference standard (N=24) | | Local Radiology Result | UIP reference standard (N=23) | Non-UIP reference standard (N=23) |
|---|---|---|---|---|---|---|
| Definite/Probable/Possible UIP | 9 | 0 | | Definite/Probable/Possible UIP | 14 | 7 |
| Inconsistent with UIP | 13 | 24 | | Inconsistent with UIP | 9 | 16 |
| Sensitivity | 41% [21-64%] | | | Sensitivity | 61% [39-80%] | |
| Specificity | 100% [86-100%] | | | Specificity | 70% [47-87%] | |
| NPV | 65% [47-80%] | | | NPV | 64% [43-82%] | |
| PPV | 100% [66-100%] | | | PPV | 67% [43-85%] | |

| Subjects with Definite/Probable/Possible UIP by Central Radiology | | | | Subjects with Definite/Probable/Possible UIP by Local Radiology | | |
|---|---|---|---|---|---|---|
| Envisia Result | UIP reference standard (N=9) | Non-UIP reference standard (N=0) | | Envisia Result | UIP reference standard (N=14) | Non-UIP reference standard (N=7) |
| UIP | 7 | 0 | | UIP | 8 | 3 |
| Non-UIP | 2 | 0 | | Non-UIP | 6 | 4 |
| Sensitivity | 78% [40-97%] | | | Sensitivity | 57% [29-82%] | |
| Specificity | N/A | | | Specificity | 57% [18-90%] | |
| NPV | N/A | | | NPV | 40% [12-74%] | |
| PPV | 100% [59-100%] | | | PPV | 73% [39-94%] | |

| Subjects with Inconsistent UIP by Central Radiology | | | | Subjects with Inconsistent UIP by Local Radiology | | |
|---|---|---|---|---|---|---|
| Envisia Result | UIP reference standard (N=13) | Non-UIP reference standard (N=24) | | Envisia Result | UIP reference standard (N=9) | Non-UIP reference standard (N=16) |
| UIP | 8 | 3 | | UIP | 7 | 0 |
| Non-UIP | 5 | 21 | | Non-UIP | 2 | 16 |
| Sensitivity | 62% [32-86%] | | | Sensitivity | 78% [40-97%] | |
| Specificity | 88% [68-97%] | | | Specificity | 100% [79-100%] | |
| NPV | 81% [61-93%] | | | NPV | 89% [65-99%] | |
| PPV | 73% [39-94%] | | | PPV | 100% [59-100%] | |

FIG. 12

|  | Age | P-value* | Correlation with classification score | |
|---|---|---|---|---|
|  |  |  | cor | P-value for testing H0: cor = 0 |
| UIP | 66.4 (10.3) | 0.13 | 0.57 | 0.003 |
| Non-UIP | 61.9 (10.0) |  | 0.20 | 0.331 |
| Total | 64.1 (10.3) |  | 0.41 | 0.004 |

FIG. 13B

METHODS AND SYSTEMS FOR DETECTING USUAL INTERSTITIAL PNEUMONIA

CROSS REFERENCE TO RELATED APPLICATIONS

The present application is a continuation application of U.S. patent application Ser. No. 17/218,123, filed Mar. 30, 2021, which is a continuation application of U.S. patent application Ser. No. 16/292,573, filed Mar. 5, 2019, which is a continuation application of International Patent Application No. PCT/US2017/050358, filed Sep. 6, 2017, which claims benefit to U.S. Provisional Application No. 62/528,899 filed Jul. 5, 2017 and U.S. Provisional Application No. 62/384,609, filed Sep. 7, 2016, the entire contents of which are hereby incorporated by reference in their entirety for all purposes.

BACKGROUND

Interstitial lung diseases (ILD) are a heterogeneous group of acute and chronic bilateral parenchymal pulmonary disorders with similar clinical manifestations, but a wide spectrum of severity and outcome including varying disease progression, treatment response, and survival.[1] Among these, idiopathic pulmonary fibrosis (IPF) is one of the most common (incidence of 14-60 per 100,000 per year in North America) and severe ILD, characterized by progressive fibrosis, worsening lung function and death.[3-6] In the appropriate clinical setting, IPF is defined by the presence of the usual interstitial pneumonia (UIP) pattern on HRCT and/or SLB. 8 The lengthy time to diagnosis, coupled with the rapid course of disease, compels the need for new tools to minimize suffering of patients during the uncertain diagnostic process. Most patients diagnosed with IPF die within five years of their initial diagnosis.[7,8] However, the recent availability of two new antifibrotic drugs pirfenidone and nintedanib, which have shown promise in stabilizing IPF disease progression, and other therapeutics in development may change this picture,[9-11] and accurate diagnosis is critical for appropriate therapeutic intervention.[5,12]

Distinguishing the diagnosis of IPF from other fibrotic IIPs has significant implications given these new possibilities for treatment with lung transplant and/or anti-fibrotic oral compounds.[2] Additionally, a number of the disorders that are often confused with IPF are treated with immunosuppressive agents. As treatment of IPF with combined immunosuppression has been shown to be harmful, choosing the correct treatment is critical.[2,33]

IPF may be challenging to diagnose. Internationally recognized guidelines recommend the multidisciplinary evaluation of clinical, radiological, and pathological disease features in the diagnosis and management of ILD. The diagnostic approach to IPF requires exclusion of other interstitial pneumonias, as well as connective tissue disease and environmental and occupational exposures.[3-6] Patients suspected of having IPF usually undergo high-resolution computed tomography (HRCT) of the chest, which confirms the disease with high specificity only if the pattern of usual interstitial pneumonia (UIP) is clearly evident.[5,13] Thus, a confident diagnosis of IPF is achievable without SLB for approximately one third of ILD patients.[34-36] In those without a confident UIP pattern diagnosis on HRCT (e.g. Possible UIP, and the working category of Probable UIP), the positive predictive value (PPV) for the presence of histologic UIP has been estimated at approximately 60%,[35,36] a level that is not considered sufficient to forgo confirmation by SLB.[8] Accordingly, because HRCT results are frequently inconclusive, a large number of patients require an invasive diagnostic surgical lung biopsy (SLB) to clarify the histopathologic features of interstitial pneumonia and/or UIP pattern[5,14] and the typical length of time to diagnose IPF from the onset of symptoms may be 1-2 years.[15] With high procedural complication rates reported for cryobiopsy,[37] and in-hospital and 90-day mortality associated with SLB reaching 1.7% and 3.9% respectively,[38] a less invasive method of diagnosing IPF is greatly needed in the art.

Reliable identification of UIP pathology in transbronchial biopsies (TBBs) is challenged by the difficulty of sufficient sampling of alveolated lung parenchyma and heterogeneous disease distribution. Discordance between pathologists occurs, and a correct diagnosis may be dependent on individual experience.[16] Despite histopathologic evaluation, a definitive diagnosis may remain elusive. In retrospective studies with high TBB sampling adequacy rates, UIP was confirmed in 30-43% of patients with clinical and radiographic features consistent with UIP,[11,12] with a third study reporting a confirmation rate of <10%.[13] This has led many to evaluate alternate bronchoscopic studies that may provide greater alveolar sampling.[14,15] These are currently limited by availability and a lack of large multicenter studies.[16] Diagnostic accuracy has been shown to increase when multidisciplinary teams (MDT) of pulmonologists, radiologists, and pathologists confer;[17] unfortunately not all patients and their physicians have access to this level of expert review by an experienced MDT. Such reviews are time consuming and require patients to be seen at regional centers of recognized expertise.

Accordingly, more effective methods of diagnosing IPF, e.g., more robust methods of detecting UIP in bronchoscopic sampling that does not rely on sufficient sampling of alveoli, are required. In addition, methods of differentiating UIP from non-UIP are required.

While gene expression profiling studies in the scientific literature have reported differential expression between IPF and other ILD subtypes,[18,19] none, except for our prior application, PCT/US2015/059309, incorporated herein by reference in its entirety, have attempted to classify UIP in datasets containing other subtypes frequently present as part of the clinician's differential diagnosis. Further, none have utilized actual or in silico sample pooling to achieve higher sensitivity and/or specificity of differential diagnosis. Additionally, none have reported classifiers that are agnostic to cellular heterogeneity.

The methods described herein are surprisingly able to obtain a higher sensitivity and/or sensitivity for differential diagnosis by utilizing physical or in silico pooling of patient samples. Further, the methods described herein are surprisingly agnostic to cellular heterogeneity despite prior indications that cellular homogeneity was required. Thus, the present disclosure provides significant improvements over the prior art for using differential gene expression to distinguish between IPF and other ILD subtypes.

SUMMARY

The present disclosure provides methods of and systems used for differentiating between samples as usual interstitial pneumonia (UIP) or non-UIP using classifiers. The accuracy of the methods described herein have been confirmed using expert pathology diagnoses as truth labels. Thus, the methods described herein provide a pathology surrogate test that accurately distinguishes UIP from non-UIP patterns in samples such as, e.g., transbronchial biopsies (TBBs).

In some embodiments, the present disclosure provides a method and/or system for detecting whether a lung tissue sample is positive for usual interstitial pneumonia (UIP) or non-usual interstitial pneumonia (non-UIP). In some embodiments, a method is provided for determining whether a lung tissue sample is positive for usual interstitial pneumonia (UIP) comprising detecting mRNA expression levels in a biological sample of one or more gene listed in Table 1, Table 5, Table 15, or a combination thereof. In particular embodiments, the present disclosure provides a method and/or system for detecting whether a lung tissue sample is positive for usual interstitial pneumonia (UIP) or non-usual interstitial pneumonia (non-UIP) comprising detecting mRNA expression levels in a biological sample of one or more gene listed in Table 5. In some embodiments, the method comprises detecting all of the genes listed in Table 5. In some embodiments, the methods further comprise transforming the expression levels (e.g., expression levels of the one or more genes listed in Table 5) determined above into an UIP-score that is indicative of the likelihood that the subject has IPF (e.g., as opposed to another ILD). In some embodiments, a risk score is determined according to a model having a Negative Predictive Value (NPV) of greater than 70% for ruling out UIP. In some embodiments, a risk score is determined according to a model having a Positive Predictive Value (PPV) of greater than 80% for diagnosing UIP. In some embodiments a method is provided for: assaying the expression level of each of a first group of transcripts and a second group of transcripts in a test sample of a subject, wherein the first group of transcripts includes any one or more of the genes overexpressed in UIP and listed in any of Table 1 and/or Table 15 and the second group of transcripts includes any one or more of the genes under-expressed in UIP and listed in any of Table 1 and/or Table 15. In some embodiments a method is provided for: assaying the expression level of each of a first group of transcripts and a second group of transcripts in a test sample of a subject, wherein the first group of transcripts includes any one or more of the genes overexpressed in UIP and listed in Table 5 and the second group of transcripts includes any one or more of the genes under-expressed in UIP and listed in Table 5. In some embodiment, the method further provides for comparing the expression level of each of the first group of transcripts and the second group of transcripts with reference expression levels of the corresponding transcripts to (1) classify the lung tissue as usual interstitial pneumonia (UIP) if there is (a) an increase in an expression level corresponding to the first group or (b) a decrease in an expression level corresponding to the second group as compared to the reference expression levels, or (2) classify the lung tissue as non-usual interstitial pneumonia (non-UIP) if there is (c) an increase in the expression level corresponding to the second group or (d) a decrease in the expression level corresponding to the first group as compared to the reference expression levels. In some embodiments, the method further provides for determining and/or comparing sequence variants for any of the one or more genes listed in Table 1 and/or Table 15. In some embodiments, the method provides for determining and/or comparing sequence variants for any of the one or more genes listed in Table 5.

In some embodiments, the present disclosure provides a method of detecting whether a lung tissue sample is positive for usual interstitial pneumonia (UIP) or non-usual interstitial pneumonia (non-UIP), comprising: Assaying the expression level of each of a first group of transcripts and a second group of transcripts in a test sample of a subject, wherein the first group of transcripts includes one or more sequences corresponding to any one of the genes overexpressed in UIP and listed in Table 1 and/or Table 15 and the second group of transcripts includes one or more sequence corresponding to any one of the genes under-expressed in UIP and listed in Table 1 and/or Table 15; and comparing the expression level of each of the first group of transcripts and the second group of transcripts with reference expression levels of the corresponding transcripts to (1) classify the lung tissue as usual interstitial pneumonia (UIP) if there is (a) an increase in an expression level corresponding to the first group and/or (b) a decrease in an expression level corresponding to the second group as compared to the reference expression levels, or (2) classify the lung tissue as non-usual interstitial pneumonia (non-UIP) if there is (c) an increase in the expression level corresponding to the second group and/or (d) a decrease in the expression level corresponding to the first group as compared to the reference expression levels.

In some embodiments, the present disclosure provides a method of detecting whether a lung tissue sample is positive for usual interstitial pneumonia (UIP) or non-usual interstitial pneumonia (non-UIP), comprising: Assaying the expression level of each of a first group of transcripts and a second group of transcripts in a test sample of a subject, wherein the first group of transcripts includes one or more sequences corresponding to any one of the genes overexpressed in UIP and Table 5 and the second group of transcripts includes one or more sequences corresponding to any one of the genes under-expressed in UIP and listed in Table 5; and comparing the expression level of each of the first group of transcripts and the second group of transcripts with reference expression levels of the corresponding transcripts to (1) classify the lung tissue as usual interstitial pneumonia (UIP) if there is (a) an increase in an expression level corresponding to the first group and/or (b) a decrease in an expression level corresponding to the second group as compared to the reference expression levels, or (2) classify the lung tissue as non-usual interstitial pneumonia (non-UIP) if there is (c) an increase in the expression level corresponding to the second group and/or (d) a decrease in the expression level corresponding to the first group as compared to the reference expression levels. In some embodiments, the present disclosures provides a method of detecting whether a lung tissue sample is positive for usual interstitial pneumonia (UIP) or non-usual interstitial pneumonia (non-UIP), comprising: assaying the expression level of each of a first group of transcripts and a second group of transcripts in a test sample of a subject, wherein the first group of transcripts includes one or more sequences corresponding to any one of the genes overexpressed in UIP and listed in Table 1, Table 5, and/or Table 15 and the second group of transcripts includes one or more sequences corresponding to any one of the genes under-expressed in UIP and listed in Table 1, Table 5, and/or Table 15; and comparing the expression level of each of the first group of transcripts and the second group of transcripts with reference expression levels of the corresponding transcripts to (1) classify the lung tissue as usual interstitial pneumonia (UIP) if there is (a) an increase in an expression level corresponding to the first group and/or (b) a decrease in an expression level corresponding to the second group as compared to the reference expression levels, or (2) classify the lung tissue as non-usual interstitial pneumonia (non-UIP) if there is (c) either no change in, or an increase in, the expression level corresponding to the second group and/or (d) no change in, or a decrease in, the expression level corresponding to the first group as compared to the reference expression levels.

In some embodiments, the present disclosure provides a method of detecting whether a lung tissue sample is positive for usual interstitial pneumonia (UIP) or non-usual interstitial pneumonia (non-UIP), comprising: assaying by sequencing, array hybridization, or nucleic acid amplification the expression level of each of a first group of transcripts and a second group of transcripts in a test sample from a lung tissue of a subject, wherein the first group of transcripts includes one or more sequences corresponding to any one of the genes overexpressed in UIP and listed in Table 1 and/or Table 15 and the second group of transcripts includes one or more sequences corresponding to any one of the genes under-expressed in UIP and listed in any of Table 1 and/or Table 15; and comparing the expression level of each of the first group of transcripts and the second group of transcripts with reference expression levels of the corresponding transcripts to (1) classify the lung tissue as usual interstitial pneumonia (UIP) if there is (a) an increase in an expression level corresponding to the first group and/or (b) a decrease in an expression level corresponding to the second group as compared to the reference expression levels, or (2) classify the lung tissue as non-usual interstitial pneumonia (non-UIP) if there is (c) an increase in the expression level corresponding to the second group and/or (d) a decrease in the expression level corresponding to the first group as compared to the reference expression levels.

In some embodiments, the present disclosure provides a method of detecting whether a lung tissue sample is positive for usual interstitial pneumonia (UIP) or non-usual interstitial pneumonia (non-UIP), comprising: assaying by sequencing, array hybridization, or nucleic acid amplification the expression level of each of a first group of transcripts and a second group of transcripts in a test sample from a lung tissue of a subject, wherein the first group of transcripts includes one or more sequences corresponding to any one of the genes overexpressed in UIP and listed in Table 5 and the second group of transcripts includes one or more sequences corresponding to any one of the genes under-expressed in UIP and listed in any of Table 5; and comparing the expression level of each of the first group of transcripts and the second group of transcripts with reference expression levels of the corresponding transcripts to (1) classify the lung tissue as usual interstitial pneumonia (UIP) if there is (a) an increase in an expression level corresponding to the first group and/or (b) a decrease in an expression level corresponding to the second group as compared to the reference expression levels, or (2) classify the lung tissue as non-usual interstitial pneumonia (non-UIP) if there is (c) an increase in the expression level corresponding to the second group and/or (d) a decrease in the expression level corresponding to the first group as compared to the reference expression levels.

In some embodiments, the first group comprises 2 or more different transcripts, or 3 or more, 4 or more, 5 or more, 10 or more, 15 or more, 20 or more, or more than 20 different transcripts.

In some embodiments, the second group comprises 2 or more different transcripts, or 3 or more, 4 or more, 5 or more, 10 or more, 15 or more, 20 or more, or more than 20 different transcripts.

In some embodiments, the present disclosure provides a method of detecting whether a lung tissue sample is positive for UIP or non-UIP, comprising: assaying the expression level of two or more transcripts expressed in a test sample; and using a computer generated classifier to classify the sample as UIP and non-UIP; wherein the classifier was trained using a heterogeneous spectrum of non-UIP pathology subtypes comprising HP, NSIP, sarcoidosis, RB, bronchiolitis, and organizing pneumonia (OP); and wherein the two or more transcripts expressed in the test sample are selected from any two or more sequences listed in Table 1 and/or Table 15.

In some embodiments, the present disclosure provides a method of detecting whether a lung tissue sample is positive for UIP or non-UIP, comprising: assaying the expression level of two or more transcripts expressed in a test sample; and using a computer generated classifier to classify the sample as UIP and non-UIP; wherein the classifier was trained using a heterogeneous spectrum of non-UIP pathology subtypes comprising HP, NSIP, sarcoidosis, RB, bronchiolitis, and organizing pneumonia (OP); and wherein the two or more transcripts expressed in the test sample are selected from any two or more sequences listed in Table 5.

In some embodiments, the test sample is a pool of a plurality of samples obtained from the subject. In some embodiments, the pool comprises 2, 3, 4, or 5 samples obtained from the subject.

In some embodiments, the method comprises pooling expression level data from a plurality of individual samples obtained from the subject. In some embodiments, expression level data from 2, 3, 4, or 5 samples obtained from the subject are pooled.

In some embodiments, the test sample is a biopsy sample or a bronchoalveolar lavage sample. In some embodiments, the biopsy sample is a transbronchial biopsy sample. In some embodiments, the test sample is fresh-frozen or fixed.

In some embodiments, assaying the expression level is accomplished using RT-PCR, DNA microarray hybridization, RNASeq, or a combination thereof. In some embodiments, the expression level is assayed by detecting a nucleotide expressed in the test sample or synthesized from a nucleotide expressed in the test sample. In some embodiments, the method comprises synthesizing cDNA from RNA expressed in the test sample prior to assaying the expression level. In some embodiments, the method comprises synthesizing double-stranded cDNA from the cDNA prior to assaying the expression level. In some embodiments, the method comprises synthesizing non-natural RNA from the double-stranded cDNA prior to assaying the expression level. In some embodiments, the non-natural RNA is cRNA. In some embodiments, the non-natural RNA is labeled. In some embodiments, the label comprises a sequencing adaptor or a biotin molecule. In some embodiments, the method comprises amplification of the nucleotide prior to assaying the expression level.

In some embodiments, the method comprises labeling one or more of the transcripts. In some embodiments, the methods further comprise measuring the expression level of at least one control nucleic acid in the test sample.

In some embodiments, the method comprises classifying the lung tissue as any one of interstitial lung diseases (ILD), a particular type of ILD, a non-ILD, or non-diagnostic. In some embodiments, the lung tissue is classified as either idiopathic pulmonary fibrosis (IPF) or nonspecific interstitial pneumonia (NSIP). In some embodiments, the method comprises using smoking status as a covariate to the classification step(s). In some embodiments, smoking status is determined by detecting an expression profile indicative of the subject's smoker status.

In some embodiments, the classification of the sample comprises detection of the expression levels of one or more transcripts that are susceptible to smoker status bias, wherein the transcripts that are susceptible to smoker status bias are weighted differently than transcripts that are not susceptible to smoker bias.

In some embodiments, the classification of the sample comprises detection of the expression levels of one or more transcripts that are susceptible to smoker status bias, and wherein the transcripts that are susceptible to smoker status bias are excluded from the classification step.

In some embodiments, the method comprises implementing a classifier trained using one or more features selected from gene expression, variants, mutations, fusions, loss of heterozygoxity (LOH), and biological pathway effect. In some embodiments, the classifier is trained using features including gene expression, sequence variants, mutations, fusions, loss of heterozygoxity (LOH), and biological pathway effect.

In some embodiments, the classification step further comprises detecting sequence variants in the test sample and comparing the sequence variants to the respective sequences in a reference sample to classify the sample as UIP or non-UIP.

In some embodiments, the methods disclosed herein for detecting whether a lung tissue sample is positive for UIP or non-UIP further comprise treating the subject with a compound capable of treating IPF if the sample is classified as UIP. In some embodiments, the compound is an anti-fibrotic. In some embodiments, the compound is selected from pirfenidone, nintedanib, pharmaceutically acceptable salts thereof, and combinations thereof.

In some embodiments, the classifying performed in the methods disclosed herein for detecting whether a lung tissue sample is positive for UIP or non-UIP, results in a specificity of at least about 90% and a sensitivity of at least about 70%.

In some embodiments, the methods disclosed herein for detecting whether a lung tissue sample is positive for UIP or non-UIP comprise assaying expression data for at least two transcripts. In some embodiments, the methods disclosed herein for detecting whether a lung tissue sample is positive for UIP or non-UIP comprises assaying expression data.

In some embodiments, the methods disclosed herein for detecting whether a lung tissue sample is positive for UIP or non-UIP comprise assaying expression data for at least two genes selected from the genes listed in Table 5. In some embodiments, the methods disclosed herein for detecting whether a lung tissue sample is positive for UIP or non-UIP comprises assaying expression data for each of the genes listed in Table 5.

In some embodiments, the methods disclosed herein further comprise (i) obtaining a sample from a subject, (ii) subjecting a first portion of the sample to cytological analysis that indicates that the first portion of the sample is ambiguous or indeterminate, and (iii) assaying a second portion of the sample as the test sample. In some embodiments, the first portion and second portion are different portions.

In some embodiments, the comparing the expression level of each of the first group of transcripts and the second group of transcripts with reference expression levels of the corresponding transcripts is performed using a trained algorithm that is trained with a plurality of samples, wherein the test sample is independent of the plurality of samples.

In some embodiments, the present disclosure presents a method of treating a patient with undiagnosed idiopathic pulmonary fibrosis (IPF), comprising, (A) measuring by array, sequencing, or qRT-PCR the level of expression of at least two genes in one or more samples obtained from a subject's airway, wherein the genes are selected from those listed in Table 1 and/or Table 15, and wherein the method comprises (i) pooling at least two samples prior to the measuring step; (ii) pooling at least two sets of expression data independently measured from two separate samples; or a combination of (i) and (ii); and (B) administering a compound effective for treating IPF if: (i) the expression level of each of the at least two genes is increased as compared to reference expression levels of the corresponding transcripts; and/or (ii) the expression level of each of the at least two genes is decreased as compared to reference expression levels of the corresponding transcripts; and/or (iii) the expression level of at least one of the at least two genes increased as compared to reference expression levels of the corresponding transcripts and at least one of the at least two genes is decreased as compared to reference expression levels of the corresponding transcripts.

In some embodiments, the administering step is performed only if the increase in (i) and/or the decrease in (ii) is significant.

In some embodiments, the present disclosure presents a method of treating a patient with undiagnosed idiopathic pulmonary fibrosis (IPF) comprising, (A) measuring by array, sequencing, or qRT-PCR the level of expression of at least two genes in one or more samples obtained from a subject's airway, wherein the genes are selected from those listed in Table 5, and wherein the method comprises (i) pooling at least two samples prior to the measuring step; (ii) pooling at least two sets of expression data independently measured from two separate samples; or a combination of (i) and (ii); and (B) administering a compound effective for treating IPF if: (i) the expression level of each of the at least two genes is increased as compared to reference expression levels of the corresponding transcripts; and/or (ii) the expression level of each of the at least two genes is decreased as compared to reference expression levels of the corresponding transcripts; and/or (iii) the expression level of at least one of the at least two genes increased as compared to reference expression levels of the corresponding transcripts and at least one of the at least two genes is decreased as compared to reference expression levels of the corresponding transcripts.

In some embodiments, the administering step is performed only if the increase in (i) and/or the decrease in (ii) is significant.

In some embodiments, the present disclosure provides a method of detecting whether a pooled lung tissue test sample is positive for UIP or non-UIP, comprising: (A) assaying the expression level of one or more transcripts expressed in a test sample; and (B) classifying the test sample as UIP or non-UIP using a computer generated trained classifier; wherein the computer generated trained classifier is trained using expression levels of one or more transcripts expressed in a plurality of individual training samples obtained from a plurality of subjects, each training sample having a confirmed diagnoses of UIP or non-UIP, wherein at least two of the training samples were obtained from a single subject; and wherein the test sample is pooled prior to the classifying.

In some embodiments, the pooling comprises physical pooling. In some embodiments, the pooling comprises in silico pooling.

In some embodiments, the classifier training uses expression levels of one or more transcripts listed in Table 1 and/or Table 15. In some embodiments, the classifier training uses expression levels of one or more genes listed in Table 5. In some embodiments, the classifier training uses expression levels of all of the transcripts listed in Table 1. In some embodiments, the classifier training uses expression levels of all of the transcripts listed in Table 15. In some embodiments, the classifier training uses expression levels of all of the transcripts listed in Table 5. In some embodiments, the classifier training uses expression levels of all of the transcripts listed in Table 5 and one or more additional gene listed in Table 1 or Table 15. In some embodiments, the classifier training uses expression levels of all of the transcripts listed in Table 1 and in Table 15. In some embodiments, the computer generated trained classifier classifies the test sample as UIP or non-UIP based upon the expression level of one or more transcripts listed in Table 1 and/or Table 15. In some embodiments, the classifier classifies the test sample as UIP or non-UIP based upon the expression level of all of the transcripts listed in Table 1. In some embodiments, the classifier classifies the test sample as UIP or non-UIP based upon the expression level of all of the transcripts listed in Table 15. In some embodiments, the classifier classifies the test sample as UIP or non-UIP based upon the expression level of all of the transcripts listed in Table 1 and in Table 15. In some embodiments, the classifier training uses expression levels of all of the genes listed in Table 5. In some embodiments, the computer generated trained classifier classifies the test sample as UIP or non-UIP based upon the expression level of one or more transcript listed in Table 5. In some embodiments, the classifier classifies the test sample as UIP or non-UIP based upon the expression level of all of the transcripts listed in Table 5.

In some embodiments, the present disclosure provides a method of detecting whether a pooled lung tissue test sample is positive for a disease or condition comprising: (A) assaying the expression level of one or more transcripts expressed in a test sample; and (B) classifying the test sample as either positive for, or negative for, the disease or condition using a computer generated trained classifier; wherein the computer generated trained classifier is trained using expression levels of one or more transcripts expressed in a plurality of individual training samples obtained from a plurality of subjects, each training sample having a confirmed diagnoses of positive or negative for the disease or condition, wherein at least two of the training samples were obtained from a single subject; and wherein the test sample is pooled prior to the classifying.

In some embodiments, the pooling comprises physical pooling. In some embodiments, the pooling comprises in silico pooling. In some embodiments, the classifier classifies the sample based on the expression level of one or more gene listed in Table 5. In particular embodiments the classifier classifies the sample based on the expression level of all the genes listed in Table 5.

In some embodiments, the disease or condition is selected from: a lung disorder, lung cancer, interstitial lung disease (ILD), idiopathic pulmonary fibrosis (IPF), usual interstitial pneumonia (UIP) or non-usual interstitial pneumonia (non-UIP), acute lung injury, bronchiolitis, desquamative interstitial pneumonia, diffuse alveolar damage, emphysema, eosinophilic pneumonia, nonspecific interstitial pneumonia (NSIP) (including subtypes of cellular, mixed, or Favor), granulomatous disease, hypersensitivity pneumonitis (HP), Favor subtype hypersensitivity pneumonitis (Favor HP), organizing pneumonia, *pneumocystis* pneumonia, pulmonary hypertension, respiratory bronchiolitis, pulmonary sarcoidosis, smoking-related interstitial fibrosis, chronic obstructive pulmonary disease (COPD), a history of exposure to smoke, long-term exposure to smoke, short-term exposure to smoke, and chronic interstitial fibrosis.

In some embodiments, the present disclosure provides a method of treating a subject in need thereof with a therapeutic effective for treating idiopathic pulmonary fibrosis (IPF) comprising administering an effective dose of a compound effective for treating IPF to the subject in need thereof, wherein the subject in need thereof has an expression level of one or more genes in Table 5 that indicates the subject is in need of treatment for IPF as determined by a computer-generated trained classifier.

In some embodiments, the computer-generated trained classifier is trained using expression levels of one or more transcripts expressed in a plurality of individual training samples obtained from a plurality of subjects, each training sample having a confirmed diagnoses of UIP or non-UIP, wherein at least two of the training samples were obtained from a single subject; and wherein the test sample is pooled prior to the classifying. In particular embodiments, the computer-generated trained classifier identifies a sample obtained from the subject as UIP. In particular embodiments, the computer-generated trained classifier identifies a sample obtained from the subject as IPF.

In some embodiments, the present disclosure provides a method for identifying whether a subject is positive for a lung disorder, comprising: (a) obtaining a tissue sample of the subject; (b) subjecting a first portion of the tissue sample to cytological testing that indicates that the first portion is ambiguous or suspicious; (c) upon identifying that the first portion is ambiguous or suspicious, assaying a second portion of the tissue sample for an expression level of one or more markers associated with the lung disorder; (d) processing the expression level with a trained algorithm to generate a classification of the tissue sample as positive for the lung disorder at an accuracy of at least about 90%, wherein the trained algorithm is trained with a training set comprising a plurality of training samples, and wherein the tissue sample is independent of the plurality of samples; and (e) electronically outputting the classification, thereby identifying whether the subject is positive for the lung disorder.

In some embodiments, the tissue sample is a lung tissue sample. In some embodiments, the tissue sample is a non-lung tissue sample. In some embodiments, the non-lung tissue sample is a respiratory epithelium sample. In some embodiments, the respiratory epithelium sample is from a nose or mouth of the subject.

In some embodiments, the expression level is of a plurality of markers associated with UIP.

In some embodiments, the accuracy is at least about 95%.

In some embodiments, the classification is generated at a specificity of at least about 90%. In some embodiments, the classification is generated at a sensitivity of at least about 70%.

In some embodiments, the trained algorithm is configured to classify a lung tissue sample at an accuracy of at least about 90% across at least 100 independent test samples.

In some embodiments, the classification is electronically outputted on a graphical user interface of an electronic display of a user.

In some embodiments, the lung disorder is usual interstitial pneumonia (UIP) or non-usual interstitial pneumonia (non-UIP).

In some embodiments, the first portion is different than the second portion.

In some embodiments, the present disclosure provides a method for identifying whether a subject is positive for usual interstitial pneumonia (UIP) or non-usual interstitial pneumonia (non-UIP), comprising: (a) obtaining a tissue sample of the subject; (b) subjecting a first portion of the tissue sample to cytological testing that indicates that the first portion is ambiguous or suspicious; (c) upon identifying that the first portion is ambiguous or suspicious, assaying a second portion of the tissue sample for an expression level of one or more markers associated with UIP; (d) processing the expression level with a trained algorithm to generate a classification of the tissue sample as positive for UIP or non-UIP at an accuracy of at least about 90%, wherein the trained algorithm is trained with a training set comprising a plurality of training samples, and wherein the tissue sample is independent of the plurality of samples; and (e) electronically outputting the classification, thereby identifying whether the subject is positive for UIP or non-UIP.

Another aspect of the present disclosure provides a non-transitory computer readable medium comprising machine-executable code that, upon execution by one or more computer processors, implements any of the methods above or elsewhere herein.

Another aspect of the present disclosure provides a computer system comprising one or more computer processors and a non-transitory computer readable medium coupled thereto. The non-transitory computer-readable medium comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "Figure" and "FIG." herein), of which:

FIG. 2 shows a flow diagram of the 113 patients and associated TBB samples screened for use in this study. The figure illustrates the cohorts (central squares), processing steps (trapezoids), and exclusions (lateral squares), of patients and samples at each sequential step of processing.

FIG. 3A-3D. Classifier performance. FIGS. 1A-1D show single-sample classification performance. A classifier trained on 53 patients was used to score, by cross validation, the individual TBB samples used in training (FIG. 3A, FIG. 3B) and to prospectively score TBB samples from an independent test cohort of 31 patients (FIG. 1C, FIG. 3D). Classification scores (y-axis), organized vertically by patient, are plotted for each TBB sample in the training (FIG. 3A) and validation (FIG. 3C) sets. Individual samples are colored by lobe-level pathology diagnoses, with symbols denoting the lobe of origin (legends). Patient level pathology diagnoses are provided on the lower x-axis and radiology diagnoses are provided on the upper x-axis of each plot. The decision boundary, determined in cross validation on the training set and applied prospectively to the test set, is shown as a horizontal dashed line. Overall performance summaries when all samples are scored are provided in cross-validation on the training set (FIG. 3B) and prospectively on the validation set (FIG. 3D). The total numbers of true positive, true negative, false positive and false negative samples in each cohort are summarized in 2×2 tables. Receiver-operator characteristic areas under the curve (ROC-AUC), sensitivity and specificity, with associated 90% confidence intervals, are listed. Pathology and radiology acronyms used in FIG. 3: ACL, acute lung injury; BR, bronchiolitis; CIF, NOC, chronic interstitial fibrosis, not otherwise classified; DIP, desquamative interstitial pneumonia; DAD, diffuse alveolar damage; EMP, emphysema; EO-PN, eosinophilic pneumonia; NA, not available/missing; ND, non-diagnostic; NSIP, nonspecific interstitial pneumonia; NSIP-C, cellular NSIP; NSIP-F, Favor NSIP; GR, granulomatous disease; HP, hypersensitivity pneumonitis; HP-F, Favor HP; OP, organizing pneumonia; OTHR, other; PN-PN, *pneumocystis* pneumonia; PL-HY, pulmonary hypertension; RB, respiratory bronchiolitis; SRC, sarcoidosis; SRIF, smoking-related interstitial fibrosis; UIP, usual interstitial pneumonia; UIP-C, classic UIP; UIP-D, difficult UIP; UIP-F, Favor UIP; UIP-DE, definite UIP; UIP-P, probable UIP.

FIG. 4A shows TBB samples from eight patients (x-axis), which were processed in vitro as individual samples and scored (y-axis) by the 84 patient classifier (blue squares). The average score for the individual TBB samples from each patient is shown for comparison (dark blue triangles). FIG. 4B shows in silico simulation of mixtures of multiple (2-5 per patient) TBB samples for the entire 84 patient cohort by random sampling of single-sample TBB data. Mixtures were scored by the 84 patient UIP classifier, and ROC-AUC point estimates for classification performance across the entire cohort were generated 100-fold, and plotted for each mixture condition. Box plots denote median ROC-AUCs at each sampling condition. FIG. 4C shows the performance shown in FIG. 4B, expressed as test sensitivity in mixtures at a targeted specificity of 90%. Test sensitivity improves to ~72% with reduced variability.

The horizontal dashed red lines shows the ROC-AUC for the single sample classifier as a reference point. FIG. 4D shows mixture simulation in a set of 33 subjects with two upper lobe and three lower lobe TBBs available for every subject. There is no improvement in performance when sampling is restricted to the upper or lower lobes.

FIG. 5A shows unsupervised clustering by principal components using 24 markers (a subset of the 44); TBB samples in blue, SLB samples in orange. FIG. 5B shows bimodal expression within the population of TBBs for 9 genes: SFTPB, SFTPC, SFTPD, ABCA3, CEBPA, AGER, GPRCSA, HOPX, and SFTPA1; TBB expression counts in blue, SLB expression counts in orange). FIG. 5C shows correlated, directionally consistent expression between SFTPA1, SFTPB, SFTPC, and SFTPD, but not between PDPN and AQP5, or between members of these two groups; TBB expression counts in blue, SLB expression counts in orange).

FIG. 6A shows the summed expression (type I alveolar statistic) of two markers of type I alveolar cells (y-axis) for multiple tissue, cell line and tumor types (x-axis). Expression in normal lung tissue, lung tumors, surgical lung biopsies (SLBs, n=22) and transbronchial biopsies in the current study is also shown for comparison (n=283). FIG. 6B shows type I alveolar statistics plotted for each TBB sample, grouped as a function of classification correctness relative to pathology truth labels (e.g., true negatives, false negatives, true positives, and false positives). FIG. 6C shows the summed expression (type II alveolar statistic) of four markers of alveolar cells (y-axis) for multiple tissue, cell line and tumor types (x-axis). Expression in normal lung tissue, lung tumors, surgical lung biopsies (SLBs, n=22) and transbronchial biopsies in the current study is also shown for comparison (n=283). FIG. 6D shows type II alveolar statistics plotted for each TBB sample, grouped as a function of classification correctness relative to pathology truth labels (e.g., true negatives, false negatives, true positives, and false positives). Pairwise correlation on explant samples obtained from three patients diagnosed with IPF (Patients P1, P2, and P3). Locations (upper or lower, central or peripheral) are indicated for each sample. The top 200 differentially expressed genes separating IPF samples from normal lung samples were used to compute pairwise Pearson correlation coefficients and plotted as a heatmap with higher correlation represented in magenta color, and lower correlation represented in green color. Correlation between and with normal lung samples are in the 0.7 range (not shown).

FIG. 7A shows an illustration of a computer system usable for implementing aspects disclosed herein. FIG. 7B shows a detailed illustration of the processor of the computer system of FIG. 7A. FIG. 7C shows a detailed illustration of one non-limiting method of the present disclosure, wherein gene product expression data for known UIP and non-UIP samples are used to train a classifier (e.g., using a classifier training module) for differentiating UIP vs. non-UIP, wherein the classifier in some cases considers smoker status as a covariant, and wherein gene product expression data from unknown samples are input into the trained classifier to identify the unknown samples as either UIP or non-UIP, and wherein the results of the classification via the classifier are defined and output via a report.

FIG. 10A-10B. Validation performance of the Envisia Genomic Classifier. FIG. 10A shows ROC-AUC curve for Envisia on the 49 subject final validation group, with the pre-specified decision boundary marked on the ROC curve with an asterisk. FIG. 10B shows a 2×2 table of Envisia classification results for the final validation group.

FIG. 12. Envisia performance in subject subgroups defined by radiology. 2×2 tables of central and local radiology diagnoses for 46 of the final validation subjects with available radiology are shown, against pathology as the reference standard. Envisia test performance against pathology is shown for the subsets of subjects with radiology consistent with UIP (Definite, Probable, and Possible UIP) and inconsistent with UIP. Envisia test results are evaluated separately against central and local radiology diagnoses.

FIG. 13A-13D. Subgroup analysis of Envisia test performance against subject clinical factors. UIP subjects are marked in solid red circles, non-UIP subjects with hollow or blue circles. FIG. 13A: Envisia classification score as a function of validation cohort subject age. FIG. 13B: There is no significant correlation between subject age and classification score. FIG. 13C: Envisia score as a function of subject gender. Male patients with UIP have a greater tendency to be missed by the Envisia test (10 of 17 males with pathology UIP were called UIP by Envisia; 41% sensitivity, vs. 6 of 7 UIP females). D) Envisia score as a function of subject smoking history. Male UIP patients with smoking history are misclassified by Envisia at a higher rate than nonsmokers.

FIGS. 14A and 14B: Summed gene expression statistics for estimating alveolar content. FIG. 14A shows alveolar type I cellular content (x-axis) and FIG. 14B shows alveolar type II content (x-axis)$^{E10}$, each are plotted against the Envisia score (y-axis). FIG. 14C: Envisia test true positives (TP), false negatives (FN), true negatives (TN), and false positives (FP) are plotted by alveolar type II content. There is no enrichment of low alveolar type II content among the subjects miscalled by the Envisia test. FIG. 14D: Correlation of Envisia classification score to sample quality (RIN or DV200), separated by UIP reference label. There is a correlation between stronger (more negative) classification scores and higher sample quality among non-UIP samples that is not evident in UIP samples.

DETAILED DESCRIPTION

Figure 1:
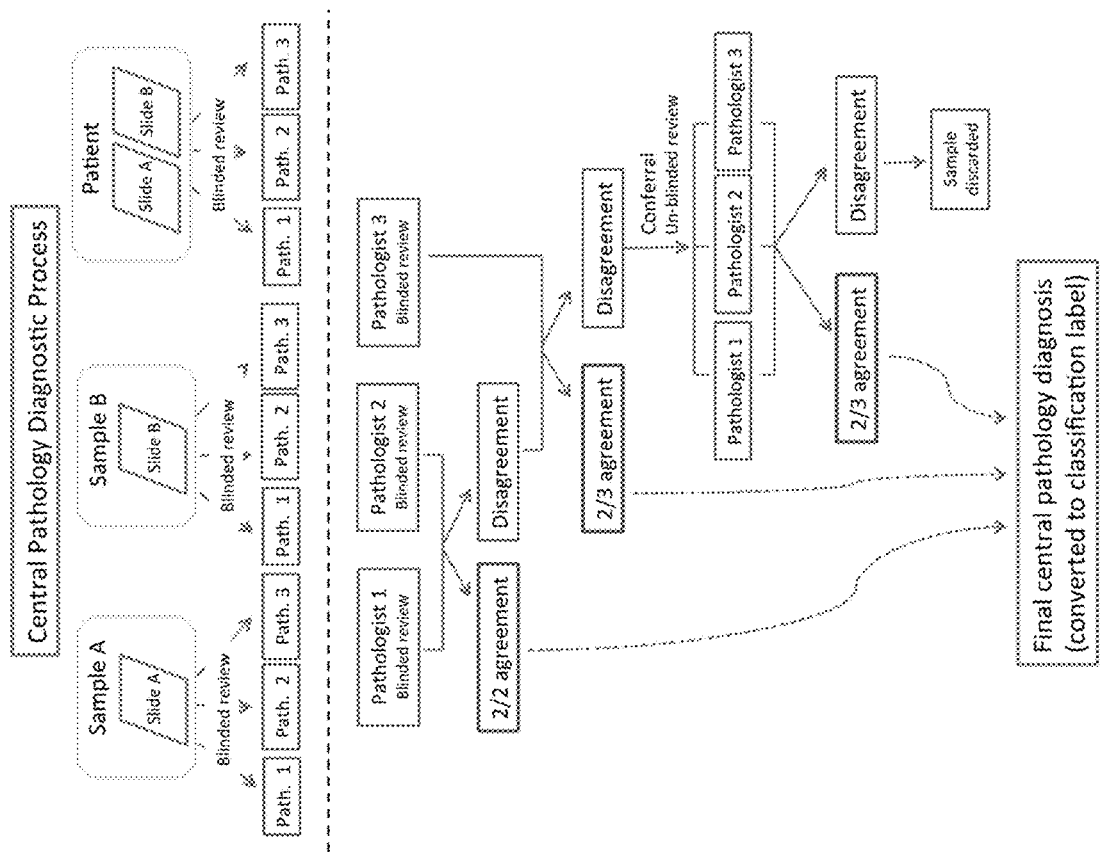
FIG. 1. Central pathology diagnostic process for a hypothetical patient with two samples (sample A and sample B). Three expert pathologists participate in the review process. For sample-level diagnosis, the glass slides for each sample are reviewed by each pathologist (Pathologist is abbreviated as Path.). For patient-level diagnosis, glass slides from all samples (two in this exercise) are gathered and reviewed together by each pathologist. Both sample-level and patient-level diagnoses go through the same review process. A majority vote is used as the final diagnosis, unless expert pathologists disagree even after the conferral, in which case, the sample is omitted due to lack of confidence in the diagnosis. Only a single such case was observed among all banked tissues (n=128).

While various embodiments of the disclosure have been shown and described herein, it will be obvious to those skilled in the art that such embodiments are provided by way of example only. Numerous variations, changes, and substitutions may occur to those skilled in the art without departing from the disclosure. It should be understood that various alternatives to the embodiments of the disclosure described herein may be employed.

"Interstitial lung disease" or "ILD" (also known as diffuse parenchymal lung disease (DPLD)) as used herein refers to a group of lung diseases affecting the interstitium (the tissue and space around the air sacs of the lungs). ILD may be classified according to a suspected or known cause, or may be idiopathic. For example, ILD may be classified as caused by inhaled substances (inorganic or organic), drug induced (e.g., antibiotics, chemotherapeutic drugs, antiarrhythmic agents, statins), associated with connective tissue disease (e.g., systemic sclerosis, polymyositis, dermatomyositis, systemic lupus erythematous, rheumatoid arthritis), associated with pulmonary infection (e.g., atypical pneumonia, *pneumocystis* pneumonia (PCP), tuberculosis, *Chlamydia trachomatis*, respiratory syncytial virus), associated with a malignancy (e.g., lymphangitic carcinomatosis), or may be idiopathic (e.g., sarcoidosis, idiopathic pulmonary fibrosis, Hamman-Rich syndrome, antisynthetase syndrome).

"ILD Inflammation" as used herein refers to an analytical grouping of inflammatory ILD subtypes characterized by underlying inflammation. These subtypes may be used collectively as a comparator against IPF and/or any other non-inflammation lung disease subtype. "ILD inflammation" can include HP, NSIP, sarcoidosis, and/or organizing pneumonia.

"Idiopathic interstitial pneumonia" or "IIP" (also referred to as noninfectious pneumonia" refers to a class of ILDs which includes, for example, desquamative interstitial pneumonia, nonspecific interstitial pneumonia, lymphoid interstitial pneumonia, cryptogenic organizing pneumonia, and idiopathic pulmonary fibrosis.

"Idiopathic pulmonary fibrosis" or "IPF" as used herein refers to a chronic, progressive form of lung disease characterized by fibrosis of the supporting framework (interstitium) of the lungs. By definition, the term is used when the cause of the pulmonary fibrosis is unknown ("idiopathic"). Microscopically, lung tissue from patients having IPF shows a characteristic set of histologic/pathologic features known as usual interstitial pneumonia (UIP), which is a pathologic counterpart of IPF.

"Nonspecific interstitial pneumonia" or "NSIP" is a form of idiopathic interstitial pneumonia generally characterized by a cellular pattern defined by chronic inflammatory cells with collagen deposition that is consistent or patchy, and a fibrosing pattern defined by a diffuse patchy fibrosis. In contrast to UIP, there is no honeycomb appearance nor fibroblast foci that characterize usual interstitial pneumonia.

"Hypersensitivity pneumonitis" or "HP" refers to also called extrinsic allergic alveolitis, (EAA) refers to an inflammation of the alveoli within the lung caused by an exaggerated immune response and hypersensitivity to as a result of an inhaled antigen (e.g., organic dust).

"Pulmonary sarcoidosis" or "PS" refers to a syndrome involving abnormal collections of chronic inflammatory cells (granulomas) that can form as nodules. The inflammatory process for HP generally involves the alveoli, small bronchi, and small blood vessels. In acute and subacute cases of HP, physical examination usually reveals dry rales.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucle-otides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" can also include DNAs (e.g., cDNAs) and RNAs that contain one or more modified bases (e.g., to provide a detectable signal, such as a fluorophore). Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide (e.g., 100, 50, 20 or fewer nucleotides) including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides may be made by a variety of other methods, including in vitro recombinant DNA-mediated techniques and by expression of DNAs in cells and organisms.

The terms "gene product" or "expression product" are used herein interchangeably to refer to the RNA transcription products (RNA transcript) of a gene, including mRNA, and the polypeptide translation product of such RNA transcripts. A gene product may be, for example, a polynucleotide gene expression product (e.g., an unspliced RNA, an mRNA, a splice variant mRNA, a microRNA, a fragmented RNA, and the like) or a protein expression product (e.g., a mature polypeptide, a post-translationally modified polypeptide, a splice variant polypeptide, and the like). In some embodiments the gene expression product may be a sequence variant including mutations, fusions, loss of heterozygoxity (LOH), and/or biological pathway effects.

The term "normalized expression level" as applied to a gene expression product refers to a level of the gene product normalized relative to one or more reference (or control) gene expression products.

A "reference expression level" as applied to a gene expression product refers to an expression level for one or more reference (or "control") gene expression products. A "reference normalized expression level" as applied to a gene expression product refers to a normalized expression level value for one or more reference (or control) gene expression products (i.e., a normalized reference expression level). In some embodiments, a reference expression level is an expression level for one or more gene product in normal sample, as described herein. In some embodiments, a reference expression level is determined experimentally. In some embodiments, a reference expression level is a historical expression level, e.g., a database value of a reference expression level in a normal sample, which sample indicates a single reference expression level, or a summary of a plurality of reference expression levels (such as, e.g., (i) an average of two or more, preferably three or more reference expression levels from replicate analysis of the reference expression level from a single sample; (ii) an average of two or more, preferably three or more reference expression levels from analysis of the reference expression level from a plurality of different samples (e.g., normal samples); (iii) and a combination of the above mentioned steps (i) and (ii) (i.e., average of reference expression levels analyzed from a plurality of samples, wherein at least one of the reference expression levels are analyzed in replicate). In some embodiments, the "reference expression level" is an expression level of sequence variants, for example, in a sample that has been definitively determined to be UIP or non-UIP by other approaches (i.e. confirmed pathological diagnosis).

A "reference expression level value" as applied to a gene expression product refers to an expression level value for one or more reference (or control) gene expression products. A "reference normalized expression level value" as applied to a gene expression product refers to a normalized expression level value for one or more reference (or control) gene expression products.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to re-anneal when complementary strands are present in an environment below their melting temperature. The higher the degree of desired homology between the probe and hybridizable sequence, the higher the relative temperature that may be used. As a result, it follows that higher relative temperatures may tend to make the reaction conditions more stringent, while lower temperatures less so. For additional details and explanation of stringency of hybridization reactions, see Ausubel et al., Current Protocols in Molecular Biology, (Wiley Interscience, 1995).

"Stringent conditions" or "high stringency conditions", as defined herein, typically: (1) employ low ionic strength solutions and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual (Cold Spring Harbor Press, 1989), and include the use of washing solution and hybridization conditions (e.g., temperature, ionic strength and % SDS less stringent that those described above. An example of moderately stringent condition is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

"Sensitivity" as used herein refers to the proportion of true positives of the total number tested that actually have the target disorder (i.e., the proportion of patients with the target disorder who have a positive test result). "Specificity" as used herein refers to the proportion of true negatives of all the patients tested who actually do not have the target disorder (i.e., the proportion of patients without the target disorder who have a negative test result).

In the context of the present disclosure, reference to "at least one," "at least two," "at least five," etc. of the genes listed in any particular gene set means any one or any and all combinations of the genes listed.

The terms "splicing" and "RNA splicing" are used interchangeably and refer to RNA processing that removes introns and joins exons to produce mature mRNA with continuous coding sequence that moves into the cytoplasm of a eukaryotic cell.

"Therapeutically effective amount" or "Therapeutically effective dose" refers to an amount of a compound of the disclosure that, when administered to a subject, (e.g., preferably a mammal, more preferably a human), is sufficient to effect treatment, as defined below, of a disease or condition in the animal. The amount of a compound of the disclosure that constitutes a "therapeutically effective amount" will vary depending on the compound, the condition and its severity, the manner of administration, and the age of the subject to be treated, but can be determined routinely by one of ordinary skill in the art having regard to his own knowledge and to this disclosure. Accordingly when a compound administered at an "effective dose" this is intended to mean that the compound is capable of effecting treatment, as defined below, of a disease or condition (e.g., IPF) in a subject at such a dose.

"Treating" or "treatment" as used herein covers the treatment of the disease or condition of interest (e.g., IPF) in a subject, preferably a human, having the disease or condition of interest, and includes: (i) preventing or inhibiting the disease or condition from occurring in a subject, in particular, when such subject is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition. As used herein, the terms "disease," "disorder," and "condition" may be used interchangeably or may be different in that the particular malady, injury or condition may not have a known causative agent (so that etiology has not yet been worked out), and it is, therefore, not yet recognized as an injury or disease but only as an undesirable condition or syndrome, wherein a more or less specific set of symptoms have been identified by clinicians.

The term "exon" refers to any segment of an interrupted gene that is represented in a mature RNA product (B. Lewin, Genes 7V (Cell Press, 1990)). In theory the term "intron" refers to any segment of DNA that is transcribed but removed from within the transcript by splicing together the exons on either side of it. Operationally, exon sequences occur in the mRNA sequence of a gene. Operationally, intron sequences are the intervening sequences within the genomic DNA of a gene, bracketed by exon sequences and usually having GT and AG splice consensus sequences at their 5' and 3' boundaries.

A "computer-based system" refers to a system of hardware, software, and data storage medium used to analyze information. Hardware of a patient computer-based system can include a central processing unit (CPU), and hardware for data input, data output (e.g., display), and data storage. The data storage medium can include any manufacture comprising a recording of the present information as described above, or a memory access device that can access such a manufacture.

As used herein the term "module" refers to any assembly and/or set of operatively-coupled electrical components that can include, for example, a memory, a processor, electrical traces, optical connectors, software (executing in hardware), and/or the like. For example, a module executed in the processor may be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor) capable of performing one or more specific functions associated with that module.

To "record" data, programming or other information on a computer readable medium refers to a process for storing information, using various methods. Any convenient data storage structure may be chosen, based on the approaches used to access the stored information. A variety of data processor programs and formats may be used for storage, e.g. word processing text file, database format, etc.

A "processor" (or "computer processor") references any hardware and/or software combination that will perform the functions required of it. For example, a suitable processor may be a programmable digital microprocessor such as available in the form of an electronic controller, mainframe, server or personal computer (desktop or portable). Where the processor is programmable, suitable programming may be communicated from a remote location to the processor, or previously saved in a computer program product (such as a portable or fixed computer readable storage medium, whether magnetic, optical or solid state device based). For example, a magnetic medium or optical disk may carry the programming, and may be read by a suitable reader communicating with each processor at its corresponding station.

A "test sample" is a sample of one or more cells, preferable a tissue sample (e.g., a lung tissue sample such as a transbronchial biopsy (TBB) sample) obtained from a subject. In some embodiments, a test sample is a biopsy sample that may be obtained by various approaches (e.g., surgery). In particular embodiments, the test sample is a sample obtained by a video-assisted thoracoscopic surgery (VATS); a bronchoalveolar lavage (BAL); a transbronchial biopsy (TBB); or a cryo-transbronchial biopsy. A test sample may be obtained by an ancillary bronchoscopic procedure, such as brushing (such as by cytobrush, histobrush); bronchial biopsy; bronchial lavage; or needle-aspiration. The sample may be obtained by oral washings, touch preps, or sputum collection. The test sample may be obtained from a patient suspected of having a lung disease, e.g., an ILD, based on clinical signs and symptoms with which the patient presents (e.g., shortness of breath (generally aggravated by exertion), dry cough), and, in some cases the results of one or more of an imaging test (e.g., chest X-ray, computerized tomography (CT)), a pulmonary function test (e.g., spirometry, oximetry, exercise stress test), lung tissue analysis (e.g., histological and/or cytological analysis of samples obtained by bronchoscopy, bronchoalveolar lavage, surgical biopsy). In some embodiments, the test sample is obtained from a respiratory epithelium of the subject. The respiratory epithelium may be from the mouth, nose, pharynx, trachea, bronchi, bronchioles, or alveoli. However, other sources of respiratory epithelium also may be used. In some embodiments, the test sample is a pooled sample.

The term "pooling," is used herein to describe either (i) "physical pooling," i.e., actual mixing of samples together or (ii) "in silico pooling," i.e., a method of pooling expression values of one or more genes detected in a sample. A non-limiting example of how such in silico pooling may be performed is outlined in Example 6. The terms "in silico mixing" and "in silico pooling" are used interchangeably herein. A sample, (e.g., a test sample) that comprises a plurality of samples that have undergone physical pooling may be refered to herein as a "pooled sample."

The term "subject," as used herein, generally refers to a mammal. Typically, the subject is a human. However, the term embraces other species, e.g., pigs, mice, rats, dogs, cats, or other primates. In certain embodiments, the subject is an experimental subject such as a mouse or rat. The subject may be a male or female. The subject may be an infant, a toddler, a child, a young adult, an adult or a geriatric. The subject may be a smoker, a former smoker or a nonsmoker. The subject may have a personal or family history of ILD. The subject may have an ILD-free personal or family history. The subject may exhibit one or more symptoms of ILD or another lung disorder (e.g., cancer, emphysema, COPD). For example, the subject may exhibit shortness of breath (generally aggravated by exertion) and/or dry cough), and, in some cases may have obtained results of one or more of an imaging test (e.g., chest X-ray, computerized tomography (CT)), a pulmonary function test (e.g., spirometry, oximetry, exercise stress test), lung tissue analysis (e.g., histological and/or cytological analysis of samples obtained by bronchoscopy, bronchoalveolar lavage, surgical biopsy) that is indicative of the potential presence of an ILD or another lung disorder. In some embodiments, a subject has or has been diagnosed with chronic obstructive pulmonary disease (COPD). In some embodiments, a subject does not have or has not been diagnosed with COPD. A subject under the care of a physician or other health care provider may be referred to as a "patient."

A "gene signature" is a gene expression pattern (i.e., expression level of one or more gene, or fragments thereof), which is indicative of some characteristic or phenotype. In some embodiments, gene signature refers to the expression (and/or lack of expression) of a gene, a plurality of genes, a fragment of a gene or a plurality fragments of one or more genes, which expression and/or lack of expression is indicative of UIP, non-UIP, smoker-status, or non-smoker-status.

As used herein, "is a smoker" is meant to refer to a subject who currently smokes cigarettes or a person who has smoked cigarettes in the past or a person who has the gene signature of a person who currently smokes cigarettes or has smoked cigarettes in the past.

As used herein, "variant", when used to describe a feature used during training of a classifier of the present disclosure, refers to an alternative splice variant.

As used herein, "mutation", when used to describe a feature used during training of a classifier of the present disclosure, refers to a sequence deviation from a known normal reference sequence. In some embodiments, the deviation is a deviation from an accepted native gene sequence according to a publically accessible database such as the UniGene database (Pontius J U, Wagner L, Schuler G D. UniGene: a unified view of the transcriptome. In: The NCBI Handbook. Bethesda (MD): National Center for Biotechnology Information; 2003, incorporated herein), RefSeq (The NCBI handbook [Internet]. Bethesda (MD): National Library of Medicine (US), National Center for Biotechnology Information; 2002 Oct. Chapter 18, The Reference Sequence (RefSeq) Project, available at the World Wide Web address: ncbi.nlm.nih.gov/refseq/), Ensembl (EMBL, available at the World Wide Web address: ensembl.org/index.html), and the like. In some embodiments, the mutation includes an addition, deletion, or substitution of a sequence residue present in the reference sequence.

Abbreviations include: HRCT, high-resolution computed tomography; VATS, video-assisted thoracoscopic surgery; SLB, surgical lung biopsy; TBB, transbronchial biopsy; RB, respiratory bronchiolitis; OP, organizing pneumonia, DAD, diffuse alveolar damage, CIF/NOC, chronic interstitial fibrosis not otherwise classified; MDT, multidisciplinary team; CV, cross-validation; LOPO, leave-one-patient-out; ROC, receiver operator characteristic; AUC, area under the curve; RNASeq, RNA sequencing by next-generation sequencing technology; NGS, next-generation sequencing technology; H&E, hematoxylin and eosin; FDR, false discovery rate; IRB, Institutional Review Board; ATS, American Thoracic Society; COPD, chronic obstructive pulmonary disease; KEGG, Kyoto Encyclopedia of Genes and Genomes; CI, confidence interval.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure. As used herein, "about" means plus or minus 10% of the indicated value.

Methods for Detecting Usual Interstitial Pneumonia (UIP)

Disclosed herein are methods of and/or systems for using a molecular signature to differentiate UIP from non-UIP. The accurate diagnosis of UIP from samples (e.g., sample obtained from a patient) where expert pathology is not available stands to benefit ILD patients by accelerating diagnosis, thus facilitating treatment decisions and reducing surgical risk to patients and costs to the healthcare system.

Also disclosed herein are methods of and/or systems for using the smoker or non-smoker status of a subject to improve differentiation of UIP from other ILD subtypes using a molecular signature.

Thus, the methods and/or systems disclosed herein provide classifiers which can differentiate UIP from non-UIP patterns based on transcriptional data (e.g., high-dimensional transcriptional data) without prior knowledge of clinical or demographic information.

In some embodiments, the present disclosure provides methods for differentiating UIP from non-UIP using a classifier that comprises or consists of one or more sequences or fragments thereof presented in Table 1 and/or Table 15 or at least one sequence or fragment thereof from Table 1 and/or Table 15. In some embodiments, the present disclosure provides methods for differentiating UIP from non-UIP using a classifier that comprises or consists of one or more genes presented in Table 5 or at least one sequence or fragment thereof from Table 5. In some embodiments, the present disclosure provides methods for differentiating UIP from non-UIP using a classifier that comprises or consists of one or more sequences presented in Table 1 and/or Table 15 or at least one sequence from Table 1 and/or Table 15. In some embodiments, the present disclosure provides such methods that use a classifier comprising or consisting of at least 1, 2, 3, 4, 5, 6, 7, 8, 9, 10 or more of the sequences provided in Table 1 and/or Table 15. In some embodiments, the present disclosure provides such methods that use a classifier comprising or consisting of at least 1, 2, 3, 4, 5, 6, 7, 8, 9, 10 or more of the sequences provided in Table 5. For example, in some embodiments, the present disclosure provides such methods that use classifiers comprising or consisting of at least 11, 12, 13, 14, 15, 20, 30, 50, 100, 125, 150, or 151 sequences provided in Table 1, including all integers (e.g., 16, 17, 18, 19, 21, 22, 23, 24, 25 sequences, etc.) and ranges (e.g., from about 1-10 sequences from Table 1, from about 10-15 sequences, 10-20 sequences, 5-30 sequences, 5-50 sequences, 10-100 sequences, 50-151 sequences, etc.) between. In some embodiments, the present disclosure provides such methods that use classifiers comprising or consisting of at least 11, 12, 13, 14, 15, 20, 30, 50, 100, 125, 150, or 169 sequences provided in Table 15, including all integers (e.g., 16, 17, 18, 19, 21, 22, 23, 24, 25 sequences, etc. from Table 15) and ranges (e.g., from about 1-10 sequences from Table 15, from about 10-15 sequences, 10-20 sequences, 5-30 sequences, 5-50 sequences, 10-100 sequences, 50-169 sequences, etc. from Table 15) between. In some embodiments, the present disclosure provides such methods that use classifiers comprising or consisting of at least 11, 12, 13, 14, 15, 20, 30, 50, 100, 125, 150, 160, 170, 180, 181, 182, 183, 184, 185, 186, 187, 188, 189, or 190 genes provided in Table 5, including all integers (e.g., 16, 17, 18, 19, 21, 22, 23, 24, 25 sequences, etc. from Table 5) and ranges (e.g., from about 1-10 sequences from Table 1, from about 10-15 sequences, 10-20 sequences, 5-30 sequences, 5-50 sequences, 10-100 sequences, 50-169 sequences, 60-190 sequence, etc. from Table 5) between. In some embodiments, the present disclosure provides such methods that use classifiers comprising or consisting of at least 11, 12, 13, 14, 15, 20, 30, 50, 100, 125, 150, 200, 250, 300, or 320 sequences provided in one or both of Table 1 and Table 15, including all integers (e.g., 16, 17, 18, 19, 21, 22, 23, 24, 25 sequences, etc. from Table 1 and/or Table 15) and ranges (e.g., from about 1-10 sequences from Table 1 and/or Table 15, from about 10-15 sequences, 10-20 sequences, 5-30 sequences, 5-50 sequences, 10-100 sequences, 50-200, 75-250, 100-300 sequences, etc. from Table 1 and/or Table 15) between. In some embodiments, the present disclosure provides such methods that use classifiers comprising or consisting of at least 11, 12, 13, 14, 15, 20, 30, 50, 100, 125, 150, 200, 250, 300, 320, 350, or more genes provided in one, two, or all of Tables 1, 5, and Table 15, including all integers (e.g., 16, 17, 18, 19, 21, 22, 23, 24, 25 sequences, etc. from Table 1, Table 5 and/or Table 15) and ranges (e.g., from about 1-10 sequences from Table 1, Table 5, and/or Table 15, from about 10-15 sequences, 10-20 sequences, 5-30 sequences, 5-50 sequences, 10-100 sequences, 50-200, 75-250, 100-300 sequences, etc. from Table 1, Table 5, and/or Table 15) between.

TABLE 1

| gene_id | Gene_Biotype | gene_id | Gene_Biotype |
|---|---|---|---|
| ENSG00000162408 | prot_coding | ENSG00000163872 | prot_coding |
| ENSG00000116285 | prot_coding | ENSG00000197701 | prot_coding |
| ENSG00000219481 | prot_coding | ENSG00000168826 | prot_coding |
| ENSG00000204219 | prot_coding | ENSG00000178988 | prot_coding |
| ENSG00000117751 | prot_coding | ENSG00000178177 | prot_coding |
| ENSG00000159023 | prot_coding | ENSG00000109618 | prot_coding |
| ENSG00000116761 | prot_coding | ENSG00000250317 | prot_coding |
| ENSG00000117226 | prot_coding | ENSG00000081041 | prot_coding |
| ENSG00000163386 | prot_coding | ENSG00000145284 | prot_coding |
| ENSG00000186141 | prot_coding | ENSG00000163644 | prot_coding |
| ENSG00000122497 | prot_coding | ENSG00000163110 | prot_coding |
| ENSG00000203832 | prot_coding | ENSG00000138795 | prot_coding |
| ENSG00000143379 | prot_coding | ENSG00000205403 | prot_coding |
| ENSG00000143367 | prot_coding | ENSG00000153404 | prot_coding |
| ENSG00000163220 | prot_coding | ENSG00000206077 | prot_coding |
| ENSG00000007933 | prot_coding | ENSG00000145736 | prot_coding |
| ENSG00000143322 | prot_coding | ENSG00000145730 | prot_coding |
| ENSG00000174307 | prot_coding | ENSG00000168938 | prot_coding |
| ENSG00000143466 | prot_coding | ENSG00000113621 | prot_coding |
| ENSG00000135766 | prot_coding | ENSG00000120738 | prot_coding |
| ENSG00000163029 | prot_coding | ENSG00000253953 | prot_coding |
| ENSG00000115828 | prot_coding | ENSG00000261934 | prot_coding |
| ENSG00000135625 | prot_coding | ENSG00000155846 | prot_coding |
| ENSG00000115317 | prot_coding | ENSG00000186470 | prot_coding |
| ENSG00000228325 | prot_coding | ENSG00000026950 | prot_coding |
| ENSG00000074582 | prot_coding | ENSG00000137331 | prot_coding |
| ENSG00000123983 | prot_coding | ENSG00000244731 | prot_coding |
| ENSG00000144712 | prot_coding | ENSG00000240065 | prot_coding |
| ENSG00000168036 | prot_coding | ENSG00000204252 | prot_coding |
| ENSG00000187094 | prot_coding | ENSG00000137309 | prot_coding |
| ENSG00000179152 | prot_coding | ENSG00000137166 | prot_coding |
| ENSG00000173402 | prot_coding | ENSG00000124702 | prot_coding |
| ENSG00000163412 | prot_coding | ENSG00000112299 | prot_coding |
| ENSG00000227124 | prot_coding | ENSG00000111962 | prot_coding |
| ENSG00000184500 | prot_coding | ENSG00000112110 | prot_coding |
| ENSG00000181458 | prot_coding | ENSG00000048052 | prot_coding |
| ENSG00000034533 | prot_coding | ENSG00000006625 | prot_coding |
| ENSG00000198585 | prot_coding | ENSG00000075303 | prot_coding |
| ENSG00000172667 | prot_coding | ENSG00000158457 | prot_coding |
| ENSG00000078070 | prot_coding | ENSG00000050327 | prot_coding |
| ENSG00000033050 | prot_coding | ENSG00000072310 | prot_coding |
| ENSG00000105983 | prot_coding | ENSG00000108448 | prot_coding |
| ENSG00000164821 | prot_coding | ENSG00000141068 | prot_coding |
| ENSG00000012232 | prot_coding | ENSG00000196712 | prot_coding |
| ENSG00000130958 | prot_coding | ENSG00000242384 | prot_coding |
| ENSG00000041982 | prot_coding | ENSG00000073605 | prot_coding |
| ENSG00000136861 | prot_coding | ENSG00000167941 | prot_coding |
| ENSG00000136933 | prot_coding | ENSG00000154263 | prot_coding |
| ENSG00000160447 | prot_coding | ENSG00000161533 | prot_coding |
| ENSG00000148357 | prot_coding | ENSG00000181045 | prot_coding |
| ENSG00000170835 | prot_coding | ENSG00000211563 | miRNA |
| ENSG00000130653 | prot_coding | ENSG00000132199 | prot_coding |
| ENSG00000165997 | prot_coding | ENSG00000154655 | prot_coding |
| ENSG00000120539 | prot_coding | ENSG00000075643 | prot_coding |
| ENSG00000156113 | prot_coding | ENSG00000101000 | prot_coding |
| ENSG00000138166 | prot_coding | ENSG00000130005 | prot_coding |
| ENSG00000148925 | prot_coding | ENSG00000130513 | prot_coding |
| ENSG00000171714 | prot_coding | ENSG00000213965 | prot_coding |
| ENSG00000149090 | prot_coding | ENSG00000006659 | prot_coding |
| ENSG00000254761 | lincRNA | ENSG00000086544 | prot_coding |
| ENSG00000137474 | prot_coding | ENSG00000104812 | prot_coding |
| ENSG00000149289 | prot_coding | ENSG00000167757 | prot_coding |
| ENSG00000120647 | prot_coding | ENSG00000198464 | prot_coding |
| ENSG00000111679 | prot_coding | ENSG00000022556 | prot_coding |
| ENSG00000139197 | prot_coding | ENSG00000083814 | prot_coding |
| ENSG00000110900 | prot_coding | ENSG00000093072 | prot_coding |
| ENSG00000123358 | prot_coding | ENSG00000185133 | prot_coding |
| ENSG00000172789 | prot_coding | ENSG00000198792 | prot_coding |
| ENSG00000073910 | prot_coding | ENSG00000189306 | prot_coding |
| ENSG00000083544 | prot_coding | ENSG00000100376 | prot_coding |
| ENSG00000187630 | prot_coding | ENSG00000154642 | prot_coding |
| ENSG00000157379 | prot_coding | ENSG00000100557 | prot_coding |
| ENSG00000100592 | prot_coding | ENSG00000100650 | prot_coding |
| ENSG00000119711 | prot_coding | ENSG00000128891 | prot_coding |
| ENSG00000140718 | prot_coding | ENSG00000182810 | prot_coding |
| ENSG00000103044 | prot_coding | | |

The ENSG identifiers listed herein (i.e., the gene ids) refer to gene identifiers for the Ensembl database available at the worldwide web address: ensembl.org, the content of which is incorporated herein by reference in its entirety.

In some particular embodiments, the present disclosure provides methods and/or systems for differentiating UIP from non-UIP using a classifier that comprises or consists of one or more of the sequences or fragments thereof listed in Table 1 and/or Table 15. In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while in some cases including other genes.

In some particular embodiments, the present disclosure provides methods and/or systems for differentiating UIP from non-UIP using a classifier that comprises or consists of one or more of the sequences or fragments thereof listed in Table 5. In particular aspects, the classifier may contain 1, 2, 3, 4, 5, 6, 7, 8, or more additional genes. In other aspects, the classifier may omit 1, 2, 3, 4, 5, 6, 7, 8, or more, of these genes, while in some cases including other genes. In certain embodiments, the present disclosure provides a method and/or system for differentiating UIP from non-UIP using the Envisia classifier, which may contain all of the genes listed in Table 5.

In some embodiments, the present disclosure provides a method and/or system for differentiating UIP from non-UIP using a classifier that comprises or consists of 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; or 151 of the following sequences: ENSG00000162408; ENSG00000116285; ENSG00000219481; ENSG00000204219; ENSG00000117751; ENSG00000159023; ENSG00000116761; ENSG00000117226; ENSG00000163386; ENSG00000186141; ENSG00000122497; ENSG00000203832; ENSG00000143379; ENSG00000143367; ENSG00000163220; ENSG00000007933; ENSG00000143322; ENSG00000174307; ENSG00000143466; ENSG00000135766; ENSG00000163029; ENSG00000115828; ENSG00000135625; ENSG00000115317; ENSG00000228325; ENSG00000074582; ENSG00000123983; ENSG00000144712; ENSG00000168036; ENSG00000187094; ENSG00000179152; ENSG00000173402; ENSG00000163412; ENSG00000227124; ENSG00000184500; ENSG00000181458; ENSG00000034533; ENSG00000198585; ENSG00000172667; ENSG00000078070; ENSG00000033050; ENSG00000105983; ENSG00000164821; ENSG00000012232; ENSG00000130958; ENSG00000041982; ENSG00000136861; ENSG00000136933; ENSG00000160447; ENSG00000148357; ENSG00000170835; ENSG00000130653; ENSG00000165997; ENSG00000120539; ENSG00000156113; ENSG00000138166; ENSG00000148925; ENSG00000171714; ENSG00000254761; ENSG00000149289; ENSG00000111679; ENSG00000110900; ENSG00000172789; ENSG00000083544; ENSG00000157379; ENSG00000100592; ENSG00000119711; ENSG00000140718; ENSG00000103044; ENSG00000197701; ENSG00000178988; ENSG00000109618; ENSG00000081041; ENSG00000163644; ENSG00000138795; ENSG00000153404; ENSG00000145736; ENSG00000168938; ENSG00000120738; ENSG00000261934; ENSG00000186470; ENSG00000137331; ENSG00000240065; ENSG00000137309; ENSG00000124702; ENSG00000111962; ENSG00000048052; ENSG00000075303; ENSG00000050327; ENSG00000108448; ENSG00000196712; ENSG00000073605; ENSG00000154263; ENSG00000181045; ENSG00000132199; ENSG00000075643; ENSG00000130005; ENSG00000213965; ENSG00000086544; ENSG00000167757; ENSG00000022556; ENSG00000093072; ENSG00000198792; ENSG00000100376; ENSG00000154642; ENSG00000149090; ENSG00000137474; ENSG00000120647; ENSG00000139197; ENSG00000123358; ENSG00000073910; ENSG00000187630; ENSG00000100557; ENSG00000100650; ENSG00000128891; ENSG00000182810; ENSG00000163872; ENSG00000168826; ENSG00000178177; ENSG00000250317; ENSG00000145284; ENSG00000163110; ENSG00000205403; ENSG00000206077; ENSG00000145730; ENSG00000113621; ENSG00000253953; ENSG00000155846; ENSG00000026950; ENSG00000244731; ENSG00000204252; ENSG00000137166; ENSG00000112299; ENSG00000112110; ENSG00000006625; ENSG00000158457; ENSG00000072310; ENSG00000141068; ENSG00000242384; ENSG00000167941; ENSG00000161533; ENSG00000211563; ENSG00000154655; ENSG00000101000; ENSG00000130513; ENSG00000006659; ENSG00000104812; ENSG00000198464; ENSG00000083814; ENSG00000185133; ENSG00000189306; alone or in any combination. In particular aspects, such a classifier contains additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

In some embodiments, the present disclosure provides a method and/or system for differentiating UIP from non-UIP using a classifier that comprises or consists of all of the following sequences: ENSG00000162408; ENSG00000116285; ENSG00000219481; ENSG00000204219; ENSG00000117751; ENSG00000159023; ENSG00000116761; ENSG00000117226; ENSG00000163386; ENSG00000186141; ENSG00000122497; ENSG00000203832; ENSG00000143379; ENSG00000143367; ENSG00000163220; ENSG00000007933; ENSG00000143322; ENSG00000174307; ENSG00000143466; ENSG00000135766; ENSG00000163029; ENSG00000115828; ENSG00000135625;

ENSG00000115317;
ENSG00000074582;
ENSG00000144712;
ENSG00000187094;
ENSG00000173402;
ENSG00000227124;
ENSG00000181458;
ENSG00000198585;
ENSG00000078070;
ENSG00000105983;
ENSG00000012232;
ENSG00000041982;
ENSG00000136933;
ENSG00000148357;
ENSG00000130653;
ENSG00000120539;
ENSG00000138166;
ENSG00000171714;
ENSG00000254761;
ENSG00000149289;
ENSG00000111679;
ENSG00000110900;
ENSG00000172789;
ENSG00000083544;
ENSG00000157379;
ENSG00000100592;
ENSG00000119711;
ENSG00000140718;
ENSG00000103044;
ENSG00000197701;
ENSG00000178988;
ENSG00000109618;
ENSG00000081041;
ENSG00000163644;
ENSG00000138795;
ENSG00000153404;
ENSG00000145736;
ENSG00000168938;
ENSG00000120738;
ENSG00000261934;
ENSG00000186470;
ENSG00000137331;
ENSG00000240065;
ENSG00000137309;
ENSG00000124702;
ENSG00000111962;
ENSG00000048052;
ENSG00000075303;
ENSG00000050327;
ENSG00000108448;
ENSG00000196712;
ENSG00000073605;
ENSG00000154263;
ENSG00000181045;
ENSG00000132199;
ENSG00000075643;
ENSG00000130005;
ENSG00000213965;
ENSG00000086544;
ENSG00000167757;
ENSG00000022556;
ENSG00000093072;
ENSG00000198792;
ENSG00000100376; ENSG00000154642. In particular aspects, the classifier contains 1, 2, 3, 4, 5, 6, 7, 8, or more additional genes.

ENSG00000228325;
ENSG00000123983;
ENSG00000168036;
ENSG00000179152;
ENSG00000163412;
ENSG00000184500;
ENSG00000034533;
ENSG00000172667;
ENSG00000033050;
ENSG00000164821;
ENSG00000130958;
ENSG00000136861;
ENSG00000160447;
ENSG00000170835;
ENSG00000165997;
ENSG00000156113;
ENSG00000148925;
ENSG00000149090;
ENSG00000137474;
ENSG00000120647;
ENSG00000139197;
ENSG00000123358;
ENSG00000073910;
ENSG00000187630;
ENSG00000100557;
ENSG00000100650;
ENSG00000128891;
ENSG00000182810;
ENSG00000163872;
ENSG00000168826;
ENSG00000178177;
ENSG00000250317;
ENSG00000145284;
ENSG00000163110;
ENSG00000205403;
ENSG00000206077;
ENSG00000145730;
ENSG00000113621;
ENSG00000253953;
ENSG00000155846;
ENSG00000026950;
ENSG00000244731;
ENSG00000204252;
ENSG00000137166;
ENSG00000112299;
ENSG00000112110;
ENSG00000006625;
ENSG00000158457;
ENSG00000072310;
ENSG00000141068;
ENSG00000242384;
ENSG00000167941;
ENSG00000161533;
ENSG00000211563;
ENSG00000154655;
ENSG00000101000;
ENSG00000130513;
ENSG00000006659;
ENSG00000104812;
ENSG00000198464;
ENSG00000083814;
ENSG00000185133;
ENSG00000189306;

In some embodiments, the present disclosure provides a method and/or system for differentiating UIP from non-UIP using a classifier that comprises or consists of 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; or 190 of the following genes; alone or in combination: ENSG00000005381; ENSG00000005955;
ENSG00000007908; ENSG00000007933;
ENSG00000010379; ENSG00000012232;
ENSG00000022556; ENSG00000026950;
ENSG00000033050; ENSG00000038295;
ENSG00000048052; ENSG00000054803;
ENSG00000054938; ENSG00000060688;
ENSG00000071909; ENSG00000072310;
ENSG00000073605; ENSG00000078070;
ENSG00000079385; ENSG00000081041;
ENSG00000081985; ENSG00000082781;
ENSG00000083814; ENSG00000086544;
ENSG00000089902; ENSG00000092295;
ENSG00000099251; ENSG00000099974;
ENSG00000100376; ENSG00000100557;
ENSG00000101544; ENSG00000102837;
ENSG00000103044; ENSG00000103257;
ENSG00000104812; ENSG00000105255;
ENSG00000105559; ENSG00000105696;
ENSG00000105784; ENSG00000105983;
ENSG00000106018; ENSG00000106178;
ENSG00000107929; ENSG00000108312;
ENSG00000108551; ENSG00000109205;
ENSG00000110092; ENSG00000110900;
ENSG00000110975; ENSG00000111218;
ENSG00000111321; ENSG00000111328;
ENSG00000112164; ENSG00000112299;
ENSG00000112852; ENSG00000114248;
ENSG00000114923; ENSG00000115415;
ENSG00000115607; ENSG00000116285;
ENSG00000116761; ENSG00000119711;
ENSG00000119725; ENSG00000120217;
ENSG00000120738; ENSG00000120903;
ENSG00000121380; ENSG00000121417;
ENSG00000122497; ENSG00000124205;
ENSG00000124702; ENSG00000124935;
ENSG00000125255; ENSG00000128016;
ENSG00000128266; ENSG00000128791;
ENSG00000128891; ENSG00000130164;
ENSG00000130487; ENSG00000130598;
ENSG00000131095; ENSG00000131142;
ENSG00000132199; ENSG00000132204;
ENSG00000132915; ENSG00000132938;
ENSG00000133636; ENSG00000133794;
ENSG00000134028; ENSG00000134245;
ENSG00000135148; ENSG00000135447;
ENSG00000135625; ENSG00000136881;
ENSG00000136883; ENSG00000136928;
ENSG00000136933; ENSG00000137285;
ENSG00000137463; ENSG00000137573;

ENSG00000137709; ENSG00000137968;
ENSG00000138166; ENSG00000138308;
ENSG00000140274; ENSG00000140279;
ENSG00000140323; ENSG00000140450;
ENSG00000140465; ENSG00000140505;
ENSG00000140718; ENSG00000141279;
ENSG00000142178; ENSG00000142661;
ENSG00000143185; ENSG00000143195;
ENSG00000143320; ENSG00000143322;
ENSG00000143367; ENSG00000143379;
ENSG00000143603; ENSG00000144655;
ENSG00000145248; ENSG00000145284;
ENSG00000145358; ENSG00000145736;
ENSG00000148541; ENSG00000148700;
ENSG00000148702; ENSG00000149043;
ENSG00000149289; ENSG00000151012;
ENSG00000151572; ENSG00000152672;
ENSG00000153404; ENSG00000154227;
ENSG00000154451; ENSG00000156414;
ENSG00000157103; ENSG00000157680;
ENSG00000158457; ENSG00000159231;
ENSG00000159674; ENSG00000161609;
ENSG00000162594; ENSG00000163029;
ENSG00000163110; ENSG00000163285;
ENSG00000163412; ENSG00000163635;
ENSG00000163644; ENSG00000163735;
ENSG00000163817; ENSG00000163884;
ENSG00000164604; ENSG00000164821;
ENSG00000165948; ENSG00000165973;
ENSG00000165983; ENSG00000166923;
ENSG00000167748; ENSG00000168004;
ENSG00000168036; ENSG00000168062;
ENSG00000168394; ENSG00000168661;
ENSG00000168938; ENSG00000169248;
ENSG00000170113; ENSG00000170442;
ENSG00000170509; ENSG00000170837;
ENSG00000171016; ENSG00000171408;
ENSG00000171649; ENSG00000171714;
ENSG00000172137; ENSG00000172183;
ENSG00000172215; ENSG00000172667;
ENSG00000173809; ENSG00000173812;
ENSG00000173926; ENSG00000175764;
ENSG00000175806; ENSG00000176046;
ENSG00000177182; ENSG00000177294;
ENSG00000178187; and ENSG00000178229. In particular aspects, such a classifier contains additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

In some embodiments, the present disclosure provides a method and/or system for differentiating UIP from non-UIP using a classifier that comprises or consists of 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; or 190 of the following genes; alone or in combination: MPO; GGNBP2; SELE; FMO3; SLC6A13; EXTL3; NLRP2; BTN3A1; ABCF2; TLL1; HDAC9; CBLN4; CHRDL2; SNRNP40; MYO3B; SREBF1; GSDMB; MCCC1; CEACAM1; CXCL2; IL12RB2; ITGB5; ZNF671; ITPKC; RCOR1; TGM1; HSD17B7P2; DDTL; FAM118A; C14orf105; ADNP2; OLFM4; HAS3; SLC7A5; GYS1; FSD1; PLEKHA4; TMEM59L; RUNDC3B; LMBR1; VIPR2; CCL24; LARP4B; UBTF; RASD1; ODAM; CCND1; TSPAN11; SYT10; PRMT8; LTBR; CDK2AP1; GLP1R; VNN1; PCDHB2; LRRC31; SLC4A3; STAT1; IL18RAP; ERRFI1; CTH; ALDH6A1; ZNF410; CD274; EGR1; CHRNA2; BCL2L14; ZNF211; NBPF14; EDN3; KLHDC3; SCGB1D2; SLCIOA2; ZFP36; GNAZ; TWSG1; C15orf57; LDLR; KLHDC7B; TNNI2; GFAP; CCL25; ENOSF1; LINC00470; PDE6A; MTUS2; NTS; ARNTL; ADAMDEC1; WNT2B; TRAFD1; PPP1R1A; EGR4; BAAT; KIF12; GABBR2; RABEPK; TUBB2B; MGARP; SULF1; POU2F3; SLC44A5; DUSP5; PLA2G12B; DUOXA2; DUOX2; DISP2; ARRDC4; CYP1A1; CYP1A2; FTO; NPEPPS; SIK1; MYOM3; XCL2; ILDR2; CRABP2; ABL2; TUFT1; SETDB1; KCNN3; CSRNP1; SLC10A4; SCD5; DDIT4L; GTF2H2; FAM13C; ADD3; HABP2; SYT8; ZC3H12C; SLC7A11; ANO4; CLEC4F; PLEKHG4B; CERS3; GBP5; TDRD9; SLC6A1; DGKI; TSPAN33; CBR3; SPON2; CCDC155; IL23R; SMC6; PDLIM5; GABRG1; EIF4E3; ATXN7; PPM1K; CXCL5; SLC6A20; KLF15; GPR85; DEFA4; IFI27L1; NELL1; PTER; GREM1; KLK1; HRASLS5; CTNNB1; BATF2; TAP1; ZNF30; PPIC; CXCL11; NIPA1; KRT86; HSD17B13; GPR27; PYGO1; PDE7B; ZIK1; ANDS; CALB2; ISG20; CXCR6; ZMAT3; TDRD12; EIF1; MARCH3; TTLL11; MSRA; NUPR1; CLVS1; FBXO39; ZNF454; and ZNF543. In particular aspects, such a classifier contains additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

In some embodiments, the present disclosure provides a method and/or system for differentiating UIP from non-UIP using a classifier described herein, wherein the method further comprises implementing a classifier that classifies the subject as a smoker or non-smoker. Such a smoker status classification can in some cases be implemented prior to implementing a UIP vs. non-UIP classifier, or a smoker status classification step may be built in as a covariate used during the training (e.g., using a classifier training module) of a UIP vs. non-UIP classifier of the present disclosure.

In particular embodiments, the present disclosure provides a method and/or system for differentiating UIP from non-UIP using the Envisia classifier, wherein the method further comprises implementing a classifier that classifies the subject as a smoker or non-smoker. Such a smoker status classification can in some cases be implemented prior to implementing the Envisia classifier, or a smoker status classification step may be built into the Envisia classifier as a covariate used during re training (e.g., using a classifier training module) of a UIP vs. non-UIP classifier comprising the genes listed in Table 5 according to the present disclosure.

In some embodiments, alternatively, or additionally, the method of and/or system for differentiating UIP from non-UIP using a classifier described herein (e.g., the Envisia classifier) further comprises a step of excluding or assigning differential weight to certain genes or variants thereof that are susceptible to smoker-status bias during the training (e.g., using a classifier training module) or implementation of the UIP vs. non-UIP classifier. As used herein, "smoker status bias" refers to genes or variants thereof, which in non-smoker patients are differentially expressed in UIP vs. non-UIP patients, but which are not detectably differentially expressed in UIP vs. non-UIP patients that are (or have been) smokers.

In some embodiments, the method of and/or system for the present disclosure comprises a tiered classifier comprising at least a first and a second classifier, wherein the first classifier is trained (e.g., using a classifier training module) to recognize gene signatures that distinguish smokers from non-smokers, and a second classifier is trained (e.g., using a classifier training module) to distinguish UIP vs. non-UIP in smokers or non-smokers, respectively. In some such embodiments, the second classifier is the Envisia classifier.

In some embodiments, alternatively, or additionally, the method of and/or system for differentiating UIP from non-UIP using a classifier described herein comprises a step of pooling a plurality of samples obtained from a subject, and then assaying the expression level of a group of transcripts present in the pooled sample. In some embodiments, the plurality of samples equals 2, 3, 4, or 5 samples. In some embodiments, the plurality of samples equals more than 5 samples. In particular aspects, such a classifier contains additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes. In some embodiments, the classifier comprises or consists of 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; or 190 of the genes listed in Table 5. In particular aspects, such a classifier contains additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

In some embodiments, alternatively, or additionally, the method of and/or system for differentiating UIP from non-UIP using a classifier described herein comprises a step of in silico pooling of a plurality of samples obtained from a subject after assaying the expression level of a group of transcripts present in each of the plurality of samples. One example of such in silico pooling is described in Example 6. In some embodiments, a non-limiting example of in silico pooling comprises the steps of (i) assaying an expression level of a group of transcripts present in a first sample of a plurality of samples obtained from an individual subject; (ii) assaying an expression level of the same or an overlapping group of transcripts present in a second sample of the plurality of samples obtained from the individual subject; (iii) in some cases, assaying an expression level of the same or an overlapping group of transcripts (as compared to the first and second sample) in one or more additional samples in the plurality of samples obtained from the individual subject; (iv) scaling the expression levels; (v) averaging the scaled expression levels to produce an "in silico-pooled" expression level; (vi) performing variance stabilized transformation (VST) of the averaged scaled expression levels, (vii) score using VST of the in-silico pooled expressions; and (viii) compare the score to the decision boundary and assign UIP/non-UIP prediction label.

In some embodiments, the number of samples from the subject that are included in the plurality of samples pooled via in silico pooling equals 2, 3, 4, or 5 samples. In some embodiments, the number of samples in the plurality of samples equals more than 5 samples. In particular aspects, such a classifier contains additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

In some embodiments, the number of samples from the subject that are included in the plurality of samples pooled via in silico pooling equals 2, 3, 4, or 5 samples. In some embodiments, number of samples in the plurality of samples equals more than 5 samples. In some embodiments, the classifier comprises or consists of 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; or 190 of the genes listed in Table 5. In particular aspects, such a classifier contains additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

In some particular embodiments, a computer generated classifier for differentiating UIP from non-UIP is trained using expression levels of one or more transcripts expressed in a plurality of individual training samples obtained from a plurality of subjects, each training sample having a confirmed diagnoses (i.e., a "classification label" or "truth label" as disclosed herein (see, e.g., FIG. 1)) of UIP or non-UIP, wherein at least two of the training samples were obtained from a single subject. In some embodiments, the present disclosure provides a method of detecting whether a pooled lung tissue test sample is positive for UIP or non-UIP using such a classifier (e.g., the Envisia classifier), wherein the method comprises (A) assaying the expression level of one or more transcripts expressed in a test sample; and (B) classifying the test sample as UIP or non-UIP using the computer-generated and trained classifier, wherein the test sample is pooled via physical pooling or via in silico pooling.

In some embodiments, by training on all samples separately, maximum representation and sampling diversity is achieved, and a priori sub-sampling bias of available samples is mitigated. Further, in some embodiments, by using pooled samples for the classification step, sampling effects are mitigated. Thus, in some embodiments, the use of a classifier trained on individual (non-pooled) samples with a test sample that has been pooled (either physically or via in silico pooling) provides improved accuracy for differentiating UIP from non-UIP.

Thus, in one embodiment, the present disclosure provides a method of detecting whether a pooled lung tissue test sample from a subject is positive for UIP or non-UIP using the Envisia classifier, the method comprising (A) assaying the expression level of one or more transcripts expressed in a test sample from the subject; and (B) classifying the test sample as UIP or non-UIP using the computer generated Envisia classifier, wherein the test sample comprises a plurality of samples from the subject that have been pooled via physical pooling or via in silico pooling. In some embodiments, the plurality of samples comprises 2, 3, 4, or 5 samples. In some embodiments, the plurality of samples comprises more than 5 samples.

In some embodiments, the method of and/or system for differentiating UIP from non-UIP using a classifier described herein (e.g., the Envisia classifier) comprises differentiating UIP from non-UIP in samples (e.g., a single sample or a pool of samples) that have variable cellular composition. In some embodiments, the samples (e.g., a single sample or a pool of samples) with variable cellular composition comprise type 1 alveolar cells; type 2 alveolar cells, bronchiolar cells, lung progenitor cells, or a combination thereof. In some embodiments, the accuracy of the classifier for differentiating UIP from non-UIP is not dependent on alveolar content of the sample or pooled samples that are classified. As used herein, the term "agnostic to cellular composition" is used in reference to such a classifier, for which the accuracy of the classifier for differentiating UIP from non-UIP is not dependent on alveolar content of the sample (e.g., a single sample or a pool of samples) being classified.

In some embodiments, the present disclosure presents a classifier that is agnostic to cellular composition, the classifier exhibiting a Pearson's correlation between the classifier accuracy and the alveolar content of a sample or pooled samples that is less than about 0.1; 0.09; 0.08; 0.07; 0.06; 0.05; 0.04; 0.03; 0.02; or less than about 0.01. In some embodiments, the present disclosure presents a classifier that is agnostic to cellular composition, the classifier exhibiting a Pearson's correlation between the classifier accuracy and the alveolar content of a sample or pooled samples that is greater than about −0.1; −0.09; −0.08; −0.07; −0.06; −0.05; −0.04; −0.03; −0.02; or greater than about −0.01. In some embodiments, the classifier that is agnostic to cellular composition is the Envisia classifier.

Variable cellular composition in a sample may be detected via any suitable method. In some embodiments, variable cellular composition is determined using a semi-quantitative genomic measure of cellular content. In some embodiments, the semi-quantitative genomic measure of cellular content determines the relative abundance of alveolar cells in a sample.

In some embodiments, such a semi-quantitative genomic measure of alveolar content comprises a metric capable of determining the relative abundance of alveolar type 1 cells in a sample ("alveolar type 1 cell metric"). In some embodiments, the alveolar type 1 cell metric comprises one or more alveolar-specific gene. In some embodiments, the one or more alveolar-specific gene is a gene expressed primarily in alveolar type 1 cells. In certain embodiments, the one or more alveolar-specific gene expressed primarily in alveolar type 1 cells is selected from AQP5, PDPN, or a combination thereof. In particular embodiments, expression of AQP5, PDPN, or a combination thereof correlates with the abundance of alveolar type 1 cells in the sample. In particular embodiments, the method comprises detecting expression levels for AQP5 and PDPN, in some cases normalizing the expression levels, and summing the expression levels for these genes, wherein a high expression level indicates high alveolar type 1 cell content in the sample; a low expression level indicates low alveolar type 1 cell content in the sample; and a moderate expression level indicates moderate alveolar type 1 cell content in the sample.

In particular embodiments, the present disclosure provides a method of determining the relative abundance of type 1 alveolar cells present in two or more samples comprising (i) assaying an expression level in a first sample obtained from an individual subject of one or more transcripts of an alveolar-specific gene expressed primarily in alveolar type 1 cells; (ii) assaying an expression level in a second sample obtained from an individual subject of the same one or more transcript of an alveolar-specific gene expressed primarily in alveolar type 1 cells; (iii) and comparing the expression levels of the one or more transcripts between the two samples to determine the relative abundance of type 1 alveolar cells present in the samples. In some embodiments, the one or more alveolar-specific genes expressed primarily in alveolar type 1 cells is selected from AQP5, PDPN, or a combination thereof. In some embodiments, the one or more alveolar-specific genes expressed primarily in alveolar type 1 cells comprises AQP5, PDPN, or a combination thereof. In some embodiments, the one or more alveolar-specific genes expressed primarily in alveolar type 1 cells comprises both AQP5 and PDPN. In some embodiments, the first sample and the second sample are obtained from different subjects. In some embodiments, the first sample and the second sample are obtained from the same subject. In some embodiments, the method further comprises assaying an expression level in at least one additional sample obtained from an individual subject of the same one or more transcript of an alveolar-specific gene expressed primarily in alveolar type 1 cells and then comparing the expression level in the at least one additional sample to the expression level in the first and/or the second sample to determine the relative abundance of type 1 alveolar cells present in the samples. In some embodiments, at least two of the samples are obtained from the same subject. In some embodiments, at least 3, 4, 5, or more of the samples are obtained from the same subject. In some embodiments, all of the samples are obtained from different subjects.

In some embodiments, the present disclosure provides a semi-quantitative genomic measure of alveolar content comprising a metric capable of determining the relative abundance of alveolar type 2 cells in a sample ("alveolar type 2 cell metric"). In some embodiments, the metric comprises one or more alveolar-specific genes. In some embodiments, the one or more alveolar-specific genes are genes expressed primarily in alveolar type 2 cells. In certain embodiments, the one or more alveolar-specific genes expressed primarily in alveolar type 2 cells are selected from SFTPB, SFTPC, SFTPD, or a combination thereof. In certain embodiments, the one or more alveolar-specific genes expressed primarily in alveolar type 2 cells comprise SFTPB, SFTPC, SFTPD, or a combination thereof. In certain embodiments, the one or more alveolar-specific genes expressed primarily in alveolar type 2 cells comprises SFTPB, SFTPC, and SFTPD. In some embodiments, the alveolar type 2 cell metric further comprises one or more alveolar-specific genes that are expressed in both alveolar type 1 and alveolar type 2 cells. In certain embodiments, the gene expressed in both alveolar type 1 and alveolar type 2 cells is SFTPA1. In particular embodiments, the metric includes one or more alveolar-specific genes expressed primarily in alveolar type 2 cells and one or more genes expressed in both alveolar type 1 and alveolar type 2 cells. In particular embodiments, the metric comprises SFTPB, SFTPC, SFTPD, SFTPA1, or a combination thereof.

In particular embodiments, the present disclosure provides a method of determining the relative abundance of alveolar type 2 cells in a sample comprising detecting expression levels for FTPB, SFTPC, SFTPD, SFTPA1, or a combination thereof, in some cases normalizing the expression levels, and summing the expression levels for these genes, wherein a high expression level indicates high alveolar type 2 cell content in the sample; a low expression level indicates low alveolar type 2 cell content in the sample; and a moderate expression level indicates moderate alveolar type 2 cell content in the sample.

In particular embodiments, the present disclosure provides a method of determining the relative abundance of type 2 alveolar cells present in two or more samples; the method comprising (i) assaying an expression level in a first sample obtained from an individual subject of one or more transcripts of an alveolar-specific gene expressed primarily in alveolar type 2 cells; (ii) assaying an expression level in a second sample obtained from an individual subject of the same one or more transcripts of an alveolar-specific gene expressed primarily in alveolar type 2 cells; (iii) and comparing the expression levels of the one or more transcripts between the two samples to determine the relative abundance of type 2 alveolar cells present in the samples. In some such embodiments, the one or more alveolar-specific genes are expressed primarily in alveolar type 2 cells is selected from SFTPB, SFTPC, and SFTPD, and a combination thereof. In particular embodiments, the method comprises assaying the expression of each of SFTPB, SFTPC, and SFTPD in the first and second samples. Alternatively, or additionally, in various embodiments, the method further comprises assaying an expression level of one or more additional genes in the first sample and second samples. In some such embodiments, the one or more additional genes comprise genes expressed primarily in alveolar cells. In some embodiments, the additional genes are expressed in both alveolar type 1 and alveolar type 2 cells. In particular embodiments, the additional gene is SFTPA1. In some embodiments, the first sample and the second sample are obtained from different subjects. In some embodiments, the first sample and the second sample are obtained from the same subject. In some embodiments, the method further comprises assaying an expression level in at least one additional sample obtained from an individual subject of the same one or more transcripts of an alveolar-specific gene expressed primarily in alveolar type 1 cells and/or in both alveolar type 1 cells and alveolar type 2 cells and then comparing the expression level in the at least one additional sample to the expression level in the first and/or the second sample to determine the relative abundance of type 2 alveolar cells present in the samples. In some embodiments, at least two of the samples are obtained from the same subject. In some embodiments, at least 3, 4, 5, or more of the samples are obtained from the same subject. In some embodiments, all of the samples are obtained from different subjects.

Methods disclosed herein may involve comparing expression levels of informative-genes with one or more appropriate references. An "appropriate reference" is an expression level (or range of expression levels) of a particular informative-gene that is indicative of a known lung ILD status (i.e., UIP vs. non-UIP; IPF vs. non-IPF). An appropriate reference can be determined experimentally by a practitioner of the methods or can be a pre-existing value or range of values. An appropriate reference represents an expression level (or range of expression levels) indicative of UIP/non-UIP status. For example, an appropriate reference may be representative of the expression level of an informative gene in a reference (control) biological sample that is known to express UIP. When an appropriate reference is indicative of UIP, a lack of a detectable difference (e.g., lack of a statistically significant difference) between an expression level determined from a subject in need of characterization or diagnosis of UIP and the appropriate reference may be indicative of UIP in the subject. When an appropriate reference is indicative of UIP, a difference between an expression level determined from a subject in need of characterization or diagnosis of UIP and the appropriate reference may be indicative of the subject being free of UIP (i.e., non-UIP).

Alternatively, an appropriate reference may be an expression level (or range of expression levels) of a gene that is indicative of a subject being free of UIP (i.e., non-UIP). For example, an appropriate reference may be representative of the expression level of a particular informative gene in a reference (control) biological sample obtained from a subject who is known to be free of UIP. When an appropriate reference is indicative of a subject being free of UIP, a difference between an expression level determined from a subject in need of diagnosis of UIP and the appropriate reference may be indicative of UIP in the subject. Alternatively, when an appropriate reference is indicative of the subject being free of UIP, a lack of a detectable difference (e.g., lack of a statistically significant difference) between an expression level determined from a subject in need of diagnosis of UIP and the appropriate reference level may be indicative of the subject being free of UIP.

In some embodiments, the reference standard provides a threshold level of change, such that if the expression level of a gene in a sample is within a threshold level of change (increase or decrease depending on the particular marker) then the subject is identified as free of UIP, but if the levels are above the threshold then the subject is identified as being at risk of having UIP.

In some embodiments, the methods involve comparing the expression level of an informative gene to a reference standard that represents the expression level of the informative-gene in a control subject who is identified as not having UIP. This reference standard may be, for example, the average expression level of the informative gene in a population of control subjects who are identified as not having UIP.

The magnitude of difference between the expression level and an appropriate reference that is statistically significant may vary. For example, a significant difference that indicates UIP may be detected when the expression level of an informative gene in a biological sample is at least 1%, at least 5%, at least 10%, at least 25%, at least 50%, at least 100%, at least 250%, at least 500%, or at least 1000% higher, or lower, than an appropriate reference of that gene. Similarly, a significant difference may be detected when the expression level of an informative gene in a biological sample is at least 1.1-fold, 1.2-fold, 1.5-fold, 2-fold, at least 3-fold, at least 4-fold, at least 5-fold, at least 6-fold, at least 7-fold, at least 8-fold, at least 9-fold, at least 10-fold, at least 20-fold, at least 30-fold, at least 40-fold, at least 50-fold, at least 100-fold, or more higher, or lower, than the appropriate reference of that gene. In some embodiments, at least a 20% to 50% difference in expression between an informative gene and an appropriate reference is significant. Significant differences may be identified by using an appropriate statistical test. Examples of tests for statistical significance are provided in Applied Statistics for Engineers and Scientists by Petruccelli, Chen and Nandram 1999 Reprint Ed, which is entirely incorporated herein by reference.

It is to be understood that a plurality of expression levels may be compared with a plurality of appropriate reference levels, e.g., on a gene-by-gene basis, in order to assess the UIP status of the subject. The comparison may be made as a vector difference. In such cases, multivariate tests, e.g., Hotelling's T2 test, may be used to evaluate the significance of observed differences. Examples of such multivariate tests are provided in Applied Multivariate Statistical Analysis by Richard Arnold Johnson and Dean W. Wichern Prentice Hall; 6th edition (Apr. 2, 2007), which is entirely incorporated herein by reference.

Classification Methods

The methods may also involve comparing a set of expression levels (referred to as an expression pattern or profile) of informative genes in a biological sample obtained from a subject with a plurality of sets of reference levels (referred to as reference patterns), each reference pattern being associated with a known UIP status, identifying the reference pattern that most closely resembles the expression pattern, and associating the known UIP status of the reference pattern with the expression pattern, thereby classifying (characterizing) the UIP status of the subject.

The methods may also involve building or constructing a prediction model, which may also be referred to as a classifier or predictor that can be used to classify the disease status of a subject. As used herein, a "UIP—classifier" is a prediction model that characterizes the UIP status of a subject based on expression levels determined in a biological sample obtained from the subject. Typically the model is built using samples for which the classification (UIP status) has already been ascertained. Once the model (classifier) is built, it may then be applied to expression levels obtained from a biological sample of a subject whose UIP status is unknown in order to predict the UIP status of the subject. In particular embodiments, the UIP-classifier is the Envisia classifier. Thus, the methods may involve applying a UIP-classifier (e.g., the Envisia classifier) to the expression levels, such that the UIP-classifier characterizes the UIP status of a subject based on the expression levels. The subject may be further treated or evaluated, e.g., by a health care provider, based on the predicted UIP status. In some embodiments, the subject may be treated with a compound selected from pirfenidone, nintedanib, or pharmaceutically acceptable salts thereof, based on the predicted UIP status (e.g., based on a classification of UIP determined by applying the classifier to gene expression data from a test sample obtained from the subject. The test sample may comprise a plurality (such as at least 1, 2, 3, 4, 5, or more samples) of physical or in silico pooled samples from the subject.

The classification methods may involve transforming the expression levels into a UIP risk-score that is indicative of the likelihood that the subject has UIP. In some embodiments, such as, for example, when an elastic net regression model such as GLMNET is used, the UIP risk-score may be obtained as the combination (e.g., sum, product, or other combination) of weighted expression levels, in which the expression levels are weighted by their relative contribution to predicting increased likelihood of having UIP.

A variety of prediction models may be used as a UIP-classifier. For example, a UIP-classifier may comprise an algorithm selected from logistic regression, partial least squares, linear discriminant analysis, quadratic discriminant analysis, neural network, naïve Bayes, C4.5 decision tree, k-nearest neighbor, random forest, support vector machine, or other appropriate method.

The UIP-classifier may be trained on a data set comprising expression levels of the plurality of informative genes in biological samples obtained from a plurality of subjects identified as having UIP. For example, the UIP-classifier may be trained on a data set comprising expression levels of a plurality of informative genes in biological samples obtained from a plurality of subjects identified as having UIP based histological findings. The training set will typically also comprise control subjects identified as not having UIP. As will be appreciated by the skilled artisan, the population of subjects of the training data set may have a variety of characteristics by design, e.g., the characteristics of the population may depend on the characteristics of the subjects for whom diagnostic methods that use the classifier may be useful. For example, the population may consist of all males, all females or may consist of both males and females. The population may consist of subjects with a history of cancer, subjects without a history of cancer, or subjects from both categories. The population may include subjects who are smokers, former smokers, and/or non-smokers.

A class prediction strength can also be measured to determine the degree of confidence with which the model classifies a biological sample. This degree of confidence may serve as an estimate of the likelihood that the subject is of a particular class predicted by the model.

Accordingly, the prediction strength conveys the degree of confidence of the classification of the sample and evaluates when a sample cannot be classified. There may be instances in which a sample is tested, but does not belong, or cannot be reliably assigned to, a particular class. This may be accomplished, for example, by utilizing a threshold, or range, wherein a sample which scores above or below the determined threshold, or within the particular range, is not a sample that can be classified (e.g., a "no call").

Once a model is built, the validity of the model can be tested using various methods. One way to test the validity of the model is by cross-validation of the dataset. To perform cross-validation, one, or a subset, of the samples is eliminated and the model is built, as described above, without the eliminated sample, forming a "cross-validation model." The eliminated sample is then classified according to the model, as described herein. This process is done with all the samples, or subsets, of the initial dataset and an error rate is determined. The accuracy of the model is then assessed. This model classifies samples to be tested with high accuracy for classes that are known, or classes have been previously ascertained. Another way to validate the model is to apply the model to an independent data set, such as a new biological sample having an unknown UIP status.

As will be appreciated by the skilled artisan, the strength of the model may be assessed by a variety of parameters including, but not limited to, the accuracy, sensitivity and specificity. Various methods for computing accuracy, sensitivity and specificity are described herein (See, e.g., the Examples). The UIP-classifier may have an accuracy of at least 60%, at least 65%, at least 70%, at least 75%, at least 80%, at least 85%, at least 90%, at least 95%, at least 99%, or more. The UIP classifier may have an accuracy in a range of about 60% to 70%, 70% to 80%, 80% to 90%, or 90% to 100%. The UIP-classifier may have a sensitivity of at least 60%, at least 65%, at least 70%, at least 75%, at least 80%, at least 85%, at least 90%, at least 95%, at least 99%, or more. The UIP-classifier may have a sensitivity in a range of about 60% to 70%, 70% to 80%, 80% to 90%, or 90% to 100%. The UIP-classifier may have a specificity of at least 60%, at least 65%, at least 70%, at least 75%, at least 80%, at least 85%, at least 90%, at least 95%, at least 99%, or more. The UIP-classifier may have a specificity in a range of about 60% to 70%, 70% to 80%, 80% to 90%, or 90% to 100%.

The Negative Predictive Value (NPV) may be greater than or equal to 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% for ruling out UIP in an intended use population (e.g., a subject, such as a patient). When UIP is ruled out, non-UIP may be ruled in.

The UIP classifier may have a positive predictive value (PPV) of greater than or equal to 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% for ruling in UIP. When UIP is ruled in, non-UIP may be ruled out.

The intended use population may have a prevalence of cancer at or about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

In some embodiments, the method and/or systems of the present disclosure comprises: extracting nucleic acids (e.g., RNA, such as, e.g., total RNA) from a test sample (e.g. lung tissue); amplifying the nucleic acid to produce an expressed nucleic acid library (e.g., via polymerase chain reaction-mediated amplification of cDNAs (in some cases labeled cDNAs), which cDNAs may be produced from one or more RNA samples by reverse transcription (RT-PCR)); detecting expression of one or more nucleic acids present in the nucleic acid library (e.g., detecting RNA expression profiles by measuring cDNA species produced via RT-PCR) via an array (e.g., a microarray) or via direct sequencing (e.g., RNAseq); and determining whether the test sample is UIP or non-UIP using a trained classifier described herein (e.g., the Envisia classifier).

In some embodiments, the method and/or system of the present disclosure further comprises incorporating smoker status into the training exercise. In certain embodiments, smoker status is in some cases incorporated in one of the following ways:

(i) by using smoking status as a covariate in a UIP or non-UIP classifier during training (e.g., using a classifier training module).

(ii) by identifying a plurality of genes that are susceptible to smoker-status bias and excluding, or in some cases weighing such genes differently than genes that are not susceptible to such bias, during UIP or Non-UIP classifier training (e.g., using a classifier training module).

(iii) by constructing a tiered classification in which an initial classifier that is trained (e.g., using a classifier training module) to recognize gene signatures that distinguish smokers from non-smokers is used to pre-classify a test sample as "smoker" or "non-smoker" based upon the gene signature of the test sample; and then, subsequent to pre-classification, a distinct classifier that was trained (e.g., using a classifier training module) to distinguish UIP vs. non-UIP in either smokers or non-smokers is implemented. For example, if the pre-classifier determines that the test sample is from a smoker, a UIP vs. non-UIP classification is performed using a classifier trained (e.g., using a classifier training module) with UIP and non-UIP samples from smokers. Conversely, if the pre-classifier determines that the test sample is from a non-smoker, a UIP vs. non-UIP classification is performed using a classifier trained (e.g., using a classifier training module) with UIP and non-UIP samples from non-smokers. In some embodiments, such smoker- or non-smoker-specific classifiers provide improved diagnostic performance due, at least in part, to a reduction in background noise caused by the inclusion of genes susceptible to smoker-status bias in the classifier training.

Accordingly, the present disclosure also provides suitable classifiers for use in methods of differentiating UIP from non-UIP, as disclosed herein (e.g., the Envisia classifier). In various embodiments, the present disclosure provides a classifier suitable for differentiating UIP from non-UIP, wherein the classifier is trained (e.g., using a classifier training module such as, e.g., the Envisia classifer) using microarray, qRT-PCR, or sequencing data from a sample (e.g., an individual sample or a pooled sample) corresponding to one or more histopathology labels determined by an expert pathologist. In some embodiments, the sample is labelled UIP or non-UIP.

In some embodiments, the present disclosure presents a classifier comprising or consisting of one or more sequences or fragments thereof presented in Table 1 and/or Table 15, or at least one sequence or fragment thereof from Table 1 and/or Table 15. In some embodiments, the present disclosure provides a classifier comprising or consisting of at least 1, 2, 3, 4, 5, 6, 7, 8, 9, 10 or more of the sequences provided in any one or more or all of Table 1 and/or Table 15. For example, in some embodiments, the present disclosure provides a classifier comprising or consisting of at least 11, 12, 13, 14, 15, 20, 30, 50, 100, 150, 151 sequences provided in Table 1, including all integers (e.g., 16, 17, 18, 19, 21, 22, 23, 24, 25 sequences, etc.) and ranges (e.g., from about 1-10 sequences from any one or more or all of Tables 5, 7, 8, 9, 10, 11, or 12, from about 10-15 sequences, 10-20 sequences, 5-30 sequences, 5-50 sequences, 10-100 sequences, 50-151 sequences from any one or more or all of Table 1 and/or Table 15) between. In one embodiment, the present disclosure provides a classifier that comprises or consists of all sequences provided in Table 1 and/or Table 15.

In some embodiments, the present disclosure presents a classifier comprising or consisting of one or more sequences or fragments thereof presented in Table 5, or at least one sequence or fragment thereof from Table 5. In some embodiments, the present disclosure provides a classifier comprising or consisting of at least 1, 2, 3, 4, 5, 6, 7, 8, 9, 10 or more of the sequences provided in Table 5. For example, in some embodiments, the present disclosure provides a classifier comprising or consisting of at least 11, 12, 13, 14, 15, 20, 30, 50, 100, 150, 160, 170, 180, or 190 sequences provided in Table 5, including all integers (e.g., 16, 17, 18, 19, 21, 22, 23, 24, 25 sequences, etc.) and ranges (e.g., from about 1-10 sequences from any one or more or all of Tables 5, 7, 8, 9, 10, 11, or 12, from about 10-15 sequences, 10-20 sequences, 5-30 sequences, 5-50 sequences, 10-100 sequences, 50-150 sequences, 60-190 sequences from Table 5) between. In one embodiment, the present disclosure provides a classifier that comprises or consists of all sequences provided in Table 5.

In some embodiments, the present disclosure provides a classifier for differentiating UIP from non-UIP, wherein the classifier comprises or consists of 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; or 151 of the abovementioned 151 sequences. In particular aspects, the classifier contains 1, 2, 3, 4, 5, 6, 7, 8, or more additional genes or fragments thereof. In other aspects, the classifier omits 1, 2, 3, 4, 5, 6, 7, 8, or more, of the abovementioned 151 sequences, while in some cases including other genes. In other aspects, each of the 151 genes may be used in combination with any one or more, or up to 20 more, of the other genes.

In some particular embodiments, the present disclosure provides a classifier for differentiating UIP from non-UIP, wherein the classifier comprises or consists of one or more of the genes listed in Table 5, or fragments thereof, or any combination thereof. In one embodiment, the classifier comprises or consists of all 190 of the genes listed in Table 5. In some embodiments, the present disclosure provides a classifier for differentiating UIP from non-UIP, wherein the classifier comprises or consists of 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; or 190 of the abovementioned 190 genes listed in Table 5. In particular aspects, the classifier contains the 190 genes listed in Table 5 and 1, 2, 3, 4, 5, 6, 7, 8, or more additional genes or fragments thereof. In other aspects, the classifier omits 1, 2, 3, 4, 5, 6, 7, 8, or more, of the abovementioned 190 genes listed in Table 5, while in some cases including other genes. In other aspects, each of the 190 genes may be used in combination with any one or more, or up to 20 more, of the other genes to classify as sample as UIP or non-UIP according to the methods disclosed herein.

In certain embodiments, the present disclosure provides a method of improving the detection of a disease or condition in a lung tissue sample, the method comprising (A) assaying the expression level of one or more transcripts expressed in a test sample; and (B) classifying the test sample as either positive for, or negative for, the disease or condition using a computer generated trained classifier (e.g., the Envisia classifier); wherein the computer generated trained classifier is trained using expression levels of one or more transcripts expressed in a plurality of individual training samples obtained from a plurality of subjects, each training sample having a confirmed diagnoses of positive or negative for the disease or condition, wherein at least two of the training samples were obtained from a single subject; and wherein the test sample is pooled prior to the classifying.

Tissue Samples

A lung tissue sample for use in a subject analytical or diagnostic method may be a biopsy sample (e.g., a biopsy sample obtained by video-assisted thoracoscopic surgery; VATS); a bronchoalveolar lavage (BAL) sample; a transbronchial biopsy; a cryo-transbronchial biopsy; and the like. Lung tissue samples for analysis may be provided in a suitable preservation solution. In some embodiments, a tissue sample is obtained by an ancillary bronchoscopic procedure such as brushing (such as by cytobrush, histobrush); bronchial biopsy; bronchial lavage; or needle-aspiration. In some embodiments, the tissue sample may be obtained by oral washings, touch preps, or sputum collection. In some embodiments, the tissue sample is obtained from a respiratory epithelium of the subject. The respiratory epithelium may be from the mouth, nose, pharynx, trachea, bronchi, bronchioles, or alveoli. However, other sources of respiratory epithelium also may be used.

Tissue samples may be obtained from a patient suspected of having a lung disease, e.g., an ILD, based on clinical signs and symptoms with which the patient presents (e.g., shortness of breath (generally aggravated by exertion), dry cough), and, in some cases the results of one or more imaging tests (e.g., chest X-ray, computerized tomography (CT)), a pulmonary function test (e.g., spirometry, oximetry, exercise stress test), and/or lung tissue analysis (e.g., histological and/or cytological analysis of samples obtained by bronchoscopy, bronchoalveolar lavage, surgical biopsy). In some cases the cytological or histological analysis of the tissue sample may be ambiguous or suspicious (or indeterminate) for a presence or absence of lung disease.

The lung tissue sample may be processed in any of a variety of ways. For example, the lung tissue sample may be subjected to cell lysis. The lung tissue sample may be preserved in RNAprotect solution (a solution that inhibits RNA degradation, e.g., that inhibits nuclease digestion of RNA) and subsequently subjected to cell lysis. Components such as nucleic acids and/or proteins may be enriched or isolated from the lung tissue sample, and the enriched or isolated component may be used in a subject method. Various methods of enriching for and isolating components such nucleic acids and may be used. Various methods of isolating RNA for expression analysis may be used.

In Vitro Methods of Determining Expression Product Levels

Methods for determining gene expression product levels may include but are not limited to one or more of the following: additional cytological assays, assays for specific proteins or enzyme activities, assays for specific expression products including protein or RNA or specific RNA splice variants, in situ hybridization, whole or partial genome expression analysis, microarray hybridization assays, serial analysis of gene expression (SAGE), enzyme linked immunoabsorbance assays, mass-spectrometry, immunohistochemistry, blotting, sequencing, RNA sequencing (e.g., exome enriched RNA sequencing), DNA sequencing (e.g., sequencing of cDNA obtained from RNA); next-generation sequencing, nanopore sequencing, pyrosequencing, or Nanostring sequencing. For example, gene expression product levels may be determined according to the methods described in Kim, et. al. (Lancet Respir Med. 2015 June; 3(6):473-82, incorporated herein in its entirety, including all supplements). As used herein, the terms "assaying" or "detecting" or "determining" are used interchangeably in reference to determining gene expression product levels. In embodiments, the above-mentioned methods of determining gene expression product levels are suitable for detecting or assaying gene expression product levels. Gene expression product levels may be normalized to an internal standard such as total mRNA or the expression level of a particular gene including but not limited to glyceraldehyde-3-phosphate dehydrogenase, or tubulin.

In various embodiments, a sample comprises cells harvested from a tissue sample (e.g., a lung tissue sample such as a TBB sample). Cells may be harvested from a sample using various techniques. For example, cells may be harvested by centrifuging a cell sample and resuspending the pelleted cells. The cells may be resuspended in a buffered solution such as phosphate-buffered saline (PBS). After centrifuging the cell suspension to obtain a cell pellet, the cells may be lysed to extract nucleic acid, e.g., messenger RNA (mRNA). All samples obtained from a subject, including those subjected to any sort of further processing, are considered to be obtained from the subject.

The sample, in one embodiment, is further processed before detection of the gene expression products is performed as described herein. For example, mRNA in a cell or tissue sample may be separated from other components of the sample. The sample may be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the gene expression product. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., Proc. Natl. Acad. Sci. USA, 86:1173 (1989), incorporated by reference in its entirety for all purposes), self-sustained sequence replication (Guatelli et al., Proc. Nat. Acad. Sci. USA, 87:1874 (1990), incorporated by reference in its entirety for all purposes), incorporated by reference in its entirety for all purposes, and nucleic acid based sequence amplification (NASBA). Examples of guidelines for selecting primers for PCR amplification are provided in McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA gene expression product sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double-stranded molecules from the non-natural single-stranded cDNA, or the mRNA, by introducing additional sequences and forming non-natural hybrids. Further, amplification procedures have error rates associated with them. Therefore, amplification introduces further modifications into the cDNA molecules. In one embodiment, during amplification with the adapter-specific primers, a detectable label, e.g., a fluorophore, is added to single-stranded cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In some embodiments, the expression of a gene expression product of interest is detected at the nucleic acid level via detection of non-natural cDNA molecules.

The gene expression products described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length gene expression product polynucleotide disclosed herein. A fragment of a gene expression product polynucleotide will generally encode at least 15, 25, 30, 50, 100, 150, 200, or 250 contiguous amino acids, or up to the total number of amino acids present in a full-length gene expression product protein of the disclosure.

In certain embodiments, a gene expression profile may be obtained by whole transcriptome shotgun sequencing ("WTSS" or "RNAseq"; see, e.g., Ryan et al BioTechniques 45: 81-94), which makes the use of high-throughput sequencing technologies to sequence cDNA in order to about information about a sample's RNA content. In general terms, cDNA is made from RNA, the cDNA is amplified, and the amplification products are sequenced.

After amplification, the cDNA or derivative thereof may be sequenced using any convenient method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513: 19-39) and Morozova (Genomics. 2008 92:255-64), which are incorporated by reference for the general descriptions of the methods and the particular steps of the methods, including all starting products, reagents, and final products for each of the steps. As may be apparent, forward and reverse sequencing primer sites that compatible with a selected next-generation sequencing platform may be added to the ends of the fragments during the amplification step.

In other embodiments, the products may be sequenced using nanopore sequencing (e.g. as described in Soni et al Clin Chem 53: 1996-2001 2007, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology as disclosed in U.S. Pat. Nos. 5,795,782, 6,015,714, 6,627,067, 7,238,485 and 7,258,838 and U.S. patent application publications US2006003171 and US20090029477.

In some embodiments, the gene expression product of the subject methods is a protein, and the amount of protein in a particular biological sample is analyzed using a classifier derived from protein data obtained from cohorts of samples. The amount of protein may be determined by one or more of the following: enzyme-linked immunosorbent assay (ELISA), mass spectrometry, blotting, or immunohistochemistry.

In some embodiments, gene expression product markers and alternative splicing markers may be determined by microarray analysis using, for example, Affymetrix arrays, cDNA microarrays, oligonucleotide microarrays, spotted microarrays, or other microarray products from Biorad, Agilent, or Eppendorf. Microarrays provide particular advantages because they may contain a large number of genes or alternative splice variants that may be assayed in a single experiment. In some cases, the microarray device may contain the entire human genome or transcriptome or a substantial fraction thereof allowing a comprehensive evaluation of gene expression patterns, genomic sequence, or alternative splicing. Markers may be found using standard molecular biology and microarray analysis techniques as described in Sambrook Molecular Cloning a Laboratory Manual 2001 and Baldi, P., and Hatfield, W. G., DNA Microarrays and Gene Expression 2002.

Microarray analysis generally begins with extracting and purifying nucleic acid from a biological sample, (e.g. a biopsy or fine needle aspirate) using various approaches. For expression and alternative splicing analysis it may be advantageous to extract and/or purify RNA from DNA. It may further be advantageous to extract and/or purify niRNA from other forms of RNA, such as tRNA and rRNA.

Purified nucleic acid may further be labeled with a fluorescent label, radionuclide, or chemical label such as biotin, digoxigenin, or digoxin for example by reverse transcription, polymerase chain reaction (PCR), ligation, chemical reaction or other techniques. The labeling may be direct or indirect which may further require a coupling stage. The coupling stage can occur before hybridization, for example, using aminoallyl-UTP and NHS amino-reactive dyes (like cyanine dyes) or after, for example, using biotin and labelled streptavidin. In one example, modified nucleotides (e.g. at a 1 aaUTP: 4 TTP ratio) are added enzymatically at a lower rate compared to normal nucleotides, typically resulting in 1 every 60 bases (measured with a spectrophotometer). The aaDNA may then be purified with, for example, a column or a diafiltration device. The aminoallyl group is an amine group on a long linker attached to the nucleobase, which reacts with a reactive label (e.g. a fluorescent dye).

The labeled samples may then be mixed with a hybridization solution which may contain sodium dodecyl sulfate (SDS), SSC, dextran sulfate, a blocking agent (such as COT1 DNA, salmon sperm DNA, calf thymus DNA, PolyA or PolyT), Denhardt's solution, formamine, or a combination thereof.

A hybridization probe is a fragment of DNA or RNA of variable length, which is used to detect in DNA or RNA samples the presence of nucleotide sequences (the DNA target) that are complementary to the sequence in the probe. The probe thereby hybridizes to single-stranded nucleic acid (DNA or RNA) whose base sequence allows probe-target base pairing due to complementarity between the probe and target. The labeled probe is first denatured (by heating or under alkaline conditions) into single-stranded DNA and then hybridized to the target DNA.

To detect hybridization of the probe to its target sequence, the probe is tagged (or labeled) with a molecular marker; commonly used markers are 32P or Digoxigenin, which is nonradioactive antibody-based marker. DNA sequences or RNA transcripts that have moderate to high sequence complementarity (e.g. at least 70%, 80%, 90%, 95%, 96%, 97%, 98%, 99%, or more complementarity) to the probe are then detected by visualizing the hybridized probe via autoradiography or other imaging techniques. Detection of sequences with moderate or high complementarity depends on how stringent the hybridization conditions were applied; high stringency, such as high hybridization temperature and low salt in hybridization buffers, permits only hybridization between nucleic acid sequences that are highly similar, whereas low stringency, such as lower temperature and high salt, allows hybridization when the sequences are less similar. Hybridization probes used in DNA microarrays refer to DNA covalently attached to an inert surface, such as coated glass slides or gene chips, and to which a mobile cDNA target is hybridized.

A mix comprising target nucleic acids to be hybridized to probes on an array may be denatured by heat or chemical approaches and added to a port in a microarray. The holes may then be sealed and the microarray hybridized, for example, in a hybridization oven, where the microarray is mixed by rotation, or in a mixer. After an overnight hybridization, non-specific binding may be washed off (e.g., with SDS and SSC). The microarray may then be dried and scanned in a machine comprising a laser that excites the dye and a detector that measures emission by the dye. The image may be overlaid with a template grid and the intensities of the features (e.g., a feature comprising several pixels) may be quantified.

Various kits may be used for the amplification of nucleic acid and probe generation of the subject methods. Examples of kit that may be used in the present disclosure include but are not limited to Nugen WT-Ovation™ FFPE kit, cDNA amplification kit with Nugen Exon Module and Frag/Label module. The NuGEN WT-Ovation™ FFPE System V2 is a whole transcriptome amplification system that enables conducting global gene expression analysis on the vast archives of small and degraded RNA derived from FFPE samples. The system is comprised of reagents and a protocol required for amplification of as little as 50 ng of total FFPE RNA. The protocol may be used for qPCR, sample archiving, fragmentation, and labeling. The amplified cDNA may be fragmented and labeled in less than two hours for GeneChip™ 3' expression array analysis using NuGEN's FL-Ovation™ cDNA Biotin Module V2. For analysis using Affymetrix GeneChip™ Exon and Gene ST arrays, the amplified cDNA may be used with the WT-Ovation™ Exon Module, then fragmented and labeled using the FL-Ovation™ cDNA Biotin Module V2. For analysis on Agilent arrays, the amplified cDNA may be fragmented and labeled using NuGEN's FL-Ovation™ cDNA Fluorescent Module.

In some embodiments, Ambion™ WT-expression kit may be used. Ambion WT-expression kit allows amplification of total RNA directly without a separate ribosomal RNA (rRNA) depletion step. With the Ambion™ WT Expression Kit, samples as small as 50 ng of total RNA may be analyzed on Affymetrix™ GeneChip™ Human, Mouse, and Rat Exon and Gene 1.0 ST Arrays. In addition to the lower input RNA requirement and high concordance between the Affymetrix™ method and TaqMan™ real-time PCR data, the Ambion™ WT-expression kit provides a significant increase in sensitivity. For example, a greater number of probe sets detected above background may be obtained at the exon level with the Ambion™ WT-expression kit as a result of an increased signal-to-noise ratio. The Ambion™-expression kit may be used in combination with additional Affymetrix™ labeling kits. In some embodiments, AmpTec™ Trinucleotide Nano mRNA Amplification kit (6299-A15) may be used in the subject methods. The ExpressArt™ TRinucleotide™ mRNA amplification Nano kit is suitable for a wide range, from 1 ng to 700 ng of input total RNA. According to the amount of input total RNA and the required yields of aRNA, it may be used for 1-round (input >300 ng total RNA) or 2-rounds (minimal input amount 1 ng total RNA), with aRNA yields in the range of >10 μg. AmpTec's proprietary TRinucleotide™ priming technology results in preferential amplification of mRNAs (independent of the universal eukaryotic 3'-poly(A)-sequence), combined with selection against rRNAs. This kit may be used in combination with cDNA conversion kit and Affymetrix™ labeling kit.

The raw data may then be normalized, for example, by subtracting the background intensity and then dividing the intensities making either the total intensity of the features on each channel equal or the intensities of a reference gene and then the t-value for all the intensities may be calculated. More sophisticated methods, include z-ratio, loess and lowess regression and RMA (robust multichip analysis), such as for Affymetrix chips.

In some embodiments, the above described methods may be used for determining transcript expression levels for training (e.g., using a classifier training module) a classifier to differentiate whether a subject has UIP or non-UIP. In some embodiments, the above described methods may be used for determining transcript expression levels for inputting into a classifier module that is able to differentiate whether a sample is UIP or non-UIP.

Data Analysis (i) Comparison of Sample to Normal

In some embodiments, results of molecular profiling performed on a sample from a subject ("test sample") may be compared to a biological sample that is known or suspected to be normal ("normal sample"). In some embodiments, a normal sample is a sample that does not comprise or is expected to not comprise an ILD, or conditions under evaluation, or may test negative in the molecular profiling assay for the one or more ILDs under evaluation. In some embodiments, a normal sample is that which is or is expected to be free of any ILD, or a sample that may test negative for any ILD in the molecular profiling assay. The normal sample may be from a different subject from the subject being tested, or from the same subject. In some cases, the normal sample is a lung tissue sample obtained from a subject such as the subject being tested for example. The normal sample may be assayed at the same time, or at a different time from the test sample. In some embodiments, a normal sample is a sample that is known or suspected to be from a non-smoker. In particular embodiments, the normal sample is a sample that has been confirmed by at least two expert pathologists to be a non-UIP sample. In particular embodiments, the normal sample is a sample that has been confirmed by at least two expert pathologists to be a non-IPF sample.

The results of an assay on the test sample may be compared to the results of the same assay on a sample having a known disease state (e.g., normal, affected by a selected ILD (e.g., IPF, NSIP, etc.), smoker, non-smoker, non-UIP, UIP). In some cases the results of the assay on the normal sample are from a database, or a reference. In some cases, the results of the assay on the normal sample are a generally accepted value or range of values by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, gene product expression levels, gene product expression level changes, alternative exon usage, changes in alternative exon usage, protein levels, DNA polymorphisms, copy number variations, indications of the presence or absence of one or more DNA markers or regions, or nucleic acid sequences.

(ii) Evaluation of Results

In some embodiments, the molecular profiling results are evaluated using various approaches for correlating gene product expression levels or alternative exon usage with specific phenotypes such as a particular ILD, or normalcy (e.g. disease or condition free). In some cases, a specified statistical confidence level may be determined in order to provide a diagnostic confidence level. For example, it may be determined that a confidence level of greater than 90% may be a useful predictor of the presence of an ILD or of a smoker or non-smoker status. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen as a useful phenotypic predictor. The confidence level provided may in some cases be related to the quality of the sample, the quality of the data, the quality of the analysis, the specific methods used, and/or the number of gene expression products analyzed. The specified confidence level for providing a diagnosis may be chosen on the basis of the expected number of false positives or false negatives and/or cost. Methods for choosing parameters for achieving a specified confidence level or for identifying markers with diagnostic power include but are not limited to Receiver Operating Characteristic (ROC) curve analysis, binormal ROC, principal component analysis, partial least squares analysis, singular value decomposition, least absolute shrinkage and selection operator analysis, least angle regression, and the threshold gradient directed regularization method.

(iii) Data Analysis

Raw gene expression level and alternative splicing data may in some cases be improved through the application of methods and/or processes designed to normalize and or improve the reliability of the data. In some embodiments of the present disclosure the data analysis requires a computer or other device, machine or apparatus for application of the various methods and/or processes described herein due to the large number of individual data points that are processed. A "machine learning classifier" refers to a computational-based prediction data structure or method, employed for characterizing a gene expression profile. The signals corresponding to certain expression levels, which are obtained by, e.g., exome enriched RNA sequencing or microarray-based hybridization assays, are typically subjected to the classifier to classify the expression profile. Supervised learning generally involves "training" a classifier to recognize the distinctions among classes and then "testing" the accuracy of the classifier on an independent test set. For new, unknown samples the classifier may be used to predict the class in which the samples belong. In various embodiments, such training is be achieved, e.g., using a classifier training module.

In some cases, the robust multi-array average (RMA) method may be used to normalize raw data. The RMA method begins by computing background-corrected intensities for each matched cell on a number of microarrays. The background corrected values are restricted to positive values as described by Irizarry et al. Biostatistics 2003 April 4 (2): 249-64. After background correction, the base-2 logarithm of each background corrected matched-cell intensity is then obtained. The back-ground corrected, log-transformed, matched intensity on each microarray is then normalized using the quantile normalization method in which for each input array and each probe expression value, the array percentile probe value is replaced with the average of all array percentile points, this method is more completely described by Bolstad et al. Bioinformatics 2003. Following quantile normalization, the normalized data may then be fit to a linear model to obtain an expression measure for each probe on each microarray. Tukey's median polish algorithm (Tukey, J. W., Exploratory Data Analysis. 1977) may then be used to determine the log-scale expression level for the normalized probe set data.

Various other software and/or hardware modules or processes may be implemented. In certain methods, feature selection and model estimation may be performed by logistic regression with lasso penalty using glmnet (Friedman J, Hastie T, Tibshirani R. Regularization Paths for Generalized Linear Models via Coordinate Descent. Journal of statistical software 2010; 33(1): 1-22). Raw reads may be aligned using TopHat (Trapnell C, Pachter L, Salzberg S L. TopHat: discovering splice junctions with RNA-Seq. Bioinformatics 2009; 25(9): 1105-11.). Gene counts may be obtained using HTSeq (Anders S, Pyl P T, Huber W. HTSeq-a Python framework to work with high-throughput sequencing data. Bioinformatics 2014.) and normalized using DESeq (Love M I, Huber W, Anders S. Moderated estimation of fold change and dispersion for RNA-Seq data with DESeq2; 2014). In methods, top features (N ranging from 10 to 200) were used to train a linear support vector machine (SVM) (Suykens J A K, Vandewalle J. Least Squares Support Vector Machine Classifiers. Neural Processing Letters 1999; 9(3): 293-300) using the e1071 library (Meyer D. Support vector machines: the interface to libsvm in package e1071. 2014.). Confidence intervals may be computed using the pROC package (Robin X, Turck N, Hainard A, et al. pROC: an open-source package for R and S+ to analyze and compare ROC curves. BMC bioinformatics 2011; 12: 77)

In addition, data may be filtered to remove data that may be considered suspect. In some embodiments, data deriving from microarray probes that have fewer than about 4, 5, 6, 7 or 8 guanosine and cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine and cytosine nucleotides may be considered unreliable due to their aberrant hybridization propensity or secondary structure issues.

In some cases, unreliable probe sets may be selected for exclusion from data analysis by ranking probe-set reliability against a series of reference datasets. For example, RefSeq or Ensembl (EMBL) are considered very high quality reference datasets. Data from probe sets matching RefSeq or Ensembl sequences may in some cases be specifically included in microarray analysis experiments due to their expected high reliability. Similarly data from probe-sets matching less reliable reference datasets may be excluded from further analysis, or considered on a case by case basis for inclusion. In some cases, the Ensembl high throughput cDNA (HTC) and/or mRNA reference datasets may be used to determine the probe-set reliability separately or together. In other cases, probe-set reliability may be ranked. For example, probes and/or probe-sets that match perfectly to all reference datasets such as for example RefSeq, HTC, HTSeq, and mRNA, may be ranked as most reliable (1). Furthermore, probes and/or probe-sets that match two out of three reference datasets may be ranked as next most reliable (2), probes and/or probe-sets that match one out of three reference datasets may be ranked next (3) and probes and/or probe sets that match no reference datasets may be ranked last (4). Probes and or probe-sets may then be included or excluded from analysis based on their ranking. For example, one may choose to include data from category 1, 2, 3, and 4 probe-sets; category 1, 2, and 3 probe-sets; category 1 and 2 probe-sets; or category 1 probe-sets for further analysis. In another example, probe-sets may be ranked by the number of base pair mismatches to reference dataset entries. It is understood that there are many methods understood in the art for assessing the reliability of a given probe and/or probe-set for molecular profiling and the methods of the present disclosure encompass any of these methods and combinations thereof.

In some embodiments of the present disclosure, data from probe-sets may be excluded from analysis if they are not expressed or expressed at an undetectable level (not above background). A probe-set is judged to be expressed above background if for any group:

Integral from T0 to Infinity of the standard normal distribution<Significance (0.01)

Where: TO=Sqr(GroupSize) (T-P)/Sqr(Pvar); GroupSize=Number of CEL files in the group, T=Average of probe scores in probe-set, P=Average of Background probes averages of GC content, and Pvar=Sum of Background probe variances/(Number of probes in probe-set) 2, This allows probe-sets in which the average of probe-sets in a group is greater than the average expression of background probes of similar GC content as the probe-set probes as the center of background for the probe-set, and enables one to derive the probe-set dispersion from the background probe-set variance.

In some embodiments of the present disclosure, probe-sets that exhibit no, or low variance may be excluded from further analysis. Low-variance probe-sets are excluded from the analysis via a Chi-Square test. A probe-set is considered to be low-variance if its transformed variance is to the left of the 99 percent confidence interval of the Chi-Squared distribution with (N-1) degrees of freedom. (N-1)*Probe-set Variance/(Gene Probe-set Variance) of about Chi-Sq(N-1), where N is the number of input CEL files, (N-1) is the degrees of freedom for the Chi-Squared distribution, and the "probe-set variance for the gene" is the average of probe-set variances across the gene. In some embodiments of the present disclosure, probe-sets for a given gene or transcript cluster may be excluded from further analysis if they contain less than a minimum number of probes that pass through the previously described filter steps for GC content, reliability, variance and the like. For example, in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of data analysis of gene expression levels or of alternative splicing may further include the use of a feature selection method and/or process as provided herein. In some embodiments of the present disclosure, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420).

Methods of data analysis of gene expression levels and/or of alternative splicing may further include the use of a pre-classifier method and/or process (e.g., implemented by a pre-classifier analysis module). For example, a method and/or process may use a cell-specific molecular fingerprint to pre-classify the samples according to their composition and then apply a correction/normalization factor. This data/information may then be fed in to a final classification method and/or process which may incorporate that information to aid in the final diagnosis.

In certain embodiments, the methods of the present disclosure include the use of a pre-classifier method and/or process (e.g., implemented by a pre-classifier analysis module) that uses a molecular fingerprint to pre-classify the samples as smoker or non-smoker prior to application of a UIP/non-UIP classifier of the present disclosure.

Methods of data analysis of gene expression levels and/or of alternative splicing may further include the use of a classifier method and/or process (e.g., implemented by a classifier analysis module) as provided herein. In some embodiments of the present disclosure a diagonal linear discriminant analysis, k-nearest neighbor classifier, support vector machine (SVM) classifier, linear support vector machine, random forest classifier, or a probabilistic model-based method or a combination thereof is provided for classification of microarray data. In some embodiments, identification markers that distinguish samples (e.g. UIP from non-UIP, first ILD from second ILD, normal vs ILD), or distinguish subtypes (e.g. IPF vs. NSIP) are selected based on statistical significance of the difference in expression levels between classes of interest. In some cases, the statistical significance is adjusted by applying a Benjamini Hochberg procedure or another correction for false discovery rate (FDR).

In some cases, the classifier may be supplemented with a meta-analysis approach such as that described by Fishel and Kaufman et al. 2007 Bioinformatics 23(13): 1599-606. In some cases, the classifier may be supplemented with a meta-analysis approach such as a repeatability analysis. In some cases, the repeatability analysis selects markers that appear in at least one predictive expression product marker set.

Examples of methods for deriving and applying posterior probabilities to the analysis of microarray data are provided in Smyth, G. K. 2004 Stat. Appi. Genet. Mol. Biol. 3: Article 3, which is entirely incorporated herein by reference. In some cases, the posterior probabilities may be used to rank the markers provided by the classifier. In some cases, markers may be ranked according to their posterior probabilities and those that pass a chosen threshold may be chosen as markers whose differential expression is indicative of or diagnostic for samples that are for example UIP or non-UIP. Illustrative threshold values include prior probabilities of 0.7, 0.75, 0.8, 0.85, 0.9, 0.925, 0.95, 0.975, 0.98, 0.985, 0.99, 0.995 or higher.

A statistical evaluation of the results of the molecular profiling may provide, but is not limited to providing, a quantitative value or values indicative of one or more of the following: the likelihood of diagnostic accuracy; the likelihood a sample is UIP; the likelihood a sample is non-UIP; the likelihood of an ILD; the likelihood of a particular ILD; the likelihood of the success of a particular therapeutic intervention, the likelihood the subject is a smoker, and the likelihood the subject is a non-smoker. Thus a physician, who is not likely to be trained in genetics or molecular biology, need not understand the raw data. Rather, the data is presented directly to the physician in its most useful form to guide patient care. The results of the molecular profiling may be statistically evaluated using a number of methods, including, but not limited to: the students T test, the two-sided T test, pearson rank sum analysis, hidden Markov model analysis, analysis of q-q plots, principal component analysis, one-way ANOVA, two-way ANOVA, LIMMA and the like.

In some embodiments of the present disclosure, the use of molecular profiling alone or in combination with cytological analysis may provide a classification, identification, or diagnosis that is between about 85% accurate and about 99% or about 100% accurate. In some cases, the molecular profiling process and/or cytology provide a classification, identification, diagnosis of an ILD that is about, or at least about 85%, 86%, 87%, 88%, 90%, 91%, 92%, 93%, 94%, 95%, 96%, 97%, 97.5%, 98%, 98.5%, 99%, 99.5%, 99.75%, 99.8%, 99.85%, or 99.9% accurate. In some embodiments, the molecular profiling process and/or cytology provide a classification, identification, or diagnosis of the presence of a particular ILD type (e.g. IPF; NSIP; HP) that is about, or at least about 85%, 86%, 87%, 88%, 90%, 91%, 92%, 93%, 94%, 95%, 96%, 97%, 97.5%, 98%, 98.5%, 99%, 99.5%, 99.75%, 99.8%, 99.85%, or 99.9% accurate.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some embodiments of the present disclosure, gene expression products and compositions of nucleotides encoding for such products which are determined to exhibit the greatest difference in expression level or the greatest difference in alternative splicing between UIP and non-UIP, between UIP and normal, and/or between smoker and non-smoker may be chosen for use as molecular profiling reagents of the present disclosure. Such gene expression products may be particularly useful by providing a wider dynamic range, greater signal to noise, improved diagnostic power, lower likelihood of false positives or false negative, or a greater statistical confidence level than other methods.

In other embodiments of the present disclosure, the use of molecular profiling alone or in combination with cytological analysis may reduce the number of samples scored as non-diagnostic by about, or at least about 100%, 99%, 95%, 90%, 80%, 75%, 70%, 65%, or about 60% when compared to the use of standard cytological techniques used in the art. In some cases, the methods of the present disclosure may reduce the number of samples scored as indeterminate or suspicious by about, or at least about 100%, 99%, 98%, 97%, 95%, 90%, 85%, 80%, 75%, 70%, 65%, or about 60%, when compared to the standard cytological methods used in the art.

In some cases the results of the molecular profiling assays, are entered into a database for access by representatives or agents of a molecular profiling business, the individual, a medical provider, or insurance provider. In some cases assay results include sample classification, identification, or diagnosis by a representative, agent or consultant of the business, such as a medical professional. In other cases, a computer analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present disclosure, the results of the molecular profiling are presented as a report on a computer screen or as a paper record. In some cases, the report may include, but is not limited to, such information as one or more of the following: the number of genes differentially expressed, the suitability of the original sample, the number of genes showing differential alternative splicing, a diagnosis, a statistical confidence for the diagnosis, the likelihood the subject is a smoker, the likelihood of an ILD, and indicated therapies.

(iv) Categorization of Samples Based on Molecular Profiling Results

The results of the molecular profiling may be classified, e.g., into one of the following: smoker, non-smoker, ILD, a particular type of ILD, a non-ILD, or non-diagnostic (providing inadequate information concerning the presence or absence of an ILD). In some cases, the results of the molecular profiling may be classified into IPF versus NSIP categories. In particular cases, the results are classified as UIP or non-UIP.

In some embodiments of the present disclosure, results are classified using a trained classifier. The trained classifier may be a trained algorithm. Trained classifiers of the present disclosure implement methods and/or processes that have been developed using a reference set of known UIP and non-UIP samples. In some embodiments, training (e.g., using a classifier training module) comprises the comparison of gene expression product levels in a first set of biomarkers from a UIP sample to gene expression product levels in a second set of biomarkers from a non-UIP sample, where the first set of biomarkers includes at least one biomarker that is not in the second set. In some embodiments, training (e.g., using a classifier training module) comprises comparison of gene expression product levels in a first set of biomarkers from a first ILD that is non-UIP to gene expression product levels in a second set of biomarkers from a second ILD that is UIP, where the first set of biomarkers includes at least one biomarker that is not in the second set. In some embodiments, training (e.g., using a classifier training module) further comprises comparison of gene expression product levels in a first set biomarkers from a first subject that is a smoker to gene expression product levels in a second set of biomarkers from a second subject that is a non-smoker, where the first set of biomarkers includes at least one biomarker that is not in the second set. In some embodiments, either the entire classifier or portions of the classifier may be trained (e.g., using a classifier training module) using comparisons of expression levels of biomarker panels within a classification panel against all other biomarker panels (or all other biomarker signatures) used in the classifier. In some embodiments, either the entire classifier or portions of the classifier may be trained (e.g., using a classifier training module) using comparisons of expression levels measured in pooled samples comprising at least 2, 3, 4, 5, or more individual samples obtained from a single subject. In some embodiments, either the entire classifier or portions of the classifier may be trained (e.g., using a classifier training module) using comparisons of in silico pooled expression levels, as described herein, wherein the in silico pooled expression levels comprise pooled expression levels from at least 2, 3, 4, 5, or more individual samples obtained from a single subject. In particular aspects, such a classifier compares additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

In some embodiments, classifiers trained, as described herein, compare gene expression levels of 1; 2; 3; 4; 5; 6; 7; 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; or 190 of the genes listed in Table 5 between a test sample and a reference sample or a group of reference samples to determine whether the test sample is UIP or non-UIP. In particular aspects, such a classifier compares additional genes, e.g., 1, 2, 3, 4, 5, 6, 7, 8, or more additional genes. In other aspects, the classifier omits certain of the above-mentioned genes, e.g., 1, 2, 3, 4, 5, 6, 7, 8, or more, of these genes, while in some cases including other genes.

Classifiers suitable for categorization of samples include but are not limited to k-nearest neighbor classifiers, support vector machines, linear discriminant analysis, diagonal linear discriminant analysis, updown, naive Bayesian classifiers, neural network classifiers, hidden Markov model classifiers, genetic classifiers, or any combination thereof.

In some cases, trained classifiers of the present disclosure may incorporate data other than gene expression or alternative splicing data, such as, but not limited to, DNA polymorphism data, sequencing data, scoring or diagnosis by cytologists or pathologists of the present disclosure, information provided by the pre-classifier method and/or process of the present disclosure, or information about the medical history of the subject of the present disclosure.

When classifying a biological sample for diagnosis of ILD (e.g., with UIP), there are typically two possible outcomes from a binary classifier. Similarly, when classifying a biological sample for diagnosis of smoker, there are typically two possible outcomes from a binary classifier. When a binary classifier is compared with actual true values (e.g., values from a biological sample), there are typically four possible outcomes. If the outcome from a prediction is p (where "p" is a positive classifier output, such as a particular ILD) and the actual value is also p, then it is called a true positive (TP); however if the actual value is n then it is said to be a false positive (FP). Conversely, a true negative (TN) has occurred when both the prediction outcome and the actual value are n (where "n" is a negative classifier output, such as no ILD, or absence of a particular disease tissue as described herein), and false negative (FN) is when the prediction outcome is n while the actual value is p. In one embodiment, consider a diagnostic test that seeks to determine whether a person has a certain disease. A false positive (FP) in this case occurs when the person tests positive, but actually does not have the disease. A FN, on the other hand, occurs when the person tests negative, suggesting they are healthy, when they actually do have the disease. In some embodiments, a receiver operator characteristic (ROC) curve assuming real-world prevalence of subtypes may be generated by re-sampling errors achieved on available samples in relevant proportions.

The positive predictive value (PPV), or precision rate, or post-test probability of disease, is the proportion of patients with positive test results who are correctly diagnosed. It is the most important measure of a diagnostic method as it reflects the probability that a positive test reflects the underlying condition being tested for. Its value does however depend on the prevalence of the disease, which may vary. False positive rate (□)=FP/(FP+TN)-specificity; False negative rate (□)=FN/(TP+FN)-sensitivity; Power=sensitivity=1-□□; Likelihood-ratio positive=sensitivity/(1−specificity); Likelihood-ratio negative=(1−sensitivity)/specificity.

The negative predictive value is the proportion of patients with negative test results who are correctly diagnosed. PPV and NPV measurements may be derived using appropriate disease subtype prevalence estimates. An estimate of the pooled disease prevalence may be calculated from the pool of indeterminates which roughly classify into B vs M by surgery. For subtype specific estimates, in some embodiments, disease prevalence may sometimes be incalculable because there are not any available samples. In these cases, the subtype disease prevalence may be substituted by the pooled disease prevalence estimate.

In some embodiments, the level of expression products or alternative exon usage is indicative of one or the following: IPF, NSIP, HP, UIP, non-UIP.

In some embodiments, the level of expression products or alternative exon usage is indicative that the subject is a smoker or a non-smoker.

In some embodiments, the results of the expression analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

Reports

A subject method and/or system may include generating a report that provides an indication that a sample (a lung tissue sample) is a UIP sample (e.g., using a report module). A subject method and/or system may include generating a report that provides an indication that a sample (a lung tissue sample) is a non-UIP sample (e.g., using a report module). A subject method and/or system may include generating a report that provides an indication that a sample (a lung tissue sample) is an ILD sample (e.g., using a report module). A subject diagnostic method can include generating a report that provides an indication as to whether an individual being tested has an ILD. A subject diagnostic method can include generating a report that provides an indication as to whether an individual being tested is, or is not a smoker. A subject method (or report module) can include generating a report that provides an indication as to whether an individual being tested has IPF (and not, e.g., an ILD other than IPF; e.g., the report can indicate that the individual has IPF and not NSIP).

In some embodiments, a subject method of diagnosing UIP vs. non-UIP involves generating a report (e.g., using a report module). Such a report can include information such as a likelihood that the patient has UIP; a likelihood that the patient has non-UIP; a likelihood that the patient has IPF; a likelihood that the patient is a smoker; a recommendation regarding further evaluation; a recommendation regarding therapeutic drug and/or device intervention; and the like.

For example, the methods disclosed herein can further include a step of generating or outputting a report providing the results of a subject diagnostic method, the report may be provided in the form of an electronic medium (e.g., an electronic display on a computer monitor), or in the form of a tangible medium (e.g., a report printed on paper or other tangible medium). An assessment as to the results of a subject diagnostic method (e.g., a likelihood that the patient has UIP; a likelihood that the patient has non-UIP; a likelihood that the patient has IPF; a likelihood that an individual has an ILD; a likelihood that an individual has IPF; a likelihood that an individual is a smoker) may be referred to as a "report" or, simply, a "score." A person or entity that prepares a report ("report generator") may also perform steps such as sample gathering, sample processing, and the like. Alternatively, an entity other than the report generator can perform steps such as sample gathering, sample processing, and the like. A diagnostic assessment report may be provided to a user. A "user" may be a health professional (e.g., a clinician, a laboratory technician, a physician (e.g., a cardiologist), etc.).

A subject report can further include one or more of: 1) service provider information; 2) patient data; 3) data regarding the expression level of a given gene product or set of gene products, a score or classifier decision; 4) follow-up evaluation recommendations; 5) therapeutic intervention or recommendations; and 6) other features.

Further Evaluation

Based on the expression level of a given gene product or set of gene products, and/or based on a report (as described above), a physician or other qualified medical personnel can determine whether further evaluation of the test subject (the patient) is required. Further evaluation can include, e.g., spirometry.

Therapeutic Intervention

Based on the expression level of a given gene product or set of gene products, and/or based on a report (as described above), a physician or other qualified medical personnel can determine whether appropriate therapeutic intervention is advised. Therapeutic intervention includes drug-based therapeutic intervention, device-based therapeutic intervention, and surgical intervention. Where a report indicates a likelihood that an individual has UIP and/or IPF, drug-based therapeutic intervention includes, e.g., administering to the individual an effective amount of pirfenidone, prednisone, azathioprine, and/or N-acetylcysteine. Surgical intervention includes, e.g., arterial bypass surgery.

Computer-Implemented Methods, Systems and Devices

The methods of the present disclosure may be computer-implemented, such that method steps (e.g., assaying, comparing, calculating, and the like) are automated in whole or in part.

Accordingly, the present disclosure provides methods, computer systems, devices and the like in connection with computer-implemented methods of facilitating a diagnosis of an interstitial lung disease (e.g., a diagnosis of UIP, non-UIP, IPF, NSIP, HP, etc.), including differential diagnosis.

The present disclosure further provides methods, computer systems, devices and the like in connection with computer-implemented methods of facilitating determination of smoker status (e.g., smoker vs. non-smoker).

The present disclosure further provides methods, computer systems, devices and the like in connection with computer-implemented methods of facilitating a diagnosis of an interstitial lung disease (e.g., a diagnosis of UIP, non-UIP, IPF, NSIP, HP, etc.), including differential diagnosis, wherein the methods further comprise determining a subjects smoker status (smoker vs. non-smoker) and incorporating smoker status into the determination of the subjects interstitial lung disease diagnosis. In some embodiments, (i) smoker status is incorporated into the interstitial lung disease diagnosis as a covariate in the model used during training (e.g., using a classifier training module). This approach boosts signal-to-noise ratio, particularly in data derived from smokers (where noise is higher), and allows data derived from smokers and non-smokers to be combined and used simultaneously. In some embodiments, (ii) smoker status is incorporated into the interstitial lung disease diagnosis by identifying one or more genes that are susceptible to smoker status bias and excluding such genes or weighing such genes differently than other genes that are not susceptible to smoker-status during interstitial lung disease diagnosis classifier training. In some embodiments, (iii) smoker status is incorporated into the interstitial lung disease diagnosis by constructing a tiered classification in which an initial classifier is trained to recognize the gene signatures that distinguish smokers from non-smokers (e.g., using a classifier training module). Once patient samples are pre-classified as "smoker" or "non-smoker" (e.g., using a pre-classifier analysis module), distinct classifiers that were each trained to distinguish UIP vs. non-UIP in smokers or non-smokers, respectively may be implemented to diagnose interstitial lung disease. In still further embodiments, such methods comprising the step of incorporating smoker status into the determination of the subjects interstitial lung disease diagnosis include a combination of one or more of the above mentioned methods of such incorporation (i.e., a combination of two or more of embodiments (i) to (iii) in the instant paragraph.

For example, the method steps, including obtaining values for biomarker levels, comparing normalized biomarker (gene) expression levels to a control level, calculating the likelihood of UIP or non-UIP (and in some cases the likelihood a subject is a smoker), generating a report, and the like, may be completely or partially performed by a computer program product. Values obtained may be stored electronically, e.g., in a database, and may be subjected to a classifier executed by a programmed computer (e.g., using a classifier analysis module).

For example, the methods and/or systems of the present disclosure can involve inputting a biomarker level (e.g., a normalized expression level of a gene product) into a classifier analysis module to execute a method and/or process to perform the comparing and calculating step(s) described herein, and generate a report (e.g., using a report module) as described herein, e.g., by displaying or printing a report to an output device at a location local or remote to the computer. The output to the report may be a score (e.g., numerical score (representative of a numerical value) or a non-numerical score (e.g., non-numerical output (e.g., "IPF", "No evidence of IPF") representative of a numerical value or range of numerical values. In other aspects, the output may indicate "UIP" vs. "non-UIP." In other aspects, the output may indicate "Smoker" vs. "Non-smoker"

The present disclosure thus provides a computer program product including a computer readable storage medium having software and/or hardware modules stored on it. The software and/or hardware modules can, when executed by a processor, execute relevant calculations based on values obtained from analysis of one or more biological sample (e.g., lung tissue sample) from an individual. The computer program product has stored therein a computer program for performing the calculation(s).

The present disclosure provides systems for executing the program described above, which system generally includes: a) a central computing environment or processor executing software and/or hardware modules; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) a method and/or process executed by the central computing environment (e.g., a processor), where the method and/or process is executed based on the data received by the input device, and wherein the method and/or process calculates a value, wherein the value is indicative of the likelihood the subject has UIP, non-UIP, an ILD, or IPF, as described herein.

The present disclosure also provides systems for executing the program described above, which system generally includes: a) a central computing environment or processor executing software and/or hardware modules; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) a method and/or process executed by the central computing environment (e.g., a processor), where the method and/or process is executed based on the data received by the input device, wherein the method and/or process calculates a value, which value is indicative of the likelihood the subject has UIP, non-UIP, an ILD, or IPF as described herein, and wherein the method and/or process uses smoking status (smoker vs. non-smoker) as a covariate in the model used during training. In some embodiments, the method and/or process excludes or weighs one or more genes that are susceptible to smoker status bias differently during classifier training to enrich the feature space used for training with genes that are not confounded or affected by smoking status.

Figure 7A:
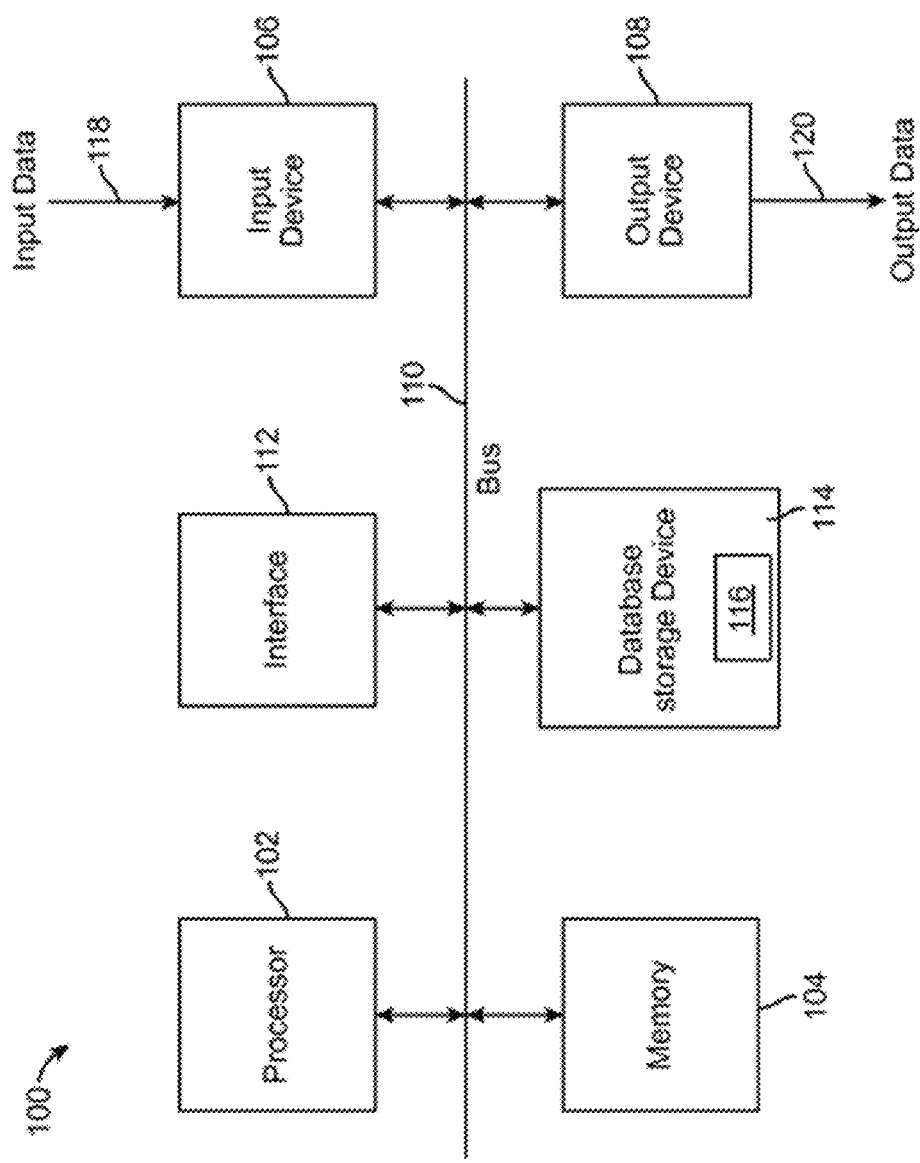
FIG. 7A-7C. Computer systems; processors; and computer executable processes for training and utilizing the classifiers disclosed herein.

In still further embodiments, the present disclosure provides systems for executing the program described above, which system generally includes: a) a central computing environment or processor executing software and/or hardware modules; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) a first method and/or process executed by the central computing environment (e.g., a processor), where the first method and/or process is executed based on the data received by the input device, wherein the first method and/or process calculates a value, which value is indicative of the likelihood a subject is a smoker or a non-smoker, as described herein, wherein the subject's status as a smoker or non-smoker causes the first method and/or process to apply a second method and/or process specifically trained (e.g., using a classifier training module) to distinguish UIP vs. non-UIP in smokers or non-smokers, respectively and e) wherein the second method and/or process is executed by the central computing environment (e.g., a processor), where the second method and/or process is executed based on the data received by the input device, and wherein the second method and/or process calculates a value, which value is indicative of the likelihood the subject has an ILD, as described herein, Computer Systems FIG. 7A illustrates a processing system 100 including at least one processor 102, or processing unit or plurality of processors, memory 104, at least one input device 106 and at least one output device 108, coupled together via a bus or group of buses 110. Processing system may be implemented on any suitable device, such as, for example, a host device, a personal computer, a handheld or laptop device, a personal digital assistant, a multiprocessor system, a microprocessor-based system, a programmable consumer electronic device, a minicomputer, a server computer, a web server computer, a mainframe computer, and/or a distributed computing environment that includes any of the above systems or devices In certain embodiments, input device 106 and output device 108 may be the same device. An interface 112 can also be provided for coupling the processing system 100 to one or more peripheral devices, for example interface 112 may be a PCI card or PC card. At least one storage device 114 which houses at least one database 116 can also be provided.

The memory 104 may be any form of memory device, for example, volatile or nonvolatile memory, solid state storage devices, magnetic devices, etc. For example, in some embodiments, the memory 104 may be a random access memory (RAM), a memory buffer, a hard drive, a read-only memory (ROM), an erasable programmable read-only memory (EPROM), a database, and/or the like.

The processor 102 can include more than one distinct processing device, for example to handle different functions within the processing system 100. The processor 100 may be any suitable processing device configured to run or execute a set of instructions or code (e.g., stored in the memory) such as a general-purpose processor (GPP), a central processing unit (CPU), an accelerated processing unit (APU), a graphics processor unit (GPU), an application specific integrated circuit (ASIC), and/or the like. Such a processor 100 can run or execute a set of instructions or code stored in the memory associated with using a personal computer application, a mobile application, an internet web browser, a cellular and/or wireless communication (e.g., via a network), and/or the like. More specifically, the processor can execute a set of instructions or code stored in the memory 104 associated with analyzing and classifying data, as described herein.

Input device 106 receives input data 118 and can comprise, for example, a keyboard, a pointer device such as a pen-like device or a mouse, audio receiving device for voice controlled activation such as a microphone, data receiver or antenna such as a modem or wireless data adaptor, data acquisition card, etc. Input data 118 can come from different sources, for example keyboard instructions in conjunction with data received via a network.

Output device 108 produces or generates output data 120 and can comprise, for example, a display device or monitor in which case output data 120 is visual, a printer in which case output data 120 is printed, a port for example a USB port, a peripheral component adaptor, a data transmitter or antenna such as a modem or wireless network adaptor, etc. Output data 120 may be distinct and derived from different output devices, for example a visual display on a monitor in conjunction with data transmitted to a network. A user can view data output, or an interpretation of the data output, on, for example, a monitor or using a printer.

In some embodiments, the input device 106 and/or the output device 108 may be a communication interface configured to send and/or receive data via a network. More specifically, in such embodiments, the processing system 100 can act as a host device to one or more client devices (not shown in FIG. 7A). As such, the processing system 100 can send data to (e.g., output data 120) and receive data from (e.g., input data 118) the client devices. Such a communication interface may be any suitable module and/or device that can place the processing system 100 in communication with a client device such as one or more network interface cards or the like. Such a network interface card can include, for example, an Ethernet port, a WiFi® radio, a Bluetooth® radio, a near field communication (NFC) radio, and/or a cellular radio that can place the client device 150 in communication with the host device 110 via a network or the like.

The storage device 114 may be any form of data or information storage system or method, for example, volatile or non-volatile memory, solid state storage devices, magnetic devices, etc. For example, in some embodiments, the storage device 114 may be a random access memory (RAM), a memory buffer, a hard drive, a read-only memory (ROM), an erasable programmable read-only memory (EPROM), a database, and/or the like.

In use, the processing system 100 is adapted to allow data or information to be stored in and/or retrieved from, via a wired or wireless communication system or method, at least one database 116. The interface 112 may allow wired and/or wireless communication between the processing unit 102 and peripheral components that may serve a specialized purpose. In general, the processor 102 can receive instructions as input data 118 via input device 106 and can display processed results or other output to a user by utilizing output device 108. More than one input device 106 and/or output device 108 may be provided. The processing system 100 may be any suitable form of terminal, server, specialized hardware, or the like. The processing system 100 may be a part of a networked communications system.

Processing system 100 can connect to a network, for example, a local area network (LAN), a virtual network such as a virtual local area network (VLAN), a wide area network (WAN), a metropolitan area network (MAN), a worldwide interoperability for microwave access network (WiMAX), a cellular network, the Internet, and/or any other suitable network implemented as a wired and/or wireless network. For instance, when used in a LAN networking environment, the computing system environment 100 is connected to the LAN through a network interface or adapter. When used in a WAN networking environment, the computing system environment typically includes a modem or other system or method for establishing communications over the WAN, such as the Internet. The modem, which may be internal or external, may be connected to a system bus via a user input interface, or via another appropriate mechanism. In a networked environment, program modules depicted relative to the computing system environment 100, or portions thereof, may be stored in a remote memory storage device. It is to be appreciated that the illustrated network connections of FIG. 7 are examples and other systems and methods of establishing a communications link between multiple computers may be used.

Input data 118 and output data 120 may be communicated to other devices via the network. The transfer of information and/or data over the network may be achieved using wired or wireless systems and methods of communication. A server can facilitate the transfer of data between the network and one or more databases. A server and one or more databases provide an example of an information source.

Thus, the processing computing system environment 100 illustrated in FIG. 7A may operate in a networked environment using logical connections to one or more remote computers. The remote computer may be a personal computer, a server, a router, a network PC, a peer device, or other common network node, and typically includes many or all of the elements described above.

Figure 7B:
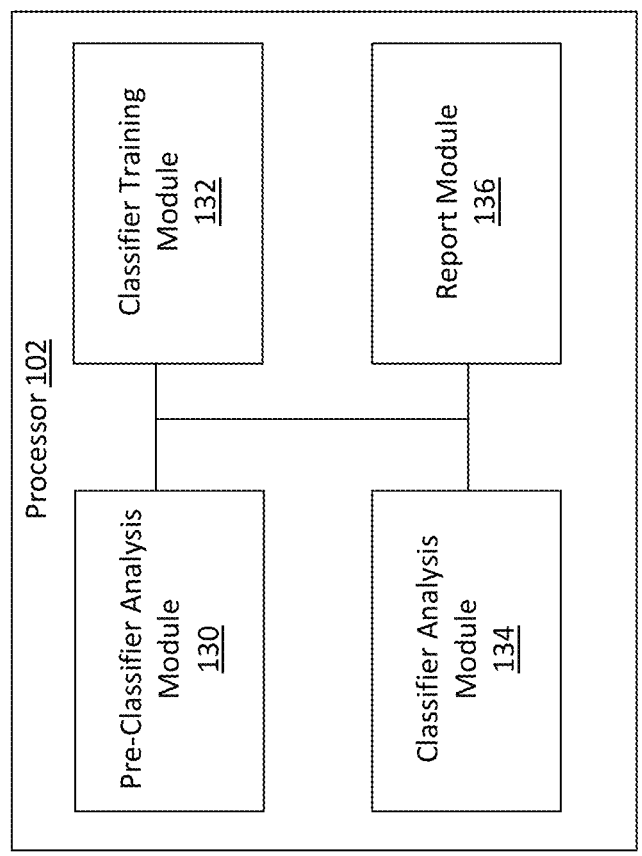

FIG. 7B illustrates the processor 102 of FIG. 7A in greater detail. The processor 102 may be configured to execute specific modules. The modules may be, for example, hardware modules, software modules stored in the memory 104 and/or executed in the processor 102, and/or any combination thereof. For example, as shown in FIG. 7B, the processor 102 includes and/or executes a pre-classifier analysis module 130, a classifier training module 132, a classifier analysis module 134 and a report module 136. As shown in FIG. 7B, the pre-classifier analysis module 130, the classifier training module 132, the classifier analysis module 134 and the report module 136 may be connected and/or electrically coupled. As such, signals may be sent between the pre-classifier analysis module 130, the classifier training module 132, the classifier analysis module 134 and the report module 136.

The classifier training module 132 may be configured to receive a corpora of data (e.g. gene expression data, sequencing data) and train a classifier. For example, clinical annotation data from samples previously identified as UIP and non-UIP (e.g., by an expert) may be received by the input device 106 and used by the classifier training module 132 to identify correlations between the samples previously identified as UIP and non-UIP. For example, expert TBB histopathology labels (i.e., UIP or non-UIP), expert HRCT labels, and/or expert patient-level clinical outcome labels may be obtained and used alone or in combination to train the classifier using microarray and/or sequencing data. The feature space used can include gene expression, variants, mutations, fusions, loss of heterozygoxity (LOH), biological pathway effect and/or any other dimension of the data that may be extracted as a feature for the purposes of training a machine-learning algorithm. In some embodiments, the feature space used for training a UIP vs. non-UIP classifier, a smoker vs. non-smoker classifier, or a UIP vs. non-UIP and smoker vs. non-smoker classifier includes gene expression, variants, mutations, fusions, loss of heterozygoxity (LOH), and biological pathway effect. In some embodiments, the feature space used for training a UIP vs. non-UIP classifier, a smoker vs. non-smoker classifier, or a UIP vs. non-UIP and smoker vs. non-smoker classifier includes gene expression and variant dimensions.

In some embodiments, the classifier training module 132 can train a smoker classifier and a non-smoker classifier based on an indication associated with whether a received sample is associated with a smoker or non-smoker. In other embodiments, the smoker/non-smoker may be used as an attribute (a model covariate) to train a single classifier. After the classifier is trained, it may be used to identify and/or classify newly received and unknown samples as described herein.

The pre-classifier analysis module 130 can identify whether a sample is associated with a smoker or a non-smoker. Specifically, the pre-classifier analysis module 130 can use any suitable method to identify and/or classify a sample as coming from an individual that smokes (or has a past history of heavy smoking) versus an individual that does not smoke (or has no smoking history). The classification may be done in any suitable manner such as, receiving an indication from a user, identification of genes that are susceptible to smoker-status bias, using a machine-learning classifier, and/or any other suitable method described herein.

The classifier analysis module 134 can input the sample into the classifier to identify and/or classify the received sample as associated with UIP and non-UIP. Specifically, the classifier analysis module 134 can use a trained classifier to identify whether the sample indicates UIP or non-UIP. In some embodiments, the classifier analysis module 134 can indicate a percentage or confidence score of the sample being associated with UIP or non-UIP. In some embodiments, the classifier analysis module 134 can execute two separate classifiers: one for smoker samples and the other for non-smoker samples (as determined by the pre-classifier analysis module 130). In other embodiments, a single classifier is executed for both smoker and non-smoker samples with an input for smoker status.

The report module 136 may be configured to generate any suitable report based on the outcome of the classifier analysis module 134 as described in further detail herein. In some cases, the report may include, but is not limited to, such information as one or more of the following: the number of genes differentially expressed, the suitability of the original sample, the number of genes showing differential alternative splicing, a diagnosis, a statistical confidence for the diagnosis, the likelihood the subject is a smoker, the likelihood of an ILD, and indicated therapies.

Figure 7C:
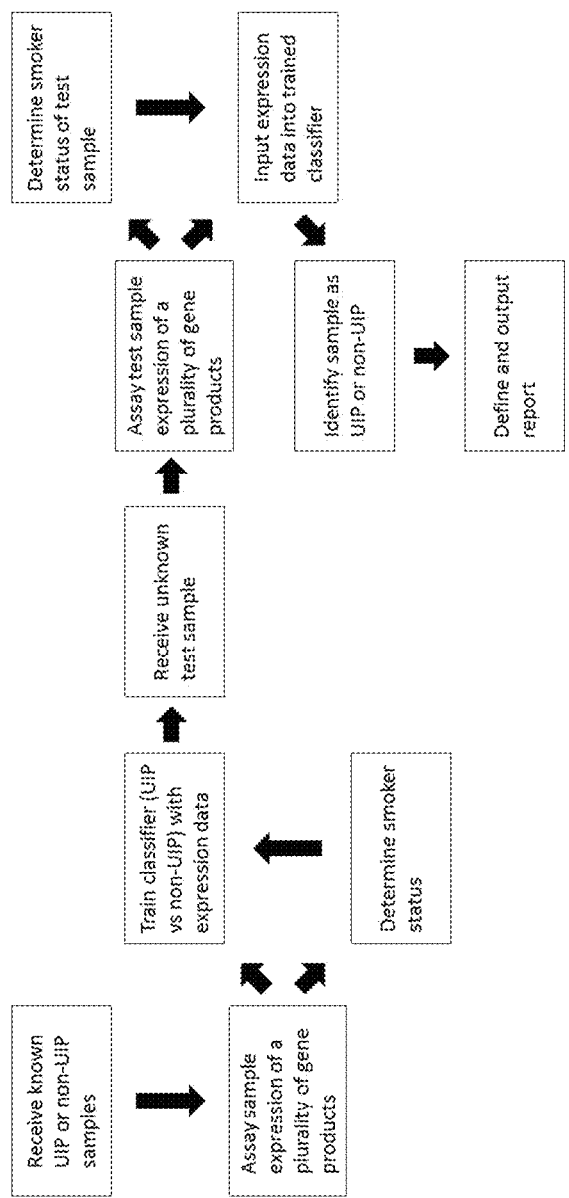

FIG. 7C illustrates a flow chart of one non-limiting embodiment of the present disclosure wherein gene product expression data for known UIP and non-UIP samples are used to train (e.g., using a classifier training module) a classifier for differentiating UIP vs. non-UIP, wherein the classifier in some cases considers smoker status as a covariant, and wherein gene product expression data from unknown samples are input into the trained classifier to identify the unknown samples as either UIP or non-UIP, and wherein the results of the classification via the classifier are defined and output via a report.

Certain embodiments may be described with reference to acts and symbolic representations of operations that are performed by one or more computing devices, such as the computing system environment 100 of FIG. 7A. As such, it will be understood that such acts and operations, which are at times referred to as being computer-executed, include the manipulation by the processor of the computer of electrical signals representing data in a structured form. This manipulation transforms the data or maintains them at locations in the memory system of the computer, which reconfigures or otherwise alters the operation of the computer in a manner understood by those skilled in the art. The data structures in which data is maintained are physical locations of the memory that have particular properties defined by the format of the data. However, while an embodiment is being described in the foregoing context, it is not meant to be limiting as those of skill in the art will appreciate that the acts and operations described hereinafter may also be implemented in hardware.

Embodiments may be implemented with numerous other general-purpose or special-purpose computing devices and computing system environments or configurations. Examples of other computing systems, environments, and configurations that may be suitable for use with an embodiment include, but are not limited to, personal computers, handheld or laptop devices, personal digital assistants, multiprocessor systems, microprocessor-based systems, programmable consumer electronics, network, minicomputers, server computers, web server computers, mainframe computers, and distributed computing environments that include any of the above systems or devices.

Embodiments may be described in a general context of computer-executable instructions, such as hardware and/or software modules. An embodiment may also be practiced in a distributed computing environment where tasks are performed by remote processing devices that are linked through a communications network. In a distributed computing environment, program modules may be located in both local and remote computer storage media including memory storage devices.

Computer Program Products

The present disclosure provides computer program products that, when executed on a programmable computer such as that described above with reference to FIG. 7, can carry out the methods of the present disclosure. As discussed above, the subject matter described herein may be embodied in systems, apparatus, methods, and/or articles depending on the desired configuration. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. display monitor, printer, etc.).

Computer programs (also known as programs, software, software applications, applications, components, or code) include instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, etc.) used to provide machine instructions and/or data to a programmable processor, including a machine-readable medium that receives machine instructions as a machine-readable signal.

It will be apparent from this description that aspects of the present disclosure may be embodied, at least in part, in software, hardware, firmware, or any combination thereof. Thus, the techniques described herein are not limited to any specific combination of hardware circuitry and/or software, or to any particular source for the instructions executed by a computer or other data processing system. Rather, these techniques may be carried out in a computer system or other data processing system in response to one or more processors, such as a microprocessor, executing sequences of instructions stored in memory or other computer-readable medium including any type of ROM, RAM, cache memory, network memory, floppy disks, hard drive disk (HDD), solid-state devices (SSD), optical disk, CD-ROM, and magnetic-optical disk, EPROMs, EEPROMs, flash memory, or any other type of media suitable for storing instructions in electronic format.

In addition, the processor(s) may be, or may include, one or more programmable general-purpose or special-purpose microprocessors, digital signal processors (DSPs), programmable controllers, application specific integrated circuits (ASICs), programmable logic devices (PLDs), trusted platform modules (TPMs), or the like, or a combination of such devices. In alternative embodiments, special-purpose hardware such as logic circuits or other hardwired circuitry may be used in combination with software instructions to implement the techniques described herein.

Arrays and Kits

The present disclosure provides arrays and kits for use in carrying out a subject evaluating method or a subject diagnostic method.

Arrays

A subject array can comprise a plurality of nucleic acids, each of which hybridizes to a gene differentially expressed in a cell present in a tissue sample obtained from an individual being tested for UIP, non-UIP, IPF, or an ILD.

A subject array can comprise a plurality of nucleic acids, each of which hybridizes to a gene differentially expressed in a cell present in a tissue sample obtained from an individual being tested for smoker status.

A subject array can comprise a plurality of nucleic acids, each of which hybridizes to a gene differentially expressed in a cell present in a tissue sample obtained from an individual being tested for both smoker status and UIP, non-UIP, IPF, or an ILD.

A subject array can comprise a plurality of member nucleic acids, each of which member nucleic acids hybridizes to a different gene product. In some cases, two or more member nucleic acids hybridize to the same gene product; e.g., in some cases 2, 3, 4, 5, 6, 7, 8, 9, 10, or more member nucleic acids hybridize to the same gene product. A member nucleic acid can have a length of from about 5 nucleotides (nt) to about 100 nt, e.g., 5, 6, 7, 8, 9, 10, 11, 12, 13, 14, 15, 16, 17 18, 19, 20, 20-25, 25-30, 30-40, 40-50, 50-60, 60-70, 70-80, 80-90, or 90-100 nt. A nucleic acid can have one or more phosphate backbone modifications.

A subject array can include from about 10 to about $10^5$ unique member nucleic acids, or more than $10^5$ unique member nucleic acids. For example, a subject array can include from about 10 to about $10^2$, from about $10^2$ to about $10^3$, from about $10^3$ to about $10^4$, from about $10^4$ to about $10^5$, or more than $10^5$, unique member nucleic acids.

Kits

A kit of the present disclosure can include an array, as described above; and a reagent for analyzing an expression level of a gene product.

Reagents for analyzing an expression level of a nucleic acid gene product include, e.g., reagents suitable for sequencing a nucleic acid; reagents suitable for amplifying a nucleic acid; and reagents suitable for nucleic acid hybridization.

The kit may include: a buffer; a detectable label; components for developing a detectable label (e.g., where a nucleic acid probe includes a detectable label); etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but methods for obtaining the instructions from a remote source, e.g. via the internet, are provided. An example of this embodiment is a kit that includes a web address where the instructions can be viewed and/or from which the instructions can be downloaded. As with the instructions, this method for obtaining the instructions is recorded on a suitable substrate.

Abbreviations

| | |
|---|---|
| adj.P.Value.edgeR: | False discovery rate adjusted p value of RNAseq gene expression data using edgeR analysis. |
| adj.P.Value.microarray | False discovery rate adjusted p value of RNAseq gene expression data using microarray analysis |
| adj.P.Value.npSeq: | False discovery rate adjusted p value of RNAseq gene expression data using npSeq analysis |
| BRONCH: | Broncholitis |
| CIF-NOC | Chronic Interstitial Fibrosis Not Otherwise Classified |
| edgeR: | an R package for the significance analysis of sequencing data |
| Ensembl ID: | Gene Identifier from Ensembl Genome Browser database |
| FDR: | False Discovery Rate, an adjusted p value that limits the possibility that the results are random due to the large number of genes simultaneously evaluated. |
| Gene Symbol: | Gene Identifier from HUGO Gene Nomenclature Committee |
| logFC.edgeR: | Log2 fold change of RNAseq gene expression data using edgeR analysis |
| logFC.microarray: | Log2 fold change of RNAseq gene expression data using LIMMA microarray analysis |
| logFC.npSeq: | Log2 fold change of RNAseq gene expression data using npSeq analysis |
| microarray: | Gene expression analysis using gene arrays such as from Affymetrix. |
| NML: | Normal Lung, usually obtained from human lung donor tissue that was ultimately never transplanted |
| npSeq: | an R package for the significance analysis of sequencing data |
| NSIP: | Non Specific Interstitial Pneumonia |
| OP: | Organizing Pneumonia |
| P.value.edgeR: | p value of RNAseq gene expression data using edgeR analysis |
| P.value.microarray: | p value of RNAseq gene expression data using LIMMA microarray analysis |
| P.value.npSeqp: | value of RNAseq gene expression data using npSeq analysis |
| RB: | Respiratory Broncholitis |
| REST: | A combination of all other ILDs except the subtype it is being compared to. Usually HP and NSIP, BRONCH, CIF-NOC, OP, RB and SARC. |
| SARC: | Sarcoidosis |
| SQC: | Squamous Cell Carcinoma |
| TCID: | "TCID" or "Transcript Cluster Identifier" refers to a gene level identifier used by all Affymetrix microarrays. Each TCID is associated with a fixed reference number that identifies a set of specific probes having sequences for a specific gene. Such specific probes are present on a given array commercially available from Affymetrix. TCID numbers thus refer to a gene product(s) of a specific gene, and may be found, e.g., at the following world wide web address: affymetrix.com/the sequences of which probes and gene products are hereby incorporation herein in their entirety. |
| UIP: | Usual Interstitial Pneumonia; the HRCT or histopathology pattern observed in IPF |
| LIMMA: | Linear Models for Microarray Data; an R package for the significance analysis of microarray data. |

"ENSEMBL ID" refers to a gene identifier number from the Ensembl Genome Browser database (see World Wide Web address: ensembl.org/index.html, which is entirely incorporated herein by reference). Each identifier begins with the letters ENSG to denote "Ensembl Gene". Each ENSEMBL ID number (i.e., each "gene" in the Ensembl database) refers to a gene defined by a specific start and stop position on a particular human chromosome, and therefore defines a specific locus of the human genome. As one of skill in the art may fully appreciate, all of the gene symbols disclosed herein refer to gene sequences, which are readily available on publically available databases, e.g., UniGene database (Pontius J U, Wagner L, Schuler G D. UniGene: a unified view of the transcriptome. In: The NCBI Handbook. Bethesda (MD): National Center for Biotechnology Information; 2003, available at the World Wide Web address ncbi.nlm.nih.gov/unigene, incorporated herein), RefSeq (The NCBI handbook [Internet]. Bethesda (MD): National Library of Medicine (US), National Center for Biotechnology Information; 2002 Oct. Chapter 18, The Reference Sequence (RefSeq) Project, available at the World Wide Web address: ncbi.nlm.nih.gov/refseq/, incorporate herein), Ensembl (EMBL, available at the world wide web address: ensembl.org/index.html, incorporated herein), and the like. The sequences of the genes disclosed herein via their gene symbols, Ensembl IDs, and Entrez IDs are herein incorporated in their entirety.

All references, patents, and patent applications cited herein are incorporated in their entirety for all purposes.

EXAMPLES

The diagnostic approach to ILD remains quite challenging given the complexity of diffuse parenchymal disorders. Diagnostic approaches have emphasized multidisciplinary evaluation of clinical, radiological, and pathological data. The latter has traditionally emphasized SLB to maximize the yield in sampling lung tissue. The development of molecular markers that could serve as a diagnostic surrogate is of interest. In order to be clinically useful in the diagnosis of ILD, a surrogate test for pathology needs to distinguish UIP from among similar but pathologically distinct disease processes.

We hypothesized that a genomic classifier can detect a UIP gene expression signature in TBBs with high accuracy in a diverse patient population. In the following examples, we used machine learning on exome enriched transcriptional data to train a classifier to differentiate UIP from among the wide variety of ILDs encountered in clinical practice. We then demonstrated that this classifier accurately predicts the presence of UIP in an independent multi-center validation cohort. Further, we surprisingly demonstrate that sample pooling enables improved sensitivity and specificity for diagnosis, and classifier performance is agnostic to cellular heterogeneity. This was surprising because prior studies had indicated that that the cell of interest in IPF is the alveolar cell; thus it may be expected that all the biology is contained within alveolar cells. However, our results demonstrate that signals outside the alveolar cells are sufficient to inform on IPF classification, and this has not been previously described.

Thus, the genomic classifiers disclosed herein may reduce the need for surgical lung biopsy in the diagnosis of ILD, and may eventually be used to inform the diagnosis and treatment of patients with IPF.

Example 1

Sample Collection, Pathology Diagnosis, and Labeling

Video-assisted thoracoscopic surgery (VATS) specimens were prospectively collected as a part of an Institutional Review Board (IRB) approved ongoing multi-center clinical protocol, BRonchial sAmple collection for a noVel gEnomic test (BRAVE), sponsored by Veracyte, Inc. (South San Francisco, CA). Additional VATS and surgical lung biopsy specimens were obtained from banked sources. High resolution computed tomography (HRCT) scans collected during usual clinical care were reviewed by an expert radiologist, when available. Radiology diagnoses were summarized according to ATS guidelines (Raghu G, et al., Am J Respir Crit Care Med 2011,183:788-824, incorporated herein by reference in its entirety). Pathological diagnoses were determined by expert pathologists (A-LK, TC, JM, and SG) according to a centralized review process.

Following surgery, histology slides were prepared by study sites from surgical lung biopsies (SLB), bronchoscopic lung cryobiopsies (BLC) or transbronchial biopsies (TBB), de-identified, and submitted to two pathologists for blinded, independent expert pathology review. Selected slides were scanned to construct a permanent digital file of microscopic images (Aperio, Vista, CA). Slides were evaluated according to the according to a centralized review process described in Kim S Y, et al., The Lancet Respiratory Medicine 2015; 3:473-482, incorporated herein by reference in its entirety.

Each pathologist determined diagnoses for the patient as a whole (patient level) and for the specific lung lobe(s) sampled for pathology (sample or lobe level). Diagnoses were evaluated, with agreement defined as subtype concordance. In the event of agreement, a categorical UIP or non-UIP 'truth' label was defined, otherwise blinded review by a third pathologist was used to achieve 2 of 3 ('tie-breaker') consensus. In the absence of agreement, an unblinded conferral process was used. This process is also described in FIG. 1, resulting in both sample-level and patient-level pathology diagnoses.

Truth labels for algorithm training and development were assigned to TBBs using pathology diagnoses made on surgical lung biopsy (SLB) from the same lung lobe. Pathology subtypes were translated to sample and patient labels of UIP or non-UIP for use in algorithm training and validation as described in Kim S Y et al., supra, with the exception that three patients with UIP pattern detected in a lower lobe, but non-UIP or non-diagnostic labels assigned in the upper lobe, were assigned UIP labels at the patient level (Table 14).

Up to 5 TBB samples (two upper lobe, three lower lobe) were collected from each patient for molecular testing. Sampling was performed at the discretion of the treating physician, with guidance to obtain visible tissue from areas adjacent to pathology sampling. Labels of UIP or non-UIP were assigned to TBB samples at lobe level resolution for algorithm training and sample scoring. A patient can have more than one sample-level diagnosis (i.e. one per VATS sample per patient, most often one from each of the lower and upper lobes of the right lung), but can only have one patient-level diagnosis. For mixtures (see Example 6), truth labels were inferred from sample labels so that all patients in training could be scored.

In total, 283 TBB samples from 84 patients were collected at 17 clinical sites and utilized in the studies reported herein. The following pathology diagnoses were defined as non-UIP for purposes of algorithm training and scoring: acute lung injury, bronchiolitis, desquamative interstitial pneumonia, diffuse alveolar damage, emphysema, eosinophilic pneumonia, nonspecific interstitial pneumonia (NSIP) (including subtypes of cellular, mixed, or Favor), granulomatous disease, hypersensitivity pneumonitis (including Favor subtype), organizing pneumonia, *pneumocystis* pneumonia, pulmonary hypertension, respiratory bronchiolitis, sarcoidosis, and smoking-related interstitial fibrosis.

UIP, for purposes of algorithm training and scoring, was defined as any UIP subtype (classic UIP, difficult UIP, Favor UIP, or UIP).

Diagnostic concordance was defined as subtype agreement for non-UIP pathologies or any UIP subtype for UIP. In the event of subtype disagreement (e.g. Favor HP and HP, Favor NSIP and NISP), consensus diagnoses (e.g., HP and NSIP, respectively) were accepted after consultation. Diagnoses of chronic interstitial fibrosis, not otherwise classified, non-diagnostic, or 'Other' were not assigned training labels and were excluded from training.

As mentioned above, mixtures from patients with concordant UIP or non-UIP diagnoses across lung lobes were assigned UIP or non-UIP labels for mixture scoring. Three patients with a lower-lobe UIP pattern, but a non-UIP or non-diagnostic label in their upper lobe, were assigned UIP labels for mixture scoring purposes.

Most diagnostic terminologies follow American Thoracic Society (ATS) 2011 or 2013 guidelines[5,6] but a few changes were made by the expert pathologist panel to better characterize features at the lobe level. In particular, 'Classic UIP' and 'Difficult UIP' were included instead of 'Definite UIP' and 'Probable UIP' as described in the ATS 2011 guidelines. Chronic interstitial fibrosis, not otherwise classified (CIF/NOC) corresponds to unclassifiable fibrotic ILD. Three subcategories of CIF/NOC, 'Favor UIP', 'Favor NSIP', and 'Favor HP', were defined to specify cases of unclassifiable fibrosis which, in the judgment of the expert pathology panel, exhibit features suggestive of UIP, non-specific interstitial pneumonia (NSIP), or hypersensitivity pneumonitis (HP). A diagnosis of smoking-related interstitial fibrosis (SRIF) is also included[20].

For classification, sample-level pathology diagnoses were converted into binary class labels (UIP and non-UIP). Among the pathology diagnosis categories, the 'UIP' class includes (1) UIP, (2) Classic UIP, (3) Difficult UIP, and (4) Favor UIP. All other pathology diagnoses except non-diagnostic (ND) were assigned to the 'non-UIP' class.

Example 2

Sample Processing

Pre- or intra-operative transbronchial biopsy specimens were collected from patients for molecular testing, packaged and transported at 4° C. in a nucleic acid preservative, and stored long-term in Veracyte facilities at −80° C. until processing. Briefly, frozen tissue samples were mounted for sectioning using Tissue-Tek O.C.T. medium (Sakura Finetek U.S.A.) and 2×20 μm sections generated using a CM1800 cryostat (Leica Biosystems, Buffalo Grove, Illinois). Tissue curls were immediately immersed in RNAprotect (QIAGEN, Valencia, California), incubated overnight at 4° C. and stored at −80° C. until extraction. Whenever possible, adjacent 5 μm tissue curls were mounted onto glass slides and processed for hematoxylin and eosin (H&E) staining following standard procedures.

Nucleic acids were extracted from preserved TBB samples using a modified AllPrep™ Micro Kit (QIAGEN, Valencia, CA) procedure. Briefly, TBB tissues were thoroughly disrupted and homogenized using a TissueLyzer™ and QIAshredder™ prior to column-based isolation of DNA and RNA fractions per manufacturer's instructions (QIAGEN). Total RNA sample quantity and quality was determined using QuantiFluor™ RNA System (Promega, Madison, WI) and Agilent RNA 6000 Pico assay (Agilent Technologies, Santa Clara, CA), respectively. We also obtained total RNAs derived from human brain, heart, lung, placenta, and testes (Life Technologies, Carlsbad, CA), thyroid and lung tumors (Takara Bio USA, Mountain View, CA) (Asterand USA; Cooperative Human Tissue Network), and lung epithelial cell lines (HBEC, NL-20, Beas2b; a kind gift from Dr. Avrum Spira). In addition, total RNAs extracted from the surgical lung biopsies of 22 BRAVE I patients were also used (Kim S Y et al., supra).

RNA libraries enriched for exonic sequences were prepared using the TruSeq™ RNA Access Library Prep Kit (Illumina, San Diego, CA) according to manufacturer's instructions. Briefly, RNA samples were fragmented into small pieces using divalent cations under elevated temperature, and random hexamer primers were used to convert fragmented RNAs into cDNAs via reverse transcriptase. cDNA libraries were subsequently used as templates for second strand synthesis; thus, producing libraries of double-stranded cDNAs, which were ligated to sequencing adapters according to the manufacturer's protocol. Finally, enriched libraries of high-specificity, adapter-ligated cDNAs were produced by two rounds of PCR amplification, validation, and capture probe hybridization, as per manufacturer's protocol.

Example 3

Next-Generation RNA Sequencing

In this example, exome-enriched next-generation RNA sequencing was performed on select samples that met in-process PCR yield criteria using a NextSeq™ 500 instrument (Illumina), per manufacturer's instructions, at a targeted read depth of up to 25 million paired-end reads per sample, and, after data quality filtering, expression counts for 17,601 Ensembl genes was normalized and input to machine learning algorithms. Machine learning was used to train an elastic net logistic regression model. Performance was evaluated by cross-validation and on an independent set of 31 patients. The sequencing and algorithm development was performed as follows.

Briefly, 10 ng of total RNA was amplified using the Ovation™ RNASeq System v2 (NuGEN, San Carlos, California) and TruSeq™ (Illumina, San Diego, California) sequencing libraries were prepared and sequenced on an Illumina HiSeq according to manufacturer's instructions (as described in Example 2). Raw sequencing (FASTQ) files were aligned to the Human Reference assembly 37 (Genome Reference Consortium) using the STAR RNAseq aligner software (Dobin A, et al., Bioinformatics 2013 Jan. 1; 29(1):15-21, incorporated herein by reference in its entirety). Read counts for up to 26,268 Ensembl annotated gene-level features were determined using HTSeq (Anders S, et al., Bioinformatics 2015; 31:166-169, incorporated herein by reference in its entirety).

Sequencing data quality metrics were generated using RNA-SeQC (DeLuca D S, et al., Bioinformatics 2012; 28:1530-153222, incorporated herein by reference in its entirety). Quality metrics in each replicate were evaluated against acceptance metrics for total reads, mapped unique reads, mean per-base coverage, base duplication rate, the percentage of bases aligned to coding regions, the base mismatch rate, and uniformity of coverage within genes.

Sequencing data was filtered to exclude features not targeted for enrichment by the library assay, and genes annotated in Ensembl as pseudogenes, non-expressed exons in T-cell receptor or immunoglobulin genes, or rRNAs, resulting in 17,601 Ensembl genes with high confidence of specific enrichment.

For the 84 patient classifier (see FIG. 2), genes with variable expression across multiple assays (total inter-assay SD>0.3) were also excluded, resulting in 14,811 genes with reproducible expression run-to-run. Expression count data was scaled by gene dispersion function and VST transformed, prior to downstream analysis. Principal component analysis was performed in R using the 'princomp' function. Model feature selection and parameter estimation were performed by logistic regression with elastic net penalty as described in Friedman J, et al., Journal of statistical software 2010; 33:1-22, incorporated herein by reference in its entirety. Parameter tuning and performance evaluations were determined by leave-one-patient-out cross validation (LOPO CV).

Example 4

Patient Cohort Characteristics

Figure 2:
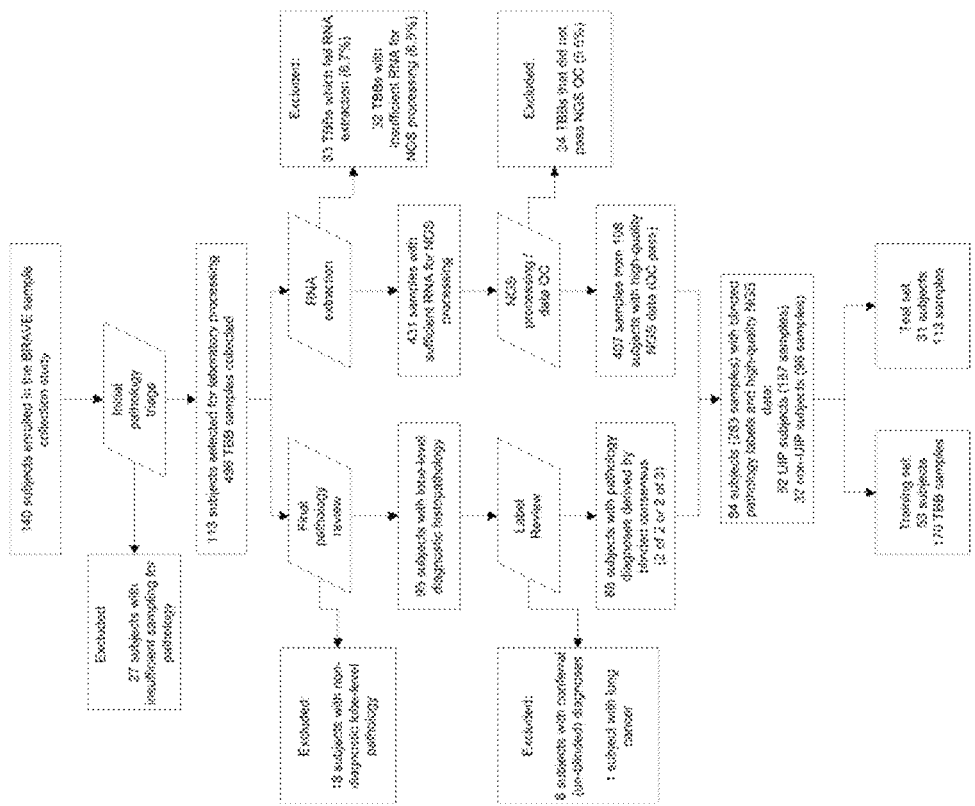
FIG. 2. Sample exclusion/inclusion procedure.

Samples from 113 ILD patients enrolled at 18 clinical sites as part of the BRAVE study (see Example 9) were screened for use in developing the molecular test for ILD. FIG. 2 shows a flow diagram of the 113 patients and associated TBB samples screened for use in this study, and it illustrates the cohorts (central squares), processing steps (trapezoids), and exclusions (lateral squares), of patients and samples at each sequential step of processing. Patients were assigned to training and test sets prospectively, prior to the availability of pathology diagnoses. Laboratory and analytical personnel remained blinded to the pathology diagnoses and labels of the test set until after algorithm lock and scoring.

We obtained pathology diagnoses specific to individual lobes of the lung for 95 of these patients using the central pathology review process described in Example 1.

We excluded diagnoses which required un-blinded review (i.e., conferral) and one patient diagnosed with lung cancer, resulting in 89 patients with high confidence ILD pathology in at least one lung lobe.

We extracted total RNA from 496 TBB samples collected from the 113 patients, and ultimately generated high quality RNAseq data for 407 samples derived from 108 patients.

The union of diagnostic patients and high-quality sample data represents 283 samples from 84 patients (52 UIP and 32 non-UIP) (FIG. 2, Table 2).

We prospectively assigned 53 patients to algorithm training and 31 patients to a validation cohort, targeting an equivalent UIP prevalence between training and test cohorts (Table 2).

TABLE 2

Demographics and UIP prevalence

|  | Training Set | Test Set | Total |
|---|---|---|---|
| Number of subjects | 53 | 31 | 84 |
| Clinical factors | | | |
| age, median (range) | 63.5 (31-88) | 62 (18-78) | 63 (18-88) |
| male gender, no. (%) | 26 (49%) | 14 (45%) | 40 (48%) |
| smoking history, yes, no. (%) | 34 (64%) | 19 (61%) | 53 (63%) |
| UIP prevalence by pathology | | | |
| by surgical lung biopsy, no. UIP (%) | 26 of 38 (68%) | 17 of 22 (77%) | 43 of 60 (72%) |
| Classic UIP | 11 | 6 | 17 |
| UIP | 9 | 6 | 15 |
| Difficult UIP | 5 | 5 | 10 |
| Favor UIP | 1 | 0 | 1 |
| by cryobiopsy, no. UIP (%) | 6 of 11 (55%) | 2 of 6 (33%) | 8 of 17 (47%) |
| UIP | 2 | 0 | 2 |
| Difficult UIP | 0 | 1 | 1 |
| Favor UIP | 4 | 1 | 5 |
| by transbronchial biopsy, no. UIP (%) | 1 of 4 (25%) | 0 of 3 (0%) | 1 of 7 (14%) |
| Difficult UIP | 1 | 0 | 1 |
| total UIP prevalence, no. UIP (%) | 33 of 53 (62%) | 19 of 31 (61%) | 52 of 84 (62%) |
| UIP prevalence by radiology | | | |
| Definite UIP | 4 | 2 | 6 |
| UIP | 4 | 2 | 6 |
| Probable UIP | 0 | 1 | 1 |
| total UIP prevalence, no. UIP (%) | 8 of 52 (15%) | 5 of 27 (19%) | 13 of 79 (16%) |

Due to several rare non-UIP ILDs in our prospective collections, some subtypes are represented by single cases in the patient cohort (Table 14, FIG. 3). Single cases of cellular NSIP, Favor HP, emphysema and *pneumocystis* pneumonia were assigned to the training cohort, whereas single cases of diffuse alveolar damage, pulmonary hypertension and eosinophilic pneumonia were assigned to the test set. The diversity and paucity of ILD subtypes prevalent in these patients illustrates the challenge of training a genomic classifier on a balanced spectrum of ILDs as encountered in clinical practice.

Radiology performed on our patient cohort as part of routine clinical care provides an independent estimate of UIP prevalence. We performed expert review of available HRCT scans and summarized the radiology findings according to ATS criteria for the UIP pattern (Raghu G., 2011, supra). The prevalence of HRCT UIP pattern in our cohort was 16%, compared to 62% by all pathology biopsy types (Table 2). The prevalence of UIP was higher in SLB than in bronchoscopic biopsies (72% vs. 47% [cryobiopsy] vs. 14% [transbronchial biopsy]), with definitive UIP typically identified in SLBs (Table 2).

Example 5

Classifier Development and Performance Using Individual TBB Samples

We evaluated multiple normalization schemes, feature selection and machine learning algorithms on our training set of 170 TBB samples from 53 patients, using a variety of genomic and clinical features. In cross validation, we observed the highest and most stable classification performance from a logistic regression model with elastic net penalty trained on expression count data, which uses 169 genes as features (Table 15). The model achieves a receiver-operator characteristic area under the curve (ROC-AUC) in cross-validation on the training set of 0.85 (FIG. 3A, FIG. 3B) based on sample level data.

Figure 3A:
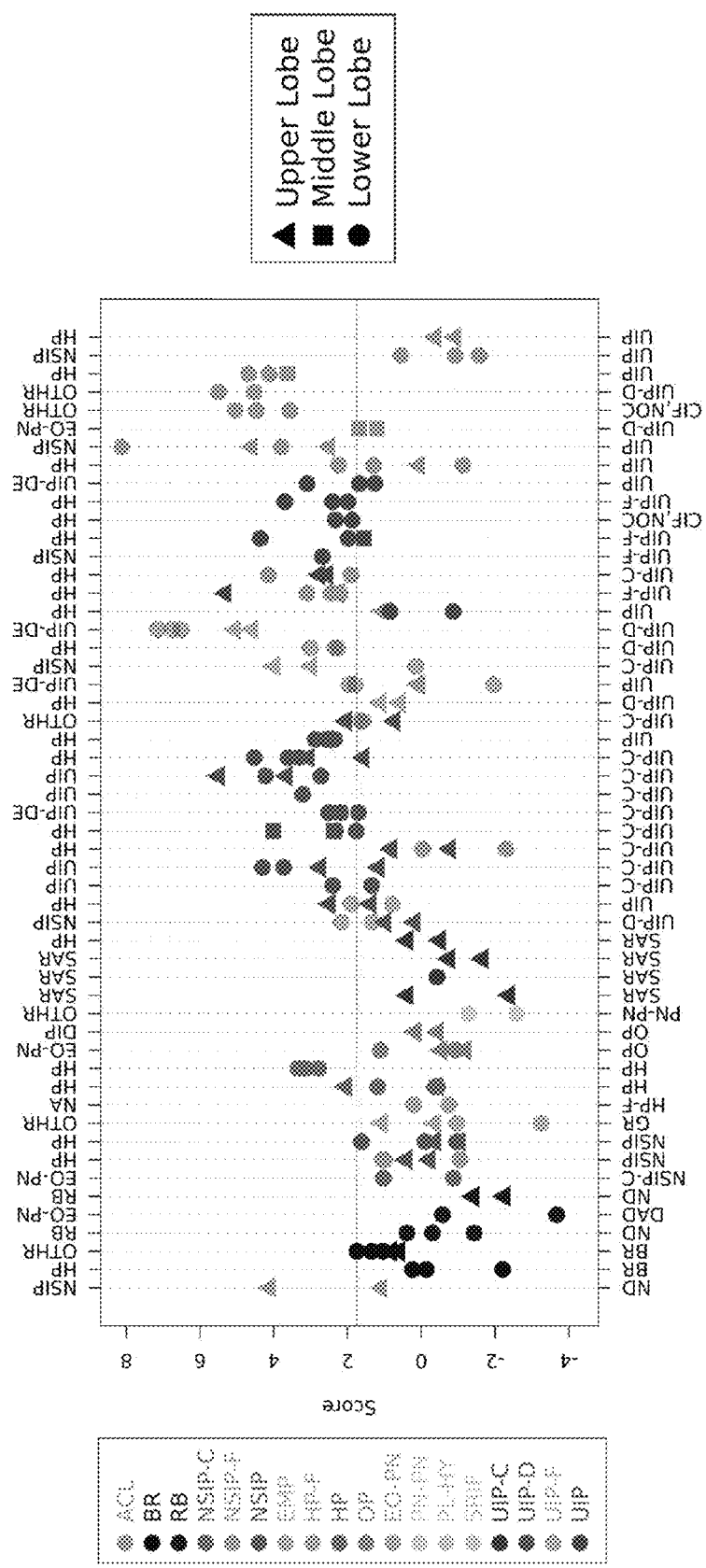
Figure 3C:
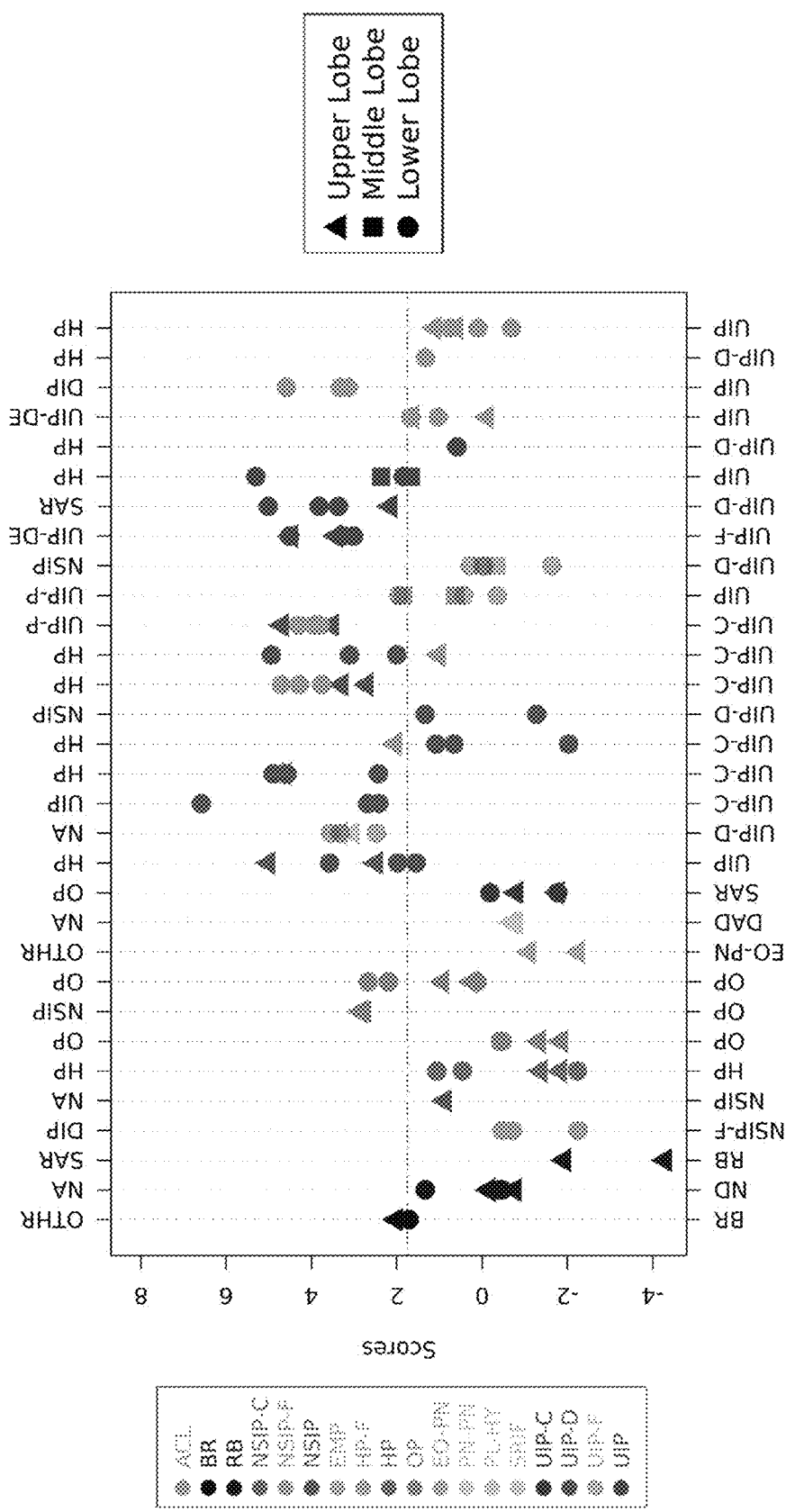

We defined a decision boundary targeting high (92%) specificity, and observed a corresponding sensitivity of 65% (FIG. 3A, FIG. 3B).

Using this classifier, TBB samples from the independent test set of 113 samples from 31 patients was prospectively scored, and the classifier showed a ROC-AUC of 0.86 with sensitivity of 63% [95% CI: 43-87] and specificity of 86% [95% CI: 73-97] (FIG. 3C, FIG. 3D) based on sample level data. Cross-validation performance that generalizes to a validation cohort suggests that robust training was achieved despite the relatively modest cohort size.

Algorithm re-training on the combined cohort of 283 TBB samples from 84 patients resulted in a cross-validated ROC-AUC of 0.87 [CI: 0.82-0.91] (sensitivity of 63% [CI: 54-72], specificity of 91% [CI: 80-98]) when all TBB samples from each patient are scored separately. Similar cross-validation results (as observed in this case) on the larger set of samples is promising, and will need to be evaluated on an additional independent test set, currently planned as prospective patients are accrued in the BRAVE studies.

Thus, we have demonstrated that a UIP genomic classifier using gene expression signature can effectively distinguish the spatially and temporally heterogeneous fibrotic disease pattern characteristic of UIP from the uniform and typically active fibrosis associated with immune responses (RB-ILD/DIP, eosinophilic pneumonia, granulomatous disease), inflammation (NSIP, HP), or as an acute response to injury[10].

All statistical analyses were carried out using R version 3.0.1[21]. For the microarray classifier, genes differentially expressed between UIP and non-UIP classes were ranked by limma[26], then the top 200 genes with lowest false discovery rate (FDR) (<0.0003) were carried forward as candidate genes for model building. Several models were built using different methods, and the one with the lowest error was chosen. Feature selection and model estimation were performed by logistic regression with lasso penalty using glmnet[27]. For the RNAseq classifier, genes were ranked by FDR resulting from a Wald-style test implemented in the DESeq2[22] package on the raw count data. The top features (N ranging from 10 to 200) were used to train a linear support vector machine (SVM)[23] using the e1071 library[24] on the normalized expression data.

Classifier performance was evaluated by CV and, when available, by an independent test set. To minimize overfitting, a single patient was maintained as the smallest unit when defining the training/test set and the CV partition; i.e. all samples belonging to the same patient were held together as a group in the training/test set or in CV partitions. The CV methods used include leave-one-patient-out (LOPO) and 10-fold patient-level CV.

FIG. 3 shows the results of single-sample classification performances.

Performance was reported as the area under the curve (AUC), and specificity (1.0—false positive rate) and sensitivity (1.0—false negative rate) at a given score threshold. We set the score threshold to require at least >90% specificity. For each performance measurement, 95% confidence intervals were computed using 2000 stratified bootstrap replicates and the pROC package[22] and reported as [CI lower-upper].

Example 6

Classifier Development and Performance Using Pooled Samples

While overall single-sample performance achieved in Example 5 was excellent, the classifier did not detect UIP in some samples from some UIP patients (FNs). As UIP was frequently detected in other samples from the same patient, sampling effects, either insufficient tissue sampling or disease heterogeneity, came under suspicion as a source of FNs.

We did not observe a systematic reduction in alveolar content in false negative samples, ruling out inadequate sampling of alveolar tissue as the cause (see Example 7). Thus, disease heterogeneity or technical sample quality effects remain possible explanations for false negatives. Importantly, we chose expert pathology review as the reference standard for the presence of UIP. Despite known issues of inter-operator disagreement[4,29,30], we achieved blinded agreement between two expert pathologists at the subtype level for 83% of our patients.

By design, our clinical study collects multiple TBB samples per patient, typically two to three per lung lobe, to mitigate possible disease and sampling heterogeneity effects, which could result in training error or false test calls. For most patients, our sample-level classifier correctly detects disease in more than one sample of the available TBBs per patient, consistent with overall high sample-level test accuracy (FIG. 3). This raises the possibility that patient-level reporting of UIP based on mixtures of multiple TBB samples is feasible by pooling multiple samples per patient, and we hypothesized that such mixtures may improve detection accuracy overall at the patient level. We therefore evaluated test designs involving combinations of multiple TBB samples.

We first used an in silico approach to derive models that simulate mixing multiple TBB samples from the same patient to yield a single test result. Herein, this approach is referred to as "in silico mixing" or, interchangeably, "in silico pooling". In silico within-patient mixtures were modeled from multiple samples by averaging scaled gene count data prior to variance stabilized transformation (VST). Simulations were performed 100 fold at each condition with gene-level technical variability added at the VST level.

Figure 4A:
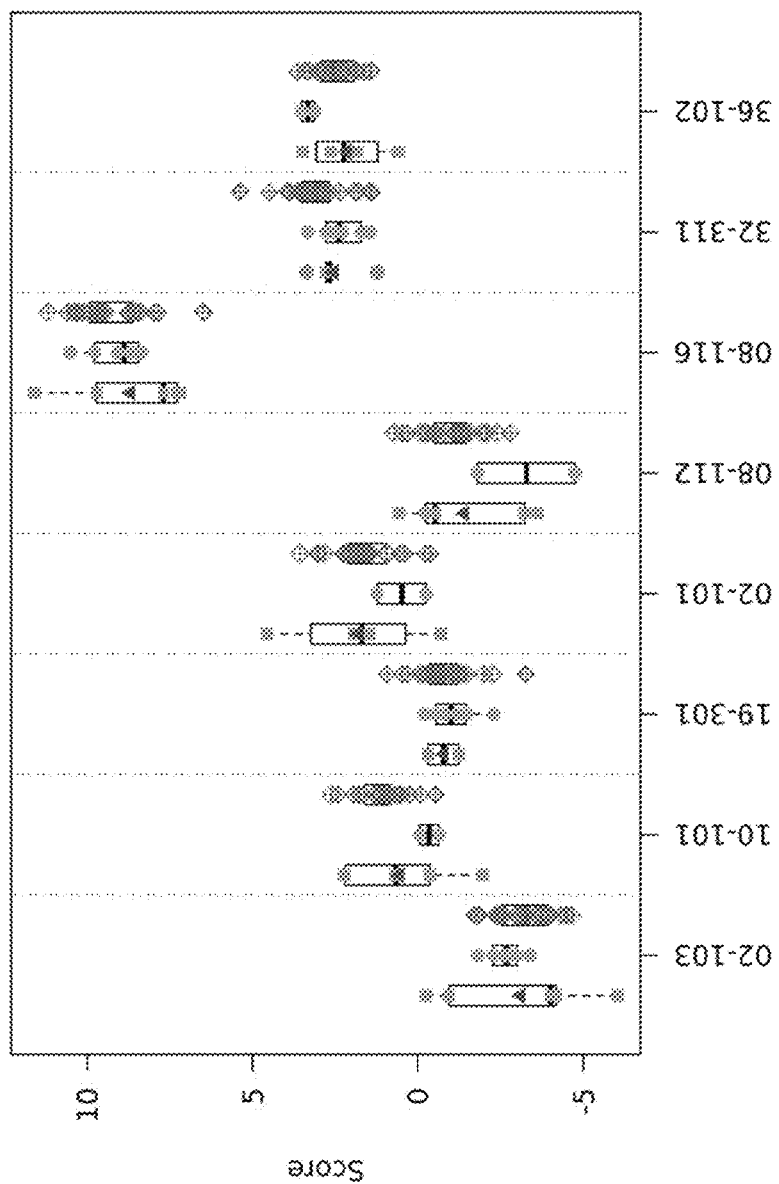
FIG. 4A-4D: Classification of UIP in mixtures of TBBs from the same patient.

The scores from the in silico simulated mixtures were then compared to actual mixtures generated in vitro for eight patients, as well as to the corresponding individual (e.g. unmixed) TBB sample scores (FIG. 4A). The results indicate that our in silico modeling reasonably approximates scores observed from actual mixtures and individual TBB samples.

Figure 4B:
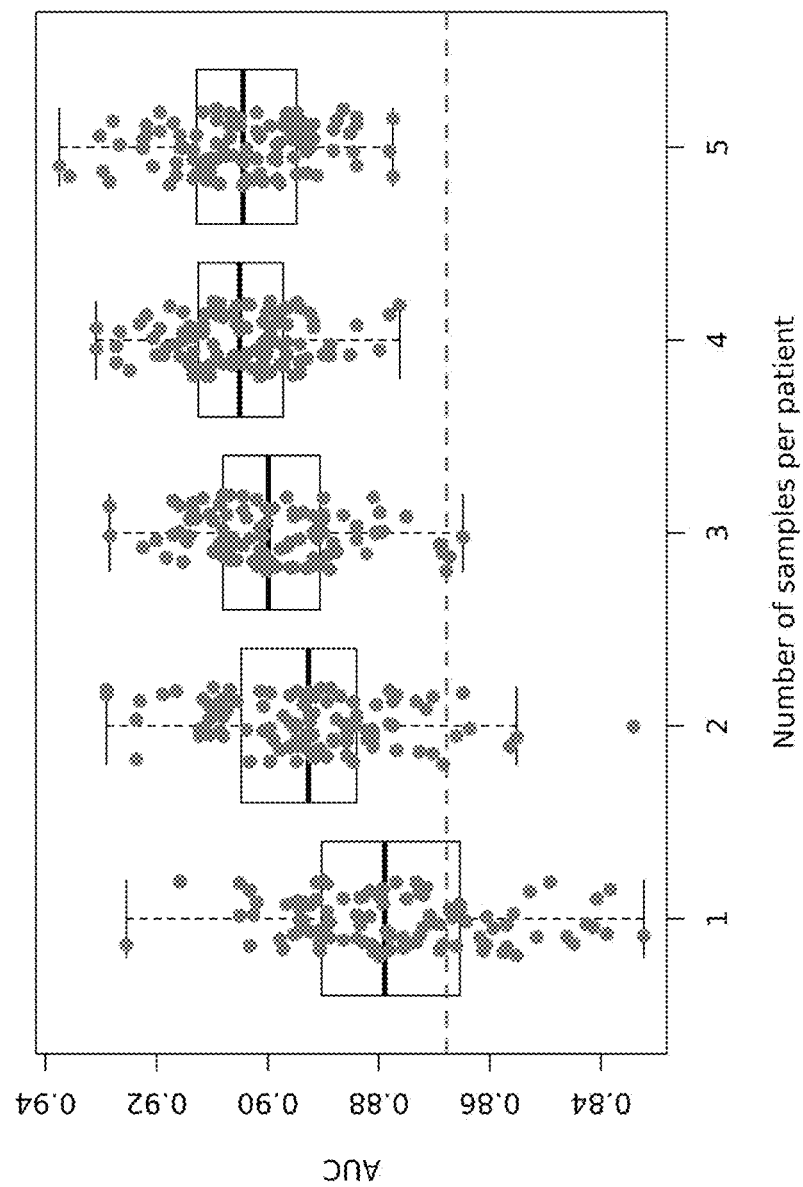
Figure 4C:
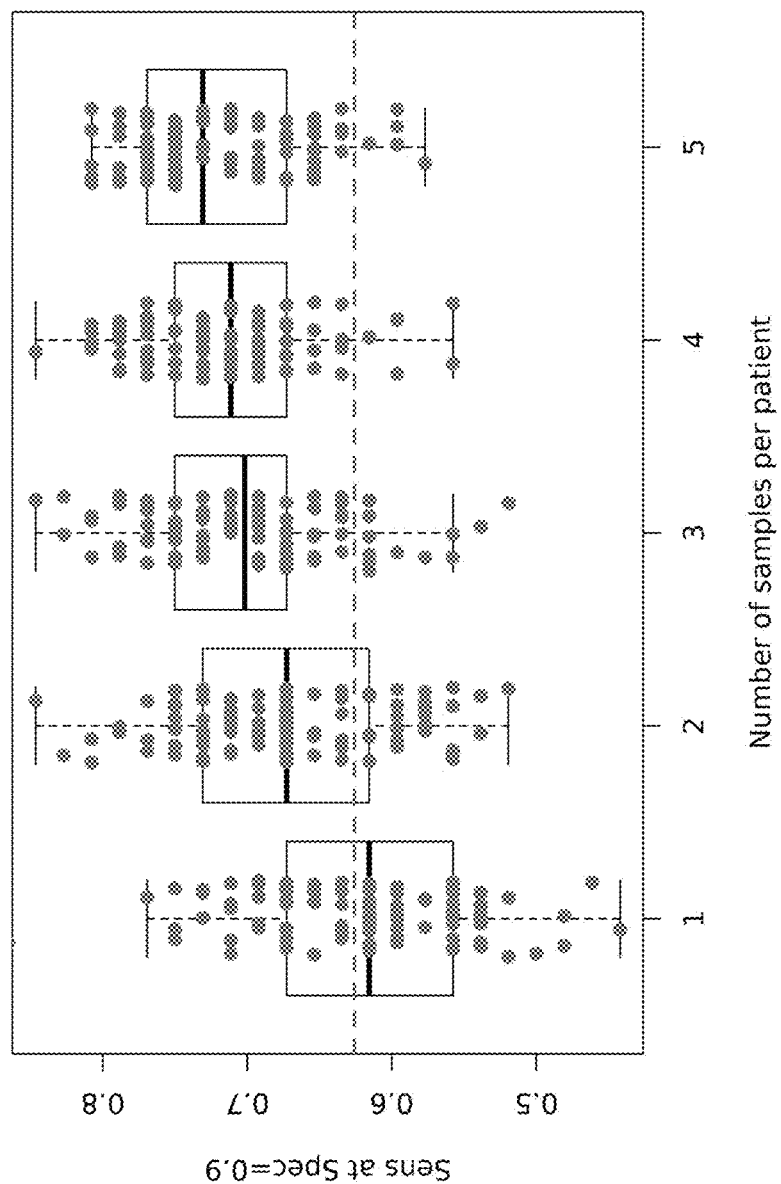
Figure 4D:
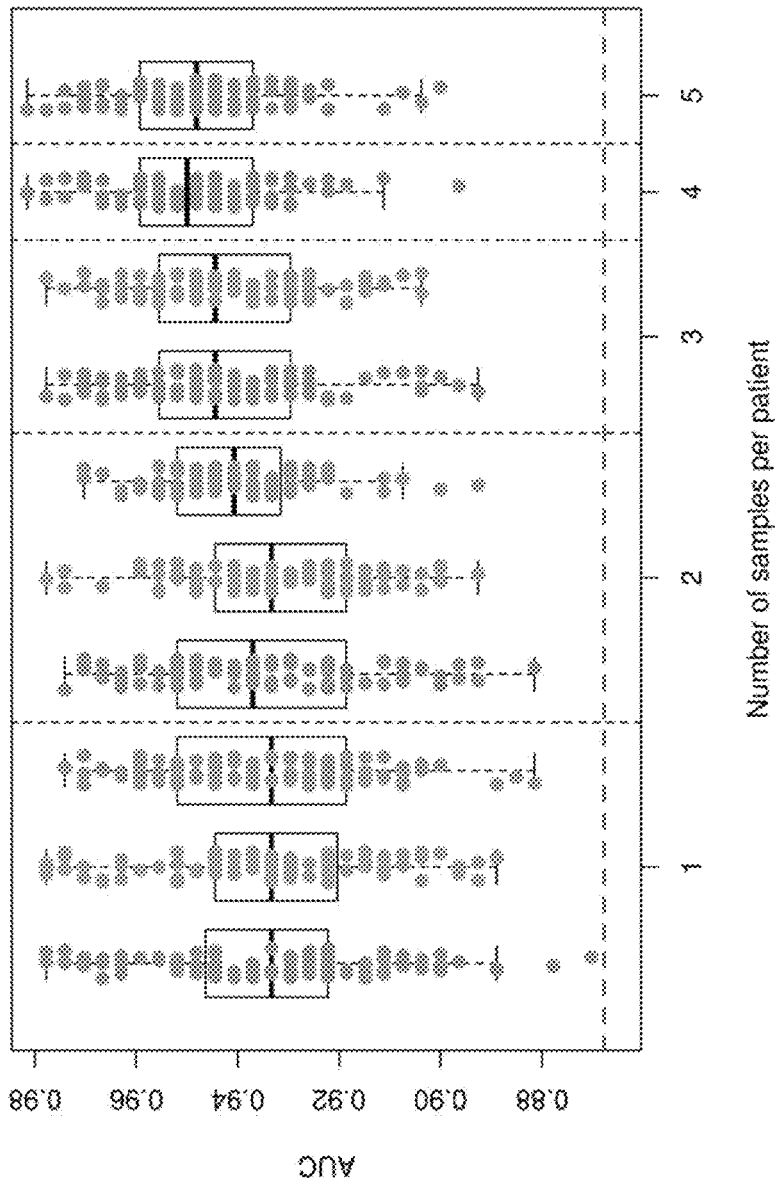

We then used this analytical method to simulate mixtures of two through five TBBs per patient, selected at random within each patient (FIG. 4B). By simulation, mixtures of two or three samples per patient show increasing classification accuracy versus a single sample per patient selected at random (FIG. 4B). Furthermore, mixtures of 4 or 5 TBBs show reduced variability (i.e., higher confidence) in the performance estimate with similar maximal accuracy (FIG. 4B). At a targeted specificity of ~90%, test sensitivity in mixtures improves to ~72%, with reduced variability (AUC=0.90 [CI 0.88-0.93], sensitivity=72% at 90% specificity [CI 60-81]) (FIG. 4C). In a set of 33 subjects with two upper lobe and three lower lobe TBBs available for every subject, mixture simulation shows no improvement in performance when sampling is restricted to the upper or lower lobes (FIG. 4D). This analysis suggests that mixtures of up to five TBB samplings per patient can maximize the accurate detection of the UIP pattern, using a single molecular test. Such a result may be surprising because pooling is expected to introduce more variability due to cellular heterogeneity.

Thus, physical or in silico mixing studies suggest that combining multiple samplings per patient results in increased accuracy.

By training on all samples separately (i.e., as described in Example 5), we maximized representation and sampling diversity, and mitigated a priori sub-sampling bias of available samples. By testing on sample mixtures, we appear to mitigate sampling effects, as demonstrated by improved test accuracy.

Example 7

Sampling Heterogeneity and Performance

Given that there is established disease heterogeneity in the lungs of patients with ILW[4,21-23], the finding that strong classifier performance may be obtained with variable sampling of the lungs prompted the question of whether adequate alveolar sampling is necessary during the TBB procedure. We hypothesized that if accurate classification of UIP versus non-UIP required gene signals from alveolar cells, then those samples with a paucity of alveolar cells should give rise to more classifier errors (particularly FNs) than samples with greater alveolar content. To address whether classifier accuracy depends upon adequate alveolar sampling, we tested the correlation between classifier accuracy and alveolar-specific genes.

Figure 5A:
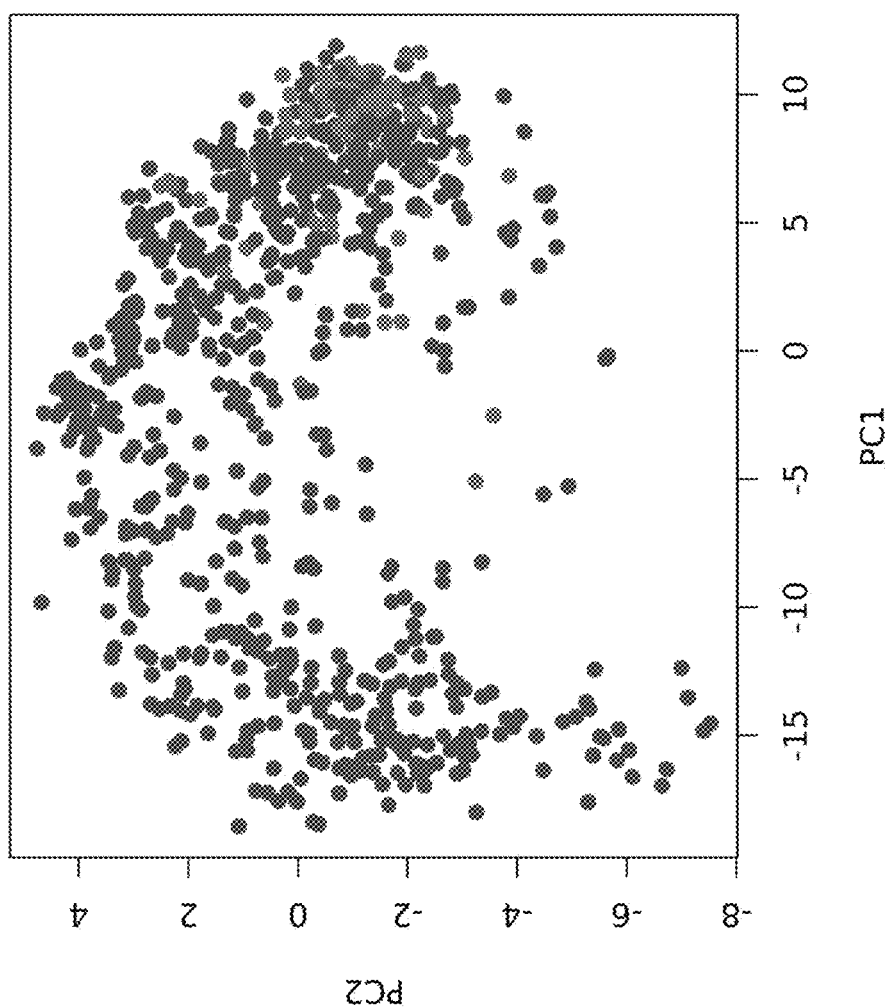
FIG. 5A-5C.

Specifically, we first developed a semi-quantitative genomic measure of alveolar content in the TBBs and then used this metric to determine whether it was correlated with classifier accuracy. TBB samples were evaluated for the expression of 44 lung specific genes, reported in the literature to be markers of bronchiolar, alveolar, and lung progenitor cells[E5-E9] (Table 16). Unsupervised clustering by principal components using the 44 markers suggests that this TBB cohort represents a continuous spectrum of sampled lung tissue, a subset of which overlaps with surgical lung biopsies (FIG. 5A; TBB samples in blue, SLB samples in orange).

We developed two alveolar metrics, one for type I and one for type II alveolar cells.

For the type I alveolar statistic we summed the expression of two genes, PDPN and AQP5. These genes show a continuous pattern of gene expression amongst the sample set.

Figure 5B:
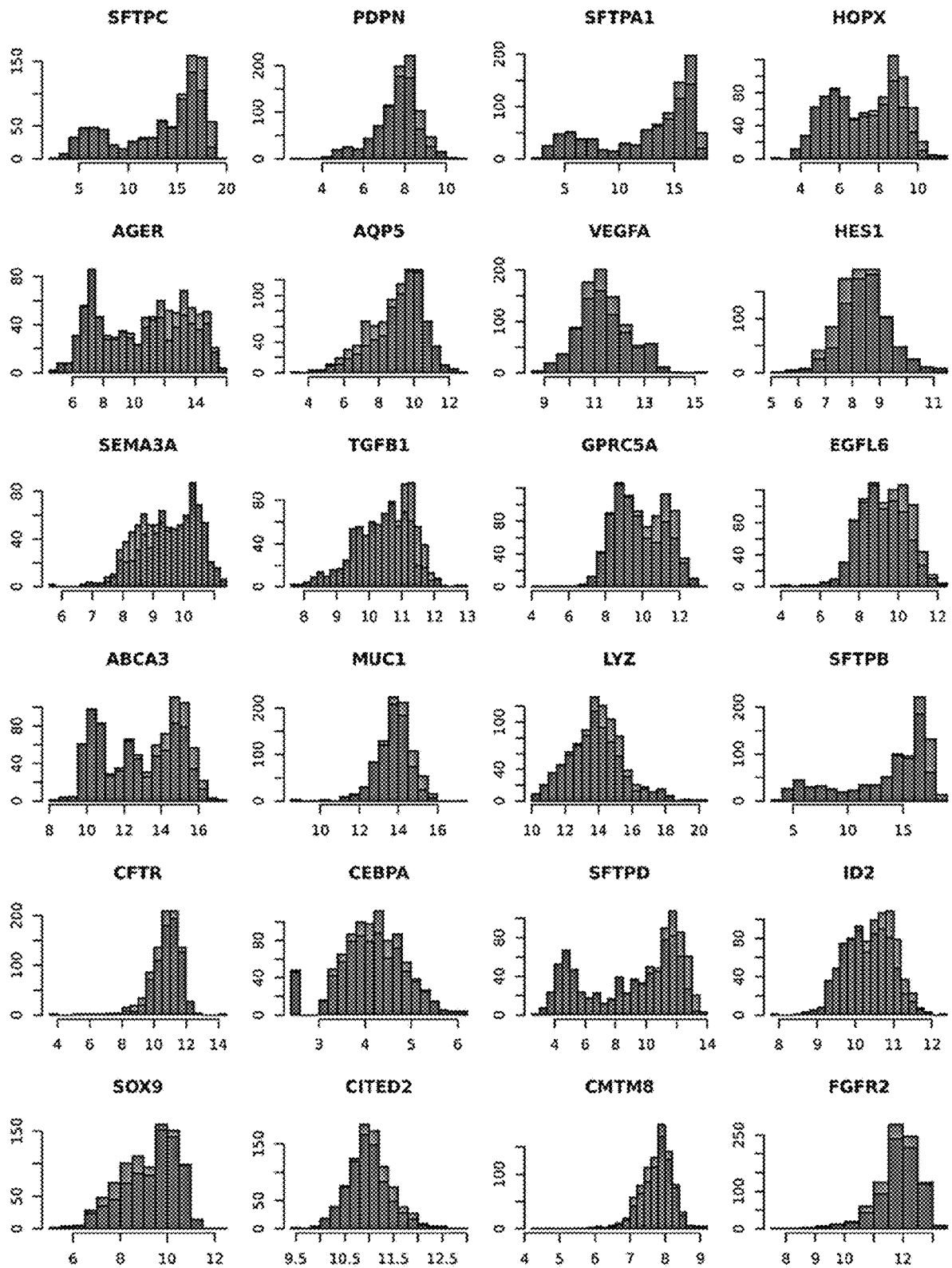
Figure 5C:
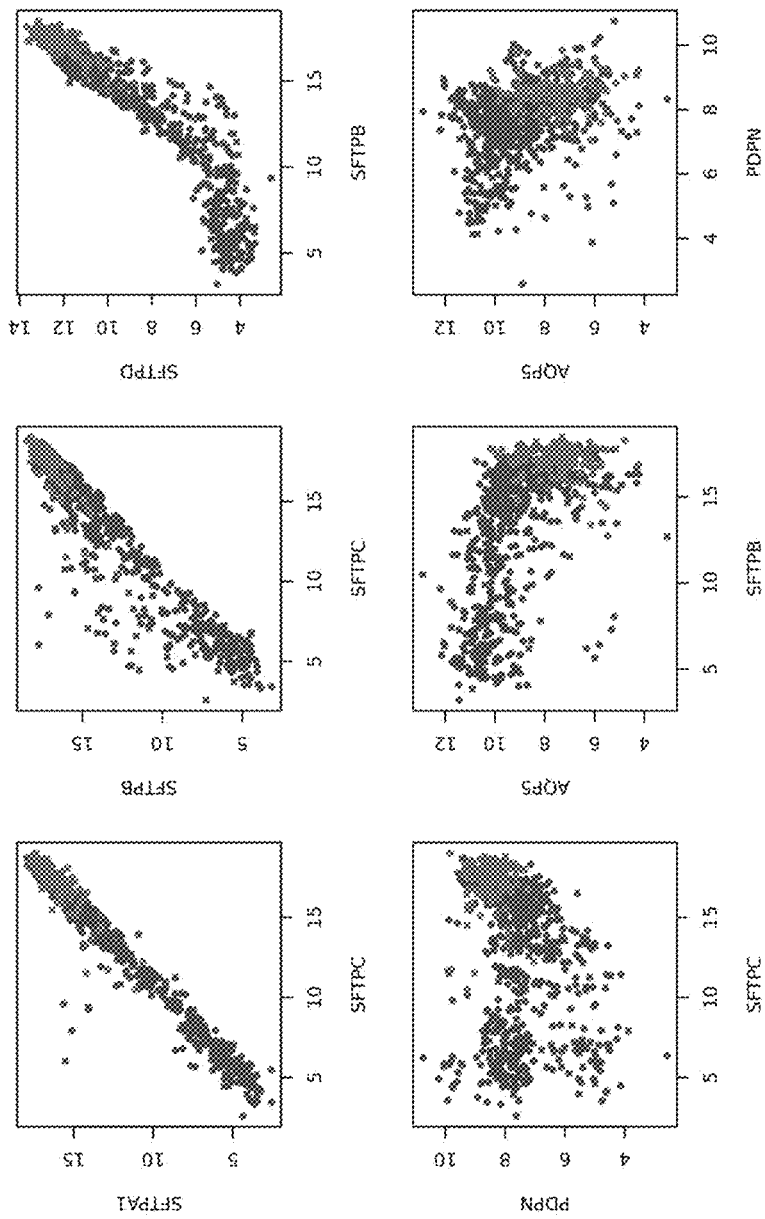

Our second approach, used for the type II alveolar metric, was to examine markers that showed evidence of bimodal expression within the population of TBBs. This pattern is seen for nine genes, five of which (SFTPB, SFTPC, SFTPD, ABCA3, CEBPA) are alveolar type II (ATII) specific, three (AGER, GPRC5A, HOPX) are alveolar type I (ATI) specific, and one (SFTPA1) is seen in both type I and II cells (FIG. 5B; TBB expression counts in blue, SLB expression counts in orange). Correlated, directionally consistent expression is seen between SFTPA1, SFTPB, SFTPC, and SFTPD, but not between PDPN and AQP5, or between members of these two groups (FIG. 5C; TBB expression counts in blue, SLB expression counts in orange). We therefore selected the four surfactant proteins SFTPA1, SFTPB, SFTPC and SFTPD as markers of type II alveolar content, and summed their expression within samples as a proxy measure of alveolar content within each sample.

Figure 6A:
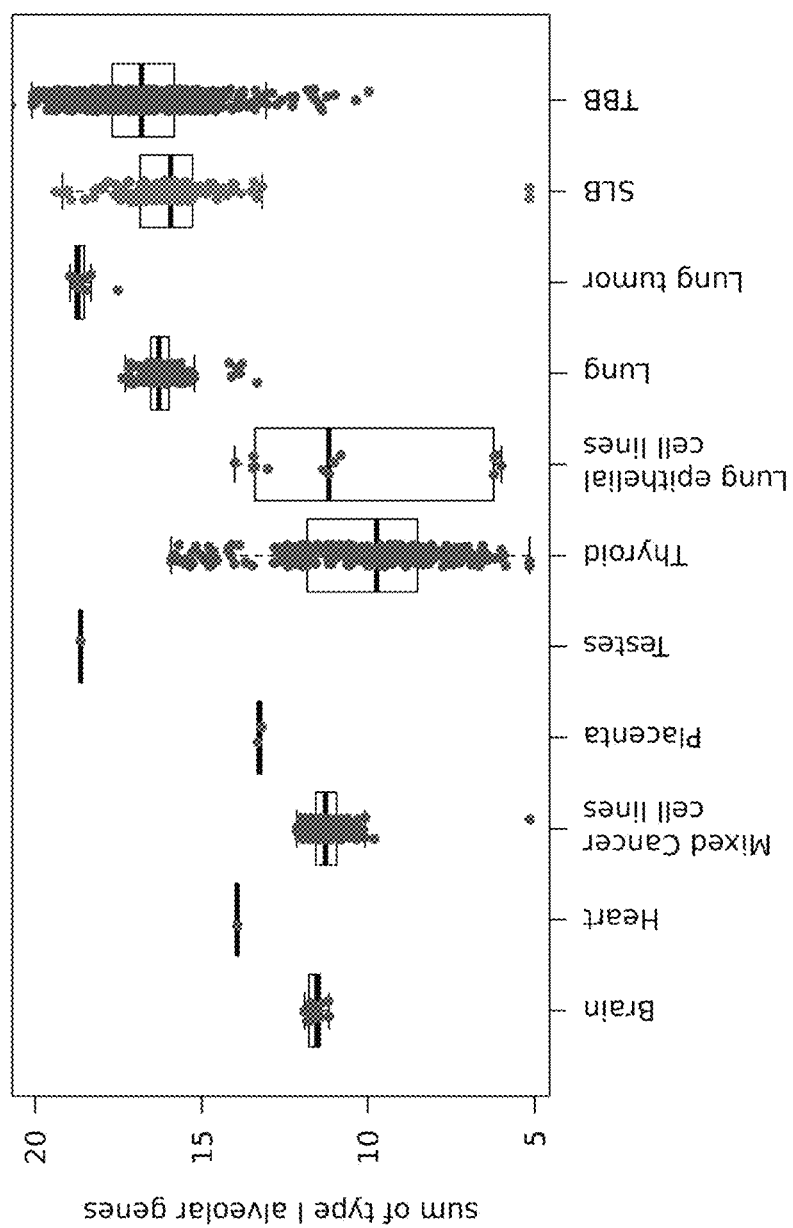
FIG. 6A-6D: Distribution of alveolar gene expression in transbronchial biopsies.
Figure 6B:
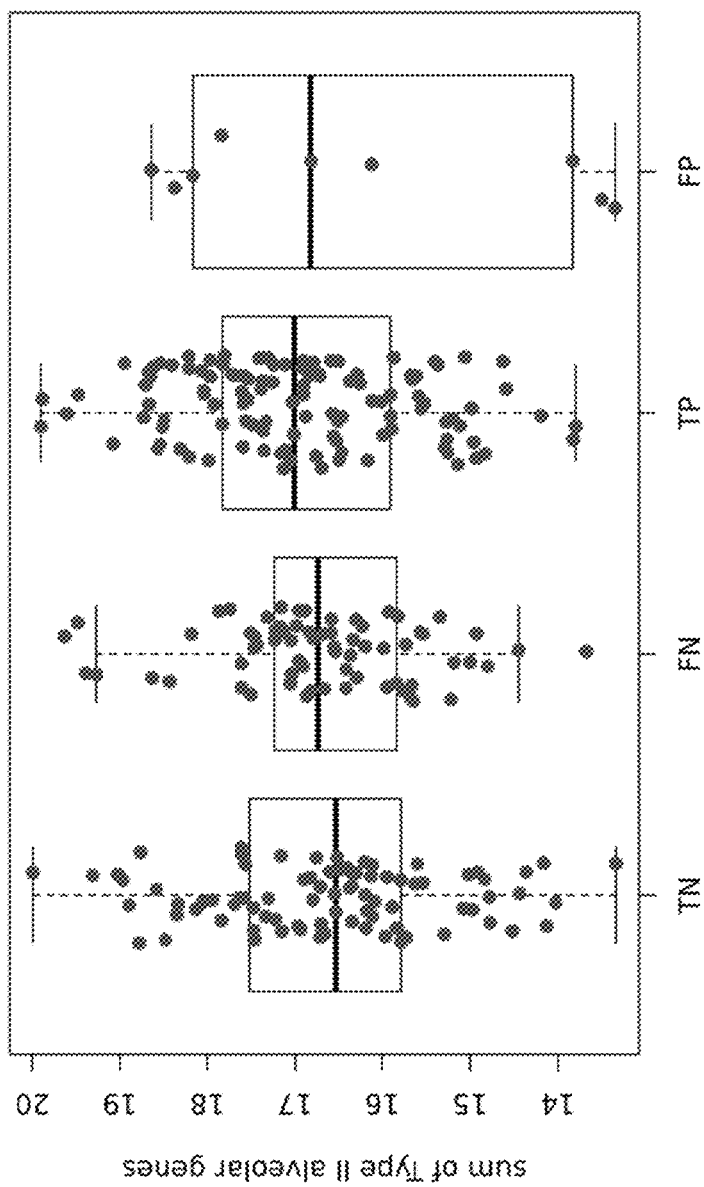
Figure 6C:
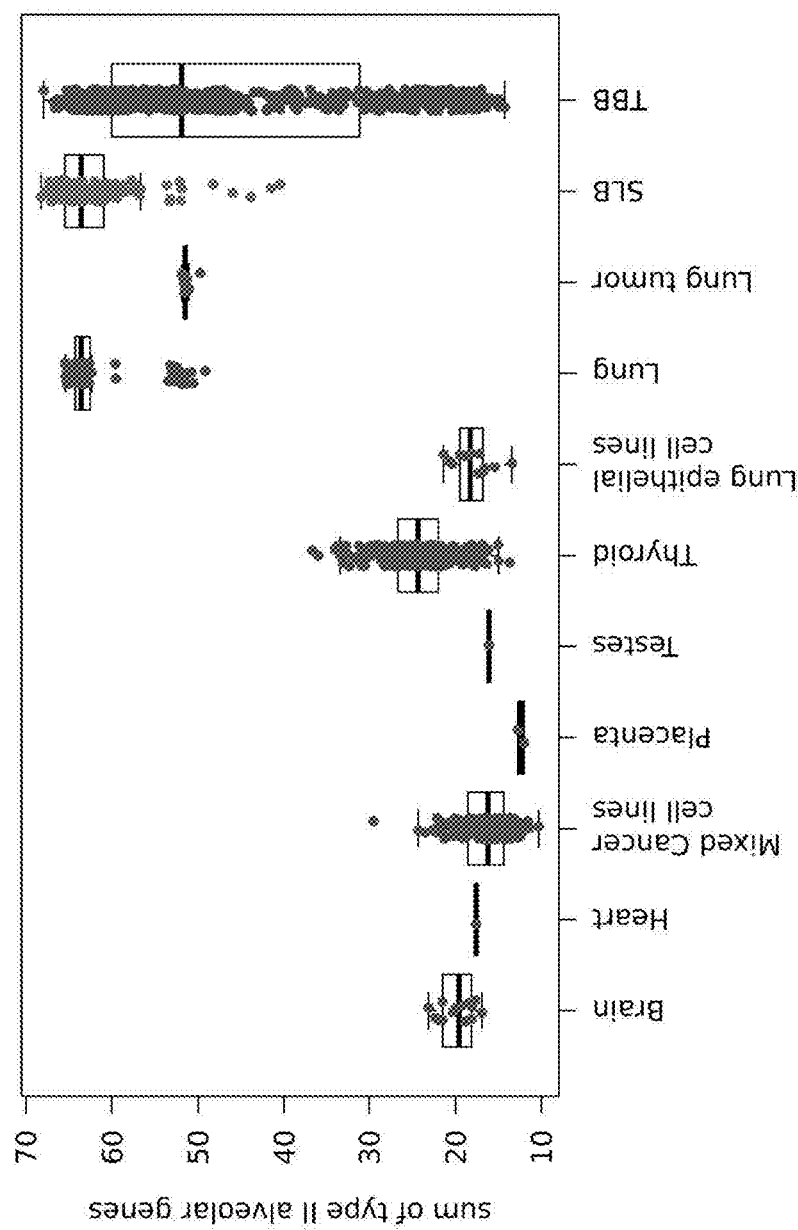
Figure 6D:
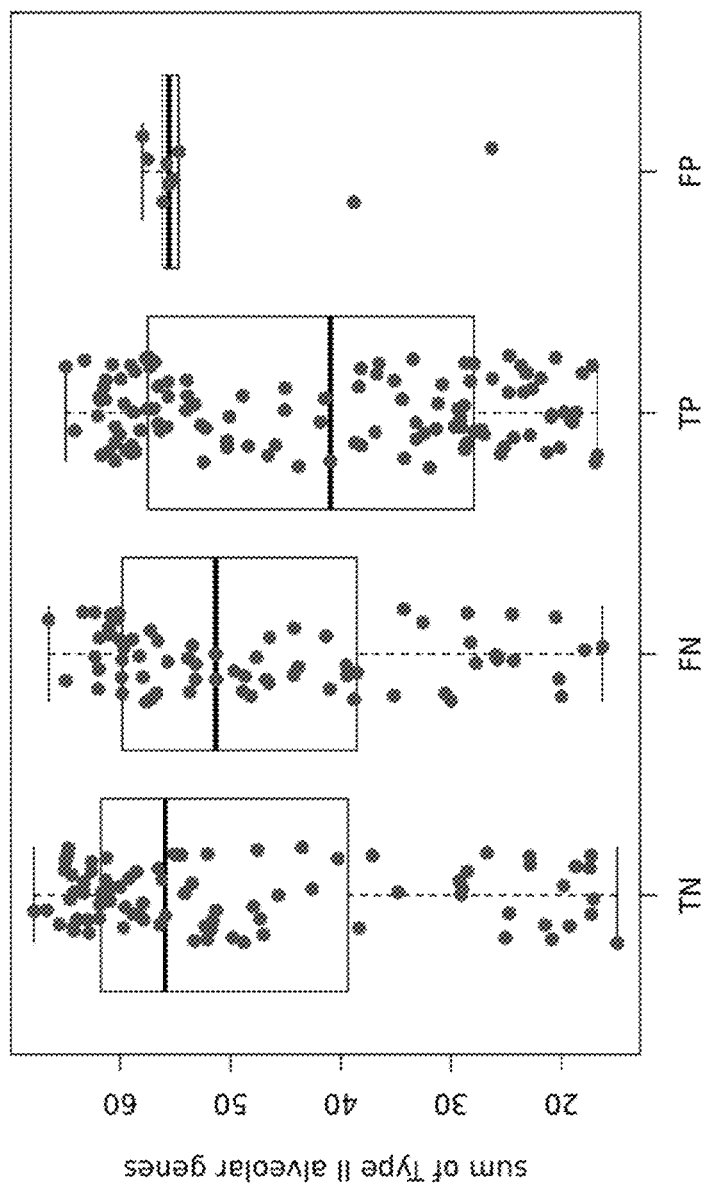

While these metrics show a wide range of type I and type II alveolar specific gene expression across various samples types, with high expression in SLBs and many TBBs, and low expression in a variety of non-lung tissue types and in three bronchial epithelial cell lines (Beas2b, HBEC, and NL-20) (FIG. 6A), the expression of these transcripts did not correlate with classifier accuracy (Pearson's correlation, 0.03, p-value=0.61). Thus, these results show that neither false negative nor false positive errors are associated with lower type I or II alveolar I content, suggesting that accurate classification results may be achieved in TBB samples with variable cellular composition (FIG. 6B).

We also found no significant correlation between classifier accuracy on individual samples and TBB alveolar gene expression, RNA quality, or RNA yield (Table 3).

TABLE 3

Pearson's correlations of TBB sample properties to classification accuracy

| Sample property | Correlation | p-value |
|---|---|---|
| Alveolar I expression statistic | −0.07 | 0.27 |
| Alveolar II expression statistic | 0.03 | 0.61 |
| RNA quality | | |
| RIN | −0.07 | 0.24 |
| $DV_{200}$ | −0.10 | 0.09 |
| RNA yield in nanograms | 0.06 | 0.32 |

These results suggest that accurate classification results can be achieved in TBB samples with variable alveolar content.

Example 8

Biological Pathways Associated With Genes Used By The Classifiers

PANTHER™ Pathway Analysis

We used DESeq2[19] to identify differential expression between UIP and non-UIP TBBs derived from 84 patients with pathology truth. Ensembl genes significantly upregulated in UIP (n=926) and in non-UIP (n=1330) at false-discovery rate (FDR) adjusted p-values <0.05 were used as input to the PANTHER™ classification system for pathway over-representation analysis (web version 11.0, released 2016-07-15)(Mi H, Lazareva-Ulitsky B. et al., Nucleic Acids Res 2005; 33:D284-D288, incorporated herein by reference in its entirety). PANTHER™ pathways were curated to remove general or redundant pathway classifications, and ordered by significance (Table 4). We found that TBBs with UIP are significantly enriched for the expression of markers of cellular metabolism, adhesion and developmental processes while non-UIP TBBs show evidence of immune activation, lipid metabolism, stress responses and cell death (Table 4). Aberrant re-activation of developmental pathways and cellular proliferation are hallmarks of IPF[24-27].

TABLE 4

Biological Processes Over Represented in UIP and non-UIP TBB Samples

| Biological Process | Number expected | Number observed | Fold Increase | P-value |
|---|---|---|---|---|
| Over Represented in UIP | | | | |
| Cell-cell adhesion | 13 | 44 | 3.4 | <0.0001 |
| Cellular component morphogenesis | 23 | 53 | 2.3 | <0.0001 |
| Nervous system development | 29 | 63 | 2.2 | <0.0001 |
| Transcription, DNA-dependent | 65 | 122 | 1.9 | <0.0001 |
| RNA metabolic process | 88 | 144 | 1.6 | <0.0001 |
| Nucleobase metabolic process | 135 | 189 | 1.4 | 0.0002 |
| Nitrogen compound metabolic process | 86 | 129 | 1.5 | 0.0008 |
| Ectoderm development | 17 | 39 | 2.3 | 0.0010 |
| Visual perception | 8 | 23 | 2.8 | 0.0036 |
| Mesoderm development | 19 | 37 | 1.9 | 0.0371 |
| Muscle contraction | 7 | 18 | 2.7 | 0.0398 |
| Over Represented in non-UIP | | | | |
| Antigen processing and presentation | 4 | 20 | 5.3 | <0.0001 |
| Cellular defense response | 13 | 39 | 3.0 | <0.0001 |
| Lipid metabolic process | 33 | 68 | 2.1 | <0.0001 |
| Immune system process | 79 | 131 | 1.7 | <0.0001 |
| Cholesterol metabolic process | 5 | 19 | 3.8 | 0.0003 |
| Steroid metabolic process | 11 | 30 | 2.7 | 0.0004 |
| Immune response | 44 | 74 | 1.7 | 0.0054 |
| Apoptotic process | 26 | 49 | 1.9 | 0.0057 |
| Phosphate-containing compound metabolism | 77 | 114 | 1.5 | 0.0076 |
| I-kappaB kinase/NF-kappaB cascade | 4 | 15 | 3.4 | 0.0157 |
| Response to stress | 53 | 83 | 1.6 | 0.0172 |
| Transmembrane tyrosine kinase signaling | 12 | 28 | 2.3 | 0.0213 |
| Catabolic process | 49 | 77 | 1.6 | 0.0222 |
| Hemopoiesis | 6 | 17 | 2.9 | 0.0328 |

Example 9

BRAVE Study Design

The purpose of the BRAVE (BRonchial sAmple collection for a noVel gEnomic test) study is to collect bronchoscopic specimens, clinical data, and associated pathology slides for external review in order to optimize a molecular profiling test that will provide a range of diagnostic and prognostic information about interstitial lung disease (ILD).

BRAVE is divided into three arms: BRAVE-1 is intended to enroll patients scheduled for a diagnostic surgical lung biopsy (SLB) as part of their usual care clinical diagnosis. BRAVE-2 is intended for patients scheduled for diagnostic bronchoscopy only. BRAVE-3 is intended for patients scheduled for a diagnostic cryobiopsy.

Bronchoalveolar lavage, blood, serum and buccal swabs are also collected. Subjects will be enrolled until a sufficient number of samples are collected to satisfy power and sample size requirements for the development and prospective validation of a molecular test for ILD.

Subjects are followed for up to one year after sample collection in order to assess progression of disease. Patients aged less than 18 years, or for whom SLB is not medically indicated, or who are undergoing SLB for non-ILD medical conditions, are not eligible for study enrollment. Patients with medical conditions which are contraindications to performing bronchoscopic biopsy, or for whom bronchoscopic sampling is not recommended or difficult, are also excluded from the BRAVE study.

Example 10

Generation of the Envisia Classifier

Having demonstrated that machine learning can detect a UIP histopathologic pattern in lung tissue obtained by SLB and TBB (see Examples 1-9), we sought to extend the classifier training in a larger and more diverse group of patients, and to validate a locked algorithm on an independent, prospectively collected set of subjects.

Methods

A total of 201 subjects were enrolled in a prospective, multi-center study at 18 U.S. and European sites. We collected up to five TBBs per subject, paired at the lobe level with standard-of-care lung tissue biopsy samples. A histologic pattern diagnosis, made using a panel of three expert pathologists, was obtained on 139 subjects. Exome-enriched RNA sequencing was performed on pooled TBBs and the resulting sequences were aligned and transcript counts extracted for xyx genes. We trained and locked a machine learning algorithm, the Envisia Genomic Classifier, using approximately 90 patients and then validated the test on an independent set of 49 subjects with histology reference labels. We optimized the test decision boundary to give high specificity, i.e., to reduce false positives as this may create harm by overcalling the UIP pattern, potentially leading to the unnecessary risk and expense of IPF therapy. We locked all classifier parameters, and defined the patient and sample characteristics that are within indication for testing. We report here the prospective clinical validation of the Envisia Genomic Classifier in TBBs from an independent cohort of 49 subjects, and compare its classification performance to HRCT.

Study Design and Oversight

For this independent validation study, a total of 88 subjects were enrolled into three separate BRAVE studies (FIG. 1). In BRAVE-1, subjects underwent a clinically-indicated SLB (n=43); BRAVE-2 subjects underwent a clinically indicated TBB (n=9); and BRAVE-3 subjects underwent a clinically indicated cryobiopsy (n=36). BRAVE-2 subjects had only TBB for histopathology evaluation, BRAVE-1 and 3 subjects were diagnosed by SLB or cryobiopsy, respectively.

Up to five dedicated transbronchial biopsies (TBB) (two upper lobe and three lower lobe, typically) were collected for molecular testing from the same lung lobes identified by participating physicians for clinically-indicated biopsy for histopathologic diagnosis. The study-indicated TBB specimens; study site-prepared histopathology slides and de-identified patient clinical data; HRCT of the chest; local clinical diagnoses; and one year and two year follow up, where available, were provided to Veracyte. Results of molecular testing were not provided to participating physicians, nor were they used to inform patient diagnosis or treatment.

HRCT scans were reviewed and classified by an expert thoracic radiologist (D. Lynch) as Definite UIP, Probable UIP, or Possible UIP9, desquamative interstitial pneumonia (DIP), hypersensitivity pneumonitis (HP), Langerhans cell histiocytosis (LCH), nonspecific interstitial pneumonia (NSIP), organizing pneumonia (OP), respiratory bronchiolitis (RB), Sarcoidosis or 'other' (unclassifiable). Veracyte clinical personnel reviewed and interpreted study site radiology descriptions using the same criteria, but with "Inconsistent with UIP" in place of the specific non-UIP diagnoses[35].

Histopathology slides from the clinically-indicated SLB, cryobiopsy, or TBB were independently reviewed by two or three expert lung pathologists blinded to patient clinical information, as previously described[E1,E10] Each pathologist independently determined a histopathologic pattern diagnosis for each lung lobe sampled. We defined consensus as blinded agreement at the histologic pattern level between two of two or two of three reviewing pathologists, or by agreement after unblinded consultation between three pathologists (conferral), if blinded agreement was not achieved.

Figure 9:
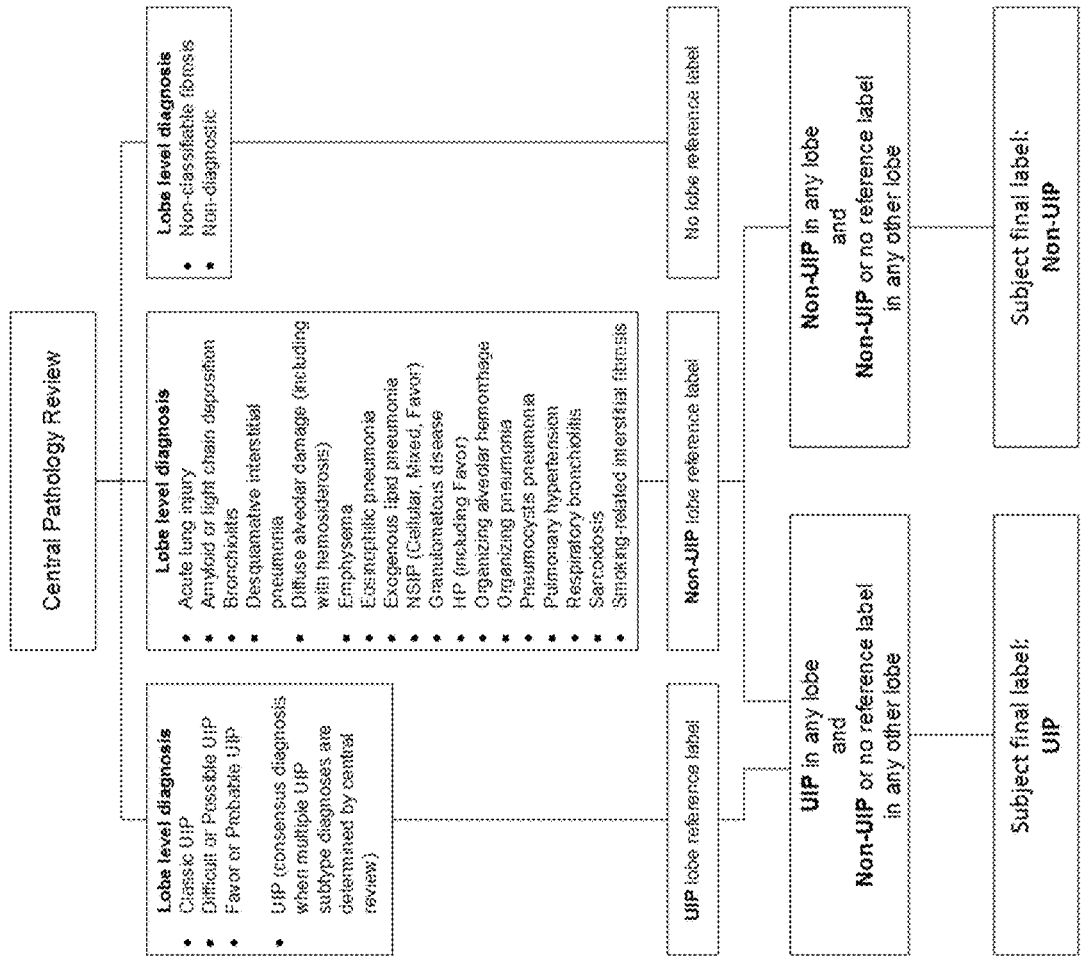
FIG. 9. Diagram of the central pathology review process used in the Example 10 study to determine reference labels for study subjects.

Veracyte personnel assigned reference labels of UIP or non-UIP to each study subject based on the consensus of the lobe-level diagnoses, according to the following categories (FIG. 9). If any lobe was diagnostic of UIP by pathology, that subject was assigned a UIP label[4]. A subject diagnostic for non-UIP pathology in any lobe was assigned a non-UIP reference label if all other lobes were also non-UIP or non-diagnostic (FIG. 9). All Veracyte laboratory and analysis personnel were blinded to the reference labels during testing and algorithm development.

Laboratory Test Procedure

Figure 8:
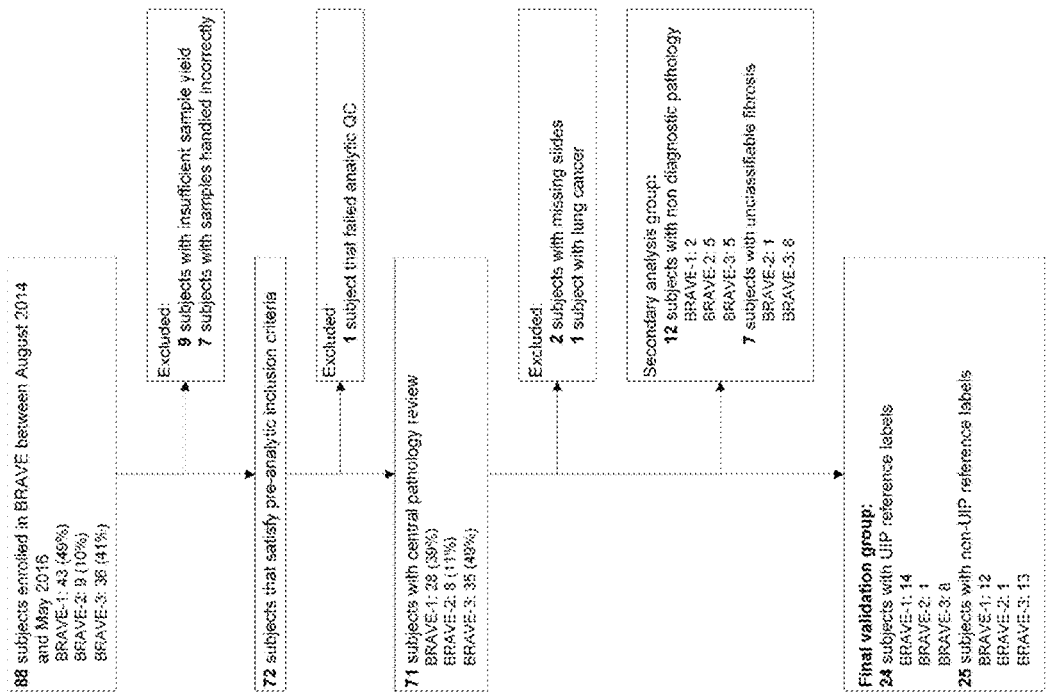
FIG. 8. Flow diagram illustrating the derivation of the Envisia final validation and secondary analysis groups from 88 BRAVE study subjects (Example 10).

Study-indicated TBB from 88 BRAVE patients were collected into a dedicated nucleic acid preservative (RNAprotect, QIAGEN, Valencia, CA), stored cold onsite for up to 14 days and shipped to Veracyte for processing. We extracted total RNA using a modified AllPrep Micro procedure (QIAGEN), followed by quantitation using RNA-binding dye fluorescence (QuantiFluor, Promega, Madison, WI). We pre-specified that a minimum of three and maximum of five TBBs per subject, each yielding at least 31 ng of total RNA, were required for study inclusion. Nine subjects were excluded due to insufficient numbers of samples or RNA yields (FIG. 8). In addition, specimens containing a foreign object (toothpicks, one subject), specimens delivered to Veracyte with missing preservative (one subject), and specimens in shipment beyond the shipping container cooling limit of 48 hours (five subjects), were also prospectively excluded (FIG. 8). The individual TBBs for 72 subjects thus satisfied our pre-specified study inclusion criteria.

Pooled RNA for each subject was input to a partially automated TruSeq RNA Access Library Prep procedure (Illumina, San Diego, CA) to enrich for expressed exonic sequences, and sequenced to a targeted depth of ≥25M paired-end reads on NextSeq 500 instruments (Illumina). Count data were evaluated against criteria for total numbers of sequenced and uniquely mapped reads, the overall proportions of mapped reads and of exonic reads, the mean per-base coverage, the uniformity of base coverage, and base duplication and mismatch rates. Data from one subject did not meet these criteria and was excluded, leaving 71 subjects (FIG. 8). Expression count data was normalized with respect to sequencing depth (scale factors) and transformed by variance stabilized transformation using DESeq216, prior to classification.

Algorithm Development 354 individual TBB samples from 90 subjects previously enrolled in the BRAVE studies from December of 2012 to July of 2015[E10] were used exclusively to train the machine learning algorithm (the classification model). Feature selection and hyperparameter optimization were performed by the algorithm using elastic net logistic regression. Performance of the model was evaluated in the training set using receiver-operator characteristic areas under the curve (ROC-AUCs), determined by leave-one-patient-out cross validation (CV). A test decision boundary was selected that optimized specificity (minimizes UIP false positive calls) in the training set. A penalized logistic classifier using 190 genes as features, with a locked decision boundary (the Envisia Genomic Classifier) was thus defined (Table 5). Envisia reports a molecular diagnosis of UIP or non-UIP for each pool of TBBs. Subjects with classification scores above the decision boundary are called UIP by Envisia while subjects with scores equal or below the decision boundary are called non-UIP. The validation was scored both internally and independently by third parties not involved in the development of the test, prior to the unveiling of the reference labels.

TABLE 5

190 genes used by the Envisia Genomic Classifier

| Gene ID | Gene Symbol |
| --- | --- |
| ENSG00000005381 | MPO |
| ENSG00000005955 | GGNBP2 |
| ENSG00000007908 | SELE |
| ENSG00000007933 | FMO3 |
| ENSG00000010379 | SLC6A13 |
| ENSG00000012232 | EXTL3 |
| ENSG00000022556 | NLRP2 |
| ENSG00000026950 | BTN3A1 |
| ENSG00000033050 | ABCF2 |
| ENSG00000038295 | TLL1 |
| ENSG00000048052 | HDAC9 |
| ENSG00000054803 | CBLN4 |
| ENSG00000054938 | CHRDL2 |
| ENSG00000060688 | SNRNP40 |
| ENSG00000071909 | MYO3B |
| ENSG00000072310 | SREBF1 |
| ENSG00000073605 | GSDMB |
| ENSG00000078070 | MCCC1 |
| ENSG00000079385 | CEACAM1 |
| ENSG00000081041 | CXCL2 |
| ENSG00000081985 | IL12RB2 |
| ENSG00000082781 | ITGB5 |
| ENSG00000083814 | ZNF671 |
| ENSG00000086544 | ITPKC |
| ENSG00000089902 | RCOR1 |
| ENSG00000092295 | TGM1 |
| ENSG00000099251 | HSD17B7P2 |

TABLE 5-continued

190 genes used by the Envisia Genomic Classifier

| Gene ID | Gene Symbol |
|---|---|
| ENSG00000099974 | DDTL |
| ENSG00000100376 | FAM118A |
| ENSG00000100557 | C14orf105 |
| ENSG00000101544 | ADNP2 |
| ENSG00000102837 | OLFM4 |
| ENSG00000103044 | HAS3 |
| ENSG00000103257 | SLC7A5 |
| ENSG00000104812 | GYS1 |
| ENSG00000105255 | FSD1 |
| ENSG00000105559 | PLEKHA4 |
| ENSG00000105696 | TMEM59L |
| ENSG00000105784 | RUNDC3B |
| ENSG00000105983 | LMBR1 |
| ENSG00000106018 | VIPR2 |
| ENSG00000106178 | CCL24 |
| ENSG00000107929 | LARP4B |
| ENSG00000108312 | UBTF |
| ENSG00000108551 | RASD1 |
| ENSG00000109205 | ODAM |
| ENSG00000110092 | CCND1 |
| ENSG00000110900 | TSPAN11 |
| ENSG00000110975 | SYT10 |
| ENSG00000111218 | PRMT8 |
| ENSG00000111321 | LTBR |
| ENSG00000111328 | CDK2AP1 |
| ENSG00000112164 | GLP1R |
| ENSG00000112299 | VNN1 |
| ENSG00000112852 | PCDHB2 |
| ENSG00000114248 | LRRC31 |
| ENSG00000114923 | SLC4A3 |
| ENSG00000115415 | STAT1 |
| ENSG00000115607 | IL18RAP |
| ENSG00000116285 | ERRFI1 |
| ENSG00000116761 | CTH |
| ENSG00000119711 | ALDH6A1 |
| ENSG00000119725 | ZNF410 |
| ENSG00000120217 | CD274 |
| ENSG00000120738 | EGR1 |
| ENSG00000120903 | CHRNA2 |
| ENSG00000121380 | BCL2L14 |
| ENSG00000121417 | ZNF211 |
| ENSG00000122497 | NBPF14 |
| ENSG00000124205 | EDN3 |
| ENSG00000124702 | KLHDC3 |
| ENSG00000124935 | SCGB1D2 |
| ENSG00000125255 | SLC10A2 |
| ENSG00000128016 | ZFP36 |
| ENSG00000128266 | GNAZ |
| ENSG00000128791 | TWSG1 |
| ENSG00000128891 | C15orf57 |
| ENSG00000130164 | LDLR |
| ENSG00000130487 | KLHDC7B |
| ENSG00000130598 | TNNI2 |
| ENSG00000131095 | GFAP |
| ENSG00000131142 | CCL25 |
| ENSG00000132199 | ENOSF1 |
| ENSG00000132204 | LINC00470 |
| ENSG00000132915 | PDE6A |
| ENSG00000132938 | MTUS2 |
| ENSG00000133636 | NTS |
| ENSG00000133794 | ARNTL |
| ENSG00000134028 | ADAMDEC1 |
| ENSG00000134245 | WNT2B |
| ENSG00000135148 | TRAFD1 |
| ENSG00000135447 | PPP1R1A |
| ENSG00000135625 | EGR4 |
| ENSG00000136881 | BAAT |
| ENSG00000136883 | KIF12 |
| ENSG00000136928 | GABBR2 |
| ENSG00000136933 | RABEPK |
| ENSG00000137285 | TUBB2B |
| ENSG00000137463 | MGARP |
| ENSG00000137573 | SULF1 |
| ENSG00000137709 | POU2F3 |
| ENSG00000137968 | SLC44A5 |
| ENSG00000138166 | DUSP5 |
| ENSG00000138308 | PLA2G12B |
| ENSG00000140274 | DUOXA2 |
| ENSG00000140279 | DUOX2 |
| ENSG00000140323 | DISP2 |
| ENSG00000140450 | ARRDC4 |
| ENSG00000140465 | CYP1A1 |
| ENSG00000140505 | CYP1A2 |
| ENSG00000140718 | FTO |
| ENSG00000141279 | NPEPPS |
| ENSG00000142178 | SIK1 |
| ENSG00000142661 | MYOM3 |
| ENSG00000143185 | XCL2 |
| ENSG00000143195 | ILDR2 |
| ENSG00000143320 | CRABP2 |
| ENSG00000143322 | ABL2 |
| ENSG00000143367 | TUFT1 |
| ENSG00000143379 | SETDB1 |
| ENSG00000143603 | KCNN3 |
| ENSG00000144655 | CSRNP1 |
| ENSG00000145248 | SLC10A4 |
| ENSG00000145284 | SCD5 |
| ENSG00000145358 | DDIT4L |
| ENSG00000145736 | GTF2H2 |
| ENSG00000148541 | FAM13C |
| ENSG00000148700 | ADD3 |
| ENSG00000148702 | HABP2 |
| ENSG00000149043 | SYT8 |
| ENSG00000149289 | ZC3H12C |
| ENSG00000151012 | SLC7A11 |
| ENSG00000151572 | ANO4 |
| ENSG00000152672 | CLEC4F |
| ENSG00000153404 | PLEKHG4B |
| ENSG00000154227 | CERS3 |
| ENSG00000154451 | GBP5 |
| ENSG00000156414 | TDRD9 |
| ENSG00000157103 | SLC6A1 |
| ENSG00000157680 | DGKI |
| ENSG00000158457 | TSPAN33 |
| ENSG00000159231 | CBR3 |
| ENSG00000159674 | SPON2 |
| ENSG00000161609 | CCDC155 |
| ENSG00000162594 | IL23R |
| ENSG00000163029 | SMC6 |
| ENSG00000163110 | PDLIM5 |
| ENSG00000163285 | GABRG1 |
| ENSG00000163412 | EIF4E3 |
| ENSG00000163635 | ATXN7 |
| ENSG00000163644 | PPM1K |
| ENSG00000163735 | CXCL5 |
| ENSG00000163817 | SLC6A20 |
| ENSG00000163884 | KLF15 |
| ENSG00000164604 | GPR85 |
| ENSG00000164821 | DEFA4 |
| ENSG00000165948 | IFI27L1 |
| ENSG00000165973 | NELL1 |
| ENSG00000165983 | PTER |
| ENSG00000166923 | GREM1 |
| ENSG00000167748 | KLK1 |
| ENSG00000168004 | HRASLS5 |
| ENSG00000168036 | CTNNB1 |
| ENSG00000168062 | BATF2 |
| ENSG00000168394 | TAP1 |
| ENSG00000168661 | ZNF30 |
| ENSG00000168938 | PPIC |
| ENSG00000169248 | CXCL11 |
| ENSG00000170113 | NIPA1 |
| ENSG00000170442 | KRT86 |
| ENSG00000170509 | HSD17B13 |
| ENSG00000170837 | GPR27 |
| ENSG00000171016 | PYGO1 |
| ENSG00000171408 | PDE7B |
| ENSG00000171649 | ZIK1 |
| ENSG00000171714 | ANO5 |
| ENSG00000172137 | CALB2 |
| ENSG00000172183 | ISG20 |
| ENSG00000172215 | CXCR6 |

TABLE 5-continued 190 genes used by the Envisia Genomic Classifier

| Gene ID | Gene Symbol |
|---|---|
| ENSG00000172667 | ZMAT3 |
| ENSG00000173809 | TDRD12 |
| ENSG00000173812 | EIF1 |
| ENSG00000173926 | MARCH3 |
| ENSG00000175764 | TTLL11 |
| ENSG00000175806 | MSRA |
| ENSG00000176046 | NUPR1 |
| ENSG00000177182 | CLVS1 |
| ENSG00000177294 | FBXO39 |
| ENSG00000178187 | ZNF454 |
| ENSG00000178229 | ZNF543 |

Statistical Analysis

Statistical analysis was performed using R software, version 3.2.3. Continuous variables were compared by Student's t-test and categorical variables were compared by chi-squared test. All confidence intervals [CI] are two-sided 95% unless otherwise noted. We assessed test performance using standard measures of prediction accuracy. We used the alveolar type I and II gene expression scores developed previously[14] to assess whether test accuracy correlated with alveolar cell gene expression. We performed a biological pathway analysis on a combined set of the top 1000 genes differentially expressed in the training cohort TBBs (UIP vs. non-UIP) and the 190 classifier genes using GeneTrail software.

Results

Demographic and Pathological Characteristics of Study Subjects

A total of 88 subjects were enrolled into one of 3 BRAVE studies at 18 US and European clinical sites between August 2014 and May 2016 (FIG. 8). We excluded 16 subjects prior to analytical testing due to specimen mis-handling or insufficient material, and one subject that failed analytical QC during testing. A total of 71 subjects satisfied study inclusion criteria. Of these, two subjects with missing histopathology slides and one subject with adenocarcinoma of the lung were subsequently excluded, leaving a total of 68 subjects for pathology review. We were unable to assign UIP/non-UIP pathology reference labels to 12 subjects with non-diagnostic pathology and 7 subjects with non-classifiable fibrosis, thus they could not be included in the final validation (FIG. 8). Final histopathologic pattern diagnoses were determined and UIP/non-UIP reference labels provided for the remaining 49 subjects. These 49 subjects became the final validation group (FIG. 8).

The 49 subjects in the final validation group showed no significant differences in subject age, gender, or smoking status when compared to the 88 enrolled subjects and the 39 excluded subjects (Table 6). The final validation set includes a diversity of UIP subtypes as well as non-UIP ILDs that may be encountered in clinical practice (Table 7).

TABLE 6

Clinical characteristics of study subjects.

| | Study eligible group N, (%) | Final validation group N, (%) | P-value |
|---|---|---|---|
| Gender - n (%) | | | 1 |
| Female | 38 (43%) | 21 (43%) | |
| Male | 50 (57%) | 28 (57%) | |
| Mean age (SD) - yr | 63.0 (11.7) | 64.1 (10.3) | 0.56 |
| Smoking status - n (%) | | | 0.73 |
| Yes | 56 (64%) | 33 (67%) | |
| No | 28 (32%) | 15 (31%) | |
| Unknown | 4 (5%) | 1 (2%) | |
| Site - n (%) | | | 0.51 |
| Academic | 36 (41%) | 20 (41%) | |
| Community | 37 (42%) | 24 (49%) | |
| European | 15 (17%) | 5 (10%) | |
| Study - n (%) | | | 0.45 |
| BRAVE 1 | 43 (49%) | 26 (53%) | |
| BRAVE 2 | 9 (10%) | 2 (4%) | |
| BRAVE 3 | 36 (41%) | 21 (43%) | |
| UIP prevalence by pathology, n (%) | N/A | 24 (49%) | |
| UIP prevalence by radiology, n/n (%) | N/A | 9/46 (20%) | |
| Radiology missing, n (%) | N/A | 3 (6%) | |
| Total subjects | 88 | 49 | |

TABLE 7

ILD pathologic patterns represented in the validation.

| Pathology Pattern Diagnosis | Final validation group N, (%) |
|---|---|
| UIP Classification labels | |
| UIP (Classic UIP, Difficult UIP or Favor UIP) | 19 (39%) |
| UIP with Favor HP; UIP with CIF, NOC; UIP with NSIP; UIP with Pulmonary hypertension | 5 (10%) |
| UIP Total | 24 (49%) |
| Non-UIP Classification labels | |
| OP; OP with CIF; NOC; OP with Acute lung injury | 1 (2%) |
| Respiratory bronchiolitis; SRIF; RB with SRIF; RB with CIF, NOC | 6 (12%) |
| Bronchiolitis; Bronchiolitis with Favor bronchiolitis | 1 (2%) |
| Sarcoidosis | 3 (6%) |
| NSIP; Cellular NSIP; Favor NSIP; Cellular NSIP with Favor HP; NSIP with Favor NSIP; Favor NSIP with CIF, NOC | 3 (6%) |
| Hypersensitivity pneumonitis; Favor HP | 4 (8%) |
| DAD; DAD with hemosiderosis | 2 (4%) |
| Eosinophilic pneumonia | 1 (2%) |
| Organizing alveolar hemorrhage | 1 (2%) |
| Exogenous lipid pneumonia | 1 (2%) |
| Amyloid or light chain deposition | 1 (2%) |
| Emphysema; Emphysema with Probable infection; Emphysema with RB | 1 (2%) |
| Non-UIP Total | 25 (51%) |
| Total | 49 |

*Subjects with different diagnoses across lung lobes are noted as "with".

Envisia Genomic Classifier performance

Figure 10A:
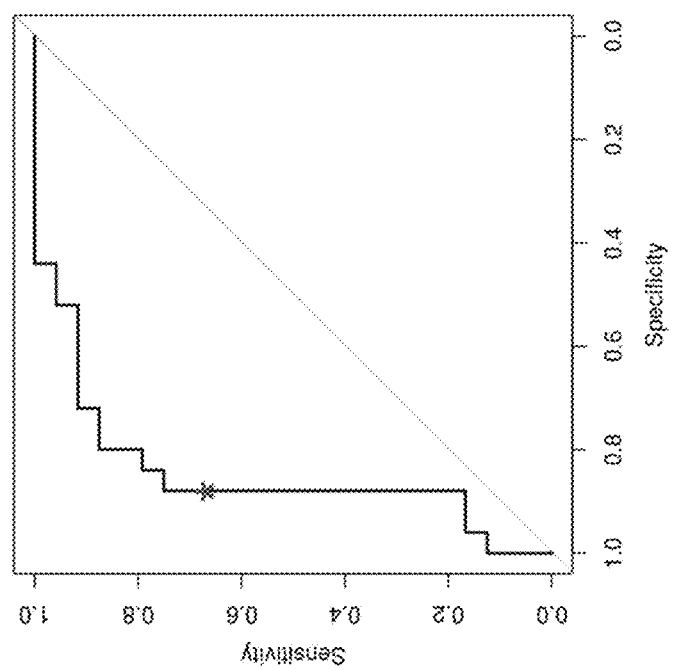

The Envisia Genomic Classifier for molecular diagnosis of UIP achieved a high specificity of 88% [CI: 68%-97%] and moderate sensitivity of 67% [CI: 45%-84%] in the validation group. The ROC-AUC was 0.85 (FIG. 10). Test performance remains within the confidence intervals when the analysis is restricted to 26 subjects with pathology derived exclusively from surgical lung biopsy or 21 subjects with pathology from cryobiopsy (data not shown). Of the 21 cryobiopsy subjects, five were from a single European study site and one, seven, and eight subjects were from three US study sites, respectively.

Figure 11:
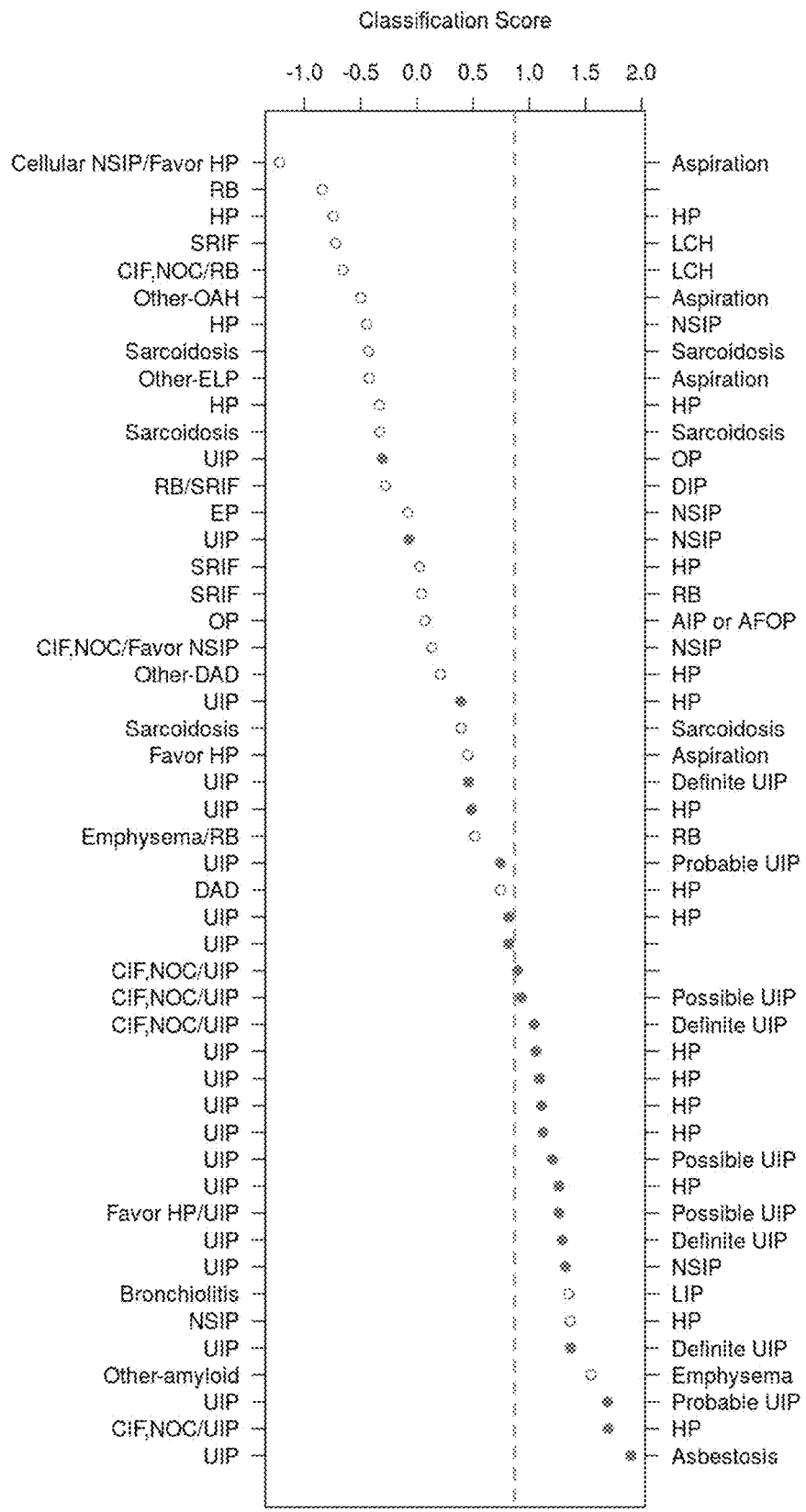
FIG. 11. Classification scores for 49 subjects in the Envisia validation group. Subjects were sorted left to right by increasing classification score (y-axis), with central pathology diagnoses on the lower x-axis and central radiology diagnoses (where available) on the upper x-axis. Solid circles represent subjects with UIP reference labels, hollow circles are subjects with non-UIP reference labels. The test decision boundary is shown with a dashed line.

In examining errors made by the classifier, three of the 25 subjects with non-UIP pathology were classified as molecular UIP (FPs) (FIG. 11). One FP had a pathologic pattern diagnosis of advanced small airway disease with follicular bronchiolitis but had a study site-derived clinical diagnosis of probable IPF. A second FP was initially diagnosed with HP by central radiology and cellular NSIP by central pathology, but showed dense fibrosis by HRCT on long term follow-up. A case of NSIP with severe emphysema by radiology and noted on histopathology to exhibit amyloid or light chain deposition was also called molecular UIP (Table 8).

TABLE 8

Clinical factors associated with three Envisia Genomic Classifier false positive subjects

| FP subject | Envisia Call | Radiology | | | Pathology | | Local Clinical Diagnosis | |
|---|---|---|---|---|---|---|---|---|
| 1 | UIP | Local IPF | Central Other (LIP) | Local Long term follow-up N/A | Loca Advanced chronic small airway disease with follicular bronchiolitis | Central SLB: Bronchiolitis (upper lobe) Bronchiolitis (lower lobe) | Initial Diagnosis Probable IPF | Updated Diagnosis N/A |
| 2 | UIP | Bibasilar infiltrates w/o honey-combing | HP | N/A | CIF, NOC | SLB: NSIP (lower lobe) | Cellular NSIP | Dense fibrosis |
| 3 | UIP | Pulmonary fibrosis | Other (Emphysema) | Severe Emphysema | UIP | Cryobiopsy: Other-amyloid or light chain deposition (upper lobe) | NSIP | NSIP |

Eight subjects with pathologic UIP were classified as molecular non-UIP by the Envisia test (FNs) (FIG. 11). While the final reference label for these subjects was UIP, half of these cases had a non-UIP diagnosis either by study site pathology, radiology or clinical diagnosis. Study site diagnoses included, HP, RB, NSIP/DIP (later updated to SRIF), and unclassifiable ILD (Table 9). The remaining four cases had a study site diagnosis of IPF, two of which had HRCT pattern diagnoses of UIP, one with NSIP, and one with HP associated with possible underlying autoimmune disease (Table 9).

TABLE 9

Clinical details associate with eight Envisia Genomic Classifier FN subjects

| FP subject | Envisia Call | Radiology | | | Pathology | | Local Clinical Diagnosis | |
|---|---|---|---|---|---|---|---|---|
| 1 | Non-UIP | Local Non-specific alveolitis | Central Organizing pneumonia | Local long term follow-up SLB-associated changes | Local NSIP | Central SLB: Classic UIP (middle lobe) Classic UIP (lower lobe) | Initial Diagnosis NSIP/DIP | Updated Diagnosis SRIF |
| 2 | Non-UIP | Possible UIP | NSIP | N/A | UIP | Cryobiopsy: UIP (lower lobe) | Possible IPF | N/A |
| 3 | Non-UIP | Bilateral pulmonary fibrosis | HP | N/A | UIP | SLB: UIP (upper lobe) UIP (middle lobe) Classic UIP (lower lobe) | Possible IPF | UIP + NSIP with autoimmune disease (possible RA) |
| 4 | Non-UIP | UIP | Definite UIP | N/A | UIP | Cryobiopsy: Favor UIP (upper lobe) UIP (middle lobe) Non-Diagnostic (lower lobe) | Definite IPF | N/A |
| 5 | Non-UIP | NSIP | HP | N/A | Chronic interstitial fibrosis, not otherwise classified | SLB: UIP (upper lobe) UIP (lower lobe) | Unclassifiable ILD | N/A |
| 6 | Non-UIP | IPF | Probable UIP | UIP | UIP | SLB: Classic UIP (upper lobe) | Definite IPF | Definite IPF |
| 7 | Non-UIP | Acute exacerbation of | HP | N/A | Chronic HP | SLB: UIP (upper lobe) | HP | N/A |

TABLE 9-continued

Clinical details associate with eight Envisia Genomic Classifier FN subjects

| FP subject | Envisia Call | Radiology | | | | Pathology | Local Clinical Diagnosis | |
|---|---|---|---|---|---|---|---|---|
| | | chronic ILD | | | | Classic UIP (middle lobe) | | |
| | | | | | | Classic UIP (lower lobe) | | |
| 8 | Non-UIP | UIP | N/A | N/A | SRIF | Cryobiopsy: | RB | N/A |
| | | | | | | Non-diagnostic (upper lobe) | | |
| | | | | | | Non-diagnostic (middle lobe) | | |
| | | | | | | Favor UIP (lower lobe) | | |

Consistent with guidelines, HRCT is used to evaluate suspect ILD patients with a goal of assessing the presence or absence of UIP pattern (e.g. "HRCT-UIP"). In the absence of a definitive UIP diagnoses by HRCT, patients should be considered for SLB to obtain a histopathologic pattern diagnosis of UIP or non-UIP[5]. To establish a performance baseline for Envisia molecular UIP calls, we evaluated the predictive value of HRCT-UIP, using histopathologic UIP as the reference standard. We examined HRCT pattern diagnoses from expert review (D. Lynch) as well as study site pattern diagnoses. In the final validation set, central radiology shows perfect specificity and positive predictive value (PPV), with marginal sensitivity (FIG. 12). This is consistent with previous reports of high specificity, but low sensitivity of expert HRCT-UIP[17]. The specificity and PPV of local radiology in this group of patients is substantially lower than expert central review, at 70% and 67%, respectively (FIG. 12).

The PPV of molecular UIP among subjects with central HRCT-UIP is 100%, similar to the overall PPV of expert radiology (versus pathology), but far superior to the overall PPV of study site HRCT-UIP (FIG. 12). The PPV of molecular UIP decreases to 73% among subjects with study site HRCT-UIP, but remains 100% among central HRCT-UIP cases (FIG. 12). Interestingly, molecular UIP calls are highly accurate among subjects with a study site radiology diagnosis of Inconsistent with UIP, showing a PPV of 100% and a NPV of 89%, similar to the 100% PPV observed by central radiology (FIG. 12). Moreover, molecular UIP shows improved sensitivity over expert radiology, at 67% versus 41%. Among 15 subjects with a specific central radiology diagnosis of HP, nine had a UIP histopathologic pattern (Table 10). Molecular UIP correctly identified histopathologic UIP in six of the nine HP patients with a UIP histopathologic pattern (Table 10), suggesting that molecular diagnosis by the Envisia test can help identify the presence of histopathologic UIP in HP patients.

TABLE 10

Performance of Envisia, relative to pathology, for 15 subjects with central radiology diagnosis of hypersensitivity pneumonitis

| Subject | Pathology | Radiology | Envisia Call |
|---|---|---|---|
| 1 | UIP | HP | UIP |
| 2 | NSIP | HP | UIP |
| 3 | UIP | HP | UIP |
| 4 | UIP | HP | UIP |
| 5 | UIP | HP | UIP |
| 6 | UIP | HP | UIP |
| 7 | UIP | HP | UIP |
| 8 | UIP | HP | nonUIP |
| 9 | DAD | HP | nonUIP |
| 10 | UIP | HP | nonUIP |
| 11 | UIP | HP | nonUIP |
| 12 | DAD | HP | nonUIP |
| 13 | SRIF | HP | nonUIP |
| 14 | HP | HP | nonUIP |
| 15 | HP | HP | nonUIP |

The recognized challenge of achieving diagnostic pathology meant that labels of UIP or non-UIP may not be determined for 19 subjects (Table 11). Patients similar to these may be encountered in the clinic and thus potentially tested by Envisia. Therefore, we compared Envisia test results to the available clinical information associated with these subjects. Among six subjects with molecular UIP by Envisia, there are two with a HRCT-UIP pattern, and two with clinical diagnoses of IPF (Table 11). Among the 13 subjects with molecular non-UIP by Envisia, seven have HRCT non-UIP pattern; three of whom have a clinical diagnosis of a non-UIP condition (Table 11).

TABLE 11

Envisia classification of subjects with non diagnostic pathology or unclassifiable fibrosis (secondary analysis group).

| Subject | Envisia score | Envisia call | Central Pathology | Central Radiology | Local Clinical Diagnosis | Local Pathology Diagnosis |
|---|---|---|---|---|---|---|
| 1 | −2.05 | NonUIP | CIF, NOC | Other- Aspiration | Bronchiolitis | |
| 2 | −1.43 | NonUIP | Non diagnostic | HP | Other | |
| 3 | −0.91 | NonUIP | Non diagnostic | Other- Aspiration | Other | Other |
| 4 | −0.49 | NonUIP | Non diagnostic | Asbestosis | | |
| 5 | −0.39 | NonUIP | CIF, NOC | | | |
| 6 | −0.25 | NonUIP | Non diagnostic | Other- Aspiration | Other | |
| 7 | 0.13 | NonUIP | Non diagnostic | | | |
| 8 | 0.15 | NonUIP | CIF, NOC | HP | Mixed NSIP | |
| 9 | 0.17 | NonUIP | CIF, NOC | Definite UIP | Mixed NSIP | |
| 10 | 0.36 | NonUIP | Non diagnostic | Probable UIP | Other | Other |
| 11 | 0.56 | NonUIP | Non diagnostic | HP | HP | Non-diagnostic |

TABLE 11-continued

Envisia classification of subjects with non diagnostic pathology or unclassifiable fibrosis (secondary analysis group).

| Subject | Envisia score | Envisia call | Central Pathology | Central Radiology | Local Clinical Diagnosis | Local Pathology Diagnosis |
|---|---|---|---|---|---|---|
| 12 | 0.74 | NonUIP | Non diagnostic | | Probable IPF | Other |
| 13 | 0.87 | NonUIP | CIF, NOC | Definite UIP | Probable IPF | CIF, NOC |
| 14 | 0.98 | UIP | Non diagnostic | RB | Other | Non-diagnostic |
| 15 | 0.98 | UIP | CIF, NOC | HP | Probable IPF | |
| 16 | 1.26 | UIP | Non diagnostic | | | Other |
| 17 | 1.39 | UIP | Non diagnostic | Possible UIP | Favor NSIP | |
| 18 | 1.42 | UIP | Non diagnostic | Definite UIP | | |
| 19 | 2.59 | UIP | Non diagnostic | | Definite IPF | |

Of the 190 genes used by the Envisia Genomic Classifier, 124 are among the top 1000 genes differentially expressed between UIP and non-UIP TBBs. The classifier features and genes upregulated in UIP are enriched for members of four biological pathways, three of which were previously identified in SLB using a microarray gene expression platform[13] (Table 12).

TABLE 12

Pathway enrichment analysis of 389 genes up-regulated in UIP in TBBs and 92 Envisia Genomic Classifier genes (55 genes are common to both sets). Pathways marked in bold are significantly enriched in surgical lung biopsies (Kim S Y et al, 2015).

| Category | Number of genes expected | Number of genes observed | P-value (corrected) | Direction of enrichment |
|---|---|---|---|---|
| Dilated cardiomyopathy | 1.9 | 11 | 0.000126 | More pathway genes than expected |
| Hypertrophic cardiomyopathy (HCM) | 1.7 | 9 | 0.003087 | More pathway genes than expected |
| Focal adhesion | 4.1 | 13 | 0.012032 | More pathway genes than expected |
| Neuroactive ligand-receptor interaction | 5.5 | 15 | 0.021914 | More pathway genes than expected |

The KEGG dilated and hypertrophic cardiomyopathy networks include genes involved in extracellular matrix interactions, growth factor response, and cytoskeletal remodeling, all reported to be upregulated in IPF[18,19].

Similarly, features and genes upregulated in non-UIP TBBs are enriched for multiple pathways also upregulated in non-UIP SLB, including immune response, cell-cell signaling and developmental pathways (Table 13). Differential upregulation of cell proliferation, immune response genes has been shown for HP in comparison to IPF[20], although some genes are co-regulated in these diseases[21].

TABLE 13

Pathway enrichment analysis of 611 genes up-regulated in non-UIP in TBBs and 98 Envisia Genomic Classifier genes (69 genes are common to both sets). Pathways marked in bold are significantly enriched in surgical lung biopsies (Kim S Y et al, 2015).

| Category | Number of genes expected | Number of genes observed | P-value (corrected) | Direction of enrichment |
|---|---|---|---|---|
| Antigen processing and presentation | 3.6 | 22 | 4.05E−10 | More pathway genes than expected |
| Leishmaniasis | 3.4 | 20 | 7.47E−09 | More pathway genes than expected |
| Graft-versus-host-disease | 2.0 | 15 | 4.75E−08 | More pathway genes than expected |
| Type I diabetes mellitus | 2.1 | 15 | 9.94E−08 | More pathway genes than expected |
| Allograft rejection | 1.8 | 14 | 1.22E−07 | More pathway genes than expected |
| Viral myocarditis | 3.5 | 18 | 5.90E−07 | More pathway genes than expected |
| Toll-like receptor signaling pathway | 4.8 | 21 | 7.52E−07 | More pathway genes than expected |
| Autoimmune thyroid disease | 2.5 | 14 | 1.39E−05 | More pathway genes than expected |
| Phagosome | 7.4 | 23 | 0.000118 | More pathway genes than expected |
| Olfactory transduction | 18.1 | 2 | 0.000145 | Fewer pathway genes than expected |
| Cytokine-cytokine receptor interaction | 12.4 | 29 | 0.001704 | More pathway genes than expected |
| Chagas disease | 4.8 | 16 | 0.002929 | More pathway genes than expected |
| Cell adhesion molecules (CAMs) | 6.3 | 18 | 0.006574 | More pathway genes than expected |
| NOD-like receptor signaling pathway | 2.9 | 11 | 0.015921 | More pathway genes than expected |
| Chemokine signaling pathway | 8.8 | 21 | 0.023401 | More pathway genes than expected |

DISCUSSION

It is common for the combination of the clinical context and radiologic pattern seen on HRCT scan of the chest to fail to provide a confident diagnosis in patients undergoing evaluation for ILD. While a histopathologic pattern diagnosis from SLB may provide a definitive diagnosis in these patients, many patients are unwilling or too ill to undergo a surgical diagnostic procedure. Even in those that do, the challenge associated with the pathologic interpretation of the biopsy findings may leave significant clinical uncertainty. An accurate and available test associated with minimal risk and not dependent on the visual and subjective skill of an experienced pulmonary pathologist to confirm the presence of histologic UIP may be very useful.

The significant challenges in accruing meaningful numbers of patients and samples to support the machine learning efforts needed to develop Envisia mirrors the challenges faced by clinicians when investigating patients with newly diagnosed ILD. Out of 201 subjects accrued through our BRAVE sample collection studies, we identified only 140 subjects with diagnostic histopathology results, despite the use of a panel of expert pulmonary pathologists. This poor yield highlights the challenge of achieving diagnostic pathology with which clinicians in the community are confronted. We trained and locked the Envisia Genomic Classifier using the first 90 subjects, and validated the test using subsequently accrued subjects. This Genomic Classifier for UIP in conventional TBBs showed high performance in both cohorts.

The accuracy of a molecular UIP call among 25 subjects with a histologic UIP pattern that was not predicted by the study site radiologists is high, with 78% of subjects with a UIP histopathologic pattern successfully identified, with no false positives. In this group of subjects, Envisia functions as a true rule-in test that recovers almost 4 in 5 of the UIP histopathologic pattern cases that were unable to be identified by HRCT. Furthermore, this subgroup is enriched with patients with HP, 60% of whom (9 of 15) in the current study had evidence of advanced fibrotic disease. Envisia detected UIP in HP patients with the same 67% sensitivity as UIP was detected overall in the 49 subject validation cohort. The NPV of the Envisia molecular UIP call in subjects with an inconsistent with UIP radiologic pattern diagnosis is >80%, suggesting substantial utility for both positive and negative Envisia test results.

Example 11

Sample Clinical and Technical Factors and Envisia Performance

Figure 13A:
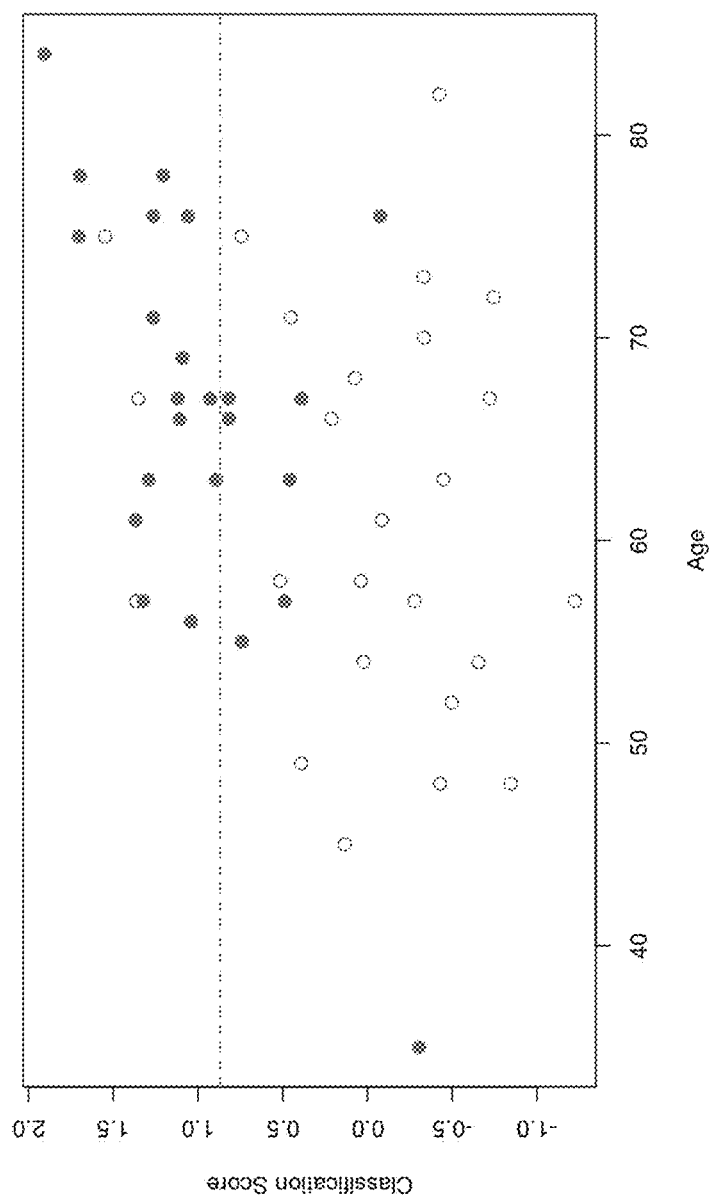
Figure 13C:
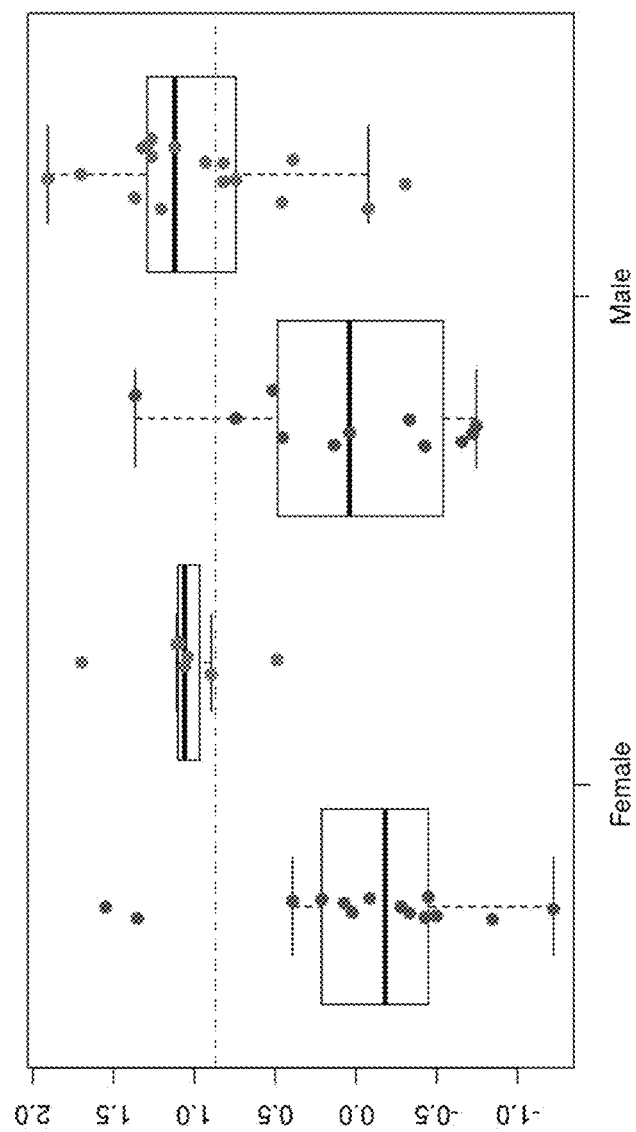
Figure 13D:
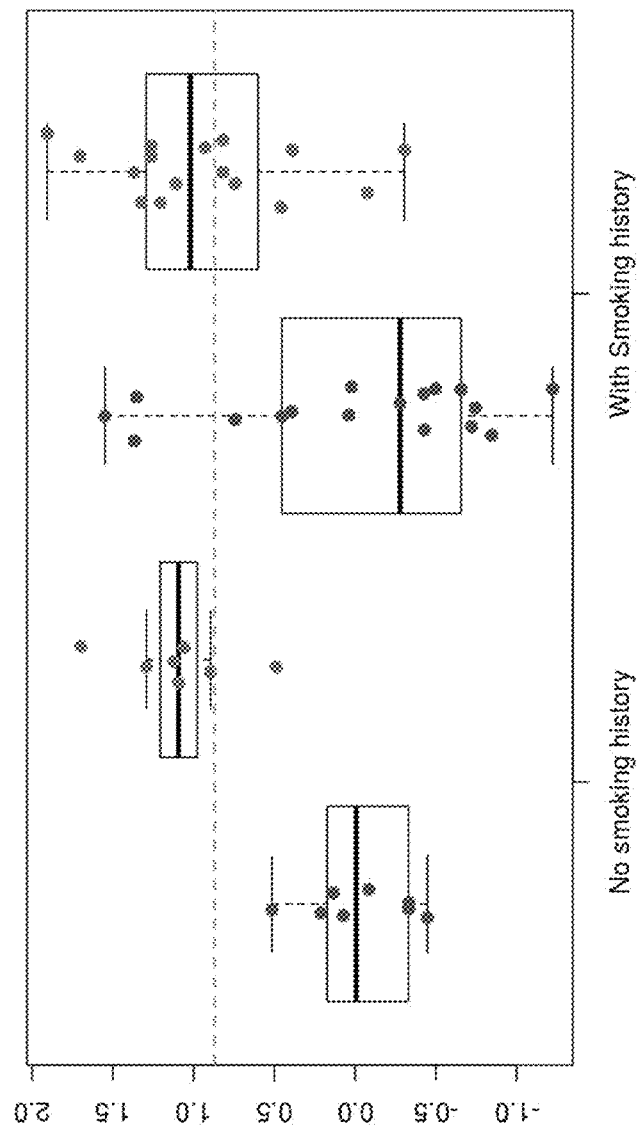
Figure 14A:
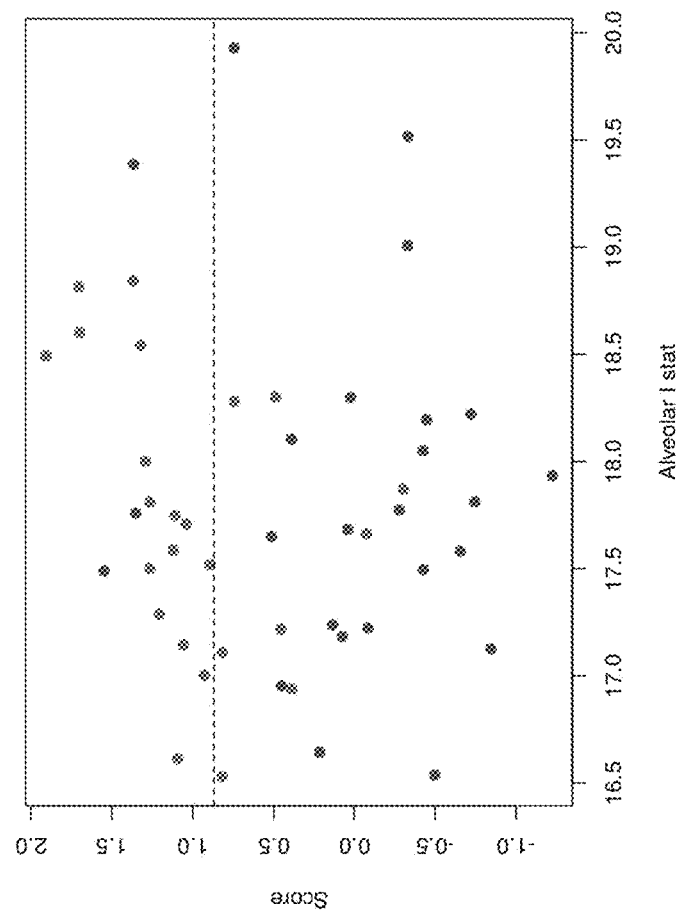
FIG. 14A-14D. Subgroup analysis of Envisia test performance against sample technical factors. UIP subjects are marked in solid red circles, non-UIP subjects with hollow or blue circles.
Figure 14B:
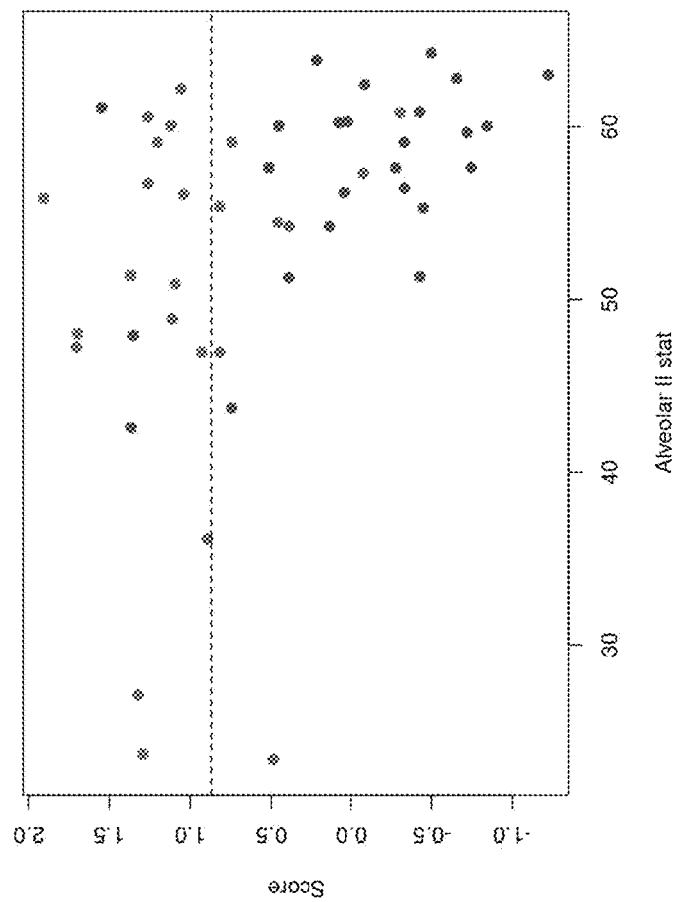
Figure 14C:
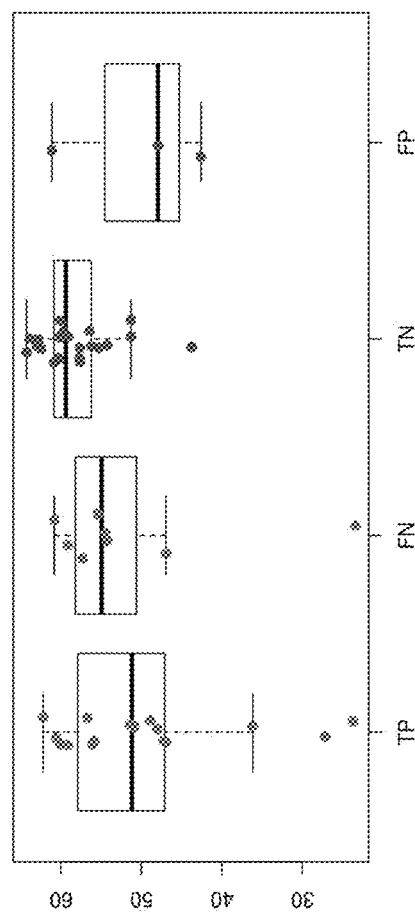
Figure 14D:
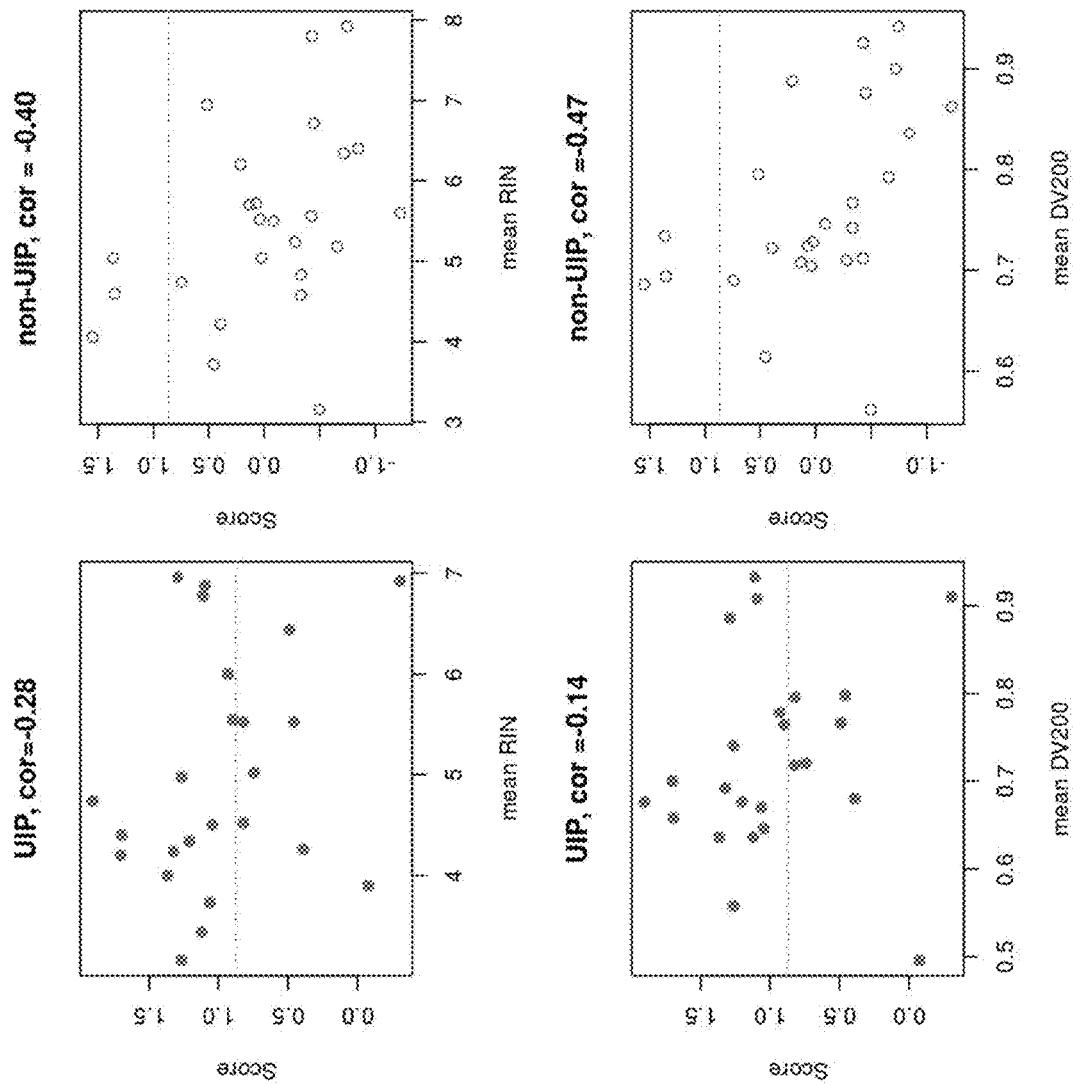

Envisia test performance shows some correlation to subject clinical and sample technical factors. UIP disease is missed at a higher rate in male subjects and subjects with a history of smoking (FIG. 13). Gene expression consistent with alveolar type II cells does not correlate strongly with Envisia test accuracy (FIG. 14), suggesting that alveolar sampling is not critical to test performance, consistent with previous observation in a cohort of 90 ILD subjects[E10]. There is a slight correlation between stronger (more negative) classification scores and higher sample quality, defined by sample size and RNA quality, among non-UIP samples that is not evident in UIP samples (FIG. 14).

The various embodiments described above may be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments may be modified, if necessary to employ concepts of the various patents, application and publications to provide yet further embodiments.

These and other changes may be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein may be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) may be expressed in a variety of software languages (e.g., computer code), including C, C++, Java™, Ruby, Visual Basic™, R, and/or other object-oriented, procedural, statistical, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, FORTRAN, etc.), functional programming languages (e.g., Haskell, Erlang, etc.), logical programming languages (e.g., Prolog), object-oriented programming languages (e.g., Java, C++, etc.), statistical programming languages and/or environments (e.g., R, etc.) or other suitable programming languages and/or development tools. Additional examples of computer code include, but are not limited to, control signals, encrypted code, and compressed code.

REFERENCES

All of the following references and all references cited herein are incorporated herein in their entirety.
1. Travis W D, Costabel U, Hansell D M, King T E, Lynch D A, Nicholson A G, Ryerson C J, Ryu J H, Selman M, Wells A U, Behr J, Bouros D, Brown K K, Colby T V, Collard H R, Cordeiro C R, Cottin V, Crestani B, Drent M, Dudden R F, Egan J, Flaherty K, Hogaboam C, Inoue Y, Johkoh T, Kim D S, Kitaichi M, Loyd J, Martinez F J, Myers J, Protzko S, Raghu G, Richeldi L, Sverzellati N, Swigris J, Valeyre D. An Official American Thoracic Society/European Respiratory Society Statement: Update of the international multidisciplinary classification of the idiopathic interstitial pneumonias. Am J Respir Crit Care Med 2013; 188:733-748.
2. Raghu G, Rochwerg B, Zhang Y, Garcia C A C, Azuma A, Behr J, Brozek J L, Collard H R, Cunningham W, Homma S, Johkoh T, Martinez F J, Myers J, Protzko S L, Richeldi L, Rind D, Selman M, Theodore A, Wells A U, Hoogsteden H, Schünemann H J. An Official ATS/ERS/JRS/ALAT Clinical Practice Guideline: Treatment of idiopathic pulmonary fibrosis. An update of the 2011 clinical practice guideline. Am J Respir Crit Care Med 2015; 192:e3-e19.
3. Bjoraker J A, Ryu J H, Edwin M K, Myers J L, Tazelaar H D, Schroeder D R, Offord K P. Prognostic significance of histopathologic subsets in idiopathic pulmonary fibrosis. Am J Respir Crit Care Med 1998; 157: 199-203.
4. Flaherty K R, Travis W D, Colby T V, Toews G B, Kazerooni E A, Gross B H, Jain A, Strawderman R L, Flint A, Lynch J P, Martinez F J. Histopathologic variability in usual and nonspecific interstitial pneumonias. Am J Respir Crit Care Med 2001; 164:1722-1727.
5. Flaherty K R, Toews G B, Travis W D, Colby T V, Kazerooni E A, Gross B H, Jain A, Strawderman R L, Paine R, Flint A, Lynch J P, Martinez F J. Clinical significance of histological classification of idiopathic interstitial pneumonia. Eur Respir J 2002; 19:275-283.
6. Flaherty K, Thwaite E, Kazerooni E, Gross B, Toews G, Colby T, Travis W, Mumford J, Murray S, Flint A, Lynch J, Martinez F. Radiological versus histological diagnosis in UIP and NSIP: Survival implications. Thorax 2003; 58:143-148.
7. Katzenstein A-L A, Mukhopadhyay S, Myers J L. Diagnosis of usual interstitial pneumonia and distinction from other fibrosing interstitial lung diseases. Hum Pathol 2008; 39:1275-1294.
8. Raghu G, Collard H R, Egan J J, Martinez F J, Behr J, Brown K K, Colby T V, Cordier J-F, Flaherty K R, Lasky J A, Lynch D A, Ryu J H, Swigris J J, Wells A U, Ancochea J, Bouros D, Carvalho C, Costabel U, Ebina M, Hansell D M, Johkoh T, Kim D S, King T E, Kondoh Y, Myers J, Müller N L, Nicholson A G, Richeldi L, Selman M, Dudden R F, Griss B S, Protzko S L, SchUnemann H J. An Official ATS/ERS/JRS/ALAT Statement: Idiopathic Pulmonary Fibrosis: Evidence-based guidelines for diagnosis and management. Am J Respir Crit Care Med 2011; 183:788-824.
9. American Thoracic S, European Respiratory S. American Thoracic Society/European Respiratory Society International Multidisciplinary Consensus Classification of the Idiopathic Interstitial Pneumonias. This joint statement of the American Thoracic Society (ATS) and the European Respiratory Society (ERS) was adopted by the ATS board of directors, June 2001 and by the ERS Executive Committee, June 2001. Am J Respir Crit Care Med 2002; 165:277-304.
10. Katzenstein A-L A, Myers J L. Idiopathic Pulmonary Fibrosis. Am J Respir Crit Care Med 1998; 157:1301-1315.
11. Berbescu E A, Katzenstein A-L A, Snow J L, Zisman D A. Transbronchial biopsy in usual interstitial pneumonia. Chest 2006; 129:1126-1131.
12. Tomassetti S, Cavazza A, Colby T V, Ryu J H, Nanni O, Scarpi E, Tantalocco P, Buccioli M, Dubini A, Piciucchi S, Ravaglia C, Gurioli C, Casoni G L, Gurioli C, Romagnoli M, Poletti V. Transbronchial biopsy is useful in predicting UIP pattern. Respir Res 2012; 13:96-96.
13. Shim H S, Park M S, Park I K. Histopathologic findings of transbronchial biopsy in usual interstitial pneumonia. Pathol Int 2010; 60:373-377.
14. Tomassetti S, Wells A U, Costabel U, Cavazza A, Colby T V, Rossi G, Sverzellati N, Carloni A, Carretta E, Buccioli M, Tantalocco P, Ravaglia C, Gurioli C, Dubini A, Piciucchi S, Ryu J H, Poletti V. Bronchoscopic lung cryobiopsy increases diagnostic confidence in the multidisciplinary diagnosis of idiopathic pulmonary fibrosis. Am J Respir Crit Care Med 2016; 193: 745-752.
15. Dhooria S, Sehgal I S, Aggarwal A N, Behera D, Agarwal R. Diagnostic yield and safety of cryoprobe transbronchial lung biopsy in diffuse parenchymal lung diseases: Systematic review and meta-analysis. Respir Care 2016; 61:700-712.
16. Poletti V, Ravaglia C, Gurioli C, Piciucchi S, Dubini A, Cavazza A, Chilosi M, Rossi A, Tomassetti S. Invasive diagnostic techniques in idiopathic interstitial pneumonias. Respirology 2016; 21:44-50.
17. Kim S Y, Diggans J, Pankratz D, Huang J, Pagan M, Sindy N, Tom E, Anderson J, Choi Y, Lynch D A, Steele M P, Flaherty K R, Brown K K, Farah H, Bukstein M J, Pardo A, Selman M, Wolters P J, Nathan S D, Colby T V, Myers J L, Katzenstein A-L A, Raghu G, Kennedy G C. Classification of usual interstitial pneumonia in patients with interstitial lung disease: Assessment of a machine learning approach using high-dimensional transcriptional data. Lancet Respir Med 2015; 3:473-482.
18. Friedman J, Hastie T, Tibshirani R. Regularization paths for generalized linear models via coordinate descent. J Stat Softw 2010; 33:1-22.
19. Love M I, Huber W, Anders S. Moderated estimation of fold change and dispersion for RNA-seq data with DESeq2. Genome Biol 2014; 15:550.
20. Mi H, Lazareva-Ulitsky B, Loo R, Kejariwal A, Vandergriff J, Rabkin S, Guo N, Muruganujan A, Doremieux O, Campbell M J, Kitano H, Thomas P D. The PANTHER database of protein families, subfamilies, functions and pathways. Nucleic Acids Res 2005; 33:D284-D288.
21. Katzenstein A-L A, Zisman D A, Litzky L A, Nguyen B T, Kotloff R M. Usual interstitial pneumonia: Histologic study of biopsy and explant specimens. Am J Surg Pathol 2002; 26:1567-1577.
22. Trahan S, Hanak V, Ryu J H, Myers J L. Role of surgical lung biopsy in separating chronic hypersensitivity pneumonia from usual interstitial pneumonia/idiopathic pulmonary fibrosis: Analysis of 31 biopsies from 15 patients. Chest 2008; 134:126-132.
23. Akashi T, Takemura T, Ando N, Eishi Y, Kitagawa M, Takizawa T, Koike M, Ohtani Y, Miyazaki Y, Inase N, Yoshizawa Y. Histopathologic analysis of sixteen autopsy cases of chronic hypersensitivity pneumonitis and comparison with idiopathic pulmonary fibrosis/usual interstitial pneumonia. Am J Clin Pathol 2009; 131:405-415.
24. Selman M, Pardo A, Barrera L, Estrada A, Watson S R, Wilson K, Aziz N, Kaminski N, Zlotnik A. Gene expression profiles distinguish idiopathic pulmonary fibrosis from hypersensitivity pneumonitis. Am J Respir Crit Care Med 2006; 173:188-198.
25. Lockstone H E, Sanderson S, Kulakova N, Baban D, Leonard A, Kok W L, McGowan S, McMichael A J, Ho L P. Gene set analysis of lung samples provides insight into pathogenesis of progressive, fibrotic pulmonary sarcoidosis. Am J Respir Crit Care Med 2010; 181: 1367-1375.
26. Selman M, Pardo A. Revealing the pathogenic and aging-related mechanisms of the enigmatic idiopathic pulmonary fibrosis. An integral model. Am J Respir Crit Care Med 2014; 189:1161-1172.
27. Bauer Y, Tedrow J, de Bernard S, Birker-Robaczewska M, Gibson K F, Guardela B J, Hess P, Klenk A, Lindell K O, Poirey S, Renault B, Rey M, Weber E, Nayler O, Kaminski N. A novel genomic signature with translational significance for human idiopathic pulmonary fibrosis. Am J Respir Cell Mol Biol 2015; 52:217-231.
28. Jonigk D, Izykowski N, Rische J, Braubach P, Kuhnel M, Warnecke G, Lippmann T, Kreipe H, Haverich A, Welte T, Gottlieb J, Laenger F. Molecular profiling in lung biopsies of human pulmonary allografts to predict chronic lung allograft dysfunction. Am J Pathol 2015; 185:3178-3188.
29. Nicholson A G, Fulford L G, Colby T V, du Bois R M, Hansell D M, Wells A U. The relationship between individual histologic features and disease progression in idiopathic pulmonary fibrosis. Am J Respir Crit Care Med 2002; 166:173-177.
30. Walsh S L, Wells A U, Desai S R, Poletti V, Piciucchi S, Dubini A, Nunes H, Valeyre D, Brillet P Y, Kambouchner M, Morais A, Pereira J M, Moura C S, Grutters J C, van den Heuvel D A, van Es H W, van Oosterhout M F, Seldenrijk C A, Bendstrup E, Rasmussen F, Madsen L B, Gooptu B, Pomplun S, Taniguchi H, Fukuoka J, Johkoh T, Nicholson A G, Sayer C, Edmunds L, Jacob J, Kokosi M A, Myers J L, Flaherty K R, Hansell D M. Multicentre evaluation of multidisciplinary team meeting agreement on diagnosis in diffuse parenchymal lung disease: A case-cohort study. Lancet Respir Med 2016; 4:557-565.
31. Flaherty K R, King T E, Raghu G, Lynch J P, Colby T V, Travis W D, Gross B H, Kazerooni E A, Toews G B, Long Q, Murray S, Lama V N, Gay S E, Martinez F J. Idiopathic Interstitial Pneumonia. Am J Respir Crit Care Med 2004; 170:904-910.
32. Tominaga J, Sakai F, Johkoh T, Noma S, Akira M, Fujimoto K, Colby T V, Ogura T, Inoue Y, Taniguchi H, Homma S, Taguchi Y, Sugiyama Y. Diagnostic certainty of idiopathic pulmonary fibrosis/usual interstitial pneumonia: The effect of the integrated clinico-radiological assessment. Eur J Radio! 2015; 84:2640-2645.
33. The Idiopathic Pulmonary Fibrosis Clinical Research Network. Prednisone, azathioprine, and n-acetylcysteine for pulmonary fibrosis. N Engl J Med 2012; 366: 1968-77.
34. Sumikawa H, Johkoh T, Colby T V, Ichikado K, Suga M, Taniguchi H, Kondoh Y, Ogura T, Arakawa H, Fujimoto K, Inoue A, Mihara N, Honda O, Tomiyama N, Nakamura H, Muller N L. Computed tomography findings in pathological usual interstitial pneumonia. Am J Respir Crit Care Med 2008; 177:433-439.
35. Chung J H, Chawla A, Peljto A L, Cool C D, Groshong S D, Talbert J L, McKean D F, Brown K K, Fingerlin T E, Schwarz M I, Schwarz D A, Lynch D A. C T scan findings of probable usual interstitial pneumonitis have a high predictive value for histologic usual interstitial pneumonitis. Chest 2015; 147:450-459.
36. Brownell R, Moua T, Henry T S, Elicker B M, White D, Vittinghoff E, Jones K D, Urisman A, Aravena C, Johannson K A, Golden J A, King T E Jr, Wolters P J. Collard H R, Ley B. The use of pretest probability increases the value of high-resolution C T in diagnosing usual interstitial pneumonia. Thorax 2017; 72(5):424-429.
37. DiBardino D M, Haas A R, Lanfranco A R, Litzky L A, Sterman D, Bessich J L. High complication rate after introduction of transbronchial cryobiopsy into clinical practice at an academic medical center. Annals Am Thorac Soc 2017; 14(6):851-857.
38. Hutchinson J P, McKeever™, Fogarty A W, Navaratnam V, Hubbard R B. Surgical lung biopsy for the diagnosis of interstitial lung disease in England: 1997-2008. Eur Respir J 2016; 48:1453-61.
E1. Kim S Y, Diggans J, Pankratz D, Huang J, Pagan M, Sindy N, Tom E, Anderson J, Choi Y, Lynch D A, Steele M P, Flaherty K R, Brown K K, Farah H, Bukstein M J, Pardo A, Selman M, Wolters P J, Nathan S D, Colby T V, Myers J L, Katzenstein A-L A, Raghu G, Kennedy G C. Classification of usual interstitial pneumonia in patients with interstitial lung disease: assessment of a machine learning approach using high-dimensional transcriptional data. Lancet Respir Med 2015; 3:473-482.
E2. Dobin A, Davis C A, Schlesinger F, Drenkow J, Zaleski C, Jha S, Batut P, Chaisson M, Gingeras T R. STAR: ultrafast universal RNA-seq aligner. Bioinformatics 2012.
E3. Anders S, Pyl P T, Huber W. HTSeq—a Python framework to work with high-throughput sequencing data. Bioinformatics 2015; 31:166-169.
E4. DeLuca D S, Levin J Z, Sivachenko A, Fennell T, Nazaire M-D, Williams C, Reich M, Winckler W, Getz G. RNA-SeQC: RNA-seq metrics for quality control and process optimization. Bioinformatics 2012; 28:1530-1532.
E5. Wuenschell C W, Sunday M E, Singh G, Minoo P, Slavkin H C, Warburton D. Embryonic mouse lung epithelial progenitor cells co-express immunohistochemical markers of diverse mature cell lineages. J Histochem Cytochem 1996; 44:113-123.
E6. Nielsen S, King L S, Christensen B M, Agre P. Aquaporins in complex tissues. II. Subcellular distribution in respiratory and glandular tissues of rat. Am J Physiol 1997; 273:C1549-1561.
E7. Kim C F, Jackson E L, Woolfenden A E, Lawrence S, Babar I, Vogel S, Crowley D, Bronson R T, Jacks T. Identification of bronchioalveolar stem cells in normal lung and lung cancer. Cell 2005; 121:823-835.

E8. Zemke A C, Snyder J C, Brockway B L, Drake J A, Reynolds S D, Kaminski N, Stripp B R. Molecular staging of epithelial maturation using secretory cell-specific genes as markers. Am J Respir Cell Mol Biol 2009; 40:340-348.

E9. Treutlein B, Brownfield D G, Wu A R, Neff N F, Mantalas G L, Espinoza F H, Desai T J, Krasnow M A, Quake S R. Reconstructing lineage hierarchies of the distal lung epithelium using single-cell RNA-seq. Nature 2014; 509:371-375.

E10. Pankratz D G, Choi Y, Imtiaz U, Fedorowicz G M, Anderson J D, Colby T V, Myers J L, Lynch D A, Brown K K, Flaherty K R, Steele M P, Groshong S D, Raghu G, Barth N M, Walsh P S, Huang J, Kennedy G C, Martinez F J. Usual interstital pneumonia can be detected in transbronchial biopsies using machine learning. Annals Am Thorac Soc 2017.

All of the above U.S. patents, U.S. patent application publications, U.S. patent applications, foreign patents, foreign patent applications and non-patent publications referred to in this specification and/or listed in the Application Data Sheet or in the above REFERENCES list, are incorporated herein by reference, in their entirety.

TABLE 14

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 01-202 | A | Upper | 74 | F | Yes | No | 24 | HP | Difficult UIP | Difficult UIP | UIP | Train | 0.84 | N/A | 1.91 | N/A |
| 01-202 | B | Upper | | | | | | | | Difficult UIP | UIP | Train | 1.03 | N/A | 1.97 | N/A |
| 02-101 | A | Upper | | | | | | | | UIP | UIP | Train | 0.61 | N/A | 0.08 | N/A |
| 02-101 | B | Upper | 76 | F | Yes | No | 45 | HP | UIP | UIP | UIP | Train | -0.10 | N/A | -1.38 | N/A |
| 02-101 | C | Lower | | | | | | | | Favor UIP | UIP | Train | -0.68 | N/A | 1.40 | N/A |
| 02-101 | E | Lower | | | | | | | | Favor UIP | UIP | Train | 1.33 | N/A | 1.96 | N/A |
| 02-102 | A | Upper | 74 | F | Yes | No | HP | UIP | UIP | UIP | UIP | Train | 0.22 | N/A | -0.29 | N/A |
| 02-102 | C | Lower | | | | | | | | UIP | UIP | Train | -0.80 | N/A | -0.84 | N/A |
| 02-102 | D | Lower | | | | | | | | UIP | UIP | Train | 2.41 | N/A | -0.01 | N/A |
| 02-102 | E | Lower | | | | | | | | UIP | UIP | Train | 1.29 | N/A | 0.21 | N/A |
| 02-103 | C | Lower | 59 | F | No | N/A | N/A | missing | Favor HP | Favor HP Train | NonUIP | Train | 0.44 | N/A | -2.73 | N/A |
| 02-103 | E | Lower | | | | | | | | Favor HP | NonUIP | Train | -0.95 | N/A | -3.16 | N/A |
| 02-104 | A | Upper | | | | | | | | Emphysema | NonUIP | Train | 0.86 | N/A | 2.46 | N/A |
| 02-104 | B | Upper | 53 | F | Yes | No | 56 | Other | Granulom disease | Emphysema | NonUIP | Train | -0.11 | N/A | 0.16 | N/A |
| 02-104 | C | Lower | | | | | | | | Emphysema | NonUIP | Train | -0.88 | N/A | -0.10 | N/A |
| 02-104 | D | Lower | | | | | | | | Emphysema | NonUIP | Train | -3.24 | N/A | -4.21 | N/A |
| 03-102 | A | Upper | | | | | | | | Classic UIP | UIP | Train | 1.27 | N/A | 5.12 | N/A |
| 03-102 | B | Upper | 65 | F | Yes | No | 20 | HP | UIP | Classic UIP | UIP | Train | 2.49 | N/A | 6.50 | N/A |
| 03-102 | C | Lower | | | | | | | | Difficult SIP | UIP | Train | 1.59 | N/A | 4.59 | N/A |
| 03-102 | D | Lower | | | | | | | | Difficult UIP | UIP | Train | 0.61 | N/A | 3.18 | N/A |
| 05-101 | A | Upper | | | | | | | | Favor UIP | UIP | Train | 4.89 | N/A | 1.46 | N/A |
| 05-101 | B | Upper | 54 | F | Yes | No | 60 | HP | Favor UIP | Favor UIP | UIP | Train | 2.54 | N/A | 1.39 | N/A |
| 05-101 | C | Lower | | | | | | | | UIP | UIP | Train | 2.76 | N/A | 1.23 | N/A |
| 05-101 | D | Lower | | | | | | | | UIP | UIP | Train | 2.43 | N/A | 1.15 | N/A |
| 05-101 | E | Lower | | | | | | | | UIP | UIP | Train | 2.30 | N/A | 0.04 | N/A |
| 05-102 | A | Upper | | | | | | | | UIP | UIP | Train | 0.07 | N/A | -0.06 | N/A |
| 05-102 | B | Upper | 68 | M | Yes | No | 100 | Definite UIP | UIP | UIP | UIP | Train | 0.17 | N/A | -0.57 | N/A |
| 05-102 | C | Lower | | | | | | | | Difficult UIP | UIP | Train | 2.20 | N/A | 1.29 | N/A |
| 05-102 | D | Lower | | | | | | | | Difficult UIP | UIP | Train | 1.68 | N/A | 1.47 | N/A |
| 05-102 | E | Lower | | | | | | | | Difficult UIP | UIP | Train | -1.91 | N/A | -1.82 | N/A |
| 05-103 | A | Upper | | | | | | | | HP | NonUIP | Train | 2.02 | N/A | 3.43 | N/A |
| 05-103 | B | Upper | 37 | M | No | N/A | HP | HP | HP | HP | NonUIP | Train | -0.35 | N/A | -0.09 | N/A |
| 05-103 | C | Lower | | | | | | | | HP | NonUIP | Train | 1.10 | N/A | 2.35 | N/A |
| 05-103 | D | Lower | | | | | | | | HP | NonUIP | Train | -0.39 | N/A | 1.33 | N/A |
| 05-103 | E | Lower | | | | | | | | OP | NonUIP | Train | -0.56 | N/A | 1.98 | N/A |
| 06-301 | A | Upper | 70 | F | No | N/A | N/A | NSIP | Non diagnostic | OP | NonUIP | Train | 4.11 | N/A | 1.80 | N/A |
| 06-301 | B | Upper | | | | | | | | RB | NonUIP | Train | 0.86 | N/A | 0.89 | N/A |
| 06-316 | C | Lower | 62 | F | Yes | Yes | 60 | RB | Non diagnostic | RB | NonUIP | Train | 0.12 | N/A | -4.05 | N/A |
| 06-316 | D | Lower | | | | | | | | RB | NonUIP | Train | -0.36 | N/A | -0.54 | N/A |
| 08-101 | C | Lower | 60 | M | Yes | No | 36 | Eosinophilic pn. | DAD | RB | NonUIP | Train | -1.65 | N/A | 1.71 | N/A |
| 08-101 | E | Lower | | | | | | | | Cellular NSIP | NonUIP | Train | -0.02 | N/A | -0.72 | N/A |
| 08-102 | C | Lower | 76 | F | Yes | No | 45 | Eosinophilic pn. | Cellular NSIP | Cellular NSIP | NonUIP | Train | -3.38 | N/A | -7.17 | N/A |
| 08-102 | D | Lower | | | | | | | | Difficult UIP | NonUIP | Train | -1.05 | N/A | -3.32 | N/A |
| 08-103 | A | Upper | | | | | | | | Difficult UIP | UIP | Train | 0.76 | N/A | -1.58 | N/A |
| | | | | | | | | | | | | | 2.87 | N/A | 1.99 | N/A |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 08-103 | B | Upper | 78 | M | Yes | No | 60 | NSIP | Classic UIP | Difficult UIP | UIP | Train | 3.52 | N/A | 6.41 | N/A |
| 08-103 | E | Lower | | | | | | | | Difficult UIP | UIP | Train | -0.20 | N/A | 2.39 | N/A |
| 08-104 | C | Lower | 71 | F | Yes | No | 48 | UIP | Classic UIP | Classic UIP | UIP | Train | 1.25 | N/A | 0.68 | N/A |
| 08-104 | E | Lower | | | | | | | | Classic UIP | UIP | Train | 2.54 | N/A | 1.78 | N/A |
| 08-106 | A | Upper | 58 | M | No | N/A | N/A | NSIP | UIP | UIP | UIP | Train | 2.16 | N/A | 4.54 | N/A |
| 08-106 | B | Upper | | | | | | | | UIP | UIP | Train | 4.18 | N/A | 5.82 | N/A |
| 08-106 | C | Lower | | | | | | | | UIP | UIP | Train | 7.93 | N/A | 9.65 | N/A |
| 08-106 | D | Lower | | | | | | | | UIP | UIP | Train | 4.01 | N/A | 4.94 | N/A |
| 08-107 | A | Upper | 74 | F | No | N/A | N/A | UIP | Classic UIP | Classic UIP | UIP | Train | 1.15 | N/A | 2.97 | N/A |
| 08-107 | B | Upper | | | | | | | | Classic UIP | UIP | Train | 2.93 | N/A | 4.22 | N/A |
| 08-107 | C | Lower | | | | | | | | Classic UIP | UIP | Train | 3.96 | N/A | 3.36 | N/A |
| 08-107 | D | Lower | | | | | | | | Classic UIP | UIP | Train | 4.14 | N/A | 5.46 | N/A |
| 08-108 | A | Middle | 71 | M | Yes | No | 74 | Eosinophilic pn. | Difficult UIP | UIP | UIP | Train | 1.36 | N/A | -3.17 | N/A |
| 08-108 | B | Middle | | | | | | | | UIP | UIP | Train | 1.72 | N/A | 0.80 | N/A |
| 08-112 | A | Upper | 48 | F | Yes | Yes | 31 | HP | Classic UIP | Classic UIP | UIP | Train | -0.78 | N/A | -1.29 | N/A |
| 08-112 | B | Upper | | | | | | | | Classic UIP | UIP | Train | 0.93 | N/A | 1.34 | N/A |
| 08-112 | C | Lower | | | | | | | | UIP | UIP | Train | -0.24 | N/A | -1.37 | N/A |
| 08-112 | E | Lower | | | | | | | | UIP | UIP | Train | -2.10 | N/A | -1.48 | N/A |
| 08-114 | C | Lower | 61 | M | Yes | Yes | 46 | HP | Difficult UIP | Difficult UIP | UIP | Train | 2.97 | N/A | 3.56 | N/A |
| 08-114 | D | Lower | | | | | | | | Difficult UIP | UIP | Train | 2.13 | N/A | 4.03 | N/A |
| 08-116 | A | Upper | 72 | M | No | N/A | N/A | Definite UIP | Difficult UIP | Difficult UIP | UIP | Train | 1.71 | N/A | 3.10 | N/A |
| 08-116 | B | Upper | | | | | | | | Difficult UIP | UIP | Train | 4.46 | N/A | 5.36 | N/A |
| 08-116 | C | Lower | | | | | | | | Difficult UIP | UIP | Train | 5.01 | N/A | 5.22 | N/A |
| 08-116 | D | Lower | | | | | | | | Difficult UIP | UIP | Train | 6.37 | N/A | 6.26 | N/A |
| 08-116 | E | Lower | | | | | | | | Difficult UIP | UIP | Train | 7.04 | N/A | 8.26 | N/A |
| 08-117 | C | Lower | 73 | M | Yes | No | 51 | Other | CIF, NOC | UIP | UIP | Train | 6.32 | N/A | 6.41 | N/A |
| 08-117 | D | Lower | | | | | | | | UIP | UIP | Train | 4.37 | N/A | 3.16 | N/A |
| 08-117 | E | Lower | | | | | | | | UIP | UIP | Train | 5.01 | N/A | 4.28 | N/A |
| 08-118 | A | Upper | 69 | F | Yes | No | Unk. | Eosinophilic pn. | OP | OP | NonUIP | Train | 3.50 | N/A | 4.90 | N/A |
| 08-118 | B | Upper | | | | | | | | OP | NonUIP | Train | 0.26 | N/A | -5.24 | N/A |
| 08-118 | C | Lower | | | | | | | | OP | NonUIP | Train | -1.30 | N/A | -0.15 | N/A |
| 08-118 | D | Lower | | | | | | | | OP | NonUIP | Train | -0.44 | N/A | -0.35 | N/A |
| 08-118 | E | Lower | | | | | | | | OP | NonUIP | Train | 1.26 | N/A | -0.15 | N/A |
| 08-120 | A | Middle | 83 | M | Yes | No | 62 | HP | Classic UIP | Classic UIP | UIP | Train | -0.62 | N/A | -0.96 | N/A |
| 08-120 | B | Middle | | | | | | | | Classic UIP | UIP | Train | 3.94 | N/A | 2.95 | N/A |
| 08-120 | D | Lower | | | | | | | | Classic UIP | UIP | Train | 2.61 | N/A | 1.06 | N/A |
| 08-120 | E | Lower | | | | | | | | Classic UIP | UIP | Train | 1.94 | N/A | 1.24 | N/A |
| 08-123 | C | Lower | 69 | F | Yes | No | 2 | HP | HP | HP | NonUIP | Train | 2.56 | N/A | 1.79 | N/A |
| 08-123 | D | Lower | | | | | | | | HP | NonUIP | Train | 2.75 | N/A | 1.43 | N/A |
| 08-123 | E | Lower | | | | | | | | HP | NonUIP | Train | 3.09 | N/A | -0.81 | N/A |
| 08-125 | A | Middle | 71 | M | Yes | No | 30 | Definite UIP | Classic UIP | Classic UIP | UIP | Train | 3.15 | N/A | -0.06 | N/A |
| 08-125 | B | Middle | | | | | | | | Classic UIP | UIP | Train | 2.74 | N/A | 1.87 | N/A |
| 08-125 | C | Lower | | | | | | | | Classic UIP | UIP | Train | 2.17 | N/A | 1.20 | N/A |
| 08-125 | D | Lower | | | | | | | | Classic UIP | UIP | Train | 1.86 | N/A | 5.56 | N/A |
| 08-125 | E | Lower | | | | | | | | Classic UIP | UIP | Train | 2.33 | N/A | 3.34 | N/A |
| 08-201 | A | Upper | | | | | | | | RB | NonUIP | Train | 2.60 | N/A | 0.92 | N/A |
| | | | | | | | | | | | | | -1.38 | N/A | -3.67 | N/A |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 08-201 | B | Upper | 46 | M | Yes | Yes | 51 | RB | Non diagnostic | RB | NonUIP | Train | -2.50 | N/A | -2.39 | N/A |
| 08-206 | D | Lower | 53 | M | Yes | Yes | Unk. | Other | Pneumocystis pn. | Pneumocystis pn. | NonUIP | Train | -2.05 | N/A | -1.11 | N/A |
| 08-206 | E | Lower |  |  |  |  |  |  |  | Pneumocystis pn. | NonUIP | Train | -1.47 | N/A | -1.49 | N/A |
| 10-101 | C | Lower | 56 | F | Yes | No | 17 | HP | Bronchiolitis | Bronchiolitis | NonUIP | Train | -2.15 | N/A | -0.97 | N/A |
| 10-101 | D | Lower |  |  |  |  |  |  |  | Bronchiolitis | NonUIP | Train | -0.24 | N/A | -0.91 | N/A |
| 10-101 | E | Lower | 56 | M | No | N/A | N/A | UIP | Classic UIP | Classic UIP | UIP | Train | 0.30 | N/A | 1.92 | N/A |
| 11-101 | C | Lower |  |  |  |  |  |  |  | UIP | UIP | Train | 3.26 | N/A | 1.90 | N/A |
| 13-101 | C | Lower | 67 | F | Yes | No | 80 | Other | Difficult UIP | UIP | UIP | Train | 5.50 | N/A | 7.21 | N/A |
| 13-101 | E | Lower |  |  |  |  |  |  |  | Classic UIP | UIP | Train | 3.66 | N/A | 6.10 | N/A |
| 13-102 | A | Upper | 61 | F | Yes | No | 12 | UIP | Classic UIP | Classic UIP | UIP | Train | 2.70 | N/A | 2.13 | N/A |
| 13-102 | B | Upper |  |  |  |  |  |  |  | Classic UIP | UIP | Train | 5.21 | N/A | 3.44 | N/A |
| 13-102 | C | Lower |  |  |  |  |  |  |  | Classic UIP | UIP | Train | 4.26 | N/A | 4.11 | N/A |
| 13-102 | D | Lower |  |  |  |  |  |  |  | Classic UIP | UIP | Train | 3.03 | N/A | 3.04 | N/A |
| 13-105 | A | Upper | 57 | M | Yes | No | 30 | HP | Classic UIP | Classic UIP | UIP | Train | 1.94 | N/A | 2.26 | N/A |
| 13-105 | B | Upper |  |  |  |  |  |  |  | Classic UIP | UIP | Train | 2.89 | N/A | 5.20 | N/A |
| 13-105 | C | Lower |  |  |  |  |  |  |  | Classic UIP | UIP | Train | 4.38 | N/A | 5.66 | N/A |
| 13-105 | D | Lower |  |  |  |  |  |  |  | Classic UIP | UIP | Train | 2.99 | N/A | 3.47 | N/A |
| 13-105 | E | Lower |  |  |  |  |  |  |  | Classic UIP | UIP | Train | 3.58 | N/A | 4.57 | N/A |
| 13-106 | A | Upper | 65 | F | Yes | No | 14 | Other | Bronchiolitis | Bronchiolitis | NonUIP | Train | 0.85 | N/A | 2.16 | N/A |
| 13-106 | B | Upper |  |  |  |  |  |  |  | Bronchiolitis | NonUIP | Train | 0.45 | N/A | 2.73 | N/A |
| 13-106 | C | Lower |  |  |  |  |  |  |  | Bronchiolitis | NonUIP | Train | 1.43 | N/A | 2.96 | N/A |
| 13-106 | D | Lower |  |  |  |  |  |  |  | Bronchiolitis | NonUIP | Train | 1.17 | N/A | 2.47 | N/A |
| 13-106 | E | Lower |  |  |  |  |  |  |  | Bronchiolitis | NonUIP | Train | 1.79 | N/A | 2.45 | N/A |
| 13-110 | A | Upper | 52 | M | No | N/A | N/A | NSIP | Difficult UIP | NSIP | UIP | Train | 0.68 | N/A | 4.83 | N/A |
| 13-110 | B | Upper |  |  |  |  |  |  |  | NSIP | SIP | Train | 0.64 | N/A | 3.90 | N/A |
| 13-110 | C | Lower |  |  |  |  |  |  |  | Difficult UIP | UIP | Train | 2.83 | N/A | 4.31 | N/A |
| 13-110 | D | Lower |  |  |  |  |  |  |  | Difficult UIP | UIP | Train | 1.25 | N/A | 5.89 | N/A |
| 13-111 | A | Upper | 70 | M | No | N/A | N/A | HP | NSIP | NSIP | NonUIP | Train | -0.05 | N/A | -0.24 | N/A |
| 13-111 | B | Upper |  |  |  |  |  |  |  | NSIP | NonUIP | Train | 0.01 | N/A | 0.36 | N/A |
| 13-111 | C | Lower |  |  |  |  |  |  |  | Favor NSIP | NonUIP | Train | -0.60 | N/A | 0.21 | N/A |
| 13-111 | D | Lower |  |  |  |  |  |  |  | Favor NSIP | NonUIP | Train | 1.11 | N/A | 0.22 | N/A |
| 13-111 | E | Upper |  |  |  |  |  |  |  | Favor NSIP | NonUIP | Train | 1.25 | N/A | -1.46 | N/A |
| 13-112 | A | Upper | 68 | M | No | No | N/A | HP | Classic UIP | Favor UIP | UIP | Train | 2.67 | N/A | 4.79 | N/A |
| 13-112 | B | Lower |  |  |  |  |  |  |  | Favor UIP | UIP | Train | 1.97 | N/A | 6.37 | N/A |
| 13-112 | D | Lower |  |  |  |  |  |  |  | UIP | UIP | Train | 1.76 | N/A | 5.25 | N/A |
| 13-201 | A | Upper | 49 | M | Yes | No | 30 | Sarcoidosis | Sarcoidosis | UIP | UIP | Train | 4.15 | N/A | 6.85 | N/A |
| 13-201 | B | Upper |  |  |  |  |  |  |  | Sarcoidosis | NonUIP | Train | 0.41 | N/A | -2.31 | N/A |
| 13-201 | C | Lower |  |  |  |  |  |  |  | Sarcoidosis | NonUIP | Train | -2.25 | N/A | -3.63 | N/A |
| 14-101 | B | Upper | 80 | M | Yes | No | Unk. | HP | UIP | UIP | UIP | Train | 2.65 | N/A | 5.98 | N/A |
| 14-101 | C | Lower |  |  |  |  |  |  |  | Classic UIP | UIP | Train | 2.51 | N/A | 3.89 | N/A |
| 14-101 | D | Lower |  |  |  |  |  |  |  | Classic UIP | UIP | Train | 3.20 | N/A | 2.04 | N/A |
| 14-101 | E | Lower |  |  |  |  |  |  |  | Classic UIP | UIP | Train | 2.27 | N/A | 2.68 | N/A |
| 15-302 | B | Middle | 70 | F | Yes | No | 33 | HP | UIP | UIP | UIP | Train | 3.70 | N/A | 6.87 | N/A |
| 15-302 | C | Lower |  |  |  |  |  |  |  | UIP | UIP | Train | 5.22 | N/A | 5.76 | N/A |
| 15-302 | E | Lower |  |  |  |  |  |  |  | UIP | UIP | Train | 4.38 | N/A | 5.59 | N/A |
| 15-303 | C | Lower | 63 | F | No | N/A | N/A | NSIP | Favor UIP | Favor UIP | UIP | Train | 2.54 | N/A | 2.39 | N/A |
| 15-304 | B | Middle |  |  |  |  |  |  |  | Favor UIP | UIP | Train | 1.45 | N/A | 0.28 | N/A |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 15-304 | C | Lower | 52 | M | No | N/A | N/A | HP | Favor UIP | Favor UIP | UIP | Train | 1.78 | N/A | -0.36 | N/A |
| 15-304 | D | Lower | | | | | | | | Favor UIP | UIP | Train | 4.37 | N/A | 6.18 | N/A |
| 15-305 | C | Lower | 58 | M | Yes | No | Unk. | HP | | Favor UIP | UIP | Train | 1.95 | N/A | 4.20 | N/A |
| 15-305 | D | Lower | | | | | | | | Favor UIP | UIP | Train | 2.33 | N/A | 3.05 | N/A |
| 18-101 | C | Lower | 67 | F | No | N/A | N/A | Sarcoidosis | CIF, NOC | Sarcoidosis | NonUIP | Train | -0.42 | N/A | 1.37 | N/A |
| 18-102 | A | Upper | 46 | F | Yes | No | 1.5 | Sarcoidosis | Sarcoidosis | Sarcoidosis | NonUIP | Train | -0.89 | N/A | 0.30 | N/A |
| 18-102 | B | Upper | | | | | | | | Sarcoidosis | NonUIP | Train | -2.07 | N/A | 0.04 | N/A |
| 18-112 | C | Lower | 61 | F | No | N/A | N/A | NSIP | UIP | UIP | UIP | Train | -1.01 | N/A | 0.15 | N/A |
| 18-112 | D | Lower | | | | | | | | UIP | UIP | Train | -1.32 | N/A | -0.94 | N/A |
| 18-112 | E | Lower | | | | | | | | UIP | UIP | Train | 0.17 | N/A | 0.38 | N/A |
| 19-301 | A | Upper | 66 | M | Yes | No | 30 | DIP | OP | OP | NonUIP | Train | 0.20 | N/A | -0.21 | N/A |
| 19-301 | B | Upper | | | | | | | | OP | NonUIP | Train | -0.28 | N/A | -0.82 | N/A |
| 19-306 | C | Lower | 64 | F | No | N/A | N/A | HP | Favor UIP | Favor UIP | UIP | Train | 3.66 | N/A | 8.16 | N/A |
| 19-306 | D | Lower | | | | | | | | Favor UIP | UIP | Train | 2.41 | N/A | 3.36 | N/A |
| 19-306 | E | Lower | | | | | | | | Favor UIP | UIP | Train | 2.17 | N/A | 5.25 | N/A |
| 32-304 | A | Upper | 58 | F | No | N/A | N/A | HP | Sarcoidosis | Sarcoidosis | NonUIP | Train | -0.03 | N/A | -2.05 | N/A |
| 32-304 | B | Upper | | | | | | | | NSIP | NonUIP | Train | -0.24 | N/A | -2.81 | N/A |
| 32-309 | B | Upper | 31 | F | Yes | Yes | 12 | HP | NSIP | NSIP | NonUIP | Train | -0.63 | N/A | -2.12 | N/A |
| 32-309 | C | Lower | | | | | | | | NSIP | NonUIP | Train | -0.92 | N/A | -0.31 | N/A |
| 32-309 | D | Lower | | | | | | | | NSIP | NonUIP | Train | 1.64 | N/A | -1.00 | N/A |
| 32-309 | E | Lower | | | | | | | | NSIP | NonUIP | Train | 0.40 | N/A | -0.67 | N/A |
| 32-311 | C | Lower | 67 | M | No | N/A | N/A | Definite UIP | UIP | Favor UIP | UIP | Train | -0.10 | N/A | -2.39 | N/A |
| 32-311 | D | Lower | | | | | | | | Favor UIP | UIP | Train | 1.37 | N/A | 2.25 | N/A |
| 32-311 | E | Lower | | | | | | | | Favor UIP | UIP | Train | 1.74 | N/A | 3.90 | N/A |
| 36-101 | A | Upper | 53 | F | No | N/A | N/A | HP | UIP | UIP | UIP | Train | 3.46 | N/A | 4.34 | N/A |
| 36-101 | B | Upper | | | | | | | | UIP | UIP | Train | -0.87 | N/A | -1.73 | N/A |
| 36-102 | A | Upper | 88 | M | No | N/A | N/A | Other | Classic UIP | Classic UIP | UIP | Train | -0.50 | N/A | -1.02 | N/A |
| 36-102 | B | Upper | | | | | | | | Classic UIP | UIP | Train | 1.67 | N/A | 3.34 | N/A |
| 36-102 | C | Lower | | | | | | | | Difficult UIP | UIP | Train | 0.79 | N/A | 3.04 | N/A |
| 36-102 | E | Lower | | | | | | | | Difficult UIP | UIP | Train | 1.69 | N/A | 1.74 | N/A |
| 36-311 | B | Upper | 42 | M | Yes | No | 1 | missing | NSIP | NSIP | NonUIP | Train | 1.41 | N/A | 2.81 | N/A |
| 01-206 | A | Upper | 42 | F | Yes | Yes | Unk. | missing | DAD | DAD | NonUIP | Test | N/A | 0.86 | -2.88 | N/A |
| 01-207 | B | Upper | | | | | | | | DAD | NonUIP | Test | N/A | -0.61 | 3.01 | N/A |
| 06-314 | A | Upper | 76 | F | No | N/A | N/A | Definite UIP | Favor UIP | Favor UIP | UIP | Test | N/A | -0.91 | 2.97 | N/A |
| 06-314 | B | Upper | | | | | | | | Favor UIP | UIP | Test | N/A | 4.80 | 5.65 | N/A |
| 06-314 | C | Lower | | | | | | | | Favor UIP | UIP | Test | N/A | 3.51 | 4.79 | N/A |
| 06-314 | D | Lower | | | | | | | | Favor UIP | UIP | Test | N/A | 2.95 | 3.90 | N/A |
| 06-314 | E | Lower | | | | | | | | Favor UIP | UIP | Test | N/A | 3.29 | 6.67 | N/A |
| 06-318 | A | Upper | | | | | | | | RB | NonUIP | Test | N/A | 4.56 | 6.72 | N/A |
| 06-318 | B | Upper | 45 | F | Yes | Yes | 37.5 | missing | Non diagnostic | RB | NonUIP | Test | N/A | -0.27 | -0.66 | N/A |
| 06-318 | C | Lower | | | | | | | | RB | NonUIP | Test | N/A | -1.25 | -1.56 | N/A |
| 06-318 | D | Lower | | | | | | | | RB | NonUIP | Test | N/A | -0.41 | -3.03 | N/A |
| 06-318 | E | Lower | | | | | | | | RB | NonUIP | Test | N/A | 1.52 | -1.31 | N/A |
| 08-105 | A | Upper | 40 | F | No | N/A | N/A | OP | OP | OP | NonUIP | Test | N/A | 0.06 | -1.43 | N/A |
| 08-105 | B | Upper | | | | | | | | OP | NonUIP | Test | N/A | -0.95 | -2.85 | N/A |
| 08-105 | C | Lower | | | | | | | | OP | NonUIP | Test | N/A | -1.00 | -2.91 | N/A |
| | | | | | | | | | | | | | | -0.27 | -0.32 | |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 08-105 | E | Lower | | | | | | | | OP | NonUIP | Test | N/A | −0.81 | −0.77 | N/A |
| 08-109 | A | Upper | 74 | M | Yes | No | 46 | Sarcoidosis | Difficult UIP | Favor UIP | UIP | Test | N/A | 1.91 | 4.16 | N/A |
| 08-109 | C | Lower | | | | | | | | Favor UIP | UIP | Test | N/A | 5.33 | 10.36 | N/A |
| 08-109 | D | Lower | | | | | | | | Favor UIP | UIP | Test | N/A | 3.84 | 4.98 | N/A |
| 08-109 | E | Lower | | | | | | | | Favor UIP | UIP | Test | N/A | 3.74 | 5.82 | N/A |
| 08-110 | C | Lower | 72 | M | Yes | No | 52 | UIP | Classic UIP | Classic UIP | UIP | Test | N/A | 2.86 | 5.24 | N/A |
| 08-110 | D | Lower | | | | | | | | Classic UIP | UIP | Test | N/A | 2.56 | 2.82 | N/A |
| 08-110 | E | Lower | | | | | | | | Classic UIP | UIP | Test | N/A | 6.32 | 6.69 | N/A |
| 08-111 | A | Upper | 54 | F | Yes | No | 10 | HP | UIP | NSIP | UIP | Test | N/A | 5.07 | 6.02 | N/A |
| 08-111 | B | Upper | | | | | | | | NSIP | UIP | Test | N/A | 2.85 | 1.72 | N/A |
| 08-111 | C | Lower | | | | | | | | Classic UIP | UIP | Test | N/A | 2.18 | 1.02 | N/A |
| 08-111 | D | Lower | | | | | | | | Classic UIP | UIP | Test | N/A | 3.81 | 3.49 | N/A |
| 08-111 | E | Lower | | | | | | | | Classic UIP | UIP | Test | N/A | 1.47 | 2.37 | N/A |
| 08-119 | A | Upper | 43 | F | Yes | No | 10.5 | OP | Sarcoidosis | Sarcoidosis | NonUIP | Test | N/A | −0.98 | −7.24 | N/A |
| 08-119 | B | Upper | | | | | | | | Sarcoidosis | NonUIP | Test | N/A | −1.88 | −6.17 | N/A |
| 08-119 | C | Lower | | | | | | | | Sarcoidosis | NonUIP | Test | N/A | −0.07 | −1.88 | N/A |
| 08-119 | E | Lower | | | | | | | | Sarcoidosis | NonUIP | Test | N/A | −1.88 | −7.24 | N/A |
| 08-121 | A | Upper | 64 | F | Yes | No | Unk. | Definite UIP | UIP | UIP | UIP | Test | N/A | 0.02 | 0.25 | N/A |
| 08-121 | B | Upper | | | | | | | | UIP | UIP | Test | N/A | 0.96 | 3.32 | N/A |
| 08-121 | C | Lower | | | | | | | | UIP | UIP | Test | N/A | 0.75 | 2.23 | N/A |
| 08-121 | E | Lower | | | | | | | | UIP | UIP | Test | N/A | 1.24 | 2.69 | N/A |
| 08-122 | A | Upper | 50 | M | No | N/A | N/A | HP | HP | HP | NonUIP | Test | N/A | −1.27 | 0.32 | N/A |
| 08-122 | B | Upper | | | | | | | | HP | NonUIP | Test | N/A | −1.51 | −0.09 | N/A |
| 08-122 | C | Lower | | | | | | | | HP | NonUIP | Test | N/A | −2.09 | 0.10 | N/A |
| 08-122 | D | Lower | | | | | | | | HP | NonUIP | Test | N/A | 0.81 | 2.15 | N/A |
| 08-122 | E | Lower | | | | | | | | HP | NonUIP | Test | N/A | 1.24 | 1.51 | N/A |
| 08-124 | A | Middle | 68 | F | Yes | No | 10 | HP | UIP | Favor UIP | UIP | Test | N/A | 2.29 | 2.73 | N/A |
| 08-124 | B | Middle | | | | | | | | Favor UIP | UIP | Test | N/A | 1.74 | 2.77 | N/A |
| 08-124 | D | Lower | | | | | | | | Favor UIP | UIP | Test | N/A | 5.57 | 5.14 | N/A |
| 08-124 | E | Lower | | | | | | | | Favor UIP | UIP | Test | N/A | 1.85 | −2.84 | N/A |
| 08-127 | C | Lower | 71 | M | Yes | No | 25 | DIP | UIP | UIP | UIP | Test | N/A | 3.19 | 3.71 | N/A |
| 08-127 | D | Lower | | | | | | | | UIP | UIP | Test | N/A | 3.15 | 4.54 | N/A |
| 08-127 | E | Upper | | | | | | | | UIP | UIP | Test | N/A | 4.92 | 3.10 | N/A |
| 08-128 | A | Upper | 75 | M | Yes | No | Unk. | HP | Classic UIP | UIP | UIP | Test | N/A | 4.78 | 6.44 | N/A |
| 08-128 | B | Lower | | | | | | | | UIP | UIP | Test | N/A | 4.59 | 5.83 | N/A |
| 08-128 | C | Lower | | | | | | | | Classic UIP | UIP | Test | N/A | 2.29 | 6.47 | N/A |
| 08-128 | D | Lower | | | | | | | | Classic UIP | UIP | Test | N/A | 4.98 | 7.19 | N/A |
| 08-128 | E | Lower | | | | | | | | Classic UIP | UIP | Test | N/A | 4.95 | 7.99 | N/A |
| 08-129 | A | Middle | 64 | M | Yes | No | 30 | Probable UIP | UIP | UIP | UIP | Test | N/A | 0.44 | 1.08 | N/A |
| 08-129 | B | Middle | | | | | | | | UIP | UIP | Test | N/A | 0.98 | 1.02 | N/A |
| 08-129 | C | Lower | | | | | | | | Difficult UIP | UIP | Test | N/A | 0.01 | −0.74 | N/A |
| 08-129 | D | Lower | | | | | | | | Difficult UIP | UIP | Test | N/A | 1.48 | 2.58 | N/A |
| 08-129 | E | Lower | | | | | | | | Difficult UIP | UIP | Test | N/A | −0.49 | −0.04 | N/A |
| 08-203 | A | Upper | 24 | F | Yes | No | 4 | Other | Eosinophilic pn. | Eosinophilic pn. | NonUIP | Test | N/A | −1.49 | −6.21 | N/A |
| 08-203 | B | Upper | | | | | | | | Eosinophilic pn. | NonUIP | Test | N/A | −2.19 | −3.19 | N/A |
| 10-102 | A | Middle | | | | | | | | Difficult UIP | UIP | Test | N/A | −0.17 | −0.26 | N/A |
| 10-102 | B | Middle | | | | | | | | Difficult UIP | UIP | Test | N/A | −0.05 | −1.37 | N/A |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 10-102 | C | Lower | 27 | M | No | N/A | N/A | NSIP | Difficult UIP | Difficult UIP | UIP | Test | N/A | 0.46 | 3.38 | N/A |
| 10-102 | D | Lower | | | | | | | | Difficult UIP | UIP | Test | N/A | -1.57 | -1.78 | N/A |
| 10-102 | E | Lower | | | | | | | | Difficult UIP | UIP | Test | N/A | 0.17 | -3.19 | N/A |
| 13-103 | A | Upper | | | | | | | | UIP | UIP | Test | N/A | 2.74 | 0.32 | N/A |
| 13-103 | C | Lower | 75 | F | No | N/A | N/A | HP | Classic UIP | Classic UIP | UIP | Test | N/A | 0.85 | 4.06 | N/A |
| 13-103 | D | Lower | | | | | | | | Classic UIP | UIP | Test | N/A | 1.23 | -0.43 | N/A |
| 13-103 | E | Lower | | | | | | | | Classic UIP | UIP | Test | N/A | -1.71 | -0.71 | N/A |
| 13-104 | C | Lower | 66 | F | No | N/A | N/A | NSIP | Difficult UIP | Classic UIP | UIP | Test | N/A | 1.37 | 1.85 | N/A |
| 13-107 | A | Upper | | | | | | | | Classic UIP | UIP | Test | N/A | -1.15 | 1.16 | N/A |
| 13-107 | B | Upper | 69 | M | Yes | No | 13.5 | HP | Classic UIP | Classic UIP | UIP | Test | N/A | 3.02 | 3.64 | N/A |
| 13-107 | C | Lower | | | | | | | | UIP | UIP | Test | N/A | 2.61 | 3.73 | N/A |
| 13-107 | D | Lower | | | | | | | | UIP | UIP | Test | N/A | 3.60 | 3.52 | N/A |
| 13-107 | E | Lower | | | | | | | | UIP | UIP | Test | N/A | 4.64 | 5.13 | N/A |
| 13-108 | A | Upper | 78 | F | No | N/A | N/A | HP | Classic UIP | UIP | UIP | Test | N/A | 4.23 | 3.68 | N/A |
| 13-108 | B | Upper | | | | | | | | UIP | UIP | Test | N/A | 1.07 | 1.24 | N/A |
| 13-108 | C | Lower | | | | | | | | Classic UIP | UIP | Test | N/A | 1.25 | 1.22 | N/A |
| 13-108 | D | Lower | | | | | | | | Classic UIP | UIP | Test | N/A | 3.32 | 2.60 | N/A |
| 13-108 | E | Lower | | | | | | | | Classic UIP | UIP | Test | N/A | 5.06 | 4.21 | N/A |
| 13-109 | A | Upper | 71 | M | Yes | No | 106 | NSIP | OP | OP | NonUIP | Test | N/A | 2.02 | 2.69 | N/A |
| 13-109 | B | Upper | | | | | | | | OP | NonUIP | Test | N/A | 3.09 | 0.32 | N/A |
| 13-113 | B | Upper | 73 | M | Yes | No | 45 | Other | Bronchiolitis | Bronchiolitis | NonUIP | Test | N/A | 2.63 | 1.81 | N/A |
| 13-113 | E | Lower | | | | | | | | Bronchiolitis | NonUIP | Test | N/A | 2.16 | -3.20 | N/A |
| 13-115 | A | Upper | 60 | M | No | N/A | N/A | Probable UIP | Classic UIP | Classic UIP | UIP | Test | N/A | 1.81 | -2.39 | N/A |
| 13-115 | B | Upper | | | | | | | | UIP | UIP | Test | N/A | 4.99 | 7.50 | N/A |
| 13-115 | C | Lower | | | | | | | | UIP | UIP | Test | N/A | 3.80 | 5.44 | N/A |
| 13-115 | D | Lower | | | | | | | | UIP | UIP | Test | N/A | 3.74 | 10.28 | N/A |
| 13-115 | E | Lower | | | | | | | | UIP | UIP | Test | N/A | 3.92 | 6.65 | N/A |
| 18-114 | E | Lower | 77 | M | Yes | No | 18 | HP | Difficult UIP | Favor UIP | UIP | Test | N/A | 4.34 | 7.11 | N/A |
| 28-302 | E | Lower | 62 | M | Yes | No | 40 | HP | Difficult UIP | UIP | UIP | Test | N/A | 0.84 | 1.52 | N/A |
| 32-301 | C | Lower | 18 | F | No | N/A | N/A | DIP | Favor NSIP | Favor NSIP | NonUIP | Test | N/A | 1.13 | 3.92 | N/A |
| 32-301 | D | Lower | | | | | | | | Favor NSIP | NonUIP | Test | N/A | -2.35 | -4.05 | N/A |
| 32-301 | E | Lower | | | | | | | | Favor NSIP | NonUIP | Test | N/A | -0.50 | -4.92 | N/A |
| 32-313 | A | Upper | 48 | F | Yes | No | 15 | Sarcoidosis | RB | RB | NonUIP | Test | N/A | -0.68 | -3.31 | N/A |
| 32-313 | B | Upper | | | | | | | | RB | NonUIP | Test | N/A | -2.09 | -3.79 | N/A |
| 32-318 | A | Upper | | | | | | | | OP | NonUIP | Test | N/A | -4.54 | -8.06 | N/A |
| 32-318 | B | Upper | 38 | F | Unk. | N/A | N/A | OP | OP | OP | NonUIP | Test | N/A | 0.56 | 1.40 | N/A |
| 32-318 | C | Lower | | | | | | | | OP | NonUIP | Test | N/A | 1.09 | 0.24 | N/A |
| 32-318 | D | Lower | | | | | | | | OP | NonUIP | Test | N/A | 2.53 | 2.23 | N/A |
| 32-318 | E | Lower | | | | | | | | OP | NonUIP | Test | N/A | 0.67 | -0.79 | N/A |
| 36-103 | A | Upper | | | | | | | | UIP | UIP | Test | N/A | 2.85 | 3.29 | N/A |
| 36-103 | B | Upper | 62 | F | No | N/A | N/A | HP | UIP | UIP | UIP | Test | N/A | 1.05 | 3.25 | N/A |
| 36-103 | C | Lower | | | | | | | | UIP | UIP | Test | N/A | 0.69 | 3.43 | N/A |
| 36-103 | D | Lower | | | | | | | | UIP | UIP | Test | N/A | 0.76 | 2.98 | N/A |
| 36-103 | E | Lower | | | | | | | | UIP | UIP | Test | N/A | -1.01 | -0.01 | N/A |
| 47-103 | A | Upper | | | | | | | | Pulm. hypertension | UIP | Test | N/A | -0.04 | 3.12 | N/A |
| 47-103 | B | Upper | | | | | | | | Pulm. hypertension | UIP | Test | N/A | 3.50 | 3.75 | N/A |
| 47-103 | | | | | | | | | | | | Test | N/A | 3.54 | 4.50 | N/A |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 47-103 | C | Lower | 72 | F | No | N/A | N/A | missing | Difficult UIP | Difficult UIP | UIP | Test | N/A | 2.56 | 3.78 | N/A |
| 47-103 | D | Lower |  |  |  |  |  |  |  | Difficult UIP | UIP | Test | N/A | 3.71 | 5.37 | N/A |
| 47-103 | E | Lower |  |  |  |  |  |  |  | Difficult UIP | UIP | Test | N/A | 3.33 | 4.84 | N/A |
| 01-201 | C | N/A | 56 | F | Yes | No | 50 | missing | N/A | N/A | N/A | Excl. | N/A | 3.00 | N/A | 2.51 |
| 01-203 | D | N/A | 50 | M | Yes | No | 2.3 | missing | N/A | N/A | N/A | Excl. | N/A | 2.46 | N/A | 1.04 |
| 01-203 | E | N/A |  |  |  |  |  |  |  | N/A | N/A | Excl. | N/A | 2.19 | N/A | -1.32 |
| 01-203 | E | N/A |  |  |  |  |  |  |  | N/A | N/A | Excl. | N/A | 1.50 | N/A | -1.95 |
| 02-103 | A | Upper | 59 | F | No | N/A | N/A | missing | Favor HP | Favor HP | NonUIP | Excl. | N/A | N/A | N/A | N/A |
| 02-103 | D | Upper |  |  |  |  |  |  |  | Favor HP | NonUIP | Excl. | N/A | N/A | N/A | N/A |
| 02-103 | D | Lower |  |  |  |  |  |  |  | Favor HP | NonUIP | Excl. | N/A | N/A | N/A | N/A |
| 02-104 | E | Lower | 53 | F | Yes | No | 56 | Other | Granulom. disease | Emphysema | N/A | Excl. | N/A | -2.25 | N/A | -5.60 |
| 03-101 | B | N/A | 54 | F | Yes | No | 40 | NSIP | N/A | N/A | N/A | Excl. | N/A | 3.48 | N/A | 3.51 |
| 03-101 | D | N/A |  |  |  |  |  |  |  | N/A | N/A | Excl. | N/A | 3.50 | N/A | 3.44 |
| 03-101 | E | N/A |  |  |  |  |  |  |  | N/A | N/A | Excl. | N/A | 2.60 | N/A | 1.89 |
| 03-201 | A | N/A | 85 | M | Yes | No | 50 | missing | N/A | N/A | N/A | Excl. | N/A | 2.47 | N/A | -4.34 |
| 03-201 | B | N/A |  |  |  |  |  |  |  | N/A | N/A | Excl. | N/A | -2.99 | N/A | -5.50 |
| 03-201 | D | N/A |  |  |  |  |  |  |  | N/A | N/A | Excl. | N/A | 3.12 | N/A | 0.57 |
| 03-201 | E | N/A |  |  |  |  |  |  |  | N/A | N/A | Excl. | N/A | 2.58 | N/A | -6.49 |
| 06-301 | D | N/A | 70 | F | No | N/A | N/A | NSIP | Non diagnostic | OP | NonUIP | Excl. | N/A | N/A | N/A | N/A |
| 06-302 | E | N/A | 72 | F | No | N/A | N/A | Other | N/A | OP | NonUIP | Excl. | N/A | 1.31 | N/A | -1.30 |
| 06-302 | A | N/A |  |  |  |  |  |  |  | N/A | N/A | Excl. | N/A | 0.22 | N/A | -3.40 |
| 06-303 | C | N/A | 67 | M | Yes | Yes | 150 | RB | N/A | N/A | N/A | Excl. | N/A | 4.88 | N/A | 2.33 |
| 06-303 | A | N/A |  |  |  |  |  |  |  | N/A | N/A | Excl. | N/A | 1.49 | N/A | -1.00 |
| 06-303 | B | N/A |  |  |  |  |  |  |  | N/A | N/A | Excl. | N/A | 2.78 | N/A | -6.93 |
| 06-303 | D | N/A |  |  |  |  |  |  |  | N/A | N/A | Excl. | N/A | -0.87 | N/A | -0.30 |
| 06-304 | A | N/A | 77 | M | No | N/A | N/A | HP | N/A | N/A | N/A | Excl. | N/A | 4.53 | N/A | 2.64 |
| 06-304 | A | N/A |  |  |  |  |  |  |  | N/A | N/A | Excl. | N/A | 2.43 | N/A | 2.83 |
| 06-304 | B | N/A |  |  |  |  |  |  |  | N/A | N/A | Excl. | N/A | 1.60 | N/A | 1.18 |
| 06-304 | C | N/A | 77 | F | No | N/A | N/A | HP | N/A | N/A | N/A | Excl. | N/A | 1.38 | N/A | 1.56 |
| 06-304 | D | N/A |  |  |  |  |  |  |  | N/A | N/A | Excl. | N/A | 5.05 | N/A | -0.14 |
| 06-305 | E | N/A |  |  |  |  |  |  |  | N/A | N/A | Excl. | N/A | 2.82 | N/A | 4.50 |
| 06-305 | A | N/A |  |  |  |  |  |  |  | N/A | N/A | Excl. | N/A | 1.88 | N/A | 5.56 |
| 06-305 | B | N/A |  |  |  |  |  |  |  | N/A | N/A | Excl. | N/A | 2.27 | N/A | -0.75 |
| 06-305 | C | N/A | 41 | F | Yes | Yes | 30 | Other | Non diagnostic | SRIF | NonUIP | Excl. | N/A | -0.51 | N/A | 1.99 |
| 06-305 | D | N/A |  |  |  |  |  |  |  | SRIF | NonUIP | Excl. | N/A | 0.61 | N/A | -0.87 |
| 06-306 | E | N/A |  |  |  |  |  |  |  | SRIF | NonUIP | Excl. | N/A | 2.80 | N/A | 2.75 |
| 06-306 | A | N/A |  |  |  |  |  |  |  | N/A | N/A | Excl. | N/A | 0.75 | N/A | -3.18 |
| 06-306 | B | N/A |  |  |  |  |  |  |  | N/A | N/A | Excl. | N/A | 1.40 | N/A | 1.63 |
| 06-306 | C | N/A |  |  |  |  |  |  |  | N/A | N/A | Excl. | N/A | N/A | N/A | N/A |
| 06-306 | D | N/A |  |  |  |  |  |  |  | N/A | N/A | Excl. | N/A | N/A | N/A | N/A |
| 06-306 | E | N/A |  |  |  |  |  |  |  | N/A | N/A | Excl. | N/A | -0.85 | N/A | 0.34 |
| 06-312 | A | N/A | 70 | F | Yes | No | missing | missing | N/A | N/A | N/A | Excl. | N/A | 2.05 | N/A | 2.55 |
| 06-312 | B | N/A |  |  |  |  |  |  |  | N/A | N/A | Excl. | N/A | 1.60 | N/A | 0.45 |
| 06-312 | C | N/A |  |  |  |  |  |  |  | N/A | N/A | Excl. | N/A | 2.47 | N/A | 3.41 |
| 06-312 | D | N/A |  |  |  |  |  |  |  | N/A | N/A | Excl. | N/A | N/A | N/A | N/A |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 06-312 | E | N/A | | | | | | | | N/A | N/A | Excl. | N/A | 0.98 | N/A | -1.17 |
| 06-316 | A | Upper | | | | | | | | N/A | Non UIP | Excl. | N/A | N/A | N/A | N/A |
| 06-316 | B | Upper | 62 | F | Yes | Yes | 60 | RB | Non diagnostic | N/A | Non UIP | Excl. | N/A | N/A | N/A | N/A |
| 08-101 | A | Upper | 60 | M | Yes | No | 36 | Eosinophilic pn. | DAD | SRIF | Non UIP | Excl. | N/A | N/A | N/A | N/A |
| 08-102 | B | Upper | 76 | F | Yes | No | 45 | Eosinophilic pn. | Cellular NSIP | SRIF | NonUIP | Excl. | N/A | N/A | N/A | N/A |
| 08-103 | C | Lower | 78 | M | Yes | No | 60 | NSIP | Classic UIP | RB | NonUIP | Excl. | N/A | N/A | N/A | 3.89 |
| 08-104 | A | N/A | 71 | F | Yes | No | 48 | UIP | Classic UIP | Cellular NSIP | UIP | Excl. | N/A | 3.78 | N/A | -0.69 |
| 08-104 | B | N/A | | | | | | | | Difficult UIP | UIP | Excl. | N/A | 2.01 | N/A | N/A |
| 08-106 | E | Lower | 58 | M | No | N/A | N/A | NSIP | UIP | N/A | UIP | Excl. | N/A | N/A | N/A | -1.39 |
| 08-108 | C | N/A | 71 | M | Yes | No | 74 | Eosinophilic pn. | Difficult UIP | N/A | UIP | Excl. | N/A | -0.99 | N/A | 0.24 |
| 08-108 | D | N/A | | | | | | | | N/A | UIP | Excl. | N/A | 1.26 | N/A | 2.81 |
| 08-108 | E | N/A | | | | | | | | Favor UIP | UIP | Excl. | N/A | 2.22 | N/A | N/A |
| 08-109 | B | Upper | 74 | F | Yes | No | 46 | Sarcoidosis | Difficult UIP | N/A | UIP | Excl. | N/A | N/A | N/A | 1.55 |
| 08-110 | A | N/A | 72 | M | Yes | No | 52 | UIP | Classic UIP | UIP | UIP | Excl. | N/A | 2.65 | N/A | -0.23 |
| 08-110 | B | N/A | 48 | F | Yes | Yes | 31 | HP | Classic UIP | N/A | UIP | Excl. | N/A | 1.70 | N/A | N/A |
| 08-112 | D | Lower | 61 | M | Yes | Yes | 46 | HP | Difficult UIP | N/A | UIP | Excl. | N/A | N/A | N/A | -14.59 |
| 08-114 | A | N/A | | | | | | | | N/A | N/A | Excl. | N/A | -10.23 | N/A | 0.71 |
| 08-117 | B | N/A | 73 | M | Yes | No | 51 | Other | CIF, NOC | N/A | N/A | Excl. | N/A | 1.62 | N/A | 6.32 |
| 08-117 | D | Lower | 64 | F | Yes | No | Unk. | Definite UIP | UIP | UIP | UIP | Excl. | N/A | 5.57 | N/A | 2.34 |
| 08-121 | A | N/A | | | | | | | | N/A | UIP | Excl. | N/A | 3.25 | N/A | N/A |
| 08-123 | B | N/A | 69 | F | Yes | No | 2 | HP | HP | N/A | N/A | Excl. | N/A | N/A | N/A | 3.48 |
| 08-124 | C | Lower | 68 | F | Yes | No | 10 | HP | UIP | Favor UIP | UIP | Excl. | N/A | 2.50 | N/A | 1.32 |
| 08-126 | A | N/A | | | | | | | | N/A | N/A | Excl. | N/A | 2.90 | N/A | N/A |
| 08-126 | B | N/A | 74 | F | No | N/A | N/A | missing | N/A | N/A | N/A | Excl. | N/A | N/A | N/A | -0.12 |
| 08-126 | C | N/A | | | | | | | | N/A | N/A | Excl. | N/A | 1.63 | N/A | 2.16 |
| 08-126 | D | N/A | | | | | | | | N/A | N/A | Excl. | N/A | 2.62 | N/A | 3.01 |
| 08-126 | E | N/A | | | | | | | | N/A | N/A | Excl. | N/A | 2.39 | N/A | 2.30 |
| 08-127 | A | N/A | | | | | | | | N/A | N/A | Excl. | N/A | 1.88 | N/A | 1.63 |
| 08-127 | B | N/A | 71 | M | Yes | No | 25 | DIP | UIP | N/A | UIP | Excl. | N/A | 0.28 | N/A | 1.06 |
| 08-127 | D | Lower | 46 | M | Yes | Yes | 51 | RB | Non diagnostic | N/A | N/A | Excl. | N/A | 0.74 | N/A | -5.85 |
| 08-201 | D | N/A | | | | | | | | N/A | N/A | Excl. | N/A | -3.26 | N/A | -0.89 |
| 08-201 | E | N/A | | | | | | | | N/A | N/A | Excl. | N/A | 1.15 | N/A | 3.36 |
| 08-203 | C | N/A | 24 | F | Yes | No | 4 | Other | Eosinophilic pn. | N/A | N/A | Excl. | N/A | 3.13 | N/A | -5.88 |
| 08-203 | D | N/A | | | | | | | | N/A | N/A | Excl. | N/A | -2.65 | N/A | 0.27 |
| 08-203 | E | N/A | | | | | | | | N/A | N/A | Excl. | N/A | 3.94 | N/A | 2.20 |
| 08-204 | A | Upper | | | | | | | | N/A | NonUIP | Excl. | N/A | 3.25 | N/A | N/A |
| 08-204 | B | Upper | 80 | M | Yes | No | 80 | Other | Lung cancer | Lung cancer | NonUIP | Excl. | N/A | N/A | N/A | N/A |
| 08-204 | C | N/A | | | | | | | | Lung cancer | N/A | Excl. | N/A | N/A | N/A | 0.50 |
| 08-204 | D | N/A | | | | | | | | N/A | N/A | Excl. | N/A | 1.79 | N/A | 1.22 |
| 08-204 | E | N/A | | | | | | | | N/A | N/A | Excl. | N/A | -0.63 | N/A | 4.57 |
| 08-205 | A | Upper | | | | | | | | OP | NonUIP | Excl. | N/A | 4.20 | N/A | N/A |
| 08-205 | B | Upper | | | | | | | | OP | NonUIP | Excl. | N/A | N/A | N/A | N/A |
| 08-205 | C | N/A | 58 | M | Yes | No | 9 | HP | OP | N/A | N/A | Excl. | N/A | N/A | N/A | 0.50 |
| 08-205 | D | N/A | | | | | | | | N/A | N/A | Excl. | N/A | 2.98 | N/A | -6.00 |
| 08-205 | E | N/A | | | | | | | | N/A | N/A | Excl. | N/A | -3.14 | N/A | -2.48 |
| 08-206 | A | N/A | | | | | | | | N/A | N/A | Excl. | N/A | -0.06 | N/A | -3.60 |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 08-206 | B | N/A | 53 | M | Yes | Yes | Unk. | Other | Pneumocystis pn. | N/A | N/A | Excl. | N/A | 2.93 | N/A | −0.46 |
| 08-206 | C | Lower | 56 | F | Yes | No | 17 | HP | Bronchiolitis | Pneumocystis pn. | NonUIP | Excl. | N/A | N/A | N/A | N/A |
| 10-101 | A | Upper | 56 | M | No | N/A | N/A | UIP | Classic UIP | Favor bronchiolitis | NonUIP | Excl. | N/A | N/A | N/A | N/A |
| 11-101 | B | Lower | 65 | F | Yes | No | 30 | UIP | UIP | Classic UIP | UIP | Excl. | N/A | N/A | N/A | N/A |
| 11-102 | B | Upper | 69 | F | Yes | No | 15 | UIP | Classic UIP | UIP | UIP | Excl. | N/A | N/A | N/A | N/A |
| 11-102 | D | Lower | 67 | M | Yes | No | 80 | Other | Difficult UIP | Classic UIP | UIP | Excl. | N/A | N/A | N/A | N/A |
| 11-103 | D | Upper | 61 | F | Yes | No | 12 | UIP | Classic UIP | Difficult UIP | UIP | Excl. | N/A | N/A | N/A | N/A |
| 13-101 | B | Lower | 75 | F | No | N/A | N/A | HP | Classic UIP | UIP | UIP | Excl. | N/A | N/A | N/A | N/A |
| 13-101 | D | Upper | 66 | F | No | No | N/A | NSIP | Difficult UIP | N/A | N/A | Excl. | N/A | −0.87 | N/A | −1.54 |
| 13-102 | E | N/A | | | | | | | | Classic UIP | UIP | Excl. | N/A | −4.49 | N/A | −5.06 |
| 13-103 | B | Lower | 71 | M | Yes | No | 106 | NSIP | OP | N/A | N/A | Excl. | N/A | 3.82 | N/A | 2.87 |
| 13-103 | A | N/A | | | | | | | | N/A | N/A | Excl. | N/A | 4.09 | N/A | 2.75 |
| 13-104 | B | N/A | 52 | M | No | N/A | N/A | NSIP | Difficult UIP | Difficult UIP | UIP | Excl. | N/A | −0.39 | N/A | 1.38 |
| 13-104 | D | Lower | 68 | M | No | N/A | N/A | HP | Classic UIP | UIP | UIP | Excl. | N/A | N/A | N/A | N/A |
| 13-109 | C | N/A | 73 | M | Yes | No | 45 | Other | Bronchiolitis | Bronchiolitis | NonUIP | Excl. | N/A | N/A | N/A | N/A |
| 13-109 | E | Lower | | | | | | | | Bronchiolitis | NonUIP | Excl. | N/A | N/A | N/A | N/A |
| 13-110 | E | Lower | | | | | | | | N/A | N/A | Excl. | N/A | 3.00 | N/A | −0.97 |
| 13-112 | A | Upper | 49 | M | Yes | No | 30 | Sarcoidosis | Sarcoidosis | N/A | N/A | Excl. | N/A | −2.81 | N/A | −6.40 |
| 13-113 | C | N/A | 80 | M | Yes | No | Unk. | HP | UIP | N/A | N/A | Excl. | N/A | 3.36 | N/A | 2.59 |
| 13-113 | D | N/A | | | | | | | | UIP | UIP | Excl. | N/A | −0.25 | N/A | 0.75 |
| 13-201 | D | N/A | 45 | F | No | N/A | N/A | HP | N/A | N/A | N/A | Excl. | N/A | 4.35 | N/A | 3.25 |
| 13-201 | E | N/A | | | | | | | | N/A | N/A | Excl. | N/A | −1.86 | N/A | −2.89 |
| 14-101 | A | Upper | 72 | F | Yes | No | 2.5 | UIP | N/A | N/A | N/A | Excl. | N/A | 1.09 | N/A | 0.32 |
| 14-102 | C | N/A | 63 | F | No | N/A | N/A | NSIP | Favor UIP | N/A | N/A | Excl. | N/A | −0.37 | N/A | −0.99 |
| 14-102 | D | N/A | 52 | M | No | N/A | N/A | HP | Favor UIP | Favor UIP | UIP | Excl. | N/A | −0.77 | N/A | −3.90 |
| 14-102 | E | N/A | | | | | | | | N/A | N/A | Excl. | N/A | 3.87 | N/A | 0.48 |
| 15-301 | A | Middle | 58 | M | Yes | No | Unk. | HP | CIF, NOC | Favor UIP | UIP | Excl. | N/A | 4.04 | N/A | 2.01 |
| 15-301 | D | N/A | | | | | | | | N/A | N/A | Excl. | N/A | 0.65 | N/A | 0.95 |
| 15-303 | E | N/A | | | | | | | | N/A | N/A | Excl. | N/A | 4.36 | N/A | 2.34 |
| 15-304 | 8 | Lower | | | | | | | | Favor UIP | UIP | Excl. | N/A | N/A | N/A | N/A |
| 15-305 | A | N/A | | | | | | | | N/A | N/A | Excl. | N/A | 2.09 | N/A | 1.51 |
| 15-305 | B | N/A | | | | | | | | N/A | N/A | Excl. | N/A | 2.46 | N/A | 1.65 |
| 15-306 | C | Lower | 78 | F | No | N/A | N/A | Other | UIP | Favor UIP | UIP | Excl. | N/A | N/A | N/A | N/A |
| 15-306 | D | Lower | | | | | | | | Favor UIP | UIP | Excl. | N/A | N/A | N/A | N/A |
| 15-306 | E | Lower | | | | | | | | Favor UIP | UIP | Excl. | N/A | N/A | N/A | N/A |
| 18-101 | A | N/A | 67 | F | No | N/A | N/A | Sarcoidosis | Sarcoidosis | N/A | N/A | Excl. | N/A | −0.12 | N/A | −1.70 |
| 18-101 | B | N/A | | | | | | | | N/A | N/A | Excl. | N/A | 4.01 | N/A | 4.54 |

TABLE 14-continued

113 Patients and their Associated Samples Evaluated in this Study
Table EI: 113 Patients and their associated samples evaluated in this study.

| Patient | TBB | Lobe | Age | Gender | Smoking history | Current smoker | Pack years | Central radiology Dx | Patient pathology Dx | Sample path Dx | UIP label | Cohort | 53 pt LOPO score | 53 pt Test score | 84 pt LOPO score | 84 pt Test score |
|---|---|---|---|---|---|---|---|---|---|---|---|---|---|---|---|---|
| 18-101 | D | Lower | 83 | M | Yes | No | 40 | HP | Classic UIP | Sarcoidosis | NonUIP | Excl. | N/A | N/A | N/A | N/A |
| 18-104 | A | Lower | | | | | | | | Classic UIP | UIP | Excl. | N/A | N/A | N/A | N/A |
| 18-104 | D | Lower | | | | | | | | Classic UIP | UIP | Excl. | N/A | N/A | N/A | N/A |
| 18-106 | D | N/A | 75 | M | Yes | No | 20 | RB | N/A | N/A | N/A | Excl. | N/A | 0.08 | N/A | 0.65 |
| 18-106 | E | N/A | | | | | | | | N/A | N/A | Excl. | N/A | 2.72 | N/A | 1.66 |
| 18-108 | C | N/A | 70 | M | No | N/A | N/A | Other | N/A | N/A | N/A | Excl. | N/A | -1.04 | N/A | -4.09 |
| 18-108 | D | N/A | | | | | | | | N/A | N/A | Excl. | N/A | 1.04 | N/A | 0.79 |
| 18-108 | E | N/A | | | | | | | | N/A | N/A | Excl. | N/A | -2.38 | N/A | -4.27 |
| 18-109 | C | Lower | 55 | F | Yes | Yes | 21.5 | HP | RB | RB | NonUIP | Excl. | N/A | N/A | N/A | N/A |
| 18-109 | D | Lower | | | | | | | | RB | NonUIP | Excl. | N/A | N/A | N/A | N/A |
| 18-109 | E | Lower | | | | | | | | RB | NonUIP | Excl. | N/A | N/A | N/A | N/A |
| 18-110 | C | Lower | 61 | M | Yes | Yes | 30 | Bronchiolitis | Emphysema | Emphysema | NonUIP | Excl. | N/A | N/A | N/A | N/A |
| 18-110 | D | Lower | | | | | | | | Emphysema | NonUIP | Excl. | N/A | N/A | N/A | N/A |
| 18-110 | E | Lower | | | | | | | | Emphysema | NonUIP | Excl. | N/A | N/A | N/A | N/A |
| 18-113 | C | N/A | 39 | F | No | N/A | N/A | NSIP | N/A | N/A | N/A | Excl. | N/A | 1.66 | N/A | -0.98 |
| 18-115 | C | Lower | 50 | F | Yes | missing | 74 | HP | Emphysema | Emphysema | NonUIP | Excl. | N/A | N/A | N/A | N/A |
| 18-115 | D | Lower | | | | | | | | Emphysema | NonUIP | Excl. | N/A | N/A | N/A | N/A |
| 18-115 | E | Lower | | | | | | | | Emphysema | NonUIP | Excl. | N/A | N/A | N/A | N/A |
| 18-116 | C | N/A | 63 | M | No | N/A | N/A | Sarcoidosis | N/A | N/A | N/A | Excl. | N/A | -4.05 | N/A | -5.59 |
| 18-116 | D | N/A | | | | | | | | N/A | N/A | Excl. | N/A | 6.28 | N/A | 5.43 |
| 18-117 | D | N/A | 71 | F | No | N/A | N/A | Other | N/A | N/A | N/A | Excl. | N/A | -2.00 | N/A | -5.47 |
| 18-117 | E | N/A | | | | | | | | N/A | N/A | Excl. | N/A | 2.44 | N/A | 0.64 |
| 19-306 | A | N/A | 64 | F | No | N/A | N/A | HP | Favor UIP | N/A | N/A | Excl. | N/A | 1.04 | N/A | 0.79 |
| 19-306 | B | N/A | | | | | | | | N/A | N/A | Excl. | N/A | -0.85 | N/A | -1.76 |
| 20-303 | D | N/A | 73 | F | Yes | No | 1 | missing | N/A | N/A | N/A | Excl. | N/A | 1.41 | N/A | 1.02 |
| 20-303 | E | N/A | | | | | | | | N/A | N/A | Excl. | N/A | 4.28 | N/A | 2.39 |
| 28-301 | A | Upper | 58 | M | Yes | No | 25 | Eosinophilic pn. | Non diagnostic | Hemosiderosis | N/A | N/A | N/A | -0.11 | N/A | -2.97 |
| 28-301 | B | Upper | | | | | | | | Hemosiderosis | N/A | N/A | N/A | N/A | N/A | N/A |
| 32-301 | A | N/A | 18 | F | No | N/A | N/A | DIP | Favor NSIP | N/A | N/A | Excl. | N/A | 3.37 | N/A | 3.96 |
| 32-301 | B | N/A | | | | | | | | N/A | N/A | Excl. | N/A | 3.15 | N/A | 0.90 |
| 32-804 | C | N/A | 58 | F | No | N/A | N/A | HP | Sarcoidosis | N/A | N/A | Excl. | N/A | -0.72 | N/A | -0.23 |
| 32-804 | D | N/A | | | | | | | | N/A | N/A | Excl. | N/A | 0.79 | N/A | -0.46 |
| 32-804 | E | N/A | | | | | | | | N/A | N/A | Excl. | N/A | 0.56 | N/A | -0.40 |
| 32-811 | A | N/A | 67 | M | No | N/A | N/A | Definite UIP | UIP | N/A | N/A | Excl. | N/A | 2.14 | N/A | 1.91 |
| 32-811 | B | N/A | | | | | | | | N/A | N/A | Excl. | N/A | 0.94 | N/A | 1.40 |
| 32-813 | C | N/A | 48 | F | Yes | Yes | 15 | Sarcoidosis | RB | N/A | N/A | Excl. | N/A | -0.34 | N/A | -0.20 |
| 32-813 | D | N/A | | | | | | | | N/A | N/A | Excl. | N/A | -4.23 | N/A | -6.70 |
| 32-313 | E | N/A | | | | | | | | N/A | N/A | Excl. | N/A | -0.97 | N/A | 0.00 |
| 36-101 | C | N/A | 53 | F | No | N/A | N/A | HP | UIP | N/A | N/A | Excl. | N/A | 1.65 | N/A | -0.99 |
| 36-102 | D | Lower | 88 | M | No | N/A | N/A | Other | Classic UIP | Difficult UIP | UIP | Excl. | N/A | N/A | N/A | N/A |

N/A: Data or information not available
Excl.: Excluded from training and test sets
pn.: pneumonia
Pulm.: pulmonary

TABLE 15

169 Ensembl Gene IDs used in classification (53-patient classifier).

| gene_id | gene_biotype | gene_id | gene_biotype | gene_id | gene_biotype |
|---|---|---|---|---|---|
| ENSG00000189339 | prot_coding | ENSG00000105991 | prot_coding | ENSG00000248713 | prot_coding |
| ENSG00000116285 | prot_coding | ENSG00000136275 | prot_coding | ENSG00000138795 | prot_coding |
| ENSG00000219481 | prot_coding | ENSG00000146707 | prot_coding | ENSG00000172399 | prot_coding |
| ENSG00000204219 | prot_coding | ENSG00000221305 | miRNA | ENSG00000109471 | prot_coding |
| ENSG00000142661 | prot_coding | ENSG00000012232 | prot_coding | ENSG00000151005 | prot_coding |
| ENSG00000157131 | prot_coding | ENSG00000104381 | prot_coding | ENSG00000145736 | prot_coding |
| ENSG00000116761 | prot_coding | ENSG00000204844 | lincRNA | ENSG00000168938 | prot_coding |
| ENSG00000134245 | prot_coding | ENSG00000136928 | prot_coding | ENSG00000169194 | prot_coding |
| ENSG00000122497 | prot_coding | ENSG00000136881 | prot_coding | ENSG00000113621 | prot_coding |
| ENSG00000159164 | prot_coding | ENSG00000136883 | prot_coding | ENSG00000253910 | prot_coding |
| ENSG00000232671 | prot_coding | ENSG00000148200 | prot_coding | ENSG000C0261934 | prot_coding |
| ENSG00000143367 | prot_coding | ENSG00000148339 | prot_coding | ENSG00000145888 | prot_coding |
| ENSG00000143320 | prot_coding | ENSG00000176919 | prot_coding | ENSG00000055163 | prot_coding |
| ENSG00000143195 | prot_coding | ENSG00000107929 | prot_coding | ENSG00000184845 | prot_coding |
| ENSG00000007908 | prot_coding | ENSG00000207937 | miRNA | ENSG00000234284 | prot_coding |
| ENSG00000171806 | prot_coding | ENSG00000183234 | prot_coding | ENSG00000198518 | prot_coding |
| ENSG00000007933 | prot_coding | ENSG00000148S41 | prot_coding | ENSG00000261839 | lincRNA |
| ENSG00000162782 | prot_coding | ENSG00000204020 | prot_coding | ENSG00000235109 | prot_coding |
| ENSG00000177489 | prot_coding | ENSG00000148702 | prot_coding | ENSG000C0204701 | prot_coding |
| ENSG00000138075 | prot_coding | ENSG00000149043 | prot_coding | ENSG00000204632 | prot_coding |
| ENSG00000135625 | prot_coding | ENSG00000130598 | prot_coding | ENSG00000204110 | lincRNA |
| ENSG00000115317 | prot_coding | ENSG00000171987 | prot_coding | ENSG00000124641 | prot_coding |
| ENSG00000183281 | prot_coding | ENSG00000166796 | prot_coding | ENSG00000124702 | prot_coding |
| ENSG00000144057 | prot_coding | ENSG00000183908 | prot_coding | ENSG00000112818 | prot_coding |
| ENSG00000257207 | prot_coding | ENSG00000166004 | prot_coding | ENSG00000174156 | prot_coding |
| ENSG00000144320 | prot_coding | ENSG00000183560 | prot_coding | ENSG00000118402 | prot_coding |
| ENSG00000188282 | prot_coding | ENSG00000149239 | prot_coding | ENSG00000112299 | prot_coding |
| ENSG00000074582 | prot_coding | ENSG00000254842 | lincRNA | ENSG00000048052 | prot_coding |
| ENSG00000054356 | prot_coding | ENSG00000010379 | prot_coding | ENSG00000129204 | prot_coding |
| ENSG00000114923 | prot_coding | ENSG00000111321 | prot_coding | ENSG00000129221 | prot_coding |
| ENSG00000115009 | prot_coding | ENSG00000212126 | prot_coding | ENSG00000108551 | prot_coding |
| ENSG00000181798 | Proces'd_transc | ENSG00000110900 | prot_coding | ENSG00000108342 | prot_coding |
| ENSG00000144712 | prot_coding | ENSG00000139211 | prot_coding | ENSG00000131095 | prot_coding |
| ENSG00000168329 | prot_coding | ENSG00000187166 | prot_coding | ENSG00000167105 | prot_coding |
| ENSG00000168036 | prot_coding | ENSG00000086159 | prot_coding | ENSG00000258890 | prot_coding |
| ENSG00000179152 | prot_coding | ENSG00000170374 | prot_coding | ENSG00000141562 | prot_coding |
| ENSG00000256097 | prot_coding | ENSG00000221479 | miRNA | ENSG00000128791 | prot_coding |
| ENSG00000227124 | prot_coding | ENSG00000139352 | prot_coding | ENSG00000170558 | prot_coding |
| ENSG00000184500 | prot_coding | ENSG00000122966 | prot_coding | ENSG00000075643 | prot_coding |
| ENSG00000206531 | prot_coding | ENSG00000125255 | prot_coding | ENSG00000166573 | prot_coding |
| ENSG00000163884 | prot_coding | ENSG00000134905 | prot_coding | ENSG00000256463 | prot_coding |
| ENSG00000180697 | prot_coding | ENSG00000187630 | prot_coding | ENSG00000125827 | prot_coding |
| ENSG00000198685 | prot_coding | ENSG00000257365 | prot_coding | ENSG00000182931 | prot_coding |
| ENSG00000034533 | prot_coding | ENSG00000133997 | prot_coding | ENSG00000198768 | prot_coding |
| ENSG00000172667 | prot_coding | ENSG00000119725 | prot_coding | ENSG00000101188 | prot_coding |
| ENSG00000078070 | prot_coding | ENSG00000198208 | prot_coding | ENSG00000131142 | prot_coding |
| ENSG00000159674 | prot_coding | ENSG00000258945 | prot_coding | ENSG00000086544 | prot_coding |
| ENSG00000174123 | prot_coding | ENSG00000169918 | prot_coding | ENSG00000188293 | prot_coding |
| ENSG00000109158 | prot_coding | ENSG00000198838 | prot_coding | ENSG00000167748 | prot_coding |
| ENSG00000145248 | prot_coding | ENSG00000140323 | prot_coding | ENSG00000189013 | prot_coding |
| ENSG00000035720 | prot_coding | ENSG00000167014 | prot_coding | ENSG00000022556 | prot_coding |
| ENSG00000081041 | prot_coding | ENSG00000137875 | prot_coding | ENSG00000273311 | sense_intronic |
| ENSG00000145284 | prot_coding | ENSG00000067141 | prot_coding | ENSG00000183066 | prot_coding |
| ENSG00000170509 | prot_coding | ENSG00000095917 | prot_coding | ENSG00000189306 | prot_coding |
| ENSG00000170502 | prot_coding | ENSG00000155714 | prot_coding | ENSG00000142192 | prot_coding |
| ENSG00000163644 | prot_coding | ENSG00000166848 | prot_coding | | |
| ENSG00000163110 | prot_coding | ENSG00000166509 | prot_coding | | |

Prot_coding = Protein Coding;
Proces'd_transc = Processed Transcript

TABLE 16

44 bronchiolar and alveolar cell literature markers used in this study

| Gene | Gene name | Cell types | Evidence | Ensembl Gene ID |
|---|---|---|---|---|
| SFTPC | Surfactant protein C | Epithelial precursor, alveolar type II | IHC[2], qPCR[2], in-situ hyb[4], timecourse[2] | ENSG00000168484 |
| PDPN | Podoplanin | Epithelial precursor, alveolar type I | IHC[4] | ENSG00000162493 |
| CGRP | CGRP receptor component | Epithelial precursor | IHC[1,2] | ENSG00000241258 |
| CD34 | CD34 molecule | Epithelial precursor | IHC[3] | ENSG00000174059 |
| ATXN1 | Ataxin 1 | Epithelial precursor | IHC[3] | ENSG00000124788 |
| SOX11 | SRY-box 11 | Epithelial precursor | RNAseq[4] | ENSG00000176887 |

TABLE 16-continued 44 bronchiolar and alveolar cell literature markers used in this study

| Gene | Gene name | Cell types | Evidence | Ensembl Gene ID |
| --- | --- | --- | --- | --- |
| TUBA1A | Tubulin alpha 1a | Epithelial precursor | RNAseq[4] | ENSG00000167552 |
| FOXJ1 | Forkhead box J1 | Ciliated bronchiolar epithelial cells | IHC[2,4] | ENSG00000129654 |
| AQP4 | Aquaporin 4 | Ciliated bronchiolar epithelial cells | IHC[5] | ENSG00000171885 |
| ITGB4 | Integrin subunit beta 4 | Ciliated bronchiolar epithelial cells | qPCR[4] | ENSG00000132470 |
| TOP2A | Topoisomerase DNAII alpha | Ciliated bronchiolar epithelial cells | qPCR[4] | ENSG00000131747 |
| SCGB1A1 | Secretoglobin family 1A member 1 | Ciliated bronchiolar epithelial cells, Clara cells | injury timecourse[2], IHC[1,2,4] | ENSG00000149021 |
| CLDN10 | Claudin 10 | Bronchiolar Clara cells | injury timecourse[2], IHC[2] | ENSG00000134873 |
| KRT15 | Keratin 15 | Bronchiolar Clara cells | IHC[4] | ENSG00000171346 |
| AQP3 | Aquaporin 3 | Bronchiolar Clara cells | in-situ EM[5] | ENSG00000165272 |
| CYP2F2P | Cytochrome P450 family 2 subfamily F member 2, pseudogene | Bronchiolar Clara cells | injury timecourse[2] | ENSG00000237118 |
| FMO3 | Flavin containing monooxygenase 3 | Bronchiolar Clara cells | injury timecourse[2] | ENSG00000007933 |
| PON1 | Paraoxonase 1 | Bronchiolar Clara cells | injury timecourse[2] | ENSG00000005421 |
| AOX3P | Aldehyde oxidase 3, pseudogene | Bronchiolar Clara cells | injury timecourse[2] | ENSG00000244301 |
| SCGB3A2 | Secretoglobin family 3A member 2 | Bronchiolar Clara cells | microarray[2] | ENSG00000164265 |
| CES1 | Carboxylesterase 1 | Bronchiolar Clara cells | microarray[2] | ENSG00000198848 |
| GABRP | Gamma-aminobutyric acid type A receptor pi subunit | Bronchiolar Clara cells | microarray[2] | ENSG00000094755 |
| SFTPA1 | Surfactant protein A1 | Alveolar type I and II | IHC[1] | ENSG00000122852 |
| HOPX | HOP homeobox | Alveolar type I | Tg-IF[4] | ENSG00000171476 |
| AGER | Advanced glycosylation end product-specific receptor | Alveolar type I | IHC[4] | ENSG00000204305 |
| AQP5 | Aquaporin 5 | Alveolar type I | qPCR[4], RNAseq[4], IHC[5] | ENSG00000161798 |
| VEGFA | Vascular endothelial growth factor A | Alveolar type I | qPCR[4], RNAseq[4] | ENSG00000112715 |
| HES1 | Hes family bHLH transcription factor 1 | Alveolar type I | RNAseq[4] | ENSG00000114315 |
| SEMA3A | Semaphorin 3A | Alveolar type I | RNAseq[4] | ENSG00000075213 |
| TGFB1 | Transforming growth factor beta 1 | Alveolar type I | RNAseq[4] | ENSG00000105329 |
| GPRC5A | G protein-coupled receptor class C group 5 member A | Alveolar type I | RNAseq[4] | ENSG00000013588 |
| EGFL6 | EGF like domain multiple 6 | Alveolar type II | RNAseq[4], in-situ hyb[4] | ENSG00000198759 |
| ABCA3 | ATP binding cassette subfamily A member 3 | Alveolar type II | qPCR[4], RNAseq[4] | ENSG00000167972 |
| MUC1 | Mucin 1, cell surface associated | Alveolar type II | qPCR[4], RNAseq[4] | ENSG00000185499 |
| LYZ | Lysozyme | Alveolar type II | qPCR[4], RNAseq[4] | ENSG00000090382 |
| SFTPB | Surfactant protein B | Alveolar type II | qPCR[4], RNAseq[4] | ENSG00000168878 |
| CFTR | Cystic fibrosis transmembrane conductance regulator | Alveolar type II | qPCR[4], RNAseq[4] | ENSG00000001626 |
| CEBPA | CCAAT/enhancer binding protein alpha | Alveolar type II | qPCR[4], RNAseq[4] | ENSG00000245848 |
| SFTPD | Surfactant protein D | Alveolar type II | qPCR[4], RNAseq[4] | ENSG00000133661 |
| ID2 | Inhibitor of DNA binding 2, HLH protein | Alveolar type II | qPCR[4], RNAseq[4] | ENSG00000115738 |
| SOX9 | SRY-box 9 | Alveolar type II | RNAseq[4] | ENSG00000125398 |
| CITED2 | Cbp/p300 interacting transactivator with Glu/Asp rich carboxy-terminal domain 2 | Alveolar type II | RNAseq[4] | ENSG00000164442 |
| CMTM8 | CKLF like MARVEL transmembrane domain containing 8 | Alveolar type II | RNAseq[4] | ENSG00000170293 |
| FGFR2 | Fibroblast growth factor receptor 2 | Alveolar type II | RNAseq[4] | ENSG00000066468 |

[1] Wuenschell 1996;
[2] Zemke 2009;
[3] Kim 2005;
[4] Treutlein 2014;
[5] Nielsen 1997

What is claimed is:

1. A method for identifying whether a subject is positive for usual interstitial pneumonia (UIP) or non-usual interstitial pneumonia (non-UIP), the method comprising:
   (a) pooling lung tissue samples from said subject suspected of having UIP to produce a pooled lung tissue sample;
   (b) assaying said pooled lung tissue sample for a level of expression of one or more markers associated with said UIP or said non-UIP, wherein said one or more markers associated with said UIP or said non-UIP comprise a gene selected from MPO, GGNBP2, SELE, FMO3, SLC6A13, EXTL3, NLRP2, BTN3A1, ABCF2, TLL1, HDAC9, CBLN4, CHRDL2, SNRNP40, MYO3B, SREBF1, GSDMB, MCCC1, CEACAM1, CXCL2, IL12RB2, ITGB5, ZNF671, ITPKC, RCOR1, TGMI, HSD17B7P2, DDTL, FAM118A, C14orf105, ADNP2, OLFM4, HAS3, SLC7A5, GYS1, FSD1, PLEKHA4, TMEM59L, RUNDC3B, LMBR1, VIPR2, CCL24, LARP4B, UBTF, RASD1, ODAM, CCND1, TSPAN11, SYT10, PRMT8, LTBR, CDK2AP1, GLP1R, VNN1, PCDHB2, LRRC31, SLC4A3, STAT1, IL18RAP, ERRFIL, CTH, ALDH6A1, ZNF410, CD274, EGR1, CHRNA2, BCL2L14, ZNF211, NBPF14, EDN3, KLHDC3, SCGB1D2, SLC10A2, ZFP36, GNAZ, TWSG1, C15orf57, LDLR, KLHDC7B, TNNI2, GFAP, CCL25, ENOSF1, LINC00470, PDE6A, MTUS2, NTS, ARNTL, ADAM-DEC1, WNT2B, TRAFD1, PPP1R1A, EGR4, BAAT, KIF12, GABBR2, RABEPK, TUBB2B, MGARP, SULF1, POU2F3, SLC44AS, DUSP5, PLA2G12B, DUOXA2, DUOX2, DISP2, ARRDC4, CYP1A1, CYP1A2, FTO, NPEPPS, SIK1, MYOM3, XCL2, ILDR2, CRABP2, ABL2, TUFT1, SETDB1, KCNN3, CSRNP1, SLC10A4, SCD5, DDIT4L, GTF2H2, FAM13C, ADD3, HABP2, SYT8, ZC3H12C, SLC7A11, ANO4, CLEC4F, PLEKHG4B, CERS3, GBP5, TDRD9, SLC6A1, DGKI, TSPAN33, CBR3, SPON2, CCDC155, IL23R, SMC6, PDLIM5, GABRG1, EIF4E3, ATXN7, PPM1K, CXCL5, SLC6A20, KLF15, GPR8S, DEFA4, IFI27L1, NELL1, PTER, GREM1, KLK1, HRASLS5, CTNNB1, BATF2, TAP1, ZNF30, PPIC, CXCL11, NIPA1, KRT86, HSD17B13, GPR27, PYGO1, PDE7B, ZIK1, ANO5, CALB2, ISG20, CXCR6, ZMAT3, TDRD12, EIF1, MARCH3, TTLL11, MSRA, NUPR1, CLVS1, FBX039, ZNF4S4, and ZNFS43;

(c) processing said level of expression to generate a classification of said pooled lung tissue sample as being positive for said UIP or said non-UIP; and (d) outputting said classification of said pooled lung tissue sample as being positive for said UIP or non-UIP.

2. The method of claim 1, wherein said classification is generated at an accuracy of at least about 90%.

3. The method of claim 1, wherein said processing is performed using a trained algorithm.

4. The method of claim 3, wherein said trained algorithm is trained with a training set comprising a plurality of training samples, and wherein said plurality of training samples is independent of said pooled lung tissue sample.

5. The method of claim 3, wherein said trained algorithm is trained to use smoking status as a covariate.

6. The method of claim 3, wherein said trained algorithm is trained using one or more features selected from the group consisting of gene expression variants, fusions, mutations, loss of heterozygosity (LOH), and biological pathway effect.

7. The method of claim 1, wherein said processing comprises applying a weighted algorithm to said level of expression.

8. The method of claim 7, wherein said assaying comprises detection of an additional level of expression of one or more markers that are associated with smoker status bias, and wherein said weighted algorithm weighs said additional level of expression differently than a level of expression associated with one or more markers that are not susceptible to smoker status bias.

9. The method of claim 7, wherein assaying comprises detection of an additional level of expression of one or more markers that are associated with smoker status bias and wherein said weighted algorithm excludes said additional level of expression.

10. The method of claim 1, wherein said pooled lung tissue sample is a pooled epithelium sample.

11. The method of claim 1, wherein said one or more markers is a plurality of markers associated with said UIP or said non-UIP.

12. The method of claim 1, wherein said classification is generated at a specificity of at least about 90%.

13. The method of claim 1, wherein said classification is generated at a sensitivity of at least about 70%.

14. The method of claim 1, wherein said non-UIP is selected from the group consisting of hypersensitivity pneumonitis (HP), nonspecific interstitial pneumonia (NSIP), pulmonary sarcoidosis, respiratory bronchiolitis (RB), bronchiolitis, and organizing pneumonia (OP).

15. The method of claim 1, wherein said one or more markers are one or more genes.

16. The method of claim 1, further comprising determining an additional expression level of one or more markers associated with a smoker status of said subject, and wherein said classification is determined using said additional expression level.

17. The method of claim 1, wherein said pooled lung tissue sample comprises a lung tissue sample selected from the group consisting of a biopsy sample, a bronchial brushing sample, a bronchoalveolar lavage sample, and a respiratory epithelium sample.

18. The method of claim 1, wherein said pooled lung tissue sample is cytologically ambiguous or suspicious.

19. The method of claim 1, wherein said one or more marker associated with said UIP or said non-UIP comprise two or more markers associated with said UIP or said non-UIP, wherein said two or more markers comprise two or more genes selected from MPO, GGNBP2, SELE, FMO3, SLC6A13, EXTL3, NLRP2, BTN3A1, ABCF2, TLL1, HDAC9, CBLN4, CHRDL2, SNRNP40, MYO3B, SREBF1, GSDMB, MCCC1, CEACAM1, CXCL2, IL12RB2, ITGBS, ZNF671, ITPKC, RCOR1, TGM1, HSD17B7P2, DDTL, FAM118A, C14orf105, ADNP2, OLFM4, HAS3, SLC7AS, GYS1, FSD1, PLEKHA4, TMEMS9L, RUNDC3B, LMBR1, VIPR2, CCL24, LARP4B, UBTF, RASD1, ODAM, CCND1, TSPAN11, SYT10, PRMT8, LTBR, CDK2AP1, GLP1R, VNN1, PCDHB2, LRRC31, SLC4A3, STAT1, IL18RAP, ERRF11, CTH, ALDH6A1, ZNF410, CD274, EGR1, CHRNA2, BCL2L14, ZNF211, NBPF14, EDN3, KLHDC3, SCGB1D2, SLC10A2, ZFP36, GNAZ, TWSG1, C15orf57, LDLR, KLHDC7B, TNNI2, GFAP, CCL2S, ENOSF1, LINC00470, PDE6A, MTUS2, NTS, ARNTL, ADAM-DEC1, WNT2B, TRAFD1, PPP1R1A, EGR4, BAAT, KIF12, GABBR2, RABEPK, TUBB2B, MGARP, SULF1, POU2F3, SLC44A5, DUSP5, PLA2G12B, DUOXA2, DUOX2, DISP2, ARRDC4, CYP1A1, CYP1A2, FTO, NPEPPS, SIK1, MYOM3, XCL2, ILDR2, CRABP2, ABL2, TUFT1, SETDB1, KCNN3, CSRNP1, SLC10A4, SCD5, DDIT4L, GTF2H2, FAM13C, ADD3, HABP2, SYT8, ZC3H12C, SLC7A11, ANO4, CLEC4F, PLEKHG4B, CERS3, GBP5, TDRD9, SLC6A1, DGKI, TSPAN33, CBR3, SPON2, CCDC155, IL23R, SMC6, PDLIM5, GABRG1, EIF4E3, ATXN7, PPM1K, CXCL5, SLC6A20, KLF15, GPR85, DEFA4, IFI27L1, NELL1, PTER, GREM1, KLK1, HRASLS5, CTNNB1, BATF2, TAP1, ZNF30, PPIC, CXCL11, NIPA1, KRT86, HSD17B13, GPR27, PYGO1, PDE7B, ZIK1, ANO5, CALB2, ISG20, CXCR6, ZMAT3, TDRD12, EIF1, MARCH3, TTLL11, MSRA, NUPR1, CLVS1, FBX039, ZNF454, and ZNF543.

20. The method of claim 1, wherein said one or more marker associated with said UIP or said non-UIP comprise three or more markers associated with said UIP or said non-UIP, wherein said three or more markers comprise three or more genes selected from MPO, GGNBP2, SELE, FMO3, SLC6A13, EXTL3, NLRP2, BTN3A1, ABCF2, TLL1, HDAC9, CBLN4, CHRDL2, SNRNP40, MYO3B, SREBF1, GSDMB, MCCC1, CEACAM1, CXCL2, IL12RB2, ITGB5, ZNF671, ITPKC, RCOR1, TGM1, HSD17B7P2, DDTL, FAM118A, C14orf105, ADNP2, OLFM4, HAS3, SLC7A5, GYS1, FSD1, PLEKHA4, TMEM59L, RUNDC3B, LMBR1, VIPR2, CCL24, LARP4B, UBTF, RASD1, ODAM, CCND1, TSPAN11, SYT10, PRMT8, LTBR, CDK2AP1, GLP1R, VNN1, PCDHB2, LRRC31, SLC4A3, STAT1, IL18RAP, ERRF11, CTH, ALDH6A1, ZNF410, CD274, EGR1, CHRNA2, BCL2L14, ZNF211, NBPF14, EDN3, KLHDC3, SCGB1D2, SLC10A2, ZFP36, GNAZ, TWSG1, C15orf57, LDLR, KLHDC7B, TNNI2, GFAP, CCL25, ENOSF1, LINC00470, PDE6A, MTUS2, NTS, ARNTL, ADAM-DEC1, WNT2B, TRAFD1, PPP1R1A, EGR4, BAAT, KIF12, GABBR2, RABEPK, TUBB2B, MGARP, SULF1, POU2F3, SLC44A5, DUSP5, PLA2G12B, DUOXA2, DUOX2, DISP2, ARRDC4, CYP1A1, CYP1A2, FTO, NPEPPS, SIK1, MYOM3, XCL2, ILDR2, CRABP2, ABL2, TUFT1, SETDB1, KCNN3, CSRNP1, SLC10A4, SCD5, DDIT4L, GTF2H2, FAM13C, ADD3, HABP2, SYT8, ZC3H12C, SLC7A11, ANO4, CLEC4F, PLEKHG4B, CERS3, GBP5, TDRD9, SLC6A1, DGKI, TSPAN33, CBR3, SPON2, CCDC155, IL23R, SMC6, PDLIM5, GABRG1, EIF4E3, ATXN7, PPM1K, CXCL5, SLC6A20, KLF15, GPR85, DEFA4, IFI27L1, NELL1, PTER, GREM1, KLK1, HRASLS5, CTNNB1, BATF2, TAP1, ZNF30, PPIC, CXCL11, NIPA1, KRT86, HSD17B13, GPR27, PYGO1, PDE7B, ZIK1, ANO5, CALB2, ISG20, CXCR6, ZMAT3, TDRD12, EIF1, MARCH3, TTLL11, MSRA, NUPR1, CLVS1, FBX039, ZNF454, and ZNF543.

* * * * *

UNITED STATES PATENT AND TRADEMARK OFFICE
CERTIFICATE OF CORRECTION

PATENT NO. : 11,976,329 B2
APPLICATION NO. : 17/558534
DATED : May 7, 2024
INVENTOR(S) : Giulia C. Kennedy et al.

Page 1 of 1

It is certified that error appears in the above-identified patent and that said Letters Patent is hereby corrected as shown below:

On the Title Page

Item (60), Lines 3-4:
Replace "on Sep. 7, 2016, provisional application No. 61/799,754, filed on Mar. 15, 2013." with --on Sep. 7, 2016.--.

In the Claims

Column 122, Line 53:
Replace "STAT1, IL18RAP, ERRFIL CTH, ALDH6A1," with --STAT1, IL18RAP, ERRFI1, CTH, ALDH6A1,--.

Column 124, Line 22:
Replace "PCDHB2, LRRC31, SLC4A3, STAT1, IL18RAP, ERRF11," with --PCDHB2, LRRC31, SLC4A3, STAT1, IL18RAP, ERRFI1,--.

Column 124, Line 59:
Replace "PCDHB2, LRRC31, SLC4A3, STAT1, IL18RAP, ERRF11," with --PCDHB2, LRRC31, SLC4A3, STAT1, IL18RAP, ERRFI1,--.

Signed and Sealed this
Twenty-fifth Day of June, 2024

Katherine Kelly Vidal
*Director of the United States Patent and Trademark Office*